(12) United States Patent
Blois et al.

(10) Patent No.: US 11,952,574 B2
(45) Date of Patent: Apr. 9, 2024

(54) COMPOSITIONS AND METHODS FOR INHIBITING TRANSMEMBRANE SERINE PROTEASE 6 (TMPRSS6) EXPRESSION

(71) Applicants: Novo Nordisk A/S, Bagsvaerd (DK); Dicerna Pharmaceuticals, Inc., Lexington, MA (US)

(72) Inventors: Anna Linda Blois, Sudbury, MA (US); Christina Marie Priest, Lexington, MA (US); Jihye Park, Cambridge, MA (US); Henryk Dudek, Belmont, MA (US)

(73) Assignees: Novo Nordisk A/S, Bagsvaerd (DK); Dicerna Pharmaceuticals, Inc., Lexington, MA (US)

(*) Notice: Subject to any disclaimer, the term of this patent is extended or adjusted under 35 U.S.C. 154(b) by 0 days.

(21) Appl. No.: 18/213,289

(22) Filed: Jun. 23, 2023

(65) Prior Publication Data
US 2024/0002858 A1   Jan. 4, 2024

Related U.S. Application Data

(60) Provisional application No. 63/355,210, filed on Jun. 24, 2022.

(30) Foreign Application Priority Data

Nov. 23, 2022 (EP) .................................. 22209113

(51) Int. Cl.
C12N 15/11 (2006.01)
A61P 7/00 (2006.01)
C12N 15/113 (2010.01)

(52) U.S. Cl.
CPC .......... *C12N 15/1138* (2013.01); *A61P 7/00* (2018.01); *C12N 2310/14* (2013.01); *C12N 2310/315* (2013.01); *C12N 2310/531* (2013.01)

(58) Field of Classification Search
None
See application file for complete search history.

(56) References Cited

U.S. PATENT DOCUMENTS

| | | |
|---|---|---|
| 5,804,683 A | 9/1998 | Usman et al. |
| 5,831,071 A | 11/1998 | Usman et al. |
| 5,998,203 A | 12/1999 | Matulic-Adamic et al. |
| 6,008,400 A | 12/1999 | Scaringe et al. |
| 6,111,086 A | 8/2000 | Scaringe |
| 6,117,657 A | 9/2000 | Usman et al. |
| 6,353,098 B1 | 3/2002 | Usman et al. |
| 6,362,323 B1 | 3/2002 | Usman et al. |
| 6,437,117 B1 | 8/2002 | Usman et al. |
| 6,469,158 B1 | 10/2002 | Usman et al. |
| 8,372,968 B2 | 2/2013 | Tuschl |
| 8,513,207 B2 | 8/2013 | Brown |
| 8,883,996 B2 | 11/2014 | Rossi |
| 8,927,513 B2 | 1/2015 | Manoharan et al. |
| 8,927,705 B2 | 1/2015 | Brown |
| 9,012,138 B2 | 4/2015 | Tuschl |
| 9,012,621 B2 | 4/2015 | Tuschl |
| 9,193,753 B2 | 11/2015 | Tuschl |
| 9,567,587 B2 | 2/2017 | Freier |
| 10,131,912 B2 | 11/2018 | Brown |
| 2007/0254362 A1 | 11/2007 | Quay et al. |
| 2008/0274462 A1 | 11/2008 | Jeon et al. |
| 2009/0099115 A1 | 4/2009 | McSwiggen |
| 2019/0177729 A1 | 6/2019 | Wang et al. |

FOREIGN PATENT DOCUMENTS

| | | |
|---|---|---|
| WO | 20021108 A1 | 1/2002 |
| WO | 2010033225 A2 | 3/2010 |
| WO | 2011133871 A2 | 10/2011 |
| WO | 12135246 A2 | 10/2012 |
| WO | 13070786 A1 | 5/2013 |
| WO | 14190157 A1 | 11/2014 |
| WO | 16085852 A1 | 6/2016 |
| WO | 2016100401 A1 | 6/2016 |
| WO | 16161429 A1 | 10/2016 |
| WO | 2018045317 A1 | 3/2018 |
| WO | 18185240 A1 | 10/2018 |
| WO | 2022226127 A1 | 10/2022 |
| WO | 2022231999 A1 | 11/2022 |

OTHER PUBLICATIONS

Abe et al., "Dumbbell-Shaped Nanocircular RNAs for RNA Interference", J Am Chem Soc. Dec. 12, 2007; vol. 129, No. 49, pp. 15108-15109.
Alexander et al., "HFE-associated hereditary hemochromatosis", Genetics in Medicine, May 2009, vol. 11, No. 5, pp. 307-313.
Altamura et al., "SLN124, a GalNAc-siRNA Conjugate Targeting TMPRSS6, Efficiently Prevents Iron Overload in Hereditary Haemochromatosis Type 1", HemaSphere, 2019, vol. 3, No. 6, pp. 1-5.
Antao et al., "A thermodynamic study of unusually stable RNA and DNA hairpins", Nucleic Acids Res., Nov. 1991, vol. 19, No. 21, pp. 5901-5905.
Beaucage et al., "Deoxynucleoside Phosphoramidites—A New Class of Key Intermediates for Deoxypolynucleotide Synthesis", Tetrahedron Lett., 1981, vol. 22, pp. 1859-1862.
Bennett et al., "Pharmacology of Antisense Drugs", Annu Rev Pharmacol Toxicol., Jan. 2017, vol. 57, pp. 81-105.
Bramsen et al., "Improved silencing properties using small internally segmented interfering RNAs", Nucleic Acids Res., 2007, vol. 35, No. 17, pp. 5886-5897.
Butler et al., "Aln-TMP: A Subcutaneously Administered RNAi Therapeutic Targeting Tmprss6 for the Treatment of ?-Thalassemia", Blood, Nov. 2013, vol. 122, No. 21, p. 2260.

(Continued)

*Primary Examiner* — Ekaterina Poliakova-Georgantas
(74) *Attorney, Agent, or Firm* — Jianjie Hu

(57) ABSTRACT

Oligonucleotides are provided herein that inhibit TMPRSS6 expression. Also provided are compositions including the same and uses thereof, particularly uses relating to treating diseases, disorders and/or conditions associated with hepcidin deficiency or suppression.

28 Claims, 28 Drawing Sheets

Specification includes a Sequence Listing.

(56) References Cited

OTHER PUBLICATIONS

Casu et al., "Minihepcidin peptides as disease modifiers in mice affected by ?-thalassemia and polycythemia vera", Blood, Jul. 2016, vol. 128, No. 2, pp. 265-276.
Chang et al., "Asymmetric shorter-duplex siRNA structures trigger efficient gene silencing with reduced nonspecific effects", Mol Ther., Apr. 2009, vol. 17, No. 4, pp. 725-732.
Cheong et al., "Solution structure of an unusually stable RNA hairpin, 5GGAC(UUCG)GUCC", Nature, Aug. 1990, vol. 346, pp. 680-682.
Cornish-Bowden, "Nomenclature for incompletely specified bases in nucleic acid sequences: recommendations 1984", Nucleic Acids Res., May 1985, vol. 13, No. 9, pp. 3021-3030.
Damha et al., "Oligoribonucleotide synthesis. The silyl-phosphoramidite method", Methods Mol. Biol., 1993, vol. 20, pp. 81-114.
Du et al., "The Serine Protease TMPRSS6 Is Required to Sense Iron Deficiency", Science, May 2008, vol. 320, No. 5869, pp. 1088-1092.
Elsner, "Single-stranded siRNAs for in vivo gene silencing", Nat Biotechnol., Nov. 2012, vol. 30, No. 11, p. 1063.
Finberg et al., "Tmprss6 is a genetic modifier of the Hfe-hemochromatosis phenotype in mice", Blood, Feb. 2011, vol. 117, No. 17, pp. 4590-4599.
Folgueras et al., "Membrane-bound serine protease matriptase-2 (Tmprss6) is an essential regulator of iron homeostasis", Blood, Jun. 2008, vol. 112, No. 6, pp. 2539-2545.
Gardenghi et al., "Hepcidin as a therapeutic tool to limit iron overload and improve anemia in ?-thalassemic mice", J. Clin. Invest., Dec. 2010, vol. 120, No. 12, pp. 4466-4477.
Guo et al, "Inactivation of specific ? cell transcription factors in type 2 diabetes", J. Clin. Invest., Aug. 2013, vol. 123, No. 8, pp. 3305-3316.
Hamilton et al., "Two classes of short interfering RNA in RNA silencing", EMBO J., Sep. 2, 2002, vol. 21, No. 17, pp. 4671-4679.
Heus et al., "Structural features that give rise to the unusual stability of RNA hairpins containing GNRA loops", Science, Jul. 1991, vol. 253, pp. 191-194.
Hohjoh, "Enhancement of RNAi activity by improved siRNA duplexes", FEBS Lett., Jan. 2004, vol. 557, No. 1-3, pp. 193-198.
Huch et al., "In vitro expansion of single Lgr5+ liver stem cells induced by Wnt-driven regeneration", Nature, Feb. 2013, vol. 494, pp. 247-250.
Hughes et al., "Synthetic DNA Synthesis and Assembly: Putting the Synthetic in Synthetic Biology", Cold Spring Harb Perspect Biol., Jan. 2017, vol. 9, No. 1, Article No. a023812, pp. 1-17.
Imanishi et al., "BNAs: novel nucleic acid analogs with a bridged sugar moiety", Chem Commun. (Camb), Aug. 2002, vol. 21, pp. 1653-1659.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", Tetrahedon, Apr. 1998, vol. 54, pp. 3607-3630.
Kraynack and Baker, "Small interfering RNAs containing full 2?-O-methylribonucleotide-modified sense strands display Argonaute2/eIF2C2-dependent activity", RNA, 2006, vol. 12, pp. 163-176.
Livak and Schmittgen, "Analysis of relative gene expression data using real-time quantitative PCR and the 2(-Delta Delta C(T)) Method", Methods, Dec. 2001, vol. 25, No. 4, pp. 402-408.
Loakes et al., "3-Nitropyrrole and 5-nitroindole as universal bases in primers for DNA sequencing and PCR", Nucleic Acids Res., Jul. 1995, vol. 23, pp. 2361-2366.
Loakes et al., "5-Nitroindole as an universal base analogue", Nucleic Acids Res., Oct. 1994, vol. 22, pp. 4039-4043.
Matsui et al., "Argonaute 2-dependent Regulation of Gene Expression by Single-stranded miRNA Mimics", Mol Ther., May 2016, vol. 24, No. 5, pp. 946-955.
Moore et al., "Short hairpin RNA (shRNA): design, delivery, and assessment of gene knockdown", Methods Mol Biol., 2010, vol. 629, pp. 141-158.
Nakano et al., "Selection for thermodynamically stable DNA tetraloops using temperature gradient gel electrophoresis reveals four motifs: d(cGNNAg), d(cGNABg), d(cCNNGg), and d(gCNNGc)", Biochemistry, Dec. 2002, vol. 41, pp. 14281-14292.
Prakash et al., "Identification of metabolically stable 5'-phosphate analogs that support single-stranded siRNA activity", Nucleic Acids Res., Mar. 2015, vol. 43, pp. 2993-3011.
Ramos et al., "Minihepcidins prevent iron overload in a hepcidin-deficient mouse model of severe hemochromatosis", Blood, Nov. 2012, vol. 120, No. 18, pp. 3829-3836.
Scaringe et al., "Chemical synthesis of biologically active oligoribonucleotides using beta-cyanoethyl protected ribonucleoside phosphoramidites", Nucleic Acids Res., Sep. 1990, vol. 18, pp. 5433-5441.
Schmidt et al., "An RNAi therapeutic targeting Tmprss6 decreases iron overload in Hfe -/- mice and ameliorates anemia and iron overload in murine b-thalassemia intermedia", Blood, Dec. 2012, vol. 121, No. 7, pp. 1200-1208.
Schmidt et al., "RNAi-mediated reduction of hepatic Tmprss6 diminishesanemia and secondary iron overload in a splenectomized mouse model of b-thalassemia intermedia", AJH, 2018, vol. 93, pp. 745-750.
Shinji et al., Nippon Kagakkai Koen Yokoshu, 2000, vol. 78, p. 731.
Snead et al., "5' Unlocked Nucleic Acid Modification Improves siRNA Targeting", Mol. Ther-Nucl. Acids, Jul. 2013, vol. 2, No. 7, e103, pp. 1-7.
Sun et al., "Asymmetric RNA duplexes mediate RNA interference in mammalian cells", Nat Biotechnol. Dec. 2008, vol. 26, No. 12, pp. 1379-1382.
Usman et al., "The automated chemical synthesis of long oligoribuncleotides using 2'-O-silylated ribonucleoside 3'-O-phosphoramidites on a controlled-pore glass support: synthesis of a 43-nucleotide sequence similar to the 3'-half molecule of an *Escherichia coli* formylmethionine tRNA", J. Am. Chem. Soc., Dec. 1987, vol. 109, pp. 7845-7854.
Vadolas et al., "SLN124, a GalNac-siRNA targeting transmembrane serine protease 6, in combination with deferiprone therapy reduces ineffective erythropoiesis and hepatic iron-overload in a mouse model of b-thalassaemia," BJH, May 2021, vol. 194, pp. 200-210.
Van Aerschot et al., "An acyclic 5-nitroindazole nucleoside analogue as ambiguous nucleoside", Nucleic Acids Res., Dec. 1995, vol. 23, No. 21, pp. 4363-4370.
Wincott et al., "Synthesis, deprotection, analysis and purification of RNA and ribosomes", Nucleic Acids Res., Jul. 1995, vol. 23, No. 14, pp. 2677-2684.
Woese et al., "Architecture of ribosomal RNA: constraints on the sequence of "tetra-loops"", PNAS, Nov. 1990, vol. 87, pp. 8467-8471.

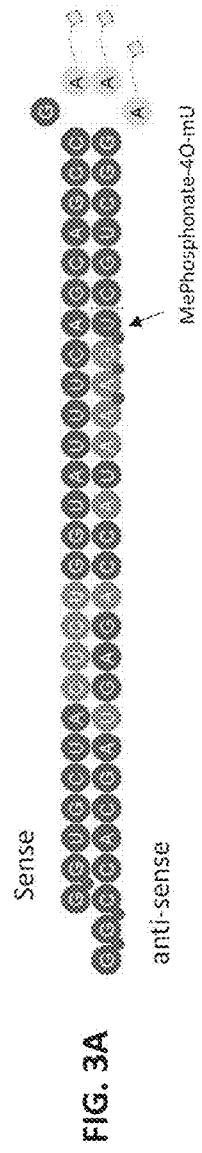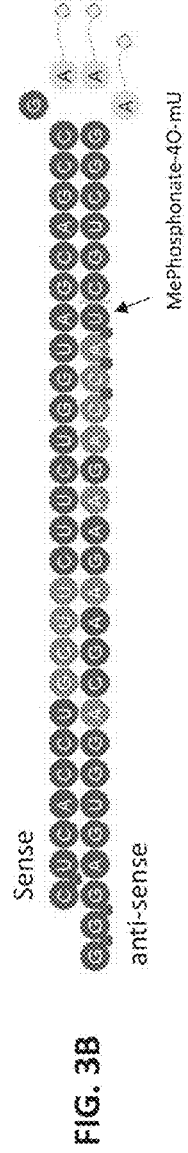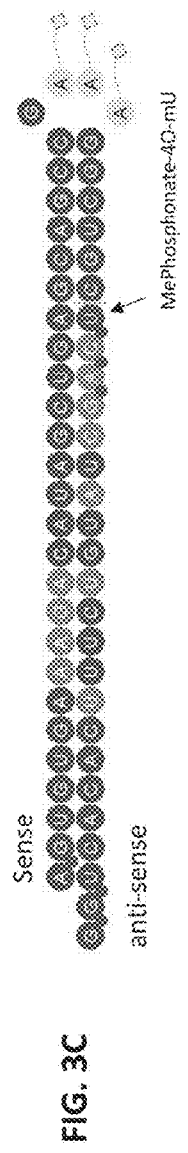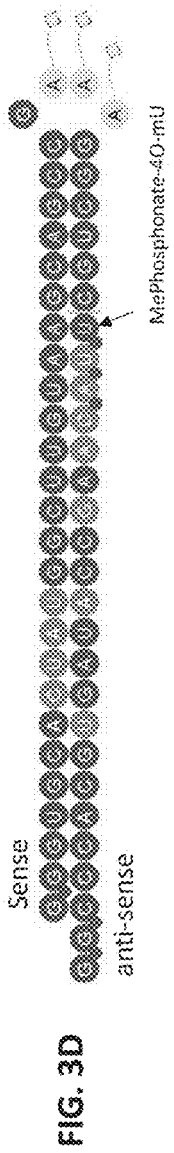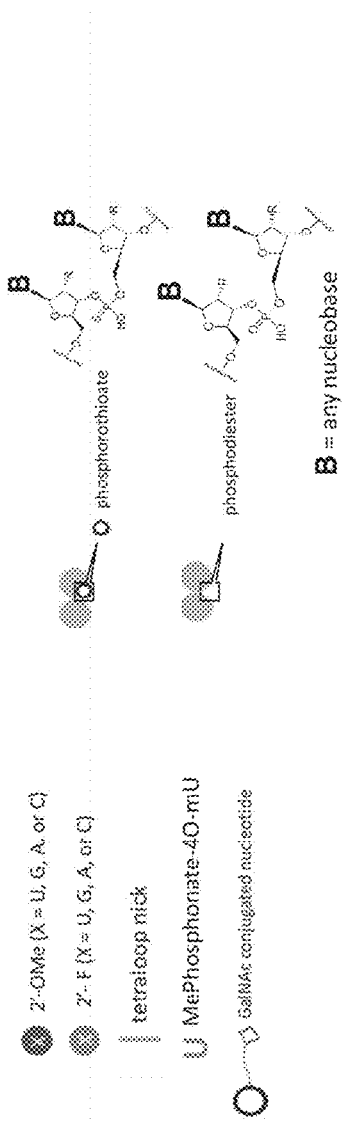
FIG. 3A  FIG. 3B  FIG. 3C  FIG. 3D

SEQUENCE LISTING

```
Sequence total quantity: 862
SEQ ID NO: 1         moltype = RNA  length = 19
FEATURE              Location/Qualifiers
source               1..19
                     mol_type = other RNA
                     organism = synthetic construct
```

```
SEQUENCE: 1
cggctcacct tgaaggaca                                                      19

SEQ ID NO: 2         moltype = RNA  length = 19
FEATURE              Location/Qualifiers
source               1..19
                     mol_type = other RNA
                     organism = synthetic construct SEQUENCE: 2
ggctcacctt gaaggacac                                                      19

SEQ ID NO: 3         moltype = RNA  length = 19
FEATURE              Location/Qualifiers
source               1..19
                     mol_type = other RNA
                     organism = synthetic construct SEQUENCE: 3
gctcaccttg aaggacacc                                                      19

SEQ ID NO: 4         moltype = RNA  length = 19
FEATURE              Location/Qualifiers
source               1..19
                     mol_type = other RNA
                     organism = synthetic construct SEQUENCE: 4
ctcaccttga aggacacct                                                      19

SEQ ID NO: 5         moltype = RNA  length = 19
FEATURE              Location/Qualifiers
source               1..19
                     mol_type = other RNA
                     organism = synthetic construct SEQUENCE: 5
tcaccttgaa ggacacctc                                                      19

SEQ ID NO: 6         moltype = RNA  length = 19
FEATURE              Location/Qualifiers
source               1..19
                     mol_type = other RNA
                     organism = synthetic construct SEQUENCE: 6
gaggccatgc tgtcctcct                                                      19

SEQ ID NO: 7         moltype = RNA  length = 19
FEATURE              Location/Qualifiers
source               1..19
                     mol_type = other RNA
                     organism = synthetic construct SEQUENCE: 7
aggccatgct gtcctcctg                                                      19

SEQ ID NO: 8         moltype = RNA  length = 19
FEATURE              Location/Qualifiers
source               1..19
                     mol_type = other RNA
                     organism = synthetic construct SEQUENCE: 8
ggccatgctg tcctcctgg                                                      19

SEQ ID NO: 9         moltype = RNA  length = 19
FEATURE              Location/Qualifiers
source               1..19
                     mol_type = other RNA
                     organism = synthetic construct SEQUENCE: 9
gccatgctgt cctcctgga                                                      19

SEQ ID NO: 10        moltype = RNA  length = 19
FEATURE              Location/Qualifiers
source               1..19
                     mol_type = other RNA
                     organism = synthetic construct SEQUENCE: 10
ccatgctgtc ctcctggaa                                                      19

SEQ ID NO: 11        moltype = RNA  length = 19
FEATURE              Location/Qualifiers
source               1..19
                     mol_type = other RNA
```

-continued

```
                            organism = synthetic construct
SEQUENCE: 11
catgctgtcc tcctggaag                                                19

SEQ ID NO: 12               moltype = RNA   length = 19
FEATURE                     Location/Qualifiers
source                      1..19
                            mol_type = other RNA
                            organism = synthetic construct
SEQUENCE: 12
atgctgtcct cctggaagc                                                19

SEQ ID NO: 13               moltype = RNA   length = 19
FEATURE                     Location/Qualifiers
source                      1..19
                            mol_type = other RNA
                            organism = synthetic construct
SEQUENCE: 13
tgctgtcctc ctggaagca                                                19

SEQ ID NO: 14               moltype = RNA   length = 19
FEATURE                     Location/Qualifiers
source                      1..19
                            mol_type = other RNA
                            organism = synthetic construct
SEQUENCE: 14
acccagcggt cagcgatga                                                19

SEQ ID NO: 15               moltype = RNA   length = 19
FEATURE                     Location/Qualifiers
source                      1..19
                            mol_type = other RNA
                            organism = synthetic construct
SEQUENCE: 15
cccagcggtc agcgatgag                                                19

SEQ ID NO: 16               moltype = RNA   length = 19
FEATURE                     Location/Qualifiers
source                      1..19
                            mol_type = other RNA
                            organism = synthetic construct
SEQUENCE: 16
cctggaggcc acagtcaca                                                19

SEQ ID NO: 17               moltype = RNA   length = 19
FEATURE                     Location/Qualifiers
source                      1..19
                            mol_type = other RNA
                            organism = synthetic construct
SEQUENCE: 17
tggaggccac agtcacagt                                                19

SEQ ID NO: 18               moltype = RNA   length = 19
FEATURE                     Location/Qualifiers
source                      1..19
                            mol_type = other RNA
                            organism = synthetic construct
SEQUENCE: 18
ggaggccaca gtcacagtg                                                19

SEQ ID NO: 19               moltype = RNA   length = 19
FEATURE                     Location/Qualifiers
source                      1..19
                            mol_type = other RNA
                            organism = synthetic construct
SEQUENCE: 19
gtgagggaga tctgggagg                                                19

SEQ ID NO: 20               moltype = RNA   length = 19
FEATURE                     Location/Qualifiers
source                      1..19
                            mol_type = other RNA
                            organism = synthetic construct
SEQUENCE: 20
agggagatct gggaggtga                                                19

SEQ ID NO: 21               moltype = RNA   length = 19
FEATURE                     Location/Qualifiers
source                      1..19
```

```
                        mol_type = other RNA
                        organism = synthetic construct
SEQUENCE: 21
gggagatctg ggaggtgaa                                                 19

SEQ ID NO: 22           moltype = RNA  length = 19
FEATURE                 Location/Qualifiers
source                  1..19
                        mol_type = other RNA
                        organism = synthetic construct
SEQUENCE: 22
ttgtacccta ggaaatacc                                                 19

SEQ ID NO: 23           moltype = RNA  length = 19
FEATURE                 Location/Qualifiers
source                  1..19
                        mol_type = other RNA
                        organism = synthetic construct
SEQUENCE: 23
tgtaccctag gaaatacca                                                 19

SEQ ID NO: 24           moltype = RNA  length = 19
FEATURE                 Location/Qualifiers
source                  1..19
                        mol_type = other RNA
                        organism = synthetic construct
SEQUENCE: 24
ttcttgccct tgcggtagc                                                 19

SEQ ID NO: 25           moltype = RNA  length = 19
FEATURE                 Location/Qualifiers
source                  1..19
                        mol_type = other RNA
                        organism = synthetic construct
SEQUENCE: 25
tcttgccctt gcggtagcc                                                 19

SEQ ID NO: 26           moltype = RNA  length = 19
FEATURE                 Location/Qualifiers
source                  1..19
                        mol_type = other RNA
                        organism = synthetic construct
SEQUENCE: 26
tggaggctgg cctgccatg                                                 19

SEQ ID NO: 27           moltype = RNA  length = 19
FEATURE                 Location/Qualifiers
source                  1..19
                        mol_type = other RNA
                        organism = synthetic construct
SEQUENCE: 27
tgccatggcc actcaccct                                                 19

SEQ ID NO: 28           moltype = RNA  length = 19
FEATURE                 Location/Qualifiers
source                  1..19
                        mol_type = other RNA
                        organism = synthetic construct
SEQUENCE: 28
ccatggccac tcaccctcg                                                 19

SEQ ID NO: 29           moltype = RNA  length = 19
FEATURE                 Location/Qualifiers
source                  1..19
                        mol_type = other RNA
                        organism = synthetic construct
SEQUENCE: 29
ccactcaccc tcggaggac                                                 19

SEQ ID NO: 30           moltype = RNA  length = 19
FEATURE                 Location/Qualifiers
source                  1..19
                        mol_type = other RNA
                        organism = synthetic construct
SEQUENCE: 30
cactcaccct cggaggaca                                                 19

SEQ ID NO: 31           moltype = RNA  length = 19
FEATURE                 Location/Qualifiers
```

```
source                       1..19
                             mol_type = other RNA
                             organism = synthetic construct
SEQUENCE: 31
actcaccctc ggaggacac                                                       19

SEQ ID NO: 32                moltype = RNA   length = 19
FEATURE                      Location/Qualifiers
source                       1..19
                             mol_type = other RNA
                             organism = synthetic construct
SEQUENCE: 32
cagtttctct catccaggc                                                       19

SEQ ID NO: 33                moltype = RNA   length = 19
FEATURE                      Location/Qualifiers
source                       1..19
                             mol_type = other RNA
                             organism = synthetic construct
SEQUENCE: 33
agtttctctc atccaggcc                                                       19

SEQ ID NO: 34                moltype = RNA   length = 19
FEATURE                      Location/Qualifiers
source                       1..19
                             mol_type = other RNA
                             organism = synthetic construct
SEQUENCE: 34
gccaagccgt agtccagag                                                       19

SEQ ID NO: 35                moltype = RNA   length = 19
FEATURE                      Location/Qualifiers
source                       1..19
                             mol_type = other RNA
                             organism = synthetic construct
SEQUENCE: 35
ccaagccgta gtccagaga                                                       19

SEQ ID NO: 36                moltype = RNA   length = 19
FEATURE                      Location/Qualifiers
source                       1..19
                             mol_type = other RNA
                             organism = synthetic construct
SEQUENCE: 36
aaccagaaga agcaggtga                                                       19

SEQ ID NO: 37                moltype = RNA   length = 19
FEATURE                      Location/Qualifiers
source                       1..19
                             mol_type = other RNA
                             organism = synthetic construct
SEQUENCE: 37
accagaagaa gcaggtgag                                                       19

SEQ ID NO: 38                moltype = RNA   length = 19
FEATURE                      Location/Qualifiers
source                       1..19
                             mol_type = other RNA
                             organism = synthetic construct
SEQUENCE: 38
gagcatcttc tgggctttg                                                       19

SEQ ID NO: 39                moltype = RNA   length = 19
FEATURE                      Location/Qualifiers
source                       1..19
                             mol_type = other RNA
                             organism = synthetic construct
SEQUENCE: 39
agcatcttct gggctttgg                                                       19

SEQ ID NO: 40                moltype = RNA   length = 19
FEATURE                      Location/Qualifiers
source                       1..19
                             mol_type = other RNA
                             organism = synthetic construct
SEQUENCE: 40
gcatcttctg ggctttggc                                                       19

SEQ ID NO: 41                moltype = RNA   length = 19
```

```
FEATURE                 Location/Qualifiers
source                  1..19
                        mol_type = other RNA
                        organism = synthetic construct
SEQUENCE: 41
caggcagctt tattccaaa                                                         19

SEQ ID NO: 42           moltype = RNA   length = 19
FEATURE                 Location/Qualifiers
source                  1..19
                        mol_type = other RNA
                        organism = synthetic construct
SEQUENCE: 42
aggcagcttt attccaaag                                                         19

SEQ ID NO: 43           moltype = RNA   length = 19
FEATURE                 Location/Qualifiers
source                  1..19
                        mol_type = other RNA
                        organism = synthetic construct
SEQUENCE: 43
gcagctttat tccaaaggg                                                         19

SEQ ID NO: 44           moltype = RNA   length = 19
FEATURE                 Location/Qualifiers
source                  1..19
                        mol_type = other RNA
                        organism = synthetic construct
SEQUENCE: 44
cagctttatt ccaaagggc                                                         19

SEQ ID NO: 45           moltype = RNA   length = 19
FEATURE                 Location/Qualifiers
source                  1..19
                        mol_type = other RNA
                        organism = synthetic construct
SEQUENCE: 45
agctttattc caaagggca                                                         19

SEQ ID NO: 46           moltype = RNA   length = 19
FEATURE                 Location/Qualifiers
source                  1..19
                        mol_type = other RNA
                        organism = synthetic construct
SEQUENCE: 46
tttattccaa agggcagct                                                         19

SEQ ID NO: 47           moltype = RNA   length = 19
FEATURE                 Location/Qualifiers
source                  1..19
                        mol_type = other RNA
                        organism = synthetic construct
SEQUENCE: 47
ttattccaaa gggcagctg                                                         19

SEQ ID NO: 48           moltype = RNA   length = 19
FEATURE                 Location/Qualifiers
source                  1..19
                        mol_type = other RNA
                        organism = synthetic construct
SEQUENCE: 48
caaagggcag ctgagctca                                                         19

SEQ ID NO: 49           moltype = RNA   length = 19
FEATURE                 Location/Qualifiers
source                  1..19
                        mol_type = other RNA
                        organism = synthetic construct
SEQUENCE: 49
aaagggcagc tgagctcac                                                         19

SEQ ID NO: 50           moltype = RNA   length = 19
FEATURE                 Location/Qualifiers
source                  1..19
                        mol_type = other RNA
                        organism = synthetic construct
SEQUENCE: 50
accaggggct tccgaagct                                                         19
```

-continued

```
SEQ ID NO: 51              moltype = RNA   length = 19
FEATURE                    Location/Qualifiers
source                     1..19
                           mol_type = other RNA
                           organism = synthetic construct
SEQUENCE: 51
ccagcattct tgctgctga                                                       19

SEQ ID NO: 52              moltype = RNA   length = 19
FEATURE                    Location/Qualifiers
source                     1..19
                           mol_type = other RNA
                           organism = synthetic construct
SEQUENCE: 52
cagcattctt gctgctgag                                                       19

SEQ ID NO: 53              moltype = RNA   length = 19
FEATURE                    Location/Qualifiers
source                     1..19
                           mol_type = other RNA
                           organism = synthetic construct
SEQUENCE: 53
agcattcttg ctgctgagc                                                       19

SEQ ID NO: 54              moltype = RNA   length = 19
FEATURE                    Location/Qualifiers
source                     1..19
                           mol_type = other RNA
                           organism = synthetic construct
SEQUENCE: 54
cattcttgct gctgagcca                                                       19

SEQ ID NO: 55              moltype = RNA   length = 19
FEATURE                    Location/Qualifiers
source                     1..19
                           mol_type = other RNA
                           organism = synthetic construct
SEQUENCE: 55
attcttgctg ctgagccac                                                       19

SEQ ID NO: 56              moltype = RNA   length = 19
FEATURE                    Location/Qualifiers
source                     1..19
                           mol_type = other RNA
                           organism = synthetic construct
SEQUENCE: 56
catcactgga gcagacatc                                                       19

SEQ ID NO: 57              moltype = RNA   length = 19
FEATURE                    Location/Qualifiers
source                     1..19
                           mol_type = other RNA
                           organism = synthetic construct
SEQUENCE: 57
atcactggag cagacatca                                                       19

SEQ ID NO: 58              moltype = RNA   length = 19
FEATURE                    Location/Qualifiers
source                     1..19
                           mol_type = other RNA
                           organism = synthetic construct
SEQUENCE: 58
tcactggagc agacatcag                                                       19

SEQ ID NO: 59              moltype = RNA   length = 19
FEATURE                    Location/Qualifiers
source                     1..19
                           mol_type = other RNA
                           organism = synthetic construct
SEQUENCE: 59
actggagcag acatcaggg                                                       19

SEQ ID NO: 60              moltype = RNA   length = 19
FEATURE                    Location/Qualifiers
source                     1..19
                           mol_type = other RNA
                           organism = synthetic construct
SEQUENCE: 60
gttcctcagg tcaccactt                                                       19
```

```
SEQ ID NO: 61            moltype = RNA   length = 19
FEATURE                  Location/Qualifiers
source                   1..19
                         mol_type = other RNA
                         organism = synthetic construct
SEQUENCE: 61
ttcctcaggt caccacttg                                                    19

SEQ ID NO: 62            moltype = RNA   length = 19
FEATURE                  Location/Qualifiers
source                   1..19
                         mol_type = other RNA
                         organism = synthetic construct
SEQUENCE: 62
tcctcaggtc accacttgc                                                    19

SEQ ID NO: 63            moltype = RNA   length = 19
FEATURE                  Location/Qualifiers
source                   1..19
                         mol_type = other RNA
                         organism = synthetic construct
SEQUENCE: 63
cctcaggtca ccacttgct                                                    19

SEQ ID NO: 64            moltype = RNA   length = 19
FEATURE                  Location/Qualifiers
source                   1..19
                         mol_type = other RNA
                         organism = synthetic construct
SEQUENCE: 64
ctcaggtcac cacttgctg                                                    19

SEQ ID NO: 65            moltype = RNA   length = 19
FEATURE                  Location/Qualifiers
source                   1..19
                         mol_type = other RNA
                         organism = synthetic construct
SEQUENCE: 65
tcaggtcacc acttgctgg                                                    19

SEQ ID NO: 66            moltype = RNA   length = 19
FEATURE                  Location/Qualifiers
source                   1..19
                         mol_type = other RNA
                         organism = synthetic construct
SEQUENCE: 66
aggtcaccac ttgctggat                                                    19

SEQ ID NO: 67            moltype = RNA   length = 19
FEATURE                  Location/Qualifiers
source                   1..19
                         mol_type = other RNA
                         organism = synthetic construct
SEQUENCE: 67
tcaccacttg ctggatcca                                                    19

SEQ ID NO: 68            moltype = RNA   length = 19
FEATURE                  Location/Qualifiers
source                   1..19
                         mol_type = other RNA
                         organism = synthetic construct
SEQUENCE: 68
caccacttgc tggatccag                                                    19

SEQ ID NO: 69            moltype = RNA   length = 19
FEATURE                  Location/Qualifiers
source                   1..19
                         mol_type = other RNA
                         organism = synthetic construct
SEQUENCE: 69
atcacacctg tgatgcggg                                                    19

SEQ ID NO: 70            moltype = RNA   length = 19
FEATURE                  Location/Qualifiers
source                   1..19
                         mol_type = other RNA
                         organism = synthetic construct
SEQUENCE: 70
```
tcacacctgt gatgcgggt                                                  19

SEQ ID NO: 71          moltype = RNA   length = 19
FEATURE                Location/Qualifiers
source                 1..19
                       mol_type = other RNA
                       organism = synthetic construct SEQUENCE: 71
tgtagacgcc gaagtagtt                                                  19

SEQ ID NO: 72          moltype = RNA   length = 19
FEATURE                Location/Qualifiers
source                 1..19
                       mol_type = other RNA
                       organism = synthetic construct SEQUENCE: 72
acaggtcctg tgggatcaa                                                  19

SEQ ID NO: 73          moltype = RNA   length = 19
FEATURE                Location/Qualifiers
source                 1..19
                       mol_type = other RNA
                       organism = synthetic construct SEQUENCE: 73
tcctgtggga tcaactgca                                                  19

SEQ ID NO: 74          moltype = RNA   length = 19
FEATURE                Location/Qualifiers
source                 1..19
                       mol_type = other RNA
                       organism = synthetic construct SEQUENCE: 74
caccttgaag gacacctct                                                  19

SEQ ID NO: 75          moltype = RNA   length = 19
FEATURE                Location/Qualifiers
source                 1..19
                       mol_type = other RNA
                       organism = synthetic construct SEQUENCE: 75
accttgaagg acacctctc                                                  19

SEQ ID NO: 76          moltype = RNA   length = 19
FEATURE                Location/Qualifiers
source                 1..19
                       mol_type = other RNA
                       organism = synthetic construct SEQUENCE: 76
ttgaaggaca cctctccag                                                  19

SEQ ID NO: 77          moltype = RNA   length = 19
FEATURE                Location/Qualifiers
source                 1..19
                       mol_type = other RNA
                       organism = synthetic construct SEQUENCE: 77
atgtgtcgac cccgaacct                                                  19

SEQ ID NO: 78          moltype = RNA   length = 19
FEATURE                Location/Qualifiers
source                 1..19
                       mol_type = other RNA
                       organism = synthetic construct SEQUENCE: 78
ctcacactgg aaggtgaat                                                  19

SEQ ID NO: 79          moltype = RNA   length = 19
FEATURE                Location/Qualifiers
source                 1..19
                       mol_type = other RNA
                       organism = synthetic construct SEQUENCE: 79
tcacactgga aggtgaatg                                                  19

SEQ ID NO: 80          moltype = RNA   length = 19
FEATURE                Location/Qualifiers
source                 1..19
                       mol_type = other RNA
                       organism = synthetic construct

```
SEQUENCE: 80
cacactggaa ggtgaatgt                                                          19

SEQ ID NO: 81         moltype = RNA   length = 19
FEATURE               Location/Qualifiers
source                1..19
                      mol_type = other RNA
                      organism = synthetic construct
SEQUENCE: 81
acactggaag gtgaatgtc                                                          19

SEQ ID NO: 82         moltype = RNA   length = 19
FEATURE               Location/Qualifiers
source                1..19
                      mol_type = other RNA
                      organism = synthetic construct
SEQUENCE: 82
cactggaagg tgaatgtcc                                                          19

SEQ ID NO: 83         moltype = RNA   length = 19
FEATURE               Location/Qualifiers
source                1..19
                      mol_type = other RNA
                      organism = synthetic construct
SEQUENCE: 83
cactggaatg tggctctgc                                                          19

SEQ ID NO: 84         moltype = RNA   length = 19
FEATURE               Location/Qualifiers
source                1..19
                      mol_type = other RNA
                      organism = synthetic construct
SEQUENCE: 84
actggaatgt ggctctgca                                                          19

SEQ ID NO: 85         moltype = RNA   length = 19
FEATURE               Location/Qualifiers
source                1..19
                      mol_type = other RNA
                      organism = synthetic construct
SEQUENCE: 85
ctggaatgtg gctctgcaa                                                          19

SEQ ID NO: 86         moltype = RNA   length = 19
FEATURE               Location/Qualifiers
source                1..19
                      mol_type = other RNA
                      organism = synthetic construct
SEQUENCE: 86
tggaatgtgg ctctgcaaa                                                          19

SEQ ID NO: 87         moltype = RNA   length = 19
FEATURE               Location/Qualifiers
source                1..19
                      mol_type = other RNA
                      organism = synthetic construct
SEQUENCE: 87
ggctctgcaa acgcagttt                                                          19

SEQ ID NO: 88         moltype = RNA   length = 19
FEATURE               Location/Qualifiers
source                1..19
                      mol_type = other RNA
                      organism = synthetic construct
SEQUENCE: 88
gctctgcaaa cgcagtttc                                                          19

SEQ ID NO: 89         moltype = RNA   length = 19
FEATURE               Location/Qualifiers
source                1..19
                      mol_type = other RNA
                      organism = synthetic construct
SEQUENCE: 89
ctctgcaaac gcagtttct                                                          19

SEQ ID NO: 90         moltype = RNA   length = 19
FEATURE               Location/Qualifiers
source                1..19
                      mol_type = other RNA
```

```
                              organism = synthetic construct
SEQUENCE: 90
tctgcaaacg cagtttctc                                                    19

SEQ ID NO: 91          moltype = RNA   length = 19
FEATURE                Location/Qualifiers
source                 1..19
                       mol_type = other RNA
                       organism = synthetic construct
SEQUENCE: 91
ctgcaaacgc agtttctct                                                    19

SEQ ID NO: 92          moltype = RNA   length = 19
FEATURE                Location/Qualifiers
source                 1..19
                       mol_type = other RNA
                       organism = synthetic construct
SEQUENCE: 92
tgcaaacgca gtttctctc                                                    19

SEQ ID NO: 93          moltype = RNA   length = 19
FEATURE                Location/Qualifiers
source                 1..19
                       mol_type = other RNA
                       organism = synthetic construct
SEQUENCE: 93
gcaaacgcag tttctctca                                                    19

SEQ ID NO: 94          moltype = RNA   length = 19
FEATURE                Location/Qualifiers
source                 1..19
                       mol_type = other RNA
                       organism = synthetic construct
SEQUENCE: 94
caaacgcagt ttctctcat                                                    19

SEQ ID NO: 95          moltype = RNA   length = 19
FEATURE                Location/Qualifiers
source                 1..19
                       mol_type = other RNA
                       organism = synthetic construct
SEQUENCE: 95
aaacgcagtt tctctcatc                                                    19

SEQ ID NO: 96          moltype = RNA   length = 19
FEATURE                Location/Qualifiers
source                 1..19
                       mol_type = other RNA
                       organism = synthetic construct
SEQUENCE: 96
aacgcagttt ctctcatcc                                                    19

SEQ ID NO: 97          moltype = RNA   length = 19
FEATURE                Location/Qualifiers
source                 1..19
                       mol_type = other RNA
                       organism = synthetic construct
SEQUENCE: 97
acgcagtttc tctcatcca                                                    19

SEQ ID NO: 98          moltype = RNA   length = 19
FEATURE                Location/Qualifiers
source                 1..19
                       mol_type = other RNA
                       organism = synthetic construct
SEQUENCE: 98
cgcagtttct ctcatccag                                                    19

SEQ ID NO: 99          moltype = RNA   length = 19
FEATURE                Location/Qualifiers
source                 1..19
                       mol_type = other RNA
                       organism = synthetic construct
SEQUENCE: 99
gcagtttctc tcatccagg                                                    19

SEQ ID NO: 100         moltype = RNA   length = 19
FEATURE                Location/Qualifiers
source                 1..19
```

| | |
|---|---|
| | moltype = other RNA<br>organism = synthetic construct |
| SEQUENCE: 100 | |
| tccttgaccc catcacagg | 19 |
| SEQ ID NO: 101<br>FEATURE<br>source | moltype = RNA length = 19<br>Location/Qualifiers<br>1..19<br>mol_type = other RNA<br>organism = synthetic construct |
| SEQUENCE: 101 | |
| ggtccgactg gttgtacaa | 19 |
| SEQ ID NO: 102<br>FEATURE<br>source | moltype = RNA length = 19<br>Location/Qualifiers<br>1..19<br>mol_type = other RNA<br>organism = synthetic construct |
| SEQUENCE: 102 | |
| gtccgactgg ttgtacaag | 19 |
| SEQ ID NO: 103<br>FEATURE<br>source | moltype = RNA length = 19<br>Location/Qualifiers<br>1..19<br>mol_type = other RNA<br>organism = synthetic construct |
| SEQUENCE: 103 | |
| tccgactggt tgtacaagc | 19 |
| SEQ ID NO: 104<br>FEATURE<br>source | moltype = RNA length = 19<br>Location/Qualifiers<br>1..19<br>mol_type = other RNA<br>organism = synthetic construct |
| SEQUENCE: 104 | |
| cgactggttg tacaagcca | 19 |
| SEQ ID NO: 105<br>FEATURE<br>source | moltype = RNA length = 19<br>Location/Qualifiers<br>1..19<br>mol_type = other RNA<br>organism = synthetic construct |
| SEQUENCE: 105 | |
| gactggttgt acaagccat | 19 |
| SEQ ID NO: 106<br>FEATURE<br>source | moltype = RNA length = 19<br>Location/Qualifiers<br>1..19<br>mol_type = other RNA<br>organism = synthetic construct |
| SEQUENCE: 106 | |
| actggttgta caagccata | 19 |
| SEQ ID NO: 107<br>FEATURE<br>source | moltype = RNA length = 19<br>Location/Qualifiers<br>1..19<br>mol_type = other RNA<br>organism = synthetic construct |
| SEQUENCE: 107 | |
| ctggttgtac aagccatag | 19 |
| SEQ ID NO: 108<br>FEATURE<br>source | moltype = RNA length = 19<br>Location/Qualifiers<br>1..19<br>mol_type = other RNA<br>organism = synthetic construct |
| SEQUENCE: 108 | |
| tggttgtaca agccatagt | 19 |
| SEQ ID NO: 109<br>FEATURE<br>source | moltype = RNA length = 19<br>Location/Qualifiers<br>1..19<br>mol_type = other RNA<br>organism = synthetic construct |
| SEQUENCE: 109 | |
| ggttgtacaa gccatagtg | 19 |
| SEQ ID NO: 110<br>FEATURE | moltype = RNA length = 19<br>Location/Qualifiers |

```
source                         1..19
                               mol_type = other RNA
                               organism = synthetic construct
SEQUENCE: 110
gttgtacaag ccatagtgc                                                     19

SEQ ID NO: 111                 moltype = RNA   length = 19
FEATURE                        Location/Qualifiers
source                         1..19
                               mol_type = other RNA
                               organism = synthetic construct
SEQUENCE: 111
ttgtacaagc catagtgca                                                     19

SEQ ID NO: 112                 moltype = RNA   length = 19
FEATURE                        Location/Qualifiers
source                         1..19
                               mol_type = other RNA
                               organism = synthetic construct
SEQUENCE: 112
tgtacaagcc atagtgcac                                                     19

SEQ ID NO: 113                 moltype = RNA   length = 19
FEATURE                        Location/Qualifiers
source                         1..19
                               mol_type = other RNA
                               organism = synthetic construct
SEQUENCE: 113
gtacaagcca tagtgcacc                                                     19

SEQ ID NO: 114                 moltype = RNA   length = 19
FEATURE                        Location/Qualifiers
source                         1..19
                               mol_type = other RNA
                               organism = synthetic construct
SEQUENCE: 114
tacaagccat agtgcaccc                                                     19

SEQ ID NO: 115                 moltype = RNA   length = 19
FEATURE                        Location/Qualifiers
source                         1..19
                               mol_type = other RNA
                               organism = synthetic construct
SEQUENCE: 115
acaagccata gtgcacccg                                                     19

SEQ ID NO: 116                 moltype = RNA   length = 19
FEATURE                        Location/Qualifiers
source                         1..19
                               mol_type = other RNA
                               organism = synthetic construct
SEQUENCE: 116
aagccatagt gcacccgca                                                     19

SEQ ID NO: 117                 moltype = RNA   length = 19
FEATURE                        Location/Qualifiers
source                         1..19
                               mol_type = other RNA
                               organism = synthetic construct
SEQUENCE: 117
ccatagtgca cccgcacac                                                     19

SEQ ID NO: 118                 moltype = RNA   length = 19
FEATURE                        Location/Qualifiers
source                         1..19
                               mol_type = other RNA
                               organism = synthetic construct
SEQUENCE: 118
tcctgttctg gatcgtcca                                                     19

SEQ ID NO: 119                 moltype = RNA   length = 19
FEATURE                        Location/Qualifiers
source                         1..19
                               mol_type = other RNA
                               organism = synthetic construct
SEQUENCE: 119
tgttctggat cgtccactg                                                     19

SEQ ID NO: 120                 moltype = RNA   length = 19
```

```
FEATURE              Location/Qualifiers
source               1..19
                     mol_type = other RNA
                     organism = synthetic construct
SEQUENCE: 120
tgcacggcaa atcatactt                                                    19

SEQ ID NO: 121       moltype = RNA   length = 19
FEATURE              Location/Qualifiers
source               1..19
                     mol_type = other RNA
                     organism = synthetic construct
SEQUENCE: 121
gcacggcaaa tcatacttc                                                    19

SEQ ID NO: 122       moltype = RNA   length = 19
FEATURE              Location/Qualifiers
source               1..19
                     mol_type = other RNA
                     organism = synthetic construct
SEQUENCE: 122
cacggcaaat catacttct                                                    19

SEQ ID NO: 123       moltype = RNA   length = 19
FEATURE              Location/Qualifiers
source               1..19
                     mol_type = other RNA
                     organism = synthetic construct
SEQUENCE: 123
acggcaaatc atacttctg                                                    19

SEQ ID NO: 124       moltype = RNA   length = 19
FEATURE              Location/Qualifiers
source               1..19
                     mol_type = other RNA
                     organism = synthetic construct
SEQUENCE: 124
ggcaaatcat acttctgcc                                                    19

SEQ ID NO: 125       moltype = RNA   length = 19
FEATURE              Location/Qualifiers
source               1..19
                     mol_type = other RNA
                     organism = synthetic construct
SEQUENCE: 125
gcaaatcata cttctgcct                                                    19

SEQ ID NO: 126       moltype = RNA   length = 19
FEATURE              Location/Qualifiers
source               1..19
                     mol_type = other RNA
                     organism = synthetic construct
SEQUENCE: 126
caaatcatac ttctgcctc                                                    19

SEQ ID NO: 127       moltype = RNA   length = 19
FEATURE              Location/Qualifiers
source               1..19
                     mol_type = other RNA
                     organism = synthetic construct
SEQUENCE: 127
aaatcatact tctgcctcc                                                    19

SEQ ID NO: 128       moltype = RNA   length = 19
FEATURE              Location/Qualifiers
source               1..19
                     mol_type = other RNA
                     organism = synthetic construct
SEQUENCE: 128
gagtagtagc tggggaagt                                                    19

SEQ ID NO: 129       moltype = RNA   length = 19
FEATURE              Location/Qualifiers
source               1..19
                     mol_type = other RNA
                     organism = synthetic construct
SEQUENCE: 129
tagtagctgg ggaagtacg                                                    19
```

```
SEQ ID NO: 130          moltype = RNA   length = 19
FEATURE                 Location/Qualifiers
source                  1..19
                        mol_type = other RNA
                        organism = synthetic construct
SEQUENCE: 130
gggtcgtagt agctgtgca                                                    19

SEQ ID NO: 131          moltype = RNA   length = 19
FEATURE                 Location/Qualifiers
source                  1..19
                        mol_type = other RNA
                        organism = synthetic construct
SEQUENCE: 131
tagctgtgca ggcccttct                                                    19

SEQ ID NO: 132          moltype = RNA   length = 19
FEATURE                 Location/Qualifiers
source                  1..19
                        mol_type = other RNA
                        organism = synthetic construct
SEQUENCE: 132
tcatacatgg ccagtcggt                                                    19

SEQ ID NO: 133          moltype = RNA   length = 19
FEATURE                 Location/Qualifiers
source                  1..19
                        mol_type = other RNA
                        organism = synthetic construct
SEQUENCE: 133
tagctgtagc ggtaacaac                                                    19

SEQ ID NO: 134          moltype = RNA   length = 19
FEATURE                 Location/Qualifiers
source                  1..19
                        mol_type = other RNA
                        organism = synthetic construct
SEQUENCE: 134
gctgtagcgg taacaaccc                                                    19

SEQ ID NO: 135          moltype = RNA   length = 19
FEATURE                 Location/Qualifiers
source                  1..19
                        mol_type = other RNA
                        organism = synthetic construct
SEQUENCE: 135
ctgtagcggt aacaaccca                                                    19

SEQ ID NO: 136          moltype = RNA   length = 19
FEATURE                 Location/Qualifiers
source                  1..19
                        mol_type = other RNA
                        organism = synthetic construct
SEQUENCE: 136
tgtagcggta acaacccag                                                    19

SEQ ID NO: 137          moltype = RNA   length = 19
FEATURE                 Location/Qualifiers
source                  1..19
                        mol_type = other RNA
                        organism = synthetic construct
SEQUENCE: 137
taacaaccca gcgtggaat                                                    19

SEQ ID NO: 138          moltype = RNA   length = 19
FEATURE                 Location/Qualifiers
source                  1..19
                        mol_type = other RNA
                        organism = synthetic construct
SEQUENCE: 138
aacaacccag cgtggaatt                                                    19

SEQ ID NO: 139          moltype = RNA   length = 19
FEATURE                 Location/Qualifiers
source                  1..19
                        mol_type = other RNA
                        organism = synthetic construct
SEQUENCE: 139
tgcagctatg tctttcaca                                                    19
```

```
SEQ ID NO: 140              moltype = RNA   length = 19
FEATURE                     Location/Qualifiers
source                      1..19
                            mol_type = other RNA
                            organism = synthetic construct
SEQUENCE: 140
gcagctatgt ctttcacac                                                       19

SEQ ID NO: 141              moltype = RNA   length = 19
FEATURE                     Location/Qualifiers
source                      1..19
                            mol_type = other RNA
                            organism = synthetic construct
SEQUENCE: 141
cagctatgtc tttcacact                                                       19

SEQ ID NO: 142              moltype = RNA   length = 19
FEATURE                     Location/Qualifiers
source                      1..19
                            mol_type = other RNA
                            organism = synthetic construct
SEQUENCE: 142
agctatgtct ttcacactg                                                       19

SEQ ID NO: 143              moltype = RNA   length = 19
FEATURE                     Location/Qualifiers
source                      1..19
                            mol_type = other RNA
                            organism = synthetic construct
SEQUENCE: 143
gctatgtctt tcacactgg                                                       19

SEQ ID NO: 144              moltype = RNA   length = 19
FEATURE                     Location/Qualifiers
source                      1..19
                            mol_type = other RNA
                            organism = synthetic construct
SEQUENCE: 144
ctatgtcttt cacactggc                                                       19

SEQ ID NO: 145              moltype = RNA   length = 19
FEATURE                     Location/Qualifiers
source                      1..19
                            mol_type = other RNA
                            organism = synthetic construct
SEQUENCE: 145
tatgtctttc acactggct                                                       19

SEQ ID NO: 146              moltype = RNA   length = 19
FEATURE                     Location/Qualifiers
source                      1..19
                            mol_type = other RNA
                            organism = synthetic construct
SEQUENCE: 146
atgtctttca cactggctt                                                       19

SEQ ID NO: 147              moltype = RNA   length = 19
FEATURE                     Location/Qualifiers
source                      1..19
                            mol_type = other RNA
                            organism = synthetic construct
SEQUENCE: 147
tgtctttcac actggcttc                                                       19

SEQ ID NO: 148              moltype = RNA   length = 19
FEATURE                     Location/Qualifiers
source                      1..19
                            mol_type = other RNA
                            organism = synthetic construct
SEQUENCE: 148
tgttgactgt ggacagcag                                                       19

SEQ ID NO: 149              moltype = RNA   length = 19
FEATURE                     Location/Qualifiers
source                      1..19
                            mol_type = other RNA
                            organism = synthetic construct
SEQUENCE: 149
```

```
ttgactgtgg acagcagct                                                    19

SEQ ID NO: 150          moltype = RNA   length = 19
FEATURE                 Location/Qualifiers
source                  1..19
                        mol_type = other RNA
                        organism = synthetic construct
SEQUENCE: 150
ggggatttgg agaatgaac                                                    19

SEQ ID NO: 151          moltype = RNA   length = 19
FEATURE                 Location/Qualifiers
source                  1..19
                        mol_type = other RNA
                        organism = synthetic construct
SEQUENCE: 151
gggatttgga gaatgaacc                                                    19

SEQ ID NO: 152          moltype = RNA   length = 19
FEATURE                 Location/Qualifiers
source                  1..19
                        mol_type = other RNA
                        organism = synthetic construct
SEQUENCE: 152
ggatttggag aatgaacca                                                    19

SEQ ID NO: 153          moltype = RNA   length = 19
FEATURE                 Location/Qualifiers
source                  1..19
                        mol_type = other RNA
                        organism = synthetic construct
SEQUENCE: 153
gatttggaga atgaaccag                                                    19

SEQ ID NO: 154          moltype = RNA   length = 19
FEATURE                 Location/Qualifiers
source                  1..19
                        mol_type = other RNA
                        organism = synthetic construct
SEQUENCE: 154
atttggagaa tgaaccaga                                                    19

SEQ ID NO: 155          moltype = RNA   length = 19
FEATURE                 Location/Qualifiers
source                  1..19
                        mol_type = other RNA
                        organism = synthetic construct
SEQUENCE: 155
tttggagaat gaaccagaa                                                    19

SEQ ID NO: 156          moltype = RNA   length = 19
FEATURE                 Location/Qualifiers
source                  1..19
                        mol_type = other RNA
                        organism = synthetic construct
SEQUENCE: 156
ttggagaatg aaccagaag                                                    19

SEQ ID NO: 157          moltype = RNA   length = 19
FEATURE                 Location/Qualifiers
source                  1..19
                        mol_type = other RNA
                        organism = synthetic construct
SEQUENCE: 157
gagaatgaac cagaagaag                                                    19

SEQ ID NO: 158          moltype = RNA   length = 19
FEATURE                 Location/Qualifiers
source                  1..19
                        mol_type = other RNA
                        organism = synthetic construct
SEQUENCE: 158
agaatgaacc agaagaagc                                                    19

SEQ ID NO: 159          moltype = RNA   length = 19
FEATURE                 Location/Qualifiers
source                  1..19
                        mol_type = other RNA
                        organism = synthetic construct
```

-continued

```
SEQUENCE: 159
gaatgaacca gaagaagca                                              19

SEQ ID NO: 160          moltype = RNA   length = 19
FEATURE                 Location/Qualifiers
source                  1..19
                        mol_type = other RNA
                        organism = synthetic construct
SEQUENCE: 160
aatgaaccag aagaagcag                                              19

SEQ ID NO: 161          moltype = RNA   length = 19
FEATURE                 Location/Qualifiers
source                  1..19
                        mol_type = other RNA
                        organism = synthetic construct
SEQUENCE: 161
atgaaccaga agaagcagg                                              19

SEQ ID NO: 162          moltype = RNA   length = 19
FEATURE                 Location/Qualifiers
source                  1..19
                        mol_type = other RNA
                        organism = synthetic construct
SEQUENCE: 162
tgaaccagaa gaagcaggt                                              19

SEQ ID NO: 163          moltype = RNA   length = 19
FEATURE                 Location/Qualifiers
source                  1..19
                        mol_type = other RNA
                        organism = synthetic construct
SEQUENCE: 163
gaaccagaag aagcaggtg                                              19

SEQ ID NO: 164          moltype = RNA   length = 19
FEATURE                 Location/Qualifiers
source                  1..19
                        mol_type = other RNA
                        organism = synthetic construct
SEQUENCE: 164
aaaggaatag acggagctg                                              19

SEQ ID NO: 165          moltype = RNA   length = 19
FEATURE                 Location/Qualifiers
source                  1..19
                        mol_type = other RNA
                        organism = synthetic construct
SEQUENCE: 165
gaatagacgg agctggagt                                              19

SEQ ID NO: 166          moltype = RNA   length = 19
FEATURE                 Location/Qualifiers
source                  1..19
                        mol_type = other RNA
                        organism = synthetic construct
SEQUENCE: 166
aatagacgga gctggagtt                                              19

SEQ ID NO: 167          moltype = RNA   length = 19
FEATURE                 Location/Qualifiers
source                  1..19
                        mol_type = other RNA
                        organism = synthetic construct
SEQUENCE: 167
atgagctcct tgagcatct                                              19

SEQ ID NO: 168          moltype = RNA   length = 19
FEATURE                 Location/Qualifiers
source                  1..19
                        mol_type = other RNA
                        organism = synthetic construct
SEQUENCE: 168
tgagctcctt gagcatctt                                              19

SEQ ID NO: 169          moltype = RNA   length = 19
FEATURE                 Location/Qualifiers
source                  1..19
                        mol_type = other RNA
```

```
                                       -continued
                        organism = synthetic construct
SEQUENCE: 169
gagctccttg agcatcttc                                                    19

SEQ ID NO: 170          moltype = RNA  length = 19
FEATURE                 Location/Qualifiers
source                  1..19
                        mol_type = other RNA
                        organism = synthetic construct
SEQUENCE: 170
agctccttga gcatcttct                                                    19

SEQ ID NO: 171          moltype = RNA  length = 19
FEATURE                 Location/Qualifiers
source                  1..19
                        mol_type = other RNA
                        organism = synthetic construct
SEQUENCE: 171
gctccttgag catcttctg                                                    19

SEQ ID NO: 172          moltype = RNA  length = 19
FEATURE                 Location/Qualifiers
source                  1..19
                        mol_type = other RNA
                        organism = synthetic construct
SEQUENCE: 172
ctccttgagc atcttctgg                                                    19

SEQ ID NO: 173          moltype = RNA  length = 19
FEATURE                 Location/Qualifiers
source                  1..19
                        mol_type = other RNA
                        organism = synthetic construct
SEQUENCE: 173
tccttgagca tcttctggg                                                    19

SEQ ID NO: 174          moltype = RNA  length = 19
FEATURE                 Location/Qualifiers
source                  1..19
                        mol_type = other RNA
                        organism = synthetic construct
SEQUENCE: 174
ttgagcatct tctgggctt                                                    19

SEQ ID NO: 175          moltype = RNA  length = 19
FEATURE                 Location/Qualifiers
source                  1..19
                        mol_type = other RNA
                        organism = synthetic construct
SEQUENCE: 175
tgagcatctt ctgggcttt                                                    19

SEQ ID NO: 176          moltype = RNA  length = 19
FEATURE                 Location/Qualifiers
source                  1..19
                        mol_type = other RNA
                        organism = synthetic construct
SEQUENCE: 176
ctgagtacac ctggctgac                                                    19

SEQ ID NO: 177          moltype = RNA  length = 19
FEATURE                 Location/Qualifiers
source                  1..19
                        mol_type = other RNA
                        organism = synthetic construct
SEQUENCE: 177
tgagtacacc tggctgacc                                                    19

SEQ ID NO: 178          moltype = RNA  length = 19
FEATURE                 Location/Qualifiers
source                  1..19
                        mol_type = other RNA
                        organism = synthetic construct
SEQUENCE: 178
ccctaggaaa taccagagt                                                    19

SEQ ID NO: 179          moltype = RNA  length = 19
FEATURE                 Location/Qualifiers
source                  1..19
```

```
SEQ ID NO: 179          moltype = RNA    length = 19
FEATURE                 Location/Qualifiers
source                  1..19
                        mol_type = other RNA
                        organism = synthetic construct
SEQUENCE: 179
cctaggaaat accagagta                                                    19

SEQ ID NO: 180          moltype = RNA    length = 19
FEATURE                 Location/Qualifiers
source                  1..19
                        mol_type = other RNA
                        organism = synthetic construct
SEQUENCE: 180
ctaggaaata ccagagtag                                                    19

SEQ ID NO: 181          moltype = RNA    length = 19
FEATURE                 Location/Qualifiers
source                  1..19
                        mol_type = other RNA
                        organism = synthetic construct
SEQUENCE: 181
taggaaatac cagagtagc                                                    19

SEQ ID NO: 182          moltype = RNA    length = 19
FEATURE                 Location/Qualifiers
source                  1..19
                        mol_type = other RNA
                        organism = synthetic construct
SEQUENCE: 182
aggaaatacc agagtagca                                                    19

SEQ ID NO: 183          moltype = RNA    length = 19
FEATURE                 Location/Qualifiers
source                  1..19
                        mol_type = other RNA
                        organism = synthetic construct
SEQUENCE: 183
ggaaatacca gagtagcac                                                    19

SEQ ID NO: 184          moltype = RNA    length = 19
FEATURE                 Location/Qualifiers
source                  1..19
                        mol_type = other RNA
                        organism = synthetic construct
SEQUENCE: 184
gaaataccag agtagcacc                                                    19

SEQ ID NO: 185          moltype = RNA    length = 19
FEATURE                 Location/Qualifiers
source                  1..19
                        mol_type = other RNA
                        organism = synthetic construct
SEQUENCE: 185
aaataccaga gtagcaccc                                                    19

SEQ ID NO: 186          moltype = RNA    length = 19
FEATURE                 Location/Qualifiers
source                  1..19
                        mol_type = other RNA
                        organism = synthetic construct
SEQUENCE: 186
ggcttttctc ttggagtcc                                                    19

SEQ ID NO: 187          moltype = RNA    length = 19
FEATURE                 Location/Qualifiers
source                  1..19
                        mol_type = other RNA
                        organism = synthetic construct
SEQUENCE: 187
gcttttctct tggagtcct                                                    19

SEQ ID NO: 188          moltype = RNA    length = 19
FEATURE                 Location/Qualifiers
source                  1..19
                        mol_type = other RNA
                        organism = synthetic construct
SEQUENCE: 188
ttttctcttg gagtcctca                                                    19

SEQ ID NO: 189          moltype = RNA    length = 19
FEATURE                 Location/Qualifiers
```

```
                       source             1..19
                                          mol_type = other RNA
                                          organism = synthetic construct
SEQUENCE: 189
tttctcttgg agtcctcac                                                              19

SEQ ID NO: 190         moltype = RNA   length = 19
FEATURE                Location/Qualifiers
source                 1..19
                       mol_type = other RNA
                       organism = synthetic construct
SEQUENCE: 190
ttctcttgga gtcctcaca                                                              19

SEQ ID NO: 191         moltype = RNA   length = 19
FEATURE                Location/Qualifiers
source                 1..19
                       mol_type = other RNA
                       organism = synthetic construct
SEQUENCE: 191
tctcttggag tcctcacag                                                              19

SEQ ID NO: 192         moltype = RNA   length = 19
FEATURE                Location/Qualifiers
source                 1..19
                       mol_type = other RNA
                       organism = synthetic construct
SEQUENCE: 192
ctcttggagt cctcacagg                                                              19

SEQ ID NO: 193         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 193
tgtccttcaa ggtgagccgc ctgct                                                       25

SEQ ID NO: 194         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 194
gtgtccttca aggtgagccg cctgc                                                       25

SEQ ID NO: 195         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 195
ggtgtccttc aaggtgagcc gcctg                                                       25

SEQ ID NO: 196         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 196
aggtgtcctt caaggtgagc cgcct                                                       25

SEQ ID NO: 197         moltype = DNA   length = 25
```

```
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 197
gaggtgtcct tcaaggtgag ccgcc                                              25

SEQ ID NO: 198          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 198
aggaggacag catggcctcc acggt                                              25

SEQ ID NO: 199          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 199
caggaggaca gcatggcctc cacgg                                              25

SEQ ID NO: 200          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 200
ccaggaggac agcatggcct ccacg                                              25

SEQ ID NO: 201          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 201
tccaggagga cagcatggcc tccac                                              25

SEQ ID NO: 202          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 202
ttccaggagg acagcatggc ctcca                                              25

SEQ ID NO: 203          moltype = DNA   length = 25
FEATURE                 Location/Qualifiers
misc_feature            1..23
                        note = RNA
misc_feature            24..25
                        note = DNA
source                  1..25
                        mol_type = other DNA
```

```
                         organism = synthetic construct
SEQUENCE: 203
cttccaggag gacagcatgg cctcc                                              25

SEQ ID NO: 204           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 204
gcttccagga ggacagcatg gcctc                                              25

SEQ ID NO: 205           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 205
tgcttccagg aggacagcat ggcct                                              25

SEQ ID NO: 206           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 206
tcatcgctga ccgctgggtg ataac                                              25

SEQ ID NO: 207           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 207
ctcatcgctg accgctgggt gataa                                              25

SEQ ID NO: 208           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 208
tgtgactgtg gcctccaggg cccct                                              25

SEQ ID NO: 209           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 209
actgtgactg tggcctccag ggccc                                              25

SEQ ID NO: 210           moltype = DNA   length = 25
FEATURE                  Location/Qualifiers
misc_feature             1..23
```

```
                              note = RNA
misc_feature                  24..25
                              note = DNA
source                        1..25
                              mol_type = other DNA
                              organism = synthetic construct
SEQUENCE: 210
cactgtgact gtggcctcca gggcc                                               25

SEQ ID NO: 211        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 211
cctcccagat ctccctcacc gggcc                                               25

SEQ ID NO: 212        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 212
tcacctccca gatctccctc accgg                                               25

SEQ ID NO: 213        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 213
ttcacctccc agatctccct caccg                                               25

SEQ ID NO: 214        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 214
ggtatttcct agggtacaag gcgga                                               25

SEQ ID NO: 215        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 215
tggtatttcc tagggtacaa ggcgg                                               25

SEQ ID NO: 216        moltype = DNA  length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 216
```

```
gctaccgcaa gggcaagaag gatgc                                          25

SEQ ID NO: 218           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 217
ggctaccgca agggcaagaa ggatg                                          25

SEQ ID NO: 218           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 218
catgcaggc cagcctccag gttcg                                           25

SEQ ID NO: 219           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 219
agggtgagtg gccatggcag gccag                                          25

SEQ ID NO: 220           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 220
cgagggtgag tggccatggc aggcc                                          25

SEQ ID NO: 221           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 221
gtcctccgag ggtgagtggc catgg                                          25

SEQ ID NO: 222           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 222
tgtcctccga gggtgagtgg ccatg                                          25

SEQ ID NO: 223           moltype = DNA  length = 25
FEATURE                  Location/Qualifiers
misc_feature             1..23
                         note = RNA
misc_feature             24..25
```

```
                        note = DNA
source                  1..25
                        mol_type = other DNA
                        organism = synthetic construct
SEQUENCE: 223
gtgtcctccg agggtgagtg gccat                                        25

SEQ ID NO: 224          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 224
gcctggatga gagaaactgc gtttg                                        25

SEQ ID NO: 225          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 225
ggcctggatg agagaaactg cgttt                                        25

SEQ ID NO: 226          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 226
ctctggacta cggcttggcc ctctg                                        25

SEQ ID NO: 227          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 227
tctctggact acggcttggc cctct                                        25

SEQ ID NO: 228          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 228
tcacctgctt cttctggttc attct                                        25

SEQ ID NO: 229          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 229
ctcacctgct tcttctggtt cattc                                        25
```

-continued

```
SEQ ID NO: 230           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 230
caaagcccag aagatgctca aggag                                               25

SEQ ID NO: 231           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 231
ccaaagccca gaagatgctc aagga                                               25

SEQ ID NO: 232           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 232
gccaaagccc agaagatgct caagg                                               25

SEQ ID NO: 233           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 233
tttggaataa agctgcctga tccaa                                               25

SEQ ID NO: 234           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 234
ctttggaata aagctgcctg atcca                                               25

SEQ ID NO: 235           moltype = DNA  length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 235
ccctttggaa taaagctgcc tgatc                                               25

SEQ ID NO: 236           moltype = DNA  length = 25
FEATURE                  Location/Qualifiers
misc_feature             1..23
                         note = RNA
misc_feature             24..25
                         note = DNA
source                   1..25
```

```
                        mol_type = other DNA
                        organism = synthetic construct
SEQUENCE: 236
gcccttggga ataaagctgc ctgat                                               25

SEQ ID NO: 237          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 237
tgcccttcgg aataaagctg cctga                                               25

SEQ ID NO: 238          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 238
agctgcccttt tggaataaag ctgcc                                              25

SEQ ID NO: 239          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 239
cagctgccct tggaataaa gctgc                                                25

SEQ ID NO: 240          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 240
tgagctcagc tgcccttgg aataa                                                25

SEQ ID NO: 241          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 241
gtgagctcag ctgccctttg gaata                                               25

SEQ ID NO: 242          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 242
agcttcggaa gccctggtc taact                                                25

SEQ ID NO: 243          moltype = DNA   length = 25
FEATURE                 Location/Qualifiers
```

```
misc_feature          1..23
                      note = RNA
misc_feature          24..25
                      note = DNA
source                1..25
                      mol_type = other DNA
                      organism = synthetic construct
SEQUENCE: 243
tcagcagcaa gaatgctggt tctac                                              25

SEQ ID NO: 244        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 244
ctcagcagca agaatgctgg ttcta                                              25

SEQ ID NO: 245        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 245
gctcagcagc aagaatgctg gttct                                              25

SEQ ID NO: 246        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 246
tggctcagca gcaagaatgc tggtt                                              25

SEQ ID NO: 247        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 247
gtggctcagc agcaagaatg ctggt                                              25

SEQ ID NO: 248        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 248
gatgtctgct ccagtgatgg cagga                                              25

SEQ ID NO: 249        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
```

```
SEQUENCE: 249
tgatgtctgc tccagtgatg gcagg                                              25

SEQ ID NO: 251          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 250
ctgatgtctg ctccagtgat ggcag                                              25

SEQ ID NO: 251          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 251
ccctgatgtc tgctccagtg atggc                                              25

SEQ ID NO: 252          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 252
aagtggtgac ctgaggaact gcccc                                              25

SEQ ID NO: 253          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 253
caagtggtga cctgaggaac tgccc                                              25

SEQ ID NO: 254          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 254
gcaagtggtg acctgaggaa ctgcc                                              25

SEQ ID NO: 255          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 255
agcaagtggt gacctgagga actgc                                              25

SEQ ID NO: 256          moltype = DNA  length = 25
FEATURE                 Location/Qualifiers
misc_feature            1..23
                        note = RNA
```

```
misc_feature         24..25
                     note = DNA
source               1..25
                     mol_type = other DNA
                     organism = synthetic construct
SEQUENCE: 256
cagcaagtgg tgacctgagg aactg                                              25

SEQ ID NO: 257       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 257
ccagcaagtg gtgacctgag gaact                                              25

SEQ ID NO: 258       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 258
atccagcaag tggtgacctg aggaa                                              25

SEQ ID NO: 259       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 259
tggatccagc aagtggtgac ctgag                                              25

SEQ ID NO: 260       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 260
ctggatccag caagtggtga cctga                                              25

SEQ ID NO: 261       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 261
cccgcatcac aggtgtgatc agctg                                              25

SEQ ID NO: 262       moltype = DNA  length = 25
FEATURE              Location/Qualifiers
misc_feature         1..23
                     note = RNA
misc_feature         24..25
                     note = DNA
source               1..25
                     mol_type = other DNA
                     organism = synthetic construct
SEQUENCE: 262
acccgcatca caggtgtgat cagct                                              25
```

| SEQ ID NO: 263 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 263
aactacttcg gcgtctacac ccgca                                                 25

| SEQ ID NO: 264 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 264
ttgatcccac aggacctgtg cagcg                                                 25

| SEQ ID NO: 265 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 265
tgcagttgat cccacaggac ctgtg                                                 25

| SEQ ID NO: 266 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 266
agaggtgtcc ttcaaggtga gccgc                                                 25

| SEQ ID NO: 267 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 267
gagaggtgtc cttcaaggtg agccg                                                 25

| SEQ ID NO: 268 | moltype = DNA length = 25 |
| --- | --- |
| FEATURE | Location/Qualifiers |
| misc_feature | 1..23 |
| | note = RNA |
| misc_feature | 24..25 |
| | note = DNA |
| source | 1..25 |
| | mol_type = other DNA |
| | organism = synthetic construct |

SEQUENCE: 268
ctggagaggt gtccttcaag gtgag                                                 25

| SEQ ID NO: 269 | moltype = DNA length = 25 |
| --- | --- |
| FEATURE | Location/Qualifiers |
| misc_feature | 1..23 |
| | note = RNA |
| misc_feature | 24..25 |
| | note = DNA |

```
source                  1..25
                        mol_type = other DNA
                        organism = synthetic construct
SEQUENCE: 269
aggttcgggg tcgacacatc tgtgg                                              25

SEQ ID NO: 270          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 270
attcaccttc cagtgtgagg accgg                                              25

SEQ ID NO: 271          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 271
cattcacctt ccagtgtgag gaccg                                              25

SEQ ID NO: 272          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 272
acattcacct tccagtgtga ggacc                                              25

SEQ ID NO: 273          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 273
gacattcacc ttccagtgtg aggac                                              25

SEQ ID NO: 274          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 274
ggacattcac cttccagtgt gagga                                              25

SEQ ID NO: 275          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 275
gcagagccac attccagtgc aaaga                                              25

SEQ ID NO: 276          moltype = DNA   length = 25
```

```
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 276
tgcagagcca cattccagtg caaag                                       25

SEQ ID NO: 277     moltype = DNA   length = 25
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 277
ttgcagagcc acattccagt gcaaa                                       25

SEQ ID NO: 278     moltype = DNA   length = 25
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 278
tttgcagagc cacattccag tgcaa                                       25

SEQ ID NO: 279     moltype = DNA   length = 25
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 279
aaactgcgtt tgcagagcca cattc                                       25

SEQ ID NO: 280     moltype = DNA   length = 25
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 280
gaaactgcgt ttgcagagcc acatt                                       25

SEQ ID NO: 281     moltype = DNA   length = 25
FEATURE            Location/Qualifiers
misc_feature       1..23
                   note = RNA
misc_feature       24..25
                   note = DNA
source             1..25
                   mol_type = other DNA
                   organism = synthetic construct
SEQUENCE: 281
agaaactgcg tttgcagagc cacat                                       25

SEQ ID NO: 282     moltype = DNA   length = 25
FEATURE            Location/Qualifiers
misc_feature       1..23
                   note = RNA
misc_feature       24..25
                   note = DNA
source             1..25
                   mol_type = other DNA
```

-continued

```
                              organism = synthetic construct
SEQUENCE: 282
gagaaactgc gtttgcagag ccaca                                          25

SEQ ID NO: 283                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 283
agagaaactg cgtttgcaga gccac                                          25

SEQ ID NO: 284                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 284
gagagaaact gcgtttgcag agcca                                          25

SEQ ID NO: 285                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 285
tgagagaaac tgcgtttgca gagcc                                          25

SEQ ID NO: 286                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 286
atgagagaaa ctgcgtttgc agagc                                          25

SEQ ID NO: 287                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 287
gatgagagaa actgcgtttg cagag                                          25

SEQ ID NO: 288                moltype = DNA   length = 25
FEATURE                       Location/Qualifiers
misc_feature                  1..23
                              note = RNA
misc_feature                  24..25
                              note = DNA
source                        1..25
                              mol_type = other DNA
                              organism = synthetic construct
SEQUENCE: 288
ggatgagaga aactgcgttt gcaga                                          25

SEQ ID NO: 289                moltype = DNA   length = 25
FEATURE                       Location/Qualifiers
misc_feature                  1..23
```

```
                        note = RNA
misc_feature            24..25
                        note = DNA
source                  1..25
                        mol_type = other DNA
                        organism = synthetic construct
SEQUENCE: 289
tggatgagag aaactgcgtt tgcag                                               25

SEQ ID NO: 290          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 290
ctggatgaga gaaactgcgt ttgca                                               25

SEQ ID NO: 291          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 291
cctggatgag agaaactgcg tttgc                                               25

SEQ ID NO: 292          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 292
cctgtgatgg ggtcaaggac tgccc                                               25

SEQ ID NO: 293          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 293
ttgtacaacc agtcggaccc ctgcc                                               25

SEQ ID NO: 294          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 294
cttgtacaac cagtcggacc cctgc                                               25

SEQ ID NO: 295          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 295
```

```
gcttgtacaa ccagtcggac ccctg                                              25

SEQ ID NO: 296         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 296
tggcttgtac aaccagtcgg acccc                                              25

SEQ ID NO: 297         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 297
atggcttgta caaccagtcg gaccc                                              25

SEQ ID NO: 298         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 298
tatggcttgt acaaccagtc ggacc                                              25

SEQ ID NO: 299         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 299
ctatggcttg tacaaccagt cggac                                              25

SEQ ID NO: 300         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 300
actatggctt gtacaaccag tcgga                                              25

SEQ ID NO: 301         moltype = DNA   length = 25
FEATURE                Location/Qualifiers
misc_feature           1..23
                       note = RNA
misc_feature           24..25
                       note = DNA
source                 1..25
                       mol_type = other DNA
                       organism = synthetic construct
SEQUENCE: 301
cactatggct tgtacaacca gtcgg                                              25

SEQ ID NO: 302         moltype = DNA   length = 25
FEATURE                Location/Qualifiers
misc_feature           1..23
                       note = RNA
misc_feature           24..25
```

```
                        note = DNA
source                  1..25
                        mol_type = other DNA
                        organism = synthetic construct
SEQUENCE: 302
gcactatggc ttgtacaacc agtcg                                         25

SEQ ID NO: 303          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 303
tgcactatgg cttgtacaac cagtc                                         25

SEQ ID NO: 304          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 304
gtgcactatg gcttgtacaa ccagt                                         25

SEQ ID NO: 305          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 305
ggtgcactat ggcttgtaca accag                                         25

SEQ ID NO: 306          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 306
gggtgcacta tggcttgtac aacca                                         25

SEQ ID NO: 307          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 307
cgggtgcact atggcttgta caacc                                         25

SEQ ID NO: 308          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 308
tgcgggtgca ctatggcttg tacaa                                         25
```

```
SEQ ID NO: 309          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 309
gtgtgcgggt gcactatggc ttgta                                              25

SEQ ID NO: 310          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 310
tggacgatcc agaacaggag gctgt                                              25

SEQ ID NO: 311          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 311
cagtggacga tccagaacag gaggc                                              25

SEQ ID NO: 312          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 312
aagtatgatt tgccgtgcac ccagg                                              25

SEQ ID NO: 313          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 313
gaagtatgat ttgccgtgca cccag                                              25

SEQ ID NO: 314          moltype = DNA  length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 314
agaagtatga tttgccgtgc accca                                              25

SEQ ID NO: 315          moltype = DNA  length = 25
FEATURE                 Location/Qualifiers
misc_feature            1..23
                        note = RNA
misc_feature            24..25
                        note = DNA
source                  1..25
```

```
                        mol_type = other DNA
                        organism = synthetic construct
SEQUENCE: 315
cagaagtatg atttgccgtg caccc                                              25

SEQ ID NO: 316          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 316
ggcagaagta tgatttgccg tgcac                                              25

SEQ ID NO: 317          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 317
aggcagaagt atgatttgcc gtgca                                              25

SEQ ID NO: 318          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 318
gaggcagaag tatgatttgc cgtgc                                              25

SEQ ID NO: 319          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 319
ggaggcagaa gtatgatttg ccgtg                                              25

SEQ ID NO: 320          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 320
acttccccag ctactactcg cccca                                              25

SEQ ID NO: 321          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 321
cgtacttccc cagctactac tcgcc                                              25

SEQ ID NO: 322          moltype = DNA   length = 25
FEATURE                 Location/Qualifiers
```

```
misc_feature          1..23
                      note = RNA
misc_feature          24..25
                      note = DNA
source                1..25
                      mol_type = other DNA
                      organism = synthetic construct
SEQUENCE: 322
tgcacagcta ctacgacccc ttcgt                                              25

SEQ ID NO: 323        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 323
agaagggcct gcacagctac tacga                                              25

SEQ ID NO: 324        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 324
accgactggc catgtatgac gtggc                                              25

SEQ ID NO: 325        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 325
gttgttaccg ctacagctac gtggg                                              25

SEQ ID NO: 326        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 326
gggttgttac cgctacagct acgtg                                              25

SEQ ID NO: 327        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
SEQUENCE: 327
tgggttgtta ccgctacagc tacgt                                              25

SEQ ID NO: 328        moltype = DNA   length = 25
FEATURE               Location/Qualifiers
misc_feature          1..23
                      note = RNA
misc_feature          24..25
                      note = DNA
source                1..25
                      mol_type = other DNA
                      organism = synthetic construct
```

```
SEQUENCE: 328
ctgggttgtt accgctacag ctacg                                          25

SEQ ID NO: 329           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 329
attccacgct gggttgttac cgcta                                          25

SEQ ID NO: 330           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 330
aattccacgc tgggttgtta ccgct                                          25

SEQ ID NO: 331           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 331
tgtgaaagac atagctgcat tgaat                                          25

SEQ ID NO: 332           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 332
gtgtgaaaga catagctgca ttgaa                                          25

SEQ ID NO: 333           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 333
agtgtgaaag acatagctgc attga                                          25

SEQ ID NO: 334           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 334
cagtgtgaaa gacatagctg cattg                                          25

SEQ ID NO: 335           moltype = DNA   length = 25
FEATURE                  Location/Qualifiers
misc_feature             1..23
                         note = RNA
```

```
misc_feature              24..25
                          note = DNA
source                    1..25
                          mol_type = other DNA
                          organism = synthetic construct
SEQUENCE: 335
ccagtgtgaa agacatagct gcatt                                              25

SEQ ID NO: 336            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 336
gccagtgtga agacatagc tgcat                                               25

SEQ ID NO: 337            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 337
agccagtgtg aaagacatag ctgca                                              25

SEQ ID NO: 338            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 338
aagccagtgt gaaagacata gctgc                                              25

SEQ ID NO: 339            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 339
gaagccagtg tgaaagacat agctg                                              25

SEQ ID NO: 340            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 340
ctgctgtcca cagtcaacag ctcgg                                              25

SEQ ID NO: 341            moltype = DNA  length = 25
FEATURE                   Location/Qualifiers
misc_feature              1..23
                          note = RNA
misc_feature              24..25
                          note = DNA
source                    1..25
                          mol_type = other DNA
                          organism = synthetic construct
SEQUENCE: 341
agctgctgtc cacagtcaac agctc                                              25
```

```
SEQ ID NO: 342          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 342
gttcattctc caaatccccg agcac                                               25

SEQ ID NO: 343          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 343
ggttcattct ccaaatcccc gagca                                               25

SEQ ID NO: 344          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 344
tggttcattc tccaaatccc cgagc                                               25

SEQ ID NO: 345          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 345
ctggttcatt ctccaaatcc ccgag                                               25

SEQ ID NO: 346          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 346
tctggttcat tctccaaatc cccga                                               25

SEQ ID NO: 347          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 347
ttctggttca ttctccaaat ccccg                                               25

SEQ ID NO: 348          moltype = DNA   length = 25
FEATURE                 Location/Qualifiers
misc_feature            1..23
                        note = RNA
misc_feature            24..25
                        note = DNA
```

```
source                   1..25
                         mol_type = other DNA
                         organism = synthetic construct
SEQUENCE: 348
cttctggttc attctccaaa tcccc                                              25

SEQ ID NO: 349           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 349
cttcttctgg ttcattctcc aaatc                                              25

SEQ ID NO: 350           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 350
gcttcttctg gttcattctc caaat                                              25

SEQ ID NO: 351           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 351
tgcttcttct ggttcattct ccaaa                                              25

SEQ ID NO: 352           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 352
ctgcttcttc tggttcattc tccaa                                              25

SEQ ID NO: 353           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 353
cctgcttctt ctggttcatt ctcca                                              25

SEQ ID NO: 354           moltype = DNA   length = 25
FEATURE                  Location/Qualifiers
misc_feature             1..23
                         note = RNA
misc_feature             24..25
                         note = DNA
source                   1..25
                         mol_type = other DNA
                         organism = synthetic construct
SEQUENCE: 354
acctgcttct tctggttcat tctcc                                              25

SEQ ID NO: 355           moltype = DNA   length = 25
```

```
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 355
cacctgcttc ttctggttca ttctc                                               25

SEQ ID NO: 356          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 356
cagctccgtc tattcctttg gggag                                               25

SEQ ID NO: 357          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 357
actccagctc cgtctattcc tttgg                                               25

SEQ ID NO: 358          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 358
aactccagct ccgtctattc ctttg                                               25

SEQ ID NO: 359          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 359
agatgctcaa ggagctcatc accag                                               25

SEQ ID NO: 360          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 360
aagatgctca aggagctcat cacca                                               25

SEQ ID NO: 361          moltype = DNA   length = 25
FEATURE                 Location/Qualifiers
misc_feature            1..23
                        note = RNA
misc_feature            24..25
                        note = DNA
source                  1..25
                        mol_type = other DNA
```

```
                        organism = synthetic construct
SEQUENCE: 361
gaagatgctc aaggagctca tcacc                                              25

SEQ ID NO: 362          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 362
agaagatgct caaggagctc atcac                                              25

SEQ ID NO: 363          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 363
cagaagatgc tcaaggagct catca                                              25

SEQ ID NO: 364          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 364
ccagaagatg ctcaaggagc tcatc                                              25

SEQ ID NO: 365          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 365
cccagaagat gctcaaggag ctcat                                              25

SEQ ID NO: 366          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 366
aagcccagaa gatgctcaag gagct                                              25

SEQ ID NO: 367          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 367
aaagcccaga agatgctcaa ggagc                                              25

SEQ ID NO: 368          moltype = DNA   length = 25
FEATURE                 Location/Qualifiers
misc_feature            1..23
```

```
                               -continued
                      note         = RNA
misc_feature          24..25
                      note         = DNA
source                1..25
                      mol_type     = other DNA
                      organism     = synthetic construct
SEQUENCE: 368
gtcagccagg tgtactcagg cagtc                                                25

SEQ ID NO: 369        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 369
ggtcagccag gtgtactcag gcagt                                                25

SEQ ID NO: 370        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 370
actctggtat ttcctagggt acaag                                                25

SEQ ID NO: 371        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 371
tactctggta tttcctaggg tacaa                                                25

SEQ ID NO: 372        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 372
ctactctggt atttcctagg gtaca                                                25

SEQ ID NO: 373        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 373
gctactctgg tatttcctag ggtac                                                25

SEQ ID NO: 374        moltype = DNA   length = 25
FEATURE               Location/Qualifiers
misc_feature          1..23
                      note         = RNA
misc_feature          24..25
                      note         = DNA
source                1..25
                      mol_type     = other DNA
                      organism     = synthetic construct
SEQUENCE: 374
```

```
tgctactctg gtatttccta gggta                                              25

SEQ ID NO: 375          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 375
gtgctactct ggtatttcct aggt                                               25

SEQ ID NO: 376          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 376
ggtgctactc tggtatttcc taggg                                              25

SEQ ID NO: 377          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 377
gggtgctact ctggtatttc ctagg                                              25

SEQ ID NO: 378          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 378
ggactccaag agaaaagccc ggggc                                              25

SEQ ID NO: 379          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 379
aggactccaa gagaaaagcc cgggg                                              25

SEQ ID NO: 380          moltype = DNA   length = 25
FEATURE                 Location/Qualifiers
misc_feature            1..23
                        note = RNA
misc_feature            24..25
                        note = DNA
source                  1..25
                        mol_type = other DNA
                        organism = synthetic construct
SEQUENCE: 380
tgaggactcc aagagaaaag cccgg                                              25

SEQ ID NO: 381          moltype = DNA   length = 25
FEATURE                 Location/Qualifiers
misc_feature            1..23
                        note = RNA
misc_feature            24..25
```

```
                    note = DNA
source              1..25
                    mol_type = other DNA
                    organism = synthetic construct
SEQUENCE: 381
gtgaggactc caagagaaaa gcccg                                        25

SEQ ID NO: 382       moltype = DNA   length = 25
FEATURE              Location/Qualifiers
misc_feature         1..23
                    note = RNA
misc_feature         24..25
                    note = DNA
source              1..25
                    mol_type = other DNA
                    organism = synthetic construct
SEQUENCE: 382
tgtgaggact ccaagagaaa agccc                                        25

SEQ ID NO: 383       moltype = DNA   length = 25
FEATURE              Location/Qualifiers
misc_feature         1..23
                    note = RNA
misc_feature         24..25
                    note = DNA
source              1..25
                    mol_type = other DNA
                    organism = synthetic construct
SEQUENCE: 383
ctgtgaggac tccaagagaa aagcc                                        25

SEQ ID NO: 384       moltype = DNA   length = 25
FEATURE              Location/Qualifiers
misc_feature         1..23
                    note = RNA
misc_feature         24..25
                    note = DNA
source              1..25
                    mol_type = other DNA
                    organism = synthetic construct
SEQUENCE: 384
cctgtgagga ctccaagaga aaagc                                        25

SEQ ID NO: 385       moltype = RNA   length = 27
FEATURE              Location/Qualifiers
source              1..27
                    mol_type = other RNA
                    organism = synthetic construct
SEQUENCE: 385
agcaggcggc tcaccttgaa ggacacc                                      27

SEQ ID NO: 386       moltype = RNA   length = 27
FEATURE              Location/Qualifiers
source              1..27
                    mol_type = other RNA
                    organism = synthetic construct
SEQUENCE: 386
gcaggcggct caccttgaag gacacct                                      27

SEQ ID NO: 387       moltype = RNA   length = 27
FEATURE              Location/Qualifiers
source              1..27
                    mol_type = other RNA
                    organism = synthetic construct
SEQUENCE: 387
caggcggctc accttgaagg acacctc                                      27

SEQ ID NO: 388       moltype = RNA   length = 27
FEATURE              Location/Qualifiers
source              1..27
                    mol_type = other RNA
                    organism = synthetic construct
SEQUENCE: 388
aggcggctca ccttgaagga cacctct                                      27

SEQ ID NO: 389       moltype = RNA   length = 27
FEATURE              Location/Qualifiers
source              1..27
                    mol_type = other RNA
```

```
                        organism = synthetic construct
SEQUENCE: 389
ggcggctcac cttgaaggac acctctc                                              27

SEQ ID NO: 390          moltype = RNA   length = 27
FEATURE                 Location/Qualifiers
source                  1..27
                        mol_type = other RNA
                        organism = synthetic construct
SEQUENCE: 390
accgtggagg ccatgctgtc ctcctgg                                              27

SEQ ID NO: 391          moltype = RNA   length = 27
FEATURE                 Location/Qualifiers
source                  1..27
                        mol_type = other RNA
                        organism = synthetic construct
SEQUENCE: 391
ccgtggaggc catgctgtcc tcctgga                                              27

SEQ ID NO: 392          moltype = RNA   length = 27
FEATURE                 Location/Qualifiers
source                  1..27
                        mol_type = other RNA
                        organism = synthetic construct
SEQUENCE: 392
cgtggaggcc atgctgtcct cctggaa                                              27

SEQ ID NO: 393          moltype = RNA   length = 27
FEATURE                 Location/Qualifiers
source                  1..27
                        mol_type = other RNA
                        organism = synthetic construct
SEQUENCE: 393
gtggaggcca tgctgtcctc ctggaag                                              27

SEQ ID NO: 394          moltype = RNA   length = 27
FEATURE                 Location/Qualifiers
source                  1..27
                        mol_type = other RNA
                        organism = synthetic construct
SEQUENCE: 394
tggaggccat gctgtcctcc tggaagc                                              27

SEQ ID NO: 395          moltype = RNA   length = 27
FEATURE                 Location/Qualifiers
source                  1..27
                        mol_type = other RNA
                        organism = synthetic construct
SEQUENCE: 395
ggaggccatg ctgtcctcct ggaagca                                              27

SEQ ID NO: 396          moltype = RNA   length = 27
FEATURE                 Location/Qualifiers
source                  1..27
                        mol_type = other RNA
                        organism = synthetic construct
SEQUENCE: 396
gaggccatgc tgtcctcctg gaagcag                                              27

SEQ ID NO: 397          moltype = RNA   length = 27
FEATURE                 Location/Qualifiers
source                  1..27
                        mol_type = other RNA
                        organism = synthetic construct
SEQUENCE: 397
aggccatgct gtcctcctgg aagcagt                                              27

SEQ ID NO: 398          moltype = RNA   length = 27
FEATURE                 Location/Qualifiers
source                  1..27
                        mol_type = other RNA
                        organism = synthetic construct
SEQUENCE: 398
gttatcaccc agcggtcagc gatgagg                                              27

SEQ ID NO: 399          moltype = RNA   length = 27
FEATURE                 Location/Qualifiers
source                  1..27
```

```
SEQUENCE: 399
ttatcaccca gcggtcagcg atgaggg                                            27

SEQ ID NO: 400          moltype = RNA  length = 27
FEATURE                 Location/Qualifiers
source                  1..27
                        mol_type = other RNA
                        organism = synthetic construct
SEQUENCE: 400
aggggccctg gaggccacag tcacagt                                            27

SEQ ID NO: 401          moltype = RNA  length = 27
FEATURE                 Location/Qualifiers
source                  1..27
                        mol_type = other RNA
                        organism = synthetic construct
SEQUENCE: 401
gggccctgga ggccacagtc acagtgc                                            27

SEQ ID NO: 402          moltype = RNA  length = 27
FEATURE                 Location/Qualifiers
source                  1..27
                        mol_type = other RNA
                        organism = synthetic construct
SEQUENCE: 402
ggccctggag gccacagtca cagtgct                                            27

SEQ ID NO: 403          moltype = RNA  length = 27
FEATURE                 Location/Qualifiers
source                  1..27
                        mol_type = other RNA
                        organism = synthetic construct
SEQUENCE: 403
ggcccggtga gggagatctg ggaggtg                                            27

SEQ ID NO: 404          moltype = RNA  length = 27
FEATURE                 Location/Qualifiers
source                  1..27
                        mol_type = other RNA
                        organism = synthetic construct
SEQUENCE: 404
ccggtgaggg agatctggga ggtgaag                                            27

SEQ ID NO: 405          moltype = RNA  length = 27
FEATURE                 Location/Qualifiers
source                  1..27
                        mol_type = other RNA
                        organism = synthetic construct
SEQUENCE: 405
cggtgaggga gatctgggag gtgaagt                                            27

SEQ ID NO: 406          moltype = RNA  length = 27
FEATURE                 Location/Qualifiers
source                  1..27
                        mol_type = other RNA
                        organism = synthetic construct
SEQUENCE: 406
tccgccttgt accctaggaa ataccag                                            27

SEQ ID NO: 407          moltype = RNA  length = 27
FEATURE                 Location/Qualifiers
source                  1..27
                        mol_type = other RNA
                        organism = synthetic construct
SEQUENCE: 407
ccgccttgta ccctaggaaa taccaga                                            27

SEQ ID NO: 408          moltype = RNA  length = 27
FEATURE                 Location/Qualifiers
source                  1..27
                        mol_type = other RNA
                        organism = synthetic construct
SEQUENCE: 408
gcatccttct tgcccttgcg gtagccg                                            27

SEQ ID NO: 409          moltype = RNA  length = 27
FEATURE                 Location/Qualifiers
```

```
source                   1..27
                         mol_type = other RNA
                         organism = synthetic construct
SEQUENCE: 409
catccttctt gcccttgcgg tagccgg                                           27

SEQ ID NO: 410           moltype = RNA   length = 27
FEATURE                  Location/Qualifiers
source                   1..27
                         mol_type = other RNA
                         organism = synthetic construct
SEQUENCE: 410
cgaacctgga ggctggcctg ccatggc                                           27

SEQ ID NO: 411           moltype = RNA   length = 27
FEATURE                  Location/Qualifiers
source                   1..27
                         mol_type = other RNA
                         organism = synthetic construct
SEQUENCE: 411
ctggcctgcc atggccactc accctcg                                           27

SEQ ID NO: 412           moltype = RNA   length = 27
FEATURE                  Location/Qualifiers
source                   1..27
                         mol_type = other RNA
                         organism = synthetic construct
SEQUENCE: 412
ggcctgccat ggccactcac cctcgga                                           27

SEQ ID NO: 413           moltype = RNA   length = 27
FEATURE                  Location/Qualifiers
source                   1..27
                         mol_type = other RNA
                         organism = synthetic construct
SEQUENCE: 413
ccatggccac tcaccctcgg aggacac                                           27

SEQ ID NO: 414           moltype = RNA   length = 27
FEATURE                  Location/Qualifiers
source                   1..27
                         mol_type = other RNA
                         organism = synthetic construct
SEQUENCE: 414
catggccact caccctcgga ggacaca                                           27

SEQ ID NO: 415           moltype = RNA   length = 27
FEATURE                  Location/Qualifiers
source                   1..27
                         mol_type = other RNA
                         organism = synthetic construct
SEQUENCE: 415
atggccactc accctcggag gacacag                                           27

SEQ ID NO: 416           moltype = RNA   length = 27
FEATURE                  Location/Qualifiers
source                   1..27
                         mol_type = other RNA
                         organism = synthetic construct
SEQUENCE: 416
caaacgcagt ttctctcatc caggccg                                           27

SEQ ID NO: 417           moltype = RNA   length = 27
FEATURE                  Location/Qualifiers
source                   1..27
                         mol_type = other RNA
                         organism = synthetic construct
SEQUENCE: 417
aaacgcagtt tctctcatcc aggccgt                                           27

SEQ ID NO: 418           moltype = RNA   length = 27
FEATURE                  Location/Qualifiers
source                   1..27
                         mol_type = other RNA
                         organism = synthetic construct
SEQUENCE: 418
cagagggcca agccgtagtc cagagag                                           27

SEQ ID NO: 419           moltype = RNA   length = 27
```

-continued

```
FEATURE                 Location/Qualifiers
source                  1..27
                        mol_type = other RNA
                        organism = synthetic construct
SEQUENCE: 419
agagggccaa gccgtagtcc agagagg                                              27

SEQ ID NO: 420          moltype = RNA   length = 27
FEATURE                 Location/Qualifiers
source                  1..27
                        mol_type = other RNA
                        organism = synthetic construct
SEQUENCE: 420
agaatgaacc agaagaagca ggtgagg                                              27

SEQ ID NO: 421          moltype = RNA   length = 27
FEATURE                 Location/Qualifiers
source                  1..27
                        mol_type = other RNA
                        organism = synthetic construct
SEQUENCE: 421
gaatgaacca gaagaagcag gtgaggg                                              27

SEQ ID NO: 422          moltype = RNA   length = 27
FEATURE                 Location/Qualifiers
source                  1..27
                        mol_type = other RNA
                        organism = synthetic construct
SEQUENCE: 422
ctccttgagc atcttctggg ctttggc                                              27

SEQ ID NO: 423          moltype = RNA   length = 27
FEATURE                 Location/Qualifiers
source                  1..27
                        mol_type = other RNA
                        organism = synthetic construct
SEQUENCE: 423
tccttgagca tcttctgggc tttggcg                                              27

SEQ ID NO: 424          moltype = RNA   length = 27
FEATURE                 Location/Qualifiers
source                  1..27
                        mol_type = other RNA
                        organism = synthetic construct
SEQUENCE: 424
ccttgagcat cttctgggct ttggcgg                                              27

SEQ ID NO: 425          moltype = RNA   length = 27
FEATURE                 Location/Qualifiers
source                  1..27
                        mol_type = other RNA
                        organism = synthetic construct
SEQUENCE: 425
ttggatcagg cagctttatt ccaaagg                                              27

SEQ ID NO: 426          moltype = RNA   length = 27
FEATURE                 Location/Qualifiers
source                  1..27
                        mol_type = other RNA
                        organism = synthetic construct
SEQUENCE: 426
tggatcaggc agctttattc caaaggg                                              27

SEQ ID NO: 427          moltype = RNA   length = 27
FEATURE                 Location/Qualifiers
source                  1..27
                        mol_type = other RNA
                        organism = synthetic construct
SEQUENCE: 427
gatcaggcag ctttattcca aagggca                                              27

SEQ ID NO: 428          moltype = RNA   length = 27
FEATURE                 Location/Qualifiers
source                  1..27
                        mol_type = other RNA
                        organism = synthetic construct
SEQUENCE: 428
atcaggcagc tttattccaa agggcag                                              27
```

```
SEQ ID NO: 429          moltype = RNA  length = 27
FEATURE                 Location/Qualifiers
source                  1..27
                        mol_type = other RNA
                        organism = synthetic construct
SEQUENCE: 429
tcaggcagct ttattccaaa gggcagc                                              27

SEQ ID NO: 430          moltype = RNA  length = 27
FEATURE                 Location/Qualifiers
source                  1..27
                        mol_type = other RNA
                        organism = synthetic construct
SEQUENCE: 430
ggcagcttta ttccaaaggg cagctga                                              27

SEQ ID NO: 431          moltype = RNA  length = 27
FEATURE                 Location/Qualifiers
source                  1..27
                        mol_type = other RNA
                        organism = synthetic construct
SEQUENCE: 431
gcagctttat tccaaagggc agctgag                                              27

SEQ ID NO: 432          moltype = RNA  length = 27
FEATURE                 Location/Qualifiers
source                  1..27
                        mol_type = other RNA
                        organism = synthetic construct
SEQUENCE: 432
ttattccaaa gggcagctga gctcacc                                              27

SEQ ID NO: 433          moltype = RNA  length = 27
FEATURE                 Location/Qualifiers
source                  1..27
                        mol_type = other RNA
                        organism = synthetic construct
SEQUENCE: 433
tattccaaag ggcagctgag ctcacct                                              27

SEQ ID NO: 434          moltype = RNA  length = 27
FEATURE                 Location/Qualifiers
source                  1..27
                        mol_type = other RNA
                        organism = synthetic construct
SEQUENCE: 434
agttagacca ggggcttccg aagctgg                                              27

SEQ ID NO: 435          moltype = RNA  length = 27
FEATURE                 Location/Qualifiers
source                  1..27
                        mol_type = other RNA
                        organism = synthetic construct
SEQUENCE: 435
gtagaaccag cattcttgct gctgagc                                              27

SEQ ID NO: 436          moltype = RNA  length = 27
FEATURE                 Location/Qualifiers
source                  1..27
                        mol_type = other RNA
                        organism = synthetic construct
SEQUENCE: 436
tagaaccagc attcttgctg ctgagcc                                              27

SEQ ID NO: 437          moltype = RNA  length = 27
FEATURE                 Location/Qualifiers
source                  1..27
                        mol_type = other RNA
                        organism = synthetic construct
SEQUENCE: 437
agaaccagca ttcttgctgc tgagcca                                              27

SEQ ID NO: 438          moltype = RNA  length = 27
FEATURE                 Location/Qualifiers
source                  1..27
                        mol_type = other RNA
                        organism = synthetic construct
SEQUENCE: 438
aaccagcatt cttgctgctg agccact                                              27
```

```
SEQ ID NO: 439         moltype = RNA   length = 27
FEATURE                Location/Qualifiers
source                 1..27
                       mol_type = other RNA
                       organism = synthetic construct
SEQUENCE: 439
accagcattc ttgctgctga gccactg                                              27

SEQ ID NO: 440         moltype = RNA   length = 27
FEATURE                Location/Qualifiers
source                 1..27
                       mol_type = other RNA
                       organism = synthetic construct
SEQUENCE: 440
tcctgccatc actggagcag acatcag                                              27

SEQ ID NO: 441         moltype = RNA   length = 27
FEATURE                Location/Qualifiers
source                 1..27
                       mol_type = other RNA
                       organism = synthetic construct
SEQUENCE: 441
cctgccatca ctggagcaga catcagg                                              27

SEQ ID NO: 442         moltype = RNA   length = 27
FEATURE                Location/Qualifiers
source                 1..27
                       mol_type = other RNA
                       organism = synthetic construct
SEQUENCE: 442
ctgccatcac tggagcagac atcaggg                                              27

SEQ ID NO: 443         moltype = RNA   length = 27
FEATURE                Location/Qualifiers
source                 1..27
                       mol_type = other RNA
                       organism = synthetic construct
SEQUENCE: 443
gccatcactg gagcagacat cagggac                                              27

SEQ ID NO: 444         moltype = RNA   length = 27
FEATURE                Location/Qualifiers
source                 1..27
                       mol_type = other RNA
                       organism = synthetic construct
SEQUENCE: 444
ggggcagttc ctcaggtcac cacttgc                                              27

SEQ ID NO: 445         moltype = RNA   length = 27
FEATURE                Location/Qualifiers
source                 1..27
                       mol_type = other RNA
                       organism = synthetic construct
SEQUENCE: 445
gggcagttcc tcaggtcacc acttgct                                              27

SEQ ID NO: 446         moltype = RNA   length = 27
FEATURE                Location/Qualifiers
source                 1..27
                       mol_type = other RNA
                       organism = synthetic construct
SEQUENCE: 446
ggcagttcct caggtcacca cttgctg                                              27

SEQ ID NO: 447         moltype = RNA   length = 27
FEATURE                Location/Qualifiers
source                 1..27
                       mol_type = other RNA
                       organism = synthetic construct
SEQUENCE: 447
gcagttcctc aggtcaccac ttgctgg                                              27

SEQ ID NO: 448         moltype = RNA   length = 27
FEATURE                Location/Qualifiers
source                 1..27
                       mol_type = other RNA
                       organism = synthetic construct
SEQUENCE: 448
```

-continued

```
cagttcctca ggtcaccact tgctgga                                              27

SEQ ID NO: 449          moltype = RNA   length = 27
FEATURE                 Location/Qualifiers
source                  1..27
                        mol_type = other RNA
                        organism = synthetic construct
SEQUENCE: 449
agttcctcag gtcaccactt gctggat                                              27

SEQ ID NO: 450          moltype = RNA   length = 27
FEATURE                 Location/Qualifiers
source                  1..27
                        mol_type = other RNA
                        organism = synthetic construct
SEQUENCE: 450
ttcctcaggt caccacttgc tggatcc                                              27

SEQ ID NO: 451          moltype = RNA   length = 27
FEATURE                 Location/Qualifiers
source                  1..27
                        mol_type = other RNA
                        organism = synthetic construct
SEQUENCE: 451
ctcaggtcac cacttgctgg atccagc                                              27

SEQ ID NO: 452          moltype = RNA   length = 27
FEATURE                 Location/Qualifiers
source                  1..27
                        mol_type = other RNA
                        organism = synthetic construct
SEQUENCE: 452
tcaggtcacc acttgctgga tccagct                                              27

SEQ ID NO: 453          moltype = RNA   length = 27
FEATURE                 Location/Qualifiers
source                  1..27
                        mol_type = other RNA
                        organism = synthetic construct
SEQUENCE: 453
cagctgatca cacctgtgat gcgggtg                                              27

SEQ ID NO: 454          moltype = RNA   length = 27
FEATURE                 Location/Qualifiers
source                  1..27
                        mol_type = other RNA
                        organism = synthetic construct
SEQUENCE: 454
agctgatcac acctgtgatg cgggtgt                                              27

SEQ ID NO: 455          moltype = RNA   length = 27
FEATURE                 Location/Qualifiers
source                  1..27
                        mol_type = other RNA
                        organism = synthetic construct
SEQUENCE: 455
tgcgggtgta gacgccgaag tagttag                                              27

SEQ ID NO: 456          moltype = RNA   length = 27
FEATURE                 Location/Qualifiers
source                  1..27
                        mol_type = other RNA
                        organism = synthetic construct
SEQUENCE: 456
cgctgcacag gtcctgtggg atcaact                                              27

SEQ ID NO: 457          moltype = RNA   length = 27
FEATURE                 Location/Qualifiers
source                  1..27
                        mol_type = other RNA
                        organism = synthetic construct
SEQUENCE: 457
cacaggtcct gtgggatcaa ctgcaca                                              27

SEQ ID NO: 458          moltype = RNA   length = 27
FEATURE                 Location/Qualifiers
source                  1..27
                        mol_type = other RNA
                        organism = synthetic construct
```

```
SEQUENCE: 458
gcggctcacc ttgaaggaca cctctcc                                              27

SEQ ID NO: 459           moltype = RNA   length = 27
FEATURE                  Location/Qualifiers
source                   1..27
                         mol_type = other RNA
                         organism = synthetic construct
SEQUENCE: 459
cggctcacct tgaaggacac ctctcca                                              27

SEQ ID NO: 460           moltype = RNA   length = 27
FEATURE                  Location/Qualifiers
source                   1..27
                         mol_type = other RNA
                         organism = synthetic construct
SEQUENCE: 460
ctcaccttga aggacacctc tccaggc                                              27

SEQ ID NO: 461           moltype = RNA   length = 27
FEATURE                  Location/Qualifiers
source                   1..27
                         mol_type = other RNA
                         organism = synthetic construct
SEQUENCE: 461
ccacagatgt gtcgaccccg aacctgg                                              27

SEQ ID NO: 462           moltype = RNA   length = 27
FEATURE                  Location/Qualifiers
source                   1..27
                         mol_type = other RNA
                         organism = synthetic construct
SEQUENCE: 462
ccggtcctca cactggaagg tgaatgt                                              27

SEQ ID NO: 463           moltype = RNA   length = 27
FEATURE                  Location/Qualifiers
source                   1..27
                         mol_type = other RNA
                         organism = synthetic construct
SEQUENCE: 463
cggtcctcac actggaaggt gaatgtc                                              27

SEQ ID NO: 464           moltype = RNA   length = 27
FEATURE                  Location/Qualifiers
source                   1..27
                         mol_type = other RNA
                         organism = synthetic construct
SEQUENCE: 464
ggtcctcaca ctggaaggtg aatgtcc                                              27

SEQ ID NO: 465           moltype = RNA   length = 27
FEATURE                  Location/Qualifiers
source                   1..27
                         mol_type = other RNA
                         organism = synthetic construct
SEQUENCE: 465
gtcctcacac tggaaggtga atgtccc                                              27

SEQ ID NO: 466           moltype = RNA   length = 27
FEATURE                  Location/Qualifiers
source                   1..27
                         mol_type = other RNA
                         organism = synthetic construct
SEQUENCE: 466
tcctcacact ggaaggtgaa tgtccca                                              27

SEQ ID NO: 467           moltype = RNA   length = 27
FEATURE                  Location/Qualifiers
source                   1..27
                         mol_type = other RNA
                         organism = synthetic construct
SEQUENCE: 467
tctttgcact ggaatgtggc tctgcaa                                              27

SEQ ID NO: 468           moltype = RNA   length = 27
FEATURE                  Location/Qualifiers
source                   1..27
                         mol_type = other RNA
```

```
                       organism = synthetic construct
SEQUENCE: 468
ctttgcactg gaatgtggct ctgcaaa                                              27

SEQ ID NO: 469         moltype = RNA   length = 27
FEATURE                Location/Qualifiers
source                 1..27
                       mol_type = other RNA
                       organism = synthetic construct
SEQUENCE: 469
tttgcactgg aatgtggctc tgcaaac                                              27

SEQ ID NO: 470         moltype = RNA   length = 27
FEATURE                Location/Qualifiers
source                 1..27
                       mol_type = other RNA
                       organism = synthetic construct
SEQUENCE: 470
ttgcactgga atgtggctct gcaaacg                                              27

SEQ ID NO: 471         moltype = RNA   length = 27
FEATURE                Location/Qualifiers
source                 1..27
                       mol_type = other RNA
                       organism = synthetic construct
SEQUENCE: 471
gaatgtggct ctgcaaacgc agtttct                                              27

SEQ ID NO: 472         moltype = RNA   length = 27
FEATURE                Location/Qualifiers
source                 1..27
                       mol_type = other RNA
                       organism = synthetic construct
SEQUENCE: 472
aatgtggctc tgcaaacgca gtttctc                                              27

SEQ ID NO: 473         moltype = RNA   length = 27
FEATURE                Location/Qualifiers
source                 1..27
                       mol_type = other RNA
                       organism = synthetic construct
SEQUENCE: 473
atgtggctct gcaaacgcag tttctct                                              27

SEQ ID NO: 474         moltype = RNA   length = 27
FEATURE                Location/Qualifiers
source                 1..27
                       mol_type = other RNA
                       organism = synthetic construct
SEQUENCE: 474
tgtggctctg caaacgcagt ttctctc                                              27

SEQ ID NO: 475         moltype = RNA   length = 27
FEATURE                Location/Qualifiers
source                 1..27
                       mol_type = other RNA
                       organism = synthetic construct
SEQUENCE: 475
gtggctctgc aaacgcagtt tctctca                                              27

SEQ ID NO: 476         moltype = RNA   length = 27
FEATURE                Location/Qualifiers
source                 1..27
                       mol_type = other RNA
                       organism = synthetic construct
SEQUENCE: 476
tggctctgca aacgcagttt ctctcat                                              27

SEQ ID NO: 477         moltype = RNA   length = 27
FEATURE                Location/Qualifiers
source                 1..27
                       mol_type = other RNA
                       organism = synthetic construct
SEQUENCE: 477
ggctctgcaa acgcagtttc tctcatc                                              27

SEQ ID NO: 478         moltype = RNA   length = 27
FEATURE                Location/Qualifiers
source                 1..27
```

-continued

```
                        mol_type = other RNA
                        organism = synthetic construct
SEQUENCE: 478
gctctgcaaa cgcagtttct ctcatcc                                               27

SEQ ID NO: 479          moltype = RNA   length = 27
FEATURE                 Location/Qualifiers
source                  1..27
                        mol_type = other RNA
                        organism = synthetic construct
SEQUENCE: 479
ctctgcaaac gcagtttctc tcatcca                                               27

SEQ ID NO: 480          moltype = RNA   length = 27
FEATURE                 Location/Qualifiers
source                  1..27
                        mol_type = other RNA
                        organism = synthetic construct
SEQUENCE: 480
tctgcaaacg cagtttctct catccag                                               27

SEQ ID NO: 481          moltype = RNA   length = 27
FEATURE                 Location/Qualifiers
source                  1..27
                        mol_type = other RNA
                        organism = synthetic construct
SEQUENCE: 481
ctgcaaacgc agtttctctc atccagg                                               27

SEQ ID NO: 482          moltype = RNA   length = 27
FEATURE                 Location/Qualifiers
source                  1..27
                        mol_type = other RNA
                        organism = synthetic construct
SEQUENCE: 482
tgcaaacgca gtttctctca tccaggc                                               27

SEQ ID NO: 483          moltype = RNA   length = 27
FEATURE                 Location/Qualifiers
source                  1..27
                        mol_type = other RNA
                        organism = synthetic construct
SEQUENCE: 483
gcaaacgcag tttctctcat ccaggcc                                               27

SEQ ID NO: 484          moltype = RNA   length = 27
FEATURE                 Location/Qualifiers
source                  1..27
                        mol_type = other RNA
                        organism = synthetic construct
SEQUENCE: 484
gggcagtcct tgaccccatc acaggca                                               27

SEQ ID NO: 485          moltype = RNA   length = 27
FEATURE                 Location/Qualifiers
source                  1..27
                        mol_type = other RNA
                        organism = synthetic construct
SEQUENCE: 485
ggcaggggtc cgactggttg tacaagc                                               27

SEQ ID NO: 486          moltype = RNA   length = 27
FEATURE                 Location/Qualifiers
source                  1..27
                        mol_type = other RNA
                        organism = synthetic construct
SEQUENCE: 486
gcaggggtcc gactggttgt acaagcc                                               27

SEQ ID NO: 487          moltype = RNA   length = 27
FEATURE                 Location/Qualifiers
source                  1..27
                        mol_type = other RNA
                        organism = synthetic construct
SEQUENCE: 487
caggggtccg actggttgta caagcca                                               27

SEQ ID NO: 488          moltype = RNA   length = 27
FEATURE                 Location/Qualifiers
```

```
source                  1..27
                        mol_type = other RNA
                        organism = synthetic construct
SEQUENCE: 488
ggggtccgac tggttgtaca agccata                                              27

SEQ ID NO: 489          moltype = RNA   length = 27
FEATURE                 Location/Qualifiers
source                  1..27
                        mol_type = other RNA
                        organism = synthetic construct
SEQUENCE: 489
gggtccgact ggttgtacaa gccatag                                              27

SEQ ID NO: 490          moltype = RNA   length = 27
FEATURE                 Location/Qualifiers
source                  1..27
                        mol_type = other RNA
                        organism = synthetic construct
SEQUENCE: 490
ggtccgactg gttgtacaag ccatagt                                              27

SEQ ID NO: 491          moltype = RNA   length = 27
FEATURE                 Location/Qualifiers
source                  1..27
                        mol_type = other RNA
                        organism = synthetic construct
SEQUENCE: 491
gtccgactgg ttgtacaagc catagtg                                              27

SEQ ID NO: 492          moltype = RNA   length = 27
FEATURE                 Location/Qualifiers
source                  1..27
                        mol_type = other RNA
                        organism = synthetic construct
SEQUENCE: 492
tccgactggt tgtacaagcc atagtgc                                              27

SEQ ID NO: 493          moltype = RNA   length = 27
FEATURE                 Location/Qualifiers
source                  1..27
                        mol_type = other RNA
                        organism = synthetic construct
SEQUENCE: 493
ccgactggtt gtacaagcca tagtgca                                              27

SEQ ID NO: 494          moltype = RNA   length = 27
FEATURE                 Location/Qualifiers
source                  1..27
                        mol_type = other RNA
                        organism = synthetic construct
SEQUENCE: 494
cgactggttg tacaagccat agtgcac                                              27

SEQ ID NO: 495          moltype = RNA   length = 27
FEATURE                 Location/Qualifiers
source                  1..27
                        mol_type = other RNA
                        organism = synthetic construct
SEQUENCE: 495
gactggttgt acaagccata gtgcacc                                              27

SEQ ID NO: 496          moltype = RNA   length = 27
FEATURE                 Location/Qualifiers
source                  1..27
                        mol_type = other RNA
                        organism = synthetic construct
SEQUENCE: 496
actggttgta caagccatag tgcaccc                                              27

SEQ ID NO: 497          moltype = RNA   length = 27
FEATURE                 Location/Qualifiers
source                  1..27
                        mol_type = other RNA
                        organism = synthetic construct
SEQUENCE: 497
ctggttgtac aagccatagt gcacccg                                              27

SEQ ID NO: 498          moltype = RNA   length = 27
```

| | | |
|---|---|---|
| FEATURE | Location/Qualifiers | |
| source | 1..27<br>mol_type = other RNA<br>organism = synthetic construct | |
| SEQUENCE: 498<br>tggttgtaca agccatagtg cacccgc | | 27 |
| SEQ ID NO: 499<br>FEATURE<br>source | moltype = RNA  length = 27<br>Location/Qualifiers<br>1..27<br>mol_type = other RNA<br>organism = synthetic construct | |
| SEQUENCE: 499<br>ggttgtacaa gccatagtgc acccgca | | 27 |
| SEQ ID NO: 500<br>FEATURE<br>source | moltype = RNA  length = 27<br>Location/Qualifiers<br>1..27<br>mol_type = other RNA<br>organism = synthetic construct | |
| SEQUENCE: 500<br>ttgtacaagc catagtgcac ccgcaca | | 27 |
| SEQ ID NO: 501<br>FEATURE<br>source | moltype = RNA  length = 27<br>Location/Qualifiers<br>1..27<br>mol_type = other RNA<br>organism = synthetic construct | |
| SEQUENCE: 501<br>tacaagccat agtgcacccg cacaccg | | 27 |
| SEQ ID NO: 502<br>FEATURE<br>source | moltype = RNA  length = 27<br>Location/Qualifiers<br>1..27<br>mol_type = other RNA<br>organism = synthetic construct | |
| SEQUENCE: 502<br>acagcctcct gttctggatc gtccact | | 27 |
| SEQ ID NO: 503<br>FEATURE<br>source | moltype = RNA  length = 27<br>Location/Qualifiers<br>1..27<br>mol_type = other RNA<br>organism = synthetic construct | |
| SEQUENCE: 503<br>gcctcctgtt ctggatcgtc cactggc | | 27 |
| SEQ ID NO: 504<br>FEATURE<br>source | moltype = RNA  length = 27<br>Location/Qualifiers<br>1..27<br>mol_type = other RNA<br>organism = synthetic construct | |
| SEQUENCE: 504<br>cctgggtgca cggcaaatca tacttct | | 27 |
| SEQ ID NO: 505<br>FEATURE<br>source | moltype = RNA  length = 27<br>Location/Qualifiers<br>1..27<br>mol_type = other RNA<br>organism = synthetic construct | |
| SEQUENCE: 505<br>ctgggtgcac ggcaaatcat acttctg | | 27 |
| SEQ ID NO: 506<br>FEATURE<br>source | moltype = RNA  length = 27<br>Location/Qualifiers<br>1..27<br>mol_type = other RNA<br>organism = synthetic construct | |
| SEQUENCE: 506<br>tgggtgcacg gcaaatcata cttctgc | | 27 |
| SEQ ID NO: 507<br>FEATURE<br>source | moltype = RNA  length = 27<br>Location/Qualifiers<br>1..27<br>mol_type = other RNA<br>organism = synthetic construct | |
| SEQUENCE: 507<br>gggtgcacgg caaatcatac ttctgcc | | 27 |

```
SEQ ID NO: 508          moltype = RNA   length = 27
FEATURE                 Location/Qualifiers
source                  1..27
                        mol_type = other RNA
                        organism = synthetic construct
SEQUENCE: 508
gtgcacggca aatcatactt ctgcctc                                              27

SEQ ID NO: 509          moltype = RNA   length = 27
FEATURE                 Location/Qualifiers
source                  1..27
                        mol_type = other RNA
                        organism = synthetic construct
SEQUENCE: 509
tgcacggcaa atcatacttc tgcctcc                                              27

SEQ ID NO: 510          moltype = RNA   length = 27
FEATURE                 Location/Qualifiers
source                  1..27
                        mol_type = other RNA
                        organism = synthetic construct
SEQUENCE: 510
gcacggcaaa tcatacttct gcctcct                                              27

SEQ ID NO: 511          moltype = RNA   length = 27
FEATURE                 Location/Qualifiers
source                  1..27
                        mol_type = other RNA
                        organism = synthetic construct
SEQUENCE: 511
cacggcaaat catacttctg cctcctc                                              27

SEQ ID NO: 512          moltype = RNA   length = 27
FEATURE                 Location/Qualifiers
source                  1..27
                        mol_type = other RNA
                        organism = synthetic construct
SEQUENCE: 512
tggggcgagt agtagctggg gaagtac                                              27

SEQ ID NO: 513          moltype = RNA   length = 27
FEATURE                 Location/Qualifiers
source                  1..27
                        mol_type = other RNA
                        organism = synthetic construct
SEQUENCE: 513
ggcgagtagt agctggggaa gtacggg                                              27

SEQ ID NO: 514          moltype = RNA   length = 27
FEATURE                 Location/Qualifiers
source                  1..27
                        mol_type = other RNA
                        organism = synthetic construct
SEQUENCE: 514
acgaaggggt cgtagtagct gtgcagg                                              27

SEQ ID NO: 515          moltype = RNA   length = 27
FEATURE                 Location/Qualifiers
source                  1..27
                        mol_type = other RNA
                        organism = synthetic construct
SEQUENCE: 515
tcgtagtagc tgtgcaggcc cttcttc                                              27

SEQ ID NO: 516          moltype = RNA   length = 27
FEATURE                 Location/Qualifiers
source                  1..27
                        mol_type = other RNA
                        organism = synthetic construct
SEQUENCE: 516
gccacgtcat acatggccag tcggtcc                                              27

SEQ ID NO: 517          moltype = RNA   length = 27
FEATURE                 Location/Qualifiers
source                  1..27
                        mol_type = other RNA
                        organism = synthetic construct
SEQUENCE: 517
cccacgtagc tgtagcggta acaaccc                                              27
```

```
SEQ ID NO: 518          moltype = RNA   length = 27
FEATURE                 Location/Qualifiers
source                  1..27
                        mol_type = other RNA
                        organism = synthetic construct
SEQUENCE: 518
cacgtagctg tagcggtaac aacccag                                              27

SEQ ID NO: 519          moltype = RNA   length = 27
FEATURE                 Location/Qualifiers
source                  1..27
                        mol_type = other RNA
                        organism = synthetic construct
SEQUENCE: 519
acgtagctgt agcggtaaca acccagc                                              27

SEQ ID NO: 520          moltype = RNA   length = 27
FEATURE                 Location/Qualifiers
source                  1..27
                        mol_type = other RNA
                        organism = synthetic construct
SEQUENCE: 520
cgtagctgta gcggtaacaa cccagcg                                              27

SEQ ID NO: 521          moltype = RNA   length = 27
FEATURE                 Location/Qualifiers
source                  1..27
                        mol_type = other RNA
                        organism = synthetic construct
SEQUENCE: 521
tagcggtaac aacccagcgt ggaattc                                              27

SEQ ID NO: 522          moltype = RNA   length = 27
FEATURE                 Location/Qualifiers
source                  1..27
                        mol_type = other RNA
                        organism = synthetic construct
SEQUENCE: 522
agcggtaaca acccagcgtg gaattca                                              27

SEQ ID NO: 523          moltype = RNA   length = 27
FEATURE                 Location/Qualifiers
source                  1..27
                        mol_type = other RNA
                        organism = synthetic construct
SEQUENCE: 523
attcaatgca gctatgtctt tcacact                                              27

SEQ ID NO: 524          moltype = RNA   length = 27
FEATURE                 Location/Qualifiers
source                  1..27
                        mol_type = other RNA
                        organism = synthetic construct
SEQUENCE: 524
ttcaatgcag ctatgtcttt cacactg                                              27

SEQ ID NO: 525          moltype = RNA   length = 27
FEATURE                 Location/Qualifiers
source                  1..27
                        mol_type = other RNA
                        organism = synthetic construct
SEQUENCE: 525
tcaatgcagc tatgtctttc acactgg                                              27

SEQ ID NO: 526          moltype = RNA   length = 27
FEATURE                 Location/Qualifiers
source                  1..27
                        mol_type = other RNA
                        organism = synthetic construct
SEQUENCE: 526
caatgcagct atgtctttca cactggc                                              27

SEQ ID NO: 527          moltype = RNA   length = 27
FEATURE                 Location/Qualifiers
source                  1..27
                        mol_type = other RNA
                        organism = synthetic construct
SEQUENCE: 527
```

```
aatgcagcta tgtctttcac actggct                                              27

SEQ ID NO: 528         moltype = RNA   length = 27
FEATURE                Location/Qualifiers
source                 1..27
                       mol_type = other RNA
                       organism = synthetic construct
SEQUENCE: 528
atgcagctat gtctttcaca ctggctt                                              27

SEQ ID NO: 529         moltype = RNA   length = 27
FEATURE                Location/Qualifiers
source                 1..27
                       mol_type = other RNA
                       organism = synthetic construct
SEQUENCE: 529
tgcagctatg tctttcacac tggcttc                                              27

SEQ ID NO: 530         moltype = RNA   length = 27
FEATURE                Location/Qualifiers
source                 1..27
                       mol_type = other RNA
                       organism = synthetic construct
SEQUENCE: 530
gcagctatgt ctttcacact ggcttcc                                              27

SEQ ID NO: 531         moltype = RNA   length = 27
FEATURE                Location/Qualifiers
source                 1..27
                       mol_type = other RNA
                       organism = synthetic construct
SEQUENCE: 531
cagctatgtc tttcacactg gcttcca                                              27

SEQ ID NO: 532         moltype = RNA   length = 27
FEATURE                Location/Qualifiers
source                 1..27
                       mol_type = other RNA
                       organism = synthetic construct
SEQUENCE: 532
ccgagctgtt gactgtggac agcagct                                              27

SEQ ID NO: 533         moltype = RNA   length = 27
FEATURE                Location/Qualifiers
source                 1..27
                       mol_type = other RNA
                       organism = synthetic construct
SEQUENCE: 533
gagctgttga ctgtggacag cagctcc                                              27

SEQ ID NO: 534         moltype = RNA   length = 27
FEATURE                Location/Qualifiers
source                 1..27
                       mol_type = other RNA
                       organism = synthetic construct
SEQUENCE: 534
gtgctcgggg atttggagaa tgaacca                                              27

SEQ ID NO: 535         moltype = RNA   length = 27
FEATURE                Location/Qualifiers
source                 1..27
                       mol_type = other RNA
                       organism = synthetic construct
SEQUENCE: 535
tgctcgggga tttggagaat gaaccag                                              27

SEQ ID NO: 536         moltype = RNA   length = 27
FEATURE                Location/Qualifiers
source                 1..27
                       mol_type = other RNA
                       organism = synthetic construct
SEQUENCE: 536
gctcgggpat ttggagaatg aaccaga                                              27

SEQ ID NO: 537         moltype = RNA   length = 27
FEATURE                Location/Qualifiers
source                 1..27
                       mol_type = other RNA
                       organism = synthetic construct
```

```
SEQUENCE: 537
ctcgggatt tggagaatga accagaa                                                27

SEQ ID NO: 538            moltype = RNA  length = 27
FEATURE                   Location/Qualifiers
source                    1..27
                          mol_type = other RNA
                          organism = synthetic construct
SEQUENCE: 538
tcggggatt ggagaatgaa ccagaag                                                27

SEQ ID NO: 539            moltype = RNA  length = 27
FEATURE                   Location/Qualifiers
source                    1..27
                          mol_type = other RNA
                          organism = synthetic construct
SEQUENCE: 539
cggggatttg gagaatgaac cagaaga                                               27

SEQ ID NO: 540            moltype = RNA  length = 27
FEATURE                   Location/Qualifiers
source                    1..27
                          mol_type = other RNA
                          organism = synthetic construct
SEQUENCE: 540
ggggatttgg agaatgaacc agaagaa                                               27

SEQ ID NO: 541            moltype = RNA  length = 27
FEATURE                   Location/Qualifiers
source                    1..27
                          mol_type = other RNA
                          organism = synthetic construct
SEQUENCE: 541
gatttggaga atgaaccaga agaagca                                               27

SEQ ID NO: 542            moltype = RNA  length = 27
FEATURE                   Location/Qualifiers
source                    1..27
                          mol_type = other RNA
                          organism = synthetic construct
SEQUENCE: 542
atttggagaa tgaaccagaa gaagcag                                               27

SEQ ID NO: 543            moltype = RNA  length = 27
FEATURE                   Location/Qualifiers
source                    1..27
                          mol_type = other RNA
                          organism = synthetic construct
SEQUENCE: 543
tttggagaat gaaccagaag aagcagg                                               27

SEQ ID NO: 544            moltype = RNA  length = 27
FEATURE                   Location/Qualifiers
source                    1..27
                          mol_type = other RNA
                          organism = synthetic construct
SEQUENCE: 544
ttggagaatg aaccagaaga agcaggt                                               27

SEQ ID NO: 545            moltype = RNA  length = 27
FEATURE                   Location/Qualifiers
source                    1..27
                          mol_type = other RNA
                          organism = synthetic construct
SEQUENCE: 545
tggagaatga accagaagaa gcaggtg                                               27

SEQ ID NO: 546            moltype = RNA  length = 27
FEATURE                   Location/Qualifiers
source                    1..27
                          mol_type = other RNA
                          organism = synthetic construct
SEQUENCE: 546
ggagaatgaa ccagaagaag caggtga                                               27

SEQ ID NO: 547            moltype = RNA  length = 27
FEATURE                   Location/Qualifiers
source                    1..27
                          mol_type = other RNA
```

```
                     organism = synthetic construct
SEQUENCE: 547
gagaatgaac cagaagaagc aggtgag                                              27

SEQ ID NO: 548         moltype = RNA   length = 27
FEATURE                Location/Qualifiers
source                 1..27
                       mol_type = other RNA
                       organism = synthetic construct
SEQUENCE: 548
ctccccaaag gaatagacgg agctgga                                              27

SEQ ID NO: 549         moltype = RNA   length = 27
FEATURE                Location/Qualifiers
source                 1..27
                       mol_type = other RNA
                       organism = synthetic construct
SEQUENCE: 549
ccaaaggaat agacggagct ggagttg                                              27

SEQ ID NO: 550         moltype = RNA   length = 27
FEATURE                Location/Qualifiers
source                 1..27
                       mol_type = other RNA
                       organism = synthetic construct
SEQUENCE: 550
caaaggaata gacggagctg gagttgt                                              27

SEQ ID NO: 551         moltype = RNA   length = 27
FEATURE                Location/Qualifiers
source                 1..27
                       mol_type = other RNA
                       organism = synthetic construct
SEQUENCE: 551
ctggtgatga gctccttgag catcttc                                              27

SEQ ID NO: 552         moltype = RNA   length = 27
FEATURE                Location/Qualifiers
source                 1..27
                       mol_type = other RNA
                       organism = synthetic construct
SEQUENCE: 552
tggtgatgag ctccttgagc atcttct                                              27

SEQ ID NO: 553         moltype = RNA   length = 27
FEATURE                Location/Qualifiers
source                 1..27
                       mol_type = other RNA
                       organism = synthetic construct
SEQUENCE: 553
ggtgatgagc tccttgagca tcttctg                                              27

SEQ ID NO: 554         moltype = RNA   length = 27
FEATURE                Location/Qualifiers
source                 1..27
                       mol_type = other RNA
                       organism = synthetic construct
SEQUENCE: 554
gtgatgagct ccttgagcat cttctgg                                              27

SEQ ID NO: 555         moltype = RNA   length = 27
FEATURE                Location/Qualifiers
source                 1..27
                       mol_type = other RNA
                       organism = synthetic construct
SEQUENCE: 555
tgatgagctc cttgagcatc ttctggg                                              27

SEQ ID NO: 556         moltype = RNA   length = 27
FEATURE                Location/Qualifiers
source                 1..27
                       mol_type = other RNA
                       organism = synthetic construct
SEQUENCE: 556
gatgagctcc ttgagcatct tctgggc                                              27

SEQ ID NO: 557         moltype = RNA   length = 27
FEATURE                Location/Qualifiers
source                 1..27
```

```
                        mol_type = other RNA
                        organism = synthetic construct
SEQUENCE: 557
atgagctcct tgagcatctt ctgggct                                              27

SEQ ID NO: 558          moltype = RNA   length = 27
FEATURE                 Location/Qualifiers
source                  1..27
                        mol_type = other RNA
                        organism = synthetic construct
SEQUENCE: 558
agctccttga gcatcttctg ggctttg                                              27

SEQ ID NO: 559          moltype = RNA   length = 27
FEATURE                 Location/Qualifiers
source                  1..27
                        mol_type = other RNA
                        organism = synthetic construct
SEQUENCE: 559
gctccttgag catcttctgg gctttgg                                              27

SEQ ID NO: 560          moltype = RNA   length = 27
FEATURE                 Location/Qualifiers
source                  1..27
                        mol_type = other RNA
                        organism = synthetic construct
SEQUENCE: 560
gactgcctga gtacacctgg ctgacca                                              27

SEQ ID NO: 561          moltype = RNA   length = 27
FEATURE                 Location/Qualifiers
source                  1..27
                        mol_type = other RNA
                        organism = synthetic construct
SEQUENCE: 561
actgcctgag tacacctggc tgaccat                                              27

SEQ ID NO: 562          moltype = RNA   length = 27
FEATURE                 Location/Qualifiers
source                  1..27
                        mol_type = other RNA
                        organism = synthetic construct
SEQUENCE: 562
cttgtaccct aggaaatacc agagtag                                              27

SEQ ID NO: 563          moltype = RNA   length = 27
FEATURE                 Location/Qualifiers
source                  1..27
                        mol_type = other RNA
                        organism = synthetic construct
SEQUENCE: 563
ttgtacccta ggaaataccagagtagc                                               27

SEQ ID NO: 564          moltype = RNA   length = 27
FEATURE                 Location/Qualifiers
source                  1..27
                        mol_type = other RNA
                        organism = synthetic construct
SEQUENCE: 564
tgtaccctag gaaataccag agtagca                                              27

SEQ ID NO: 565          moltype = RNA   length = 27
FEATURE                 Location/Qualifiers
source                  1..27
                        mol_type = other RNA
                        organism = synthetic construct
SEQUENCE: 565
gtaccctagg aaataccaga gtagcac                                              27

SEQ ID NO: 566          moltype = RNA   length = 27
FEATURE                 Location/Qualifiers
source                  1..27
                        mol_type = other RNA
                        organism = synthetic construct
SEQUENCE: 566
taccctagga aataccagag tagcacc                                              27

SEQ ID NO: 567          moltype = RNA   length = 27
FEATURE                 Location/Qualifiers
```

-continued

```
source                  1..27
                        mol_type = other RNA
                        organism = synthetic construct
SEQUENCE: 567
accctaggaa ataccagagt agcaccc                                           27

SEQ ID NO: 568          moltype = RNA  length = 27
FEATURE                 Location/Qualifiers
source                  1..27
                        mol_type = other RNA
                        organism = synthetic construct
SEQUENCE: 568
ccctaggaaa taccagagta gcacccc                                           27

SEQ ID NO: 569          moltype = RNA  length = 27
FEATURE                 Location/Qualifiers
source                  1..27
                        mol_type = other RNA
                        organism = synthetic construct
SEQUENCE: 569
cctaggaaat accagagtag cacccccc                                          27

SEQ ID NO: 570          moltype = RNA  length = 27
FEATURE                 Location/Qualifiers
source                  1..27
                        mol_type = other RNA
                        organism = synthetic construct
SEQUENCE: 570
gccccgggct tttctcttgg agtcctc                                           27

SEQ ID NO: 571          moltype = RNA  length = 27
FEATURE                 Location/Qualifiers
source                  1..27
                        mol_type = other RNA
                        organism = synthetic construct
SEQUENCE: 571
ccccgggctt ttctcttgga gtcctca                                           27

SEQ ID NO: 572          moltype = RNA  length = 27
FEATURE                 Location/Qualifiers
source                  1..27
                        mol_type = other RNA
                        organism = synthetic construct
SEQUENCE: 572
ccgggctttt ctcttggagt cctcaca                                           27

SEQ ID NO: 573          moltype = RNA  length = 27
FEATURE                 Location/Qualifiers
source                  1..27
                        mol_type = other RNA
                        organism = synthetic construct
SEQUENCE: 573
cgggcttttc tcttggagtc ctcacag                                           27

SEQ ID NO: 574          moltype = RNA  length = 27
FEATURE                 Location/Qualifiers
source                  1..27
                        mol_type = other RNA
                        organism = synthetic construct
SEQUENCE: 574
gggcttttct cttggagtcc tcacagg                                           27

SEQ ID NO: 575          moltype = RNA  length = 27
FEATURE                 Location/Qualifiers
source                  1..27
                        mol_type = other RNA
                        organism = synthetic construct
SEQUENCE: 575
ggcttttctc ttggagtcct cacaggc                                           27

SEQ ID NO: 576          moltype = RNA  length = 27
FEATURE                 Location/Qualifiers
source                  1..27
                        mol_type = other RNA
                        organism = synthetic construct
SEQUENCE: 576
gcttttctct tggagtcctc acaggcc                                           27

SEQ ID NO: 577          moltype = RNA  length = 36
```

```
FEATURE                 Location/Qualifiers
source                  1..36
                        mol_type = other RNA
                        organism = synthetic construct
SEQUENCE: 577
gtgaggactc caagagaaaa gcagccgaaa ggctgc                              36

SEQ ID NO: 578          moltype = RNA   length = 36
FEATURE                 Location/Qualifiers
source                  1..36
                        mol_type = other RNA
                        organism = synthetic construct
SEQUENCE: 578
gggtgctact ctggtattta gcagccgaaa ggctgc                              36

SEQ ID NO: 579          moltype = RNA   length = 36
FEATURE                 Location/Qualifiers
source                  1..36
                        mol_type = other RNA
                        organism = synthetic construct
SEQUENCE: 579
ggtgctactc tggtatttca gcagccgaaa ggctgc                              36

SEQ ID NO: 580          moltype = RNA   length = 36
FEATURE                 Location/Qualifiers
source                  1..36
                        mol_type = other RNA
                        organism = synthetic construct
SEQUENCE: 580
gctactctgg tatttcctaa gcagccgaaa ggctgc                              36

SEQ ID NO: 581          moltype = RNA   length = 36
FEATURE                 Location/Qualifiers
source                  1..36
                        mol_type = other RNA
                        organism = synthetic construct
SEQUENCE: 581
ggtatttcct agggtacaaa gcagccgaaa ggctgc                              36

SEQ ID NO: 582          moltype = RNA   length = 36
FEATURE                 Location/Qualifiers
source                  1..36
                        mol_type = other RNA
                        organism = synthetic construct
SEQUENCE: 582
cacctgcttc ttctggttca gcagccgaaa ggctgc                              36

SEQ ID NO: 583          moltype = RNA   length = 36
FEATURE                 Location/Qualifiers
source                  1..36
                        mol_type = other RNA
                        organism = synthetic construct
SEQUENCE: 583
gaagccagtg tgaaagacaa gcagccgaaa ggctgc                              36

SEQ ID NO: 584          moltype = RNA   length = 36
FEATURE                 Location/Qualifiers
source                  1..36
                        mol_type = other RNA
                        organism = synthetic construct
SEQUENCE: 584
cgtacttccc cagctactaa gcagccgaaa ggctgc                              36

SEQ ID NO: 585          moltype = RNA   length = 36
FEATURE                 Location/Qualifiers
source                  1..36
                        mol_type = other RNA
                        organism = synthetic construct
SEQUENCE: 585
ggaggcagaa gtatgattta gcagccgaaa ggctgc                              36

SEQ ID NO: 586          moltype = RNA   length = 36
FEATURE                 Location/Qualifiers
source                  1..36
                        mol_type = other RNA
                        organism = synthetic construct
SEQUENCE: 586
gggtgcacta tggcttgtaa gcagccgaaa ggctgc                              36
```

```
SEQ ID NO: 587         moltype = RNA   length = 36
FEATURE                Location/Qualifiers
source                 1..36
                       mol_type = other RNA
                       organism = synthetic construct
SEQUENCE: 587
gcactatggc ttgtacaaca gcagccgaaa ggctgc                                    36

SEQ ID NO: 588         moltype = RNA   length = 36
FEATURE                Location/Qualifiers
source                 1..36
                       mol_type = other RNA
                       organism = synthetic construct
SEQUENCE: 588
gatgagagaa actgcgttta gcagccgaaa ggctgc                                    36

SEQ ID NO: 589         moltype = RNA   length = 36
FEATURE                Location/Qualifiers
source                 1..36
                       mol_type = other RNA
                       organism = synthetic construct
SEQUENCE: 589
gaggtgtcct tcaaggtgaa gcagccgaaa ggctgc                                    36

SEQ ID NO: 590         moltype = RNA   length = 36
FEATURE                Location/Qualifiers
source                 1..36
                       mol_type = other RNA
                       organism = synthetic construct
SEQUENCE: 590
ctcacctgct tcttctggta gcagccgaaa ggctgc                                    36

SEQ ID NO: 591         moltype = RNA   length = 36
FEATURE                Location/Qualifiers
source                 1..36
                       mol_type = other RNA
                       organism = synthetic construct
SEQUENCE: 591
tcacctgctt cttctggtta gcagccgaaa ggctgc                                    36

SEQ ID NO: 592         moltype = RNA   length = 36
FEATURE                Location/Qualifiers
source                 1..36
                       mol_type = other RNA
                       organism = synthetic construct
SEQUENCE: 592
tctggttcat tctccaaata gcagccgaaa ggctgc                                    36

SEQ ID NO: 593         moltype = RNA   length = 36
FEATURE                Location/Qualifiers
source                 1..36
                       mol_type = other RNA
                       organism = synthetic construct
SEQUENCE: 593
gttcattctc caaatcccca gcagccgaaa ggctgc                                    36

SEQ ID NO: 594         moltype = RNA   length = 36
FEATURE                Location/Qualifiers
source                 1..36
                       mol_type = other RNA
                       organism = synthetic construct
SEQUENCE: 594
aaagtggatg tgcagttgaa gcagccgaaa ggctgc                                    36

SEQ ID NO: 595         moltype = RNA   length = 36
FEATURE                Location/Qualifiers
source                 1..36
                       mol_type = other RNA
                       organism = synthetic construct
SEQUENCE: 595
aactccagct ccgtctatta gcagccgaaa ggctgc                                    36

SEQ ID NO: 596         moltype = RNA   length = 36
FEATURE                Location/Qualifiers
source                 1..36
                       mol_type = other RNA
                       organism = synthetic construct
SEQUENCE: 596
acctgcttct tctggttcaa gcagccgaaa ggctgc                                    36
```

```
SEQ ID NO: 597          moltype = RNA   length = 36
FEATURE                 Location/Qualifiers
source                  1..36
                        mol_type = other RNA
                        organism = synthetic construct
SEQUENCE: 597
agtgtgaaag acatagctga gcagccgaaa ggctgc                                    36

SEQ ID NO: 598          moltype = RNA   length = 22
FEATURE                 Location/Qualifiers
source                  1..22
                        mol_type = other RNA
                        organism = synthetic construct
SEQUENCE: 598
ttttctcttg gagtcctcac gg                                                   22

SEQ ID NO: 599          moltype = RNA   length = 22
FEATURE                 Location/Qualifiers
source                  1..22
                        mol_type = other RNA
                        organism = synthetic construct
SEQUENCE: 599
taaataccag agtagcaccc gg                                                   22

SEQ ID NO: 600          moltype = RNA   length = 22
FEATURE                 Location/Qualifiers
source                  1..22
                        mol_type = other RNA
                        organism = synthetic construct
SEQUENCE: 600
tgaaatacca gagtagcacc gg                                                   22

SEQ ID NO: 601          moltype = RNA   length = 22
FEATURE                 Location/Qualifiers
source                  1..22
                        mol_type = other RNA
                        organism = synthetic construct
SEQUENCE: 601
ttaggaaata ccagagtagc gg                                                   22

SEQ ID NO: 602          moltype = RNA   length = 22
FEATURE                 Location/Qualifiers
source                  1..22
                        mol_type = other RNA
                        organism = synthetic construct
SEQUENCE: 602
tttgtaccct aggaaatacc gg                                                   22

SEQ ID NO: 603          moltype = RNA   length = 22
FEATURE                 Location/Qualifiers
source                  1..22
                        mol_type = other RNA
                        organism = synthetic construct
SEQUENCE: 603
tgaaccagaa gaagcaggtg gg                                                   22

SEQ ID NO: 604          moltype = RNA   length = 22
FEATURE                 Location/Qualifiers
source                  1..22
                        mol_type = other RNA
                        organism = synthetic construct
SEQUENCE: 604
ttgtctttca cactggcttc gg                                                   22

SEQ ID NO: 605          moltype = RNA   length = 22
FEATURE                 Location/Qualifiers
source                  1..22
                        mol_type = other RNA
                        organism = synthetic construct
SEQUENCE: 605
ttagtagctg gggaagtacg gg                                                   22

SEQ ID NO: 606          moltype = RNA   length = 22
FEATURE                 Location/Qualifiers
source                  1..22
                        mol_type = other RNA
                        organism = synthetic construct
SEQUENCE: 606
```

```
taaatcatac ttctgcctcc gg                                                    22

SEQ ID NO: 607         moltype = RNA   length = 22
FEATURE                Location/Qualifiers
source                 1..22
                       mol_type = other RNA
                       organism = synthetic construct
SEQUENCE: 607
ttacaagcca tagtgcaccc gg                                                    22

SEQ ID NO: 608         moltype = RNA   length = 22
FEATURE                Location/Qualifiers
source                 1..22
                       mol_type = other RNA
                       organism = synthetic construct
SEQUENCE: 608
tgttgtacaa gccatagtgc gg                                                    22

SEQ ID NO: 609         moltype = RNA   length = 22
FEATURE                Location/Qualifiers
source                 1..22
                       mol_type = other RNA
                       organism = synthetic construct
SEQUENCE: 609
taaacgcagt ttctctcatc gg                                                    22

SEQ ID NO: 610         moltype = RNA   length = 22
FEATURE                Location/Qualifiers
source                 1..22
                       mol_type = other RNA
                       organism = synthetic construct
SEQUENCE: 610
ttcaccttga aggacacctc gg                                                    22

SEQ ID NO: 611         moltype = RNA   length = 22
FEATURE                Location/Qualifiers
source                 1..22
                       mol_type = other RNA
                       organism = synthetic construct
SEQUENCE: 611
taccagaaga agcaggtgag gg                                                    22

SEQ ID NO: 612         moltype = RNA   length = 22
FEATURE                Location/Qualifiers
source                 1..22
                       mol_type = other RNA
                       organism = synthetic construct
SEQUENCE: 612
taaccagaag aagcaggtga gg                                                    22

SEQ ID NO: 613         moltype = RNA   length = 22
FEATURE                Location/Qualifiers
source                 1..22
                       mol_type = other RNA
                       organism = synthetic construct
SEQUENCE: 613
tatttggaga atgaaccaga gg                                                    22

SEQ ID NO: 614         moltype = RNA   length = 22
FEATURE                Location/Qualifiers
source                 1..22
                       mol_type = other RNA
                       organism = synthetic construct
SEQUENCE: 614
tggggatttg gagaatgaac gg                                                    22

SEQ ID NO: 615         moltype = RNA   length = 22
FEATURE                Location/Qualifiers
source                 1..22
                       mol_type = other RNA
                       organism = synthetic construct
SEQUENCE: 615
ttcaactgca catccacttt gg                                                    22

SEQ ID NO: 616         moltype = RNA   length = 22
FEATURE                Location/Qualifiers
source                 1..22
                       mol_type = other RNA
                       organism = synthetic construct
```

```
SEQUENCE: 616
taatagacgg agctggagtt gg                                                    22

SEQ ID NO: 617          moltype = RNA   length = 22
FEATURE                 Location/Qualifiers
source                  1..22
                        mol_type = other RNA
                        organism = synthetic construct
SEQUENCE: 617
ttgaaccaga agaagcaggt gg                                                    22

SEQ ID NO: 618          moltype = RNA   length = 22
FEATURE                 Location/Qualifiers
source                  1..22
                        mol_type = other RNA
                        organism = synthetic construct
SEQUENCE: 618
tcagctatgt ctttcacact gg                                                    22

SEQ ID NO: 619          moltype = RNA   length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl guanosine
modified_base           2
                        mod_base = OTHER
                        note = 2'-O-methyl uridine
modified_base           3
                        mod_base = OTHER
                        note = 2'-O-methyl guanosine
modified_base           4
                        mod_base = OTHER
                        note = 2'-O-methyl adenosine
modified_base           5
                        mod_base = OTHER
                        note = 2'-O-methyl guanosine
modified_base           6
                        mod_base = OTHER
                        note = 2'-O-methyl guanosine
modified_base           7
                        mod_base = OTHER
                        note = 2'-O-methyl adenosine
modified_base           8
                        mod_base = OTHER
                        note = 2'-fluoro cytidine
modified_base           9
                        mod_base = OTHER
                        note = 2'-fluoro uridine
modified_base           10
                        mod_base = OTHER
                        note = 2'-fluoro cytidine
modified_base           11
                        mod_base = OTHER
                        note = 2'-fluoro cytidine
modified_base           12
                        mod_base = OTHER
                        note = 2'-O-methyl adenosine
modified_base           13
                        mod_base = OTHER
                        note = 2'-O-methyl adenosine
modified_base           14
                        mod_base = OTHER
                        note = 2'-O-methyl guanosine
modified_base           15
                        mod_base = OTHER
                        note = 2'-O-methyl adenosine
modified_base           16
                        mod_base = OTHER
                        note = 2'-O-methyl guanosine
modified_base           17
                        mod_base = OTHER
                        note = 2'-O-methyl adenosine
modified_base           18
                        mod_base = OTHER
                        note = 2'-O-methyl adenosine
```

-continued

| | |
|---|---|
| modified_base | 19<br>mod_base = OTHER<br>note = 2'-O-methyl adenosine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl mcytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER<br>note = 2'-O-methyl guanosine |
| modified_base | 32<br>mod_base = OTHER<br>note = 2'-O-methyl guanosine |
| modified_base | 33<br>mod_base = OTHER<br>note = 2'-O-methyl cytidine |
| modified_base | 34<br>mod_base = OTHER<br>note = 2'-O-methyl uridine |
| modified_base | 35<br>mod_base = OTHER<br>note = 2'-O-methyl guanosine |
| modified_base | 36<br>mod_base = OTHER<br>note = 2'-O-methyl cytidine |
| source | 1..36<br>mol_type = other RNA<br>organism = synthetic construct |

SEQUENCE: 619
gtgaggactc caagagaaaa gcagccgaaa ggctgc        36

| | |
|---|---|
| SEQ ID NO: 620 | moltype = RNA  length = 36 |
| FEATURE | Location/Qualifiers |
| misc_feature | 1..36<br>note = synthetic construct |
| misc_feature | 1..2<br>note = linked via phosphorothioate |
| modified_base | 1<br>mod_base = OTHER<br>note = 2'-O-methyl guanosine |
| modified_base | 2<br>mod_base = OTHER<br>note = 2'-O-methyl guanosine |
| modified_base | 3<br>mod_base = OTHER<br>note = 2'-O-methyl guanosine |
| modified_base | 4<br>mod_base = OTHER<br>note = 2'-O-methyl uridine |
| modified_base | 5 |

-continued

|  |  |
|---|---|
|  | mod_base = OTHER<br>note = 2'-O-methyl guanosine |
| modified_base | 6<br>mod_base = OTHER<br>note = 2'-O-methyl cytidine |
| modified_base | 7<br>mod_base = OTHER<br>note = 2'-O-methyl uridine |
| modified_base | 8<br>mod_base = OTHER<br>note = 2'-fluoro adenosine |
| modified_base | 9<br>mod_base = OTHER<br>note = 2'-fluoro cytidine |
| modified_base | 10<br>mod_base = OTHER<br>note = 2'-fluoro uridine |
| modified_base | 11<br>mod_base = OTHER<br>note = 2'-fluoro cytidine |
| modified_base | 12<br>mod_base = OTHER<br>note = 2'-O-methyl uridine |
| modified_base | 13<br>mod_base = OTHER<br>note = 2'-O-methyl guanosine |
| modified_base | 14<br>mod_base = OTHER<br>note = 2'-O-methyl guanosine |
| modified_base | 15<br>mod_base = OTHER<br>note = 2'-O-methyl uridine |
| modified_base | 16<br>mod_base = OTHER<br>note = 2'-O-methyl adenosine |
| modified_base | 17<br>mod_base = OTHER<br>note = 2'-O-methyl uridine |
| modified_base | 18<br>mod_base = OTHER<br>note = 2'-O-methyl uridine |
| modified_base | 19<br>mod_base = OTHER<br>note = 2'-O-methyl uridine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl cytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER |

```
                      note = 2'-O-methyl guanosine
modified_base         32
                      mod_base = OTHER
                      note = 2'-O-methyl guanosine
modified_base         33
                      mod_base = OTHER
                      note = 2'-O-methyl cytidine
modified_base         34
                      mod_base = OTHER
                      note = 2'-O-methyl uridine
modified_base         35
                      mod_base = OTHER
                      note = 2'-O-methyl guanosine
modified_base         36
                      mod_base = OTHER
                      note = 2'-O-methyl cytidine
source                1..36
                      mol_type = other RNA
                      organism = synthetic construct
SEQUENCE: 620
gggtgctact ctggtattta gcagccgaaa ggctgc                            36

SEQ ID NO: 621        moltype = RNA   length = 36
FEATURE               Location/Qualifiers
misc_feature          1..36
                      note = synthetic construct
misc_feature          1..2
                      note = linked via phosphorothioate
modified_base         1
                      mod_base = OTHER
                      note = 2'-O-methyl guanosine
modified_base         2
                      mod_base = OTHER
                      note = 2'-O-methyl guanosine
modified_base         3
                      mod_base = OTHER
                      note = 2'-O-methyl uridine
modified_base         4
                      mod_base = OTHER
                      note = 2'-O-methyl guanosine
modified_base         5
                      mod_base = OTHER
                      note = 2'-O-methyl cytidine
modified_base         6
                      mod_base = OTHER
                      note = 2'-O-methyl uridine
modified_base         7
                      mod_base = OTHER
                      note = 2'-O-methyl adenosine
modified_base         8
                      mod_base = OTHER
                      note = 2'-fluoro cytidine
modified_base         9
                      mod_base = OTHER
                      note = 2'-fluoro uridine
modified_base         10
                      mod_base = OTHER
                      note = 2'-fluoro cytidine
modified_base         11
                      mod_base = OTHER
                      note = 2'-fluoro uridine
modified_base         12
                      mod_base = OTHER
                      note = 2'-O-methyl guanosine
modified_base         13
                      mod_base = OTHER
                      note = 2'-O-methyl guanosine
modified_base         14
                      mod_base = OTHER
                      note = 2'-O-methyl uridine
modified_base         15
                      mod_base = OTHER
                      note = 2'-O-methyl adenosine
modified_base         16
                      mod_base = OTHER
                      note = 2'-O-methyl uridine
modified_base         17
                      mod_base = OTHER
                      note = 2'-O-methyl uridine
```

```
modified_base       18
                    mod_base = OTHER
                    note = 2'-O-methyl uridine
modified_base       19
                    mod_base = OTHER
                    note = 2'-O-methyl cytidine
modified_base       20
                    mod_base = OTHER
                    note = 2'-O-methyl adenosine
modified_base       21
                    mod_base = OTHER
                    note = 2'-O-methyl guanosine
modified_base       22
                    mod_base = OTHER
                    note = 2'-O-methyl cytidine
modified_base       23
                    mod_base = OTHER
                    note = 2'-O-methyl adenosine
modified_base       24
                    mod_base = OTHER
                    note = 2'-O-methyl guanosine
modified_base       25
                    mod_base = OTHER
                    note = 2'-O-methyl cytidine
modified_base       26
                    mod_base = OTHER
                    note = 2'-O-methyl cytidine
modified_base       27
                    mod_base = OTHER
                    note = 2'-O-methyl guanosine
modified_base       28
                    mod_base = OTHER
                    note = 2'-aminodiethoxymethanol-Adenine-GalNAc
modified_base       29
                    mod_base = OTHER
                    note = 2'-aminodiethoxymethanol-Adenine-GalNAc
modified_base       30
                    mod_base = OTHER
                    note = 2'-aminodiethoxymethanol-Adenine-GalNAc
modified_base       31
                    mod_base = OTHER
                    note = 2'-O-methyl guanosine
modified_base       32
                    mod_base = OTHER
                    note = 2'-O-methyl guanosine
modified_base       33
                    mod_base = OTHER
                    note = 2'-O-methyl cytidine
modified_base       34
                    mod_base = OTHER
                    note = 2'-O-methyl uridine
modified_base       35
                    mod_base = OTHER
                    note = 2'-O-methyl guanosine
modified_base       36
                    mod_base = OTHER
                    note = 2'-O-methyl cytidine
source              1..36
                    mol_type = other RNA
                    organism = synthetic construct
SEQUENCE: 621
ggtgctactc tggtatttca gcagccgaaa ggctgc                      36

SEQ ID NO: 622      moltype = RNA   length = 36
FEATURE             Location/Qualifiers
misc_feature        1..36
                    note = synthetic construct
misc_feature        1..2
                    note = linked via phosphorothioate
modified_base       1
                    mod_base = OTHER
                    note = 2'-O-methyl guanosine
modified_base       2
                    mod_base = OTHER
                    note = 2'-O-methyl cytidine
modified_base       3
                    mod_base = OTHER
                    note = 2'-O-methyl uridine
modified_base       4
```

-continued

```
                        mod_base = OTHER
                        note = 2'-O-methyl adenosine
modified_base           5
                        mod_base = OTHER
                        note = 2'-O-methyl cytidine
modified_base           6
                        mod_base = OTHER
                        note = 2'-O-methyl uridine
modified_base           7
                        mod_base = OTHER
                        note = 2'-O-methyl cytidine
modified_base           8
                        mod_base = OTHER
                        note = 2'-fluoro uridine
modified_base           9
                        mod_base = OTHER
                        note = 2'-fluoro guanosine
modified_base           10
                        mod_base = OTHER
                        note = 2'-fluoro guanosine
modified_base           11
                        mod_base = OTHER
                        note = 2'-fluoro uridine
modified_base           12
                        mod_base = OTHER
                        note = 2'-O-methyl adenosine
modified_base           13
                        mod_base = OTHER
                        note = 2'-O-methyl uridine
modified_base           14
                        mod_base = OTHER
                        note = 2'-O-methyl uridine
modified_base           15
                        mod_base = OTHER
                        note = 2'-O-methyl uridine
modified_base           16
                        mod_base = OTHER
                        note = 2'-O-methyl cytidine
modified_base           17
                        mod_base = OTHER
                        note = 2'-O-methyl cytidine
modified_base           18
                        mod_base = OTHER
                        note = 2'-O-methyl uridine
modified_base           19
                        mod_base = OTHER
                        note = 2'-O-methyl adenosine
modified_base           20
                        mod_base = OTHER
                        note = 2'-O-methyl adenosine
modified_base           21
                        mod_base = OTHER
                        note = 2'-O-methyl guanosine
modified_base           22
                        mod_base = OTHER
                        note = 2'-O-methyl cytidine
modified_base           23
                        mod_base = OTHER
                        note = 2'-O-methyl adenosine
modified_base           24
                        mod_base = OTHER
                        note = 2'-O-methyl guanosine
modified_base           25
                        mod_base = OTHER
                        note = 2'-O-methyl cytidine
modified_base           26
                        mod_base = OTHER
                        note = 2'-O-methyl cytidine
modified_base           27
                        mod_base = OTHER
                        note = 2'-O-methyl guanosine
modified_base           28
                        mod_base = OTHER
                        note = 2'-aminodiethoxymethanol-Adenine-GalNAc
modified_base           29
                        mod_base = OTHER
                        note = 2'-aminodiethoxymethanol-Adenine-GalNAc
modified_base           30
                        mod_base = OTHER
```

|  |  |
|---|---|
|  | note = 2'-aminodiethoxymethanol-Adenine-GalNAc |
| modified_base | 31 |
|  | mod_base = OTHER |
|  | note = 2'-O-methyl guanosine |
| modified_base | 32 |
|  | mod_base = OTHER |
|  | note = 2'-O-methyl guanosine |
| modified_base | 33 |
|  | mod_base = OTHER |
|  | note = 2'-O-methyl cytidine |
| modified_base | 34 |
|  | mod_base = OTHER |
|  | note = 2'-O-methyl uridine |
| modified_base | 35 |
|  | mod_base = OTHER |
|  | note = 2'-O-methyl guanosine |
| modified_base | 36 |
|  | mod_base = OTHER |
|  | note = 2'-O-methyl cytidine |
| source | 1..36 |
|  | mol_type = other RNA |
|  | organism = synthetic construct |
| SEQUENCE: 622 | |

```
gctactctgg tatttcctaa gcagccgaaa ggctgc                           36
```

|  |  |
|---|---|
| SEQ ID NO: 623 | moltype = RNA  length = 36 |
| FEATURE | Location/Qualifiers |
| misc_feature | 1..36 |
|  | note = synthetic construct |
| misc_feature | 1..2 |
|  | note = linked via phosphorothioate |
| modified_base | 1 |
|  | mod_base = OTHER |
|  | note = 2'-O-methyl guanosine |
| modified_base | 2 |
|  | mod_base = OTHER |
|  | note = 2'-O-methyl guanosine |
| modified_base | 3 |
|  | mod_base = OTHER |
|  | note = 2'-O-methyl uridine |
| modified_base | 4 |
|  | mod_base = OTHER |
|  | note = 2'-O-methyl adenosine |
| modified_base | 5 |
|  | mod_base = OTHER |
|  | note = 2'-O-methyl uridine |
| modified_base | 6 |
|  | mod_base = OTHER |
|  | note = 2'-O-methyl uridine |
| modified_base | 7 |
|  | mod_base = OTHER |
|  | note = 2'-O-methyl uridine |
| modified_base | 8 |
|  | mod_base = OTHER |
|  | note = 2'-fluoro cytidine |
| modified_base | 9 |
|  | mod_base = OTHER |
|  | note = 2'-fluoro cytidine |
| modified_base | 10 |
|  | mod_base = OTHER |
|  | note = 2'-fluoro uridine |
| modified_base | 11 |
|  | mod_base = OTHER |
|  | note = 2'-fluoro adensosine |
| modified_base | 12 |
|  | mod_base = OTHER |
|  | note = 2'-O-methyl guanosine |
| modified_base | 13 |
|  | mod_base = OTHER |
|  | note = 2'-O-methyl guanosine |
| modified_base | 14 |
|  | mod_base = OTHER |
|  | note = 2'-O-methyl guanosine |
| modified_base | 15 |
|  | mod_base = OTHER |
|  | note = 2'-O-methyl uridine |
| modified_base | 16 |
|  | mod_base = OTHER |
|  | note = 2'-O-methyl adenosine |

| | |
|---|---|
| modified_base | 17<br>mod_base = OTHER<br>note = 2'-O-methyl cytidine |
| modified_base | 18<br>mod_base = OTHER<br>note = 2'-O-methyl adenosine |
| modified_base | 19<br>mod_base = OTHER<br>note = 2'-O-methyl adenosine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl cytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER<br>note = 2'-O-methyl guanosine |
| modified_base | 32<br>mod_base = OTHER<br>note = 2'-O-methyl guanosine |
| modified_base | 33<br>mod_base = OTHER<br>note = 2'-O-methyl cytidine |
| modified_base | 34<br>mod_base = OTHER<br>note = 2'-O-methyl uridine |
| modified_base | 35<br>mod_base = OTHER<br>note = 2'-O-methyl guanosine |
| modified_base | 36<br>mod_base = OTHER<br>note = 2'-O-methyl cytidine |
| source | 1..36<br>mol_type = other RNA<br>organism = synthetic construct |

SEQUENCE: 623
ggtatttcct agggtacaaa gcagccgaaa ggctgc                                    36

| | |
|---|---|
| SEQ ID NO: 624 | moltype = RNA  length = 36 |
| FEATURE | Location/Qualifiers |
| misc_feature | 1..36<br>note = synthetic construct |
| misc_feature | 1..2<br>note = linked via phosphorothioate |
| modified_base | 1<br>mod_base = OTHER<br>note = 2'-O-methyl cytidine |
| modified_base | 2<br>mod_base = OTHER<br>note = 2'-O-methyl adenosine |
| modified_base | 3 |

```
                              mod_base = OTHER
                              note = 2'-O-methyl cytidine
modified_base       4
                              mod_base = OTHER
                              note = 2'-O-methyl cytidine
modified_base       5
                              mod_base = OTHER
                              note = 2'-O-methyl uridine
modified_base       6
                              mod_base = OTHER
                              note = 2'-O-methyl guanosine
modified_base       7
                              mod_base = OTHER
                              note = 2'-O-methyl cytidine
modified_base       8
                              mod_base = OTHER
                              note = 2'-fluoro uridine
modified_base       9
                              mod_base = OTHER
                              note = 2'-fluoro uridine
modified_base       10
                              mod_base = OTHER
                              note = 2'-fluoro cytidine
modified_base       11
                              mod_base = OTHER
                              note = 2'-fluoro uridine
modified_base       12
                              mod_base = OTHER
                              note = 2'-O-methyl uridine
modified_base       13
                              mod_base = OTHER
                              note = 2'-O-methyl cytidine
modified_base       14
                              mod_base = OTHER
                              note = 2'-O-methyl uridine
modified_base       15
                              mod_base = OTHER
                              note = 2'-O-methyl guanosine
modified_base       16
                              mod_base = OTHER
                              note = 2'-O-methyl guanosine
modified_base       17
                              mod_base = OTHER
                              note = 2'-O-methyl uridine
modified_base       18
                              mod_base = OTHER
                              note = 2'-O-methyl uridine
modified_base       19
                              mod_base = OTHER
                              note = 2'-O-methyl cytidine
modified_base       20
                              mod_base = OTHER
                              note = 2'-O-methyl adenosine
modified_base       21
                              mod_base = OTHER
                              note = 2'-O-methyl guanosine
modified_base       22
                              mod_base = OTHER
                              note = 2'-O-methyl cytidine
modified_base       23
                              mod_base = OTHER
                              note = 2'-O-methyl adenosine
modified_base       24
                              mod_base = OTHER
                              note = 2'-O-methyl guanosine
modified_base       25
                              mod_base = OTHER
                              note = 2'-O-methyl cytidine
modified_base       26
                              mod_base = OTHER
                              note = 2'-O-methyl cytidine
modified_base       27
                              mod_base = OTHER
                              note = 2'-O-methyl guanosine
modified_base       28
                              mod_base = OTHER
                              note = 2'-aminodiethoxymethanol-Adenine-GalNAc
modified_base       29
                              mod_base = OTHER
```

```
                         note = 2'-aminodiethoxymethanol-Adenine-GalNAc
modified_base            30
                         mod_base = OTHER
                         note = 2'-aminodiethoxymethanol-Adenine-GalNAc
modified_base            31
                         mod_base = OTHER
                         note = 2'-O-methyl guanosine
modified_base            32
                         mod_base = OTHER
                         note = 2'-O-methyl guanosine
modified_base            33
                         mod_base = OTHER
                         note = 2'-O-methyl cytidine
modified_base            34
                         mod_base = OTHER
                         note = 2'-O-methyl uridine
modified_base            35
                         mod_base = OTHER
                         note = 2'-O-methyl guanosine
modified_base            36
                         mod_base = OTHER
                         note = 2'-O-methyl cytidine
source                   1..36
                         mol_type = other RNA
                         organism = synthetic construct
SEQUENCE: 624
cacctgcttc ttctggttca gcagccgaaa ggctgc                                    36

SEQ ID NO: 625           moltype = RNA  length = 36
FEATURE                  Location/Qualifiers
misc_feature             1..36
                         note = synthetic construct
misc_feature             1..2
                         note = linked via phosphorothioate
modified_base            1
                         mod_base = OTHER
                         note = 2'-O-methyl guanosine
modified_base            2
                         mod_base = OTHER
                         note = 2'-O-methyl adensosine
modified_base            3
                         mod_base = OTHER
                         note = 2'-O-methyl adenosine
modified_base            4
                         mod_base = OTHER
                         note = 2'-O-methyl guanosine
modified_base            5
                         mod_base = OTHER
                         note = 2'-O-methyl cytidine
modified_base            6
                         mod_base = OTHER
                         note = 2'-O-methyl cytidine
modified_base            7
                         mod_base = OTHER
                         note = 2'-O-methyl adenosine
modified_base            8
                         mod_base = OTHER
                         note = 2'-fluoro guanosine
modified_base            9
                         mod_base = OTHER
                         note = 2'-fluoro uridine
modified_base            10
                         mod_base = OTHER
                         note = 2'-fluoro guanosine
modified_base            11
                         mod_base = OTHER
                         note = 2'-fluoro uridine
modified_base            12
                         mod_base = OTHER
                         note = 2'-O-methyl guanosine
modified_base            13
                         mod_base = OTHER
                         note = 2'-O-methyl adenosine
modified_base            14
                         mod_base = OTHER
                         note = 2'-O-methyl adenosine
modified_base            15
                         mod_base = OTHER
                         note = 2'-O-methyl adenosine
```

```
modified_base       16
                    mod_base = OTHER
                    note = 2'-O-methyl guanosine
modified_base       17
                    mod_base = OTHER
                    note = 2'-O-methyl adenosine
modified_base       18
                    mod_base = OTHER
                    note = 2'-O-methyl cytidine
modified_base       19
                    mod_base = OTHER
                    note = 2'-O-methyl adenosine
modified_base       20
                    mod_base = OTHER
                    note = 2'-O-methyl adenosine
modified_base       21
                    mod_base = OTHER
                    note = 2'-O-methyl guanosine
modified_base       22
                    mod_base = OTHER
                    note = 2'-O-methyl cytidine
modified_base       23
                    mod_base = OTHER
                    note = 2'-O-methyl adenosine
modified_base       24
                    mod_base = OTHER
                    note = 2'-O-methyl guanosine
modified_base       25
                    mod_base = OTHER
                    note = 2'-O-methyl cytidine
modified_base       26
                    mod_base = OTHER
                    note = 2'-O-methyl cytidine
modified_base       27
                    mod_base = OTHER
                    note = 2'-O-methyl guanosine
modified_base       28
                    mod_base = OTHER
                    note = 2'-aminodiethoxymethanol-Adenine-GalNAc
modified_base       29
                    mod_base = OTHER
                    note = 2'-aminodiethoxymethanol-Adenine-GalNAc
modified_base       30
                    mod_base = OTHER
                    note = 2'-aminodiethoxymethanol-Adenine-GalNAc
modified_base       31
                    mod_base = OTHER
                    note = 2'-O-methyl guanosine
modified_base       32
                    mod_base = OTHER
                    note = 2'-O-methyl guanosine
modified_base       33
                    mod_base = OTHER
                    note = 2'-O-methyl cytidine
modified_base       34
                    mod_base = OTHER
                    note = 2'-O-methyl uridine
modified_base       35
                    mod_base = OTHER
                    note = 2'-O-methyl guanosine
modified_base       36
                    mod_base = OTHER
                    note = 2'-O-methyl cytidine
source              1..36
                    mol_type = other RNA
                    organism = synthetic construct
SEQUENCE: 625
gaagccagtg tgaaagacaa gcagccgaaa ggctgc                                36

SEQ ID NO: 626      moltype = RNA   length = 36
FEATURE             Location/Qualifiers
misc_feature        1..36
                    note = synthetic construct
misc_feature        1..2
                    note = linked via phosphorothioate
modified_base       1
                    mod_base = OTHER
                    note = 2'-O-methyl cytidine
modified_base       2
```

| | | |
|---|---|---|
| | | mod_base = OTHER |
| | | note = 2'-O-methyl guanosine |
| modified_base | 3 | |
| | | mod_base = OTHER |
| | | note = 2'-O-methyl uridine |
| modified_base | 4 | |
| | | mod_base = OTHER |
| | | note = 2'-O-methyl adenosine |
| modified_base | 5 | |
| | | mod_base = OTHER |
| | | note = 2'-O-methyl cytidine |
| modified_base | 6 | |
| | | mod_base = OTHER |
| | | note = 2'-O-methyl uridine |
| modified_base | 7 | |
| | | mod_base = OTHER |
| | | note = 2'-O-methyl uridine |
| modified_base | 8 | |
| | | mod_base = OTHER |
| | | note = 2'-fluoro cytidine |
| modified_base | 9 | |
| | | mod_base = OTHER |
| | | note = 2'-fluoro cytidine |
| modified_base | 10 | |
| | | mod_base = OTHER |
| | | note = 2'-fluoro cytidine |
| modified_base | 11 | |
| | | mod_base = OTHER |
| | | note = 2'-fluoro cytidine |
| modified_base | 12 | |
| | | mod_base = OTHER |
| | | note = 2'-O-methyl adenosine |
| modified_base | 13 | |
| | | mod_base = OTHER |
| | | note = 2'-O-methyl guanosine |
| modified_base | 14 | |
| | | mod_base = OTHER |
| | | note = 2'-O-methyl cytidine |
| modified_base | 15 | |
| | | mod_base = OTHER |
| | | note = 2'-O-methyl uridine |
| modified_base | 16 | |
| | | mod_base = OTHER |
| | | note = 2'-O-methyl adenosine |
| modified_base | 17 | |
| | | mod_base = OTHER |
| | | note = 2'-O-methyl cytidine |
| modified_base | 18 | |
| | | mod_base = OTHER |
| | | note = 2'-O-methyl uridine |
| modified_base | 19 | |
| | | mod_base = OTHER |
| | | note = 2'-O-methyl adenosine |
| modified_base | 20 | |
| | | mod_base = OTHER |
| | | note = 2'-O-methyl adenosine |
| modified_base | 21 | |
| | | mod_base = OTHER |
| | | note = 2'-O-methyl guanosine |
| modified_base | 22 | |
| | | mod_base = OTHER |
| | | note = 2'-O-methyl cytidine |
| modified_base | 23 | |
| | | mod_base = OTHER |
| | | note = 2'-O-methyl adenosine |
| modified_base | 24 | |
| | | mod_base = OTHER |
| | | note = 2'-O-methyl guanosine |
| modified_base | 25 | |
| | | mod_base = OTHER |
| | | note = 2'-O-methyl cytidine |
| modified_base | 26 | |
| | | mod_base = OTHER |
| | | note = 2'-O-methyl cytidine |
| modified_base | 27 | |
| | | mod_base = OTHER |
| | | note = 2'-O-methyl guanosine |
| modified_base | 28 | |
| | | mod_base = OTHER |

```
                        note = 2'-aminodiethoxymethanol-Adenine-GalNAc
modified_base           29
                        mod_base = OTHER
                        note = 2'-aminodiethoxymethanol-Adenine-GalNAc
modified_base           30
                        mod_base = OTHER
                        note = 2'-aminodiethoxymethanol-Adenine-GalNAc
modified_base           31
                        mod_base = OTHER
                        note = 2'-O-methyl guanosine
modified_base           32
                        mod_base = OTHER
                        note = 2'-O-methyl guanosine
modified_base           33
                        mod_base = OTHER
                        note = 2'-O-methyl cytidine
modified_base           34
                        mod_base = OTHER
                        note = 2'-O-methyl uridine
modified_base           35
                        mod_base = OTHER
                        note = 2'-O-methyl guanosine
modified_base           36
                        mod_base = OTHER
                        note = 2'-O-methyl cytidine
source                  1..36
                        mol_type = other RNA
                        organism = synthetic construct
SEQUENCE: 626
cgtacttccc cagctactaa gcagccgaaa ggctgc                               36

SEQ ID NO: 627          moltype = RNA  length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl guanosine
modified_base           2
                        mod_base = OTHER
                        note = 2'-O-methyl guanosine
modified_base           3
                        mod_base = OTHER
                        note = 2'-O-methyl adenosine
modified_base           4
                        mod_base = OTHER
                        note = 2'-O-methyl guanosine
modified_base           5
                        mod_base = OTHER
                        note = 2'-O-methyl guanosine
modified_base           6
                        mod_base = OTHER
                        note = 2'-O-methyl cytidine
modified_base           7
                        mod_base = OTHER
                        note = 2'-O-methyl adenosine
modified_base           8
                        mod_base = OTHER
                        note = 2'-fluoro guanosine
modified_base           9
                        mod_base = OTHER
                        note = 2'-fluoro adenosine
modified_base           10
                        mod_base = OTHER
                        note = 2'-fluoro adenosine
modified_base           11
                        mod_base = OTHER
                        note = 2'-fluoro guanosine
modified_base           12
                        mod_base = OTHER
                        note = 2'-O-methyl uridine
modified_base           13
                        mod_base = OTHER
                        note = 2'-O-methyl adenosine
modified_base           14
                        mod_base = OTHER
                        note = 2'-O-methyl uridine
```

| | |
|---|---|
| modified_base | 15<br>mod_base = OTHER<br>note = 2'-O-methyl guanosine |
| modified_base | 16<br>mod_base = OTHER<br>note = 2'-O-methyl adenosine |
| modified_base | 17<br>mod_base = OTHER<br>note = 2'-O-methyl uridine |
| modified_base | 18<br>mod_base = OTHER<br>note = 2'-O-methyl uridine |
| modified_base | 19<br>mod_base = OTHER<br>note = 2'-O-methyl uridine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl cytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER<br>note = 2'-O-methyl guanosine |
| modified_base | 32<br>mod_base = OTHER<br>note = 2'-O-methyl guanosine |
| modified_base | 33<br>mod_base = OTHER<br>note = 2'-O-methyl cytidine |
| modified_base | 34<br>mod_base = OTHER<br>note = 2'-O-methyl uridine |
| modified_base | 35<br>mod_base = OTHER<br>note = 2'-O-methyl guanosine |
| modified_base | 36<br>mod_base = OTHER<br>note = 2'-O-methyl cytidine |
| source | 1..36<br>mol_type = other RNA<br>organism = synthetic construct |

SEQUENCE: 627
ggaggcagaa gtatgattta gcagccgaaa ggctgc                                    36

SEQ ID NO: 628            moltype = RNA  length = 36
FEATURE                   Location/Qualifiers
misc_feature              1..36
                          note = synthetic construct
misc_feature              1..2
                          note = linked via phosphorothioate
modified_base             1

```
                      mod_base = OTHER
                      note = 2'-O-methyl guanosine
modified_base         2
                      mod_base = OTHER
                      note = 2'-O-methyl guanosine
modified_base         3
                      mod_base = OTHER
                      note = 2'-O-methyl guanosine
modified_base         4
                      mod_base = OTHER
                      note = 2'-O-methyl guanosine
modified_base         5
                      mod_base = OTHER
                      note = 2'-O-methyl uridine
modified_base         6
                      mod_base = OTHER
                      note = 2'-O-methyl guanosine
modified_base         7
                      mod_base = OTHER
                      note = 2'-O-methyl cytidine
modified_base         8
                      mod_base = OTHER
                      note = 2'-O-methyl adenosine
modified_base         9
                      mod_base = OTHER
                      note = 2'-fluoro cytidine
modified_base         10
                      mod_base = OTHER
                      note = 2'-fluoro uridine
modified_base         11
                      mod_base = OTHER
                      note = 2'-fluoro adenosine
modified_base         12
                      mod_base = OTHER
                      note = 2'-fluoro uridine
modified_base         13
                      mod_base = OTHER
                      note = 2'-O-methyl guanosine
modified_base         14
                      mod_base = OTHER
                      note = 2'-O-methyl guanosine
modified_base         15
                      mod_base = OTHER
                      note = 2'-O-methyl cytidine
modified_base         16
                      mod_base = OTHER
                      note = 2'-O-methyl uridine
modified_base         17
                      mod_base = OTHER
                      note = 2'-O-methyl uridine
modified_base         18
                      mod_base = OTHER
                      note = 2'-O-methyl guanosine
modified_base         19
                      mod_base = OTHER
                      note = 2'-O-methyl uridine
modified_base         20
                      mod_base = OTHER
                      note = 2'-O-methyl adenosine
modified_base         21
                      mod_base = OTHER
                      note = 2'-O-methyl adenosine
modified_base         22
                      mod_base = OTHER
                      note = 2'-O-methyl guanosine
modified_base         23
                      mod_base = OTHER
                      note = 2'-O-methyl cytidine
modified_base         24
                      mod_base = OTHER
                      note = 2'-O-methyl adenosine
modified_base         25
                      mod_base = OTHER
                      note = 2'-O-methyl guanosine
modified_base         26
                      mod_base = OTHER
                      note = 2'-O-methyl cytidine
modified_base         27
                      mod_base = OTHER
                      note = 2'-O-methyl cytidine
                      mod_base = OTHER
```

```
                        note = 2'-O-methyl guanosine
modified_base           28
                        mod_base = OTHER
                        note = 2'-aminodiethoxymethanol-Adenine-GalNAc
modified_base           29
                        mod_base = OTHER
                        note = 2'-aminodiethoxymethanol-Adenine-GalNAc
modified_base           30
                        mod_base = OTHER
                        note = 2'-aminodiethoxymethanol-Adenine-GalNAc
modified_base           31
                        mod_base = OTHER
                        note = 2'-O-methyl guanosine
modified_base           32
                        mod_base = OTHER
                        note = 2'-O-methyl guanosine
modified_base           33
                        mod_base = OTHER
                        note = 2'-O-methyl cytidine
modified_base           34
                        mod_base = OTHER
                        note = 2'-O-methyl uridine
modified_base           35
                        mod_base = OTHER
                        note = 2'-O-methyl guanosine
modified_base           36
                        mod_base = OTHER
                        note = 2'-O-methyl cytidine
source                  1..36
                        mol_type = other RNA
                        organism = synthetic construct
SEQUENCE: 628
gggtgcacta tggcttgtaa gcagccgaaa ggctgc                              36

SEQ ID NO: 629          moltype = RNA   length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl guanosine
modified_base           2
                        mod_base = OTHER
                        note = 2'-O-methyl cytidine
modified_base           3
                        mod_base = OTHER
                        note = 2'-O-methyl adenosine
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl adenosine
modified_base           7
                        mod_base = OTHER
                        note = 2'-O-methyl uridine
modified_base           8
                        mod_base = OTHER
                        note = 2'-fluoro guanosine
modified_base           9
                        mod_base = OTHER
                        note = 2'-fluoro guanosine
modified_base           10
                        mod_base = OTHER
                        note = 2'-fluoro cytidine
modified_base           11
                        mod_base = OTHER
                        note = 2'-fluoro uridine
modified_base           12
                        mod_base = OTHER
                        note = 2'-O-methyl uridine
modified_base           13
                        mod_base = OTHER
                        note = 2'-O-methyl guanosine
```

```
modified_base       14
                    mod_base = OTHER
                    note = 2'-O-methyl uridine
modified_base       15
                    mod_base = OTHER
                    note = 2'-O-methyl adenosine
modified_base       16
                    mod_base = OTHER
                    note = 2'-O-methyl cytidine
modified_base       17
                    mod_base = OTHER
                    note = 2'-O-methyl adenosine
modified_base       18
                    mod_base = OTHER
                    note = 2'-O-methyl adenosine
modified_base       19
                    mod_base = OTHER
                    note = 2'-O-methyl cytidine
modified_base       20
                    mod_base = OTHER
                    note = 2'-O-methyl adenosine
modified_base       21
                    mod_base = OTHER
                    note = 2'-O-methyl guanosine
modified_base       22
                    mod_base = OTHER
                    note = 2'-O-methyl cytidine
modified_base       23
                    mod_base = OTHER
                    note = 2'-O-methyl adenosine
modified_base       24
                    mod_base = OTHER
                    note = 2'-O-methyl guanosine
modified_base       25
                    mod_base = OTHER
                    note = 2'-O-methyl cytidine
modified_base       26
                    mod_base = OTHER
                    note = 2'-O-methyl cytidine
modified_base       27
                    mod_base = OTHER
                    note = 2'-O-methyl guanosine
modified_base       28
                    mod_base = OTHER
                    note = 2'-aminodiethoxymethanol-Adenine-GalNAc
modified_base       29
                    mod_base = OTHER
                    note = 2'-aminodiethoxymethanol-Adenine-GalNAc
modified_base       30
                    mod_base = OTHER
                    note = 2'-aminodiethoxymethanol-Adenine-GalNAc
modified_base       31
                    mod_base = OTHER
                    note = 2'-O-methyl guanosine
modified_base       32
                    mod_base = OTHER
                    note = 2'-O-methyl guanosine
modified_base       33
                    mod_base = OTHER
                    note = 2'-O-methyl cytidine
modified_base       34
                    mod_base = OTHER
                    note = 2'-O-methyl uridine
modified_base       35
                    mod_base = OTHER
                    note = 2'-O-methyl guanosine
modified_base       36
                    mod_base = OTHER
                    note = 2'-O-methyl cytidine
source              1..36
                    mol_type = other RNA
                    organism = synthetic construct
SEQUENCE: 629
gcactatggc ttgtacaaca gcagccgaaa ggctgc                              36

SEQ ID NO: 630      moltype = RNA   length = 36
FEATURE             Location/Qualifiers
misc_feature        1..36
                    note = synthetic construct
```

| | |
|---|---|
| misc_feature | 1..2<br>note = linked via phosphorothioate |
| modified_base | 1<br>mod_base = OTHER<br>note = 2'-O-methyl guanosine |
| modified_base | 2<br>mod_base = OTHER<br>note = 2'-O-methyl adenosine |
| modified_base | 3<br>mod_base = OTHER<br>note = 2'-O-methyl uridine |
| modified_base | 4<br>mod_base = OTHER<br>note = 2'-O-methyl guanosine |
| modified_base | 5<br>mod_base = OTHER<br>note = 2'-O-methyl adenosine |
| modified_base | 6<br>mod_base = OTHER<br>note = 2'-O-methyl guanosine |
| modified_base | 7<br>mod_base = OTHER<br>note = 2'-O-methyl adenosine |
| modified_base | 8<br>mod_base = OTHER<br>note = 2'-fluoro guanosine |
| modified_base | 9<br>mod_base = OTHER<br>note = 2'-fluoro adenosine |
| modified_base | 10<br>mod_base = OTHER<br>note = 2'-fluoro adenosine |
| modified_base | 11<br>mod_base = OTHER<br>note = 2'-fluoro adenosine |
| modified_base | 12<br>mod_base = OTHER<br>note = 2'-O-methyl cytidine |
| modified_base | 13<br>mod_base = OTHER<br>note = 2'-O-methyl uridine |
| modified_base | 14<br>mod_base = OTHER<br>note = 2'-O-methyl guanosine |
| modified_base | 15<br>mod_base = OTHER<br>note = 2'-O-methyl cytidine |
| modified_base | 16<br>mod_base = OTHER<br>note = 2'-O-methyl guanosine |
| modified_base | 17<br>mod_base = OTHER<br>note = 2'-O-methyl uridine |
| modified_base | 18<br>mod_base = OTHER<br>note = 2'-O-methyl uridine |
| modified_base | 19<br>mod_base = OTHER<br>note = 2'-O-methyl uridine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER |

```
                       note = 2'-O-methyl cytidine
modified_base          27
                       mod_base = OTHER
                       note = 2'-O-methyl guanosine
modified_base          28
                       mod_base = OTHER
                       note = 2'-aminodiethoxymethanol-Adenine-GalNAc
modified_base          29
                       mod_base = OTHER
                       note = 2'-aminodiethoxymethanol-Adenine-GalNAc
modified_base          30
                       mod_base = OTHER
                       note = 2'-aminodiethoxymethanol-Adenine-GalNAc
modified_base          31
                       mod_base = OTHER
                       note = 2'-O-methyl guanosine
modified_base          32
                       mod_base = OTHER
                       note = 2'-O-methyl guanosine
modified_base          33
                       mod_base = OTHER
                       note = 2'-O-methyl cytidine
modified_base          34
                       mod_base = OTHER
                       note = 2'-O-methyl uridine
modified_base          35
                       mod_base = OTHER
                       note = 2'-O-methyl guanosine
modified_base          36
                       mod_base = OTHER
                       note = 2'-O-methyl cytidine
source                 1..36
                       mol_type = other RNA
                       organism = synthetic construct
SEQUENCE: 630
gatgagagaa actgcgttta gcagccgaaa ggctgc                             36

SEQ ID NO: 631         moltype = RNA   length = 36
FEATURE                Location/Qualifiers
misc_feature           1..36
                       note = synthetic construct
misc_feature           1..2
                       note = linked via phosphorothioate
modified_base          1
                       mod_base = OTHER
                       note = 2'-O-methyl guanosine
modified_base          2
                       mod_base = OTHER
                       note = 2'-O-methyl adenosine
modified_base          3
                       mod_base = OTHER
                       note = 2'-O-methyl guanosine
modified_base          4
                       mod_base = OTHER
                       note = 2'-O-methyl guanosine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl uridine
modified_base          8
                       mod_base = OTHER
                       note = 2'-fluoro cytidine
modified_base          9
                       mod_base = OTHER
                       note = 2'-fluoro cytidine
modified_base          10
                       mod_base = OTHER
                       note = 2'-fluoro uridine
modified_base          11
                       mod_base = OTHER
                       note = 2'-fluoro uridine
modified_base          12
                       mod_base = OTHER
                       note = 2'-O-methyl cytidine
```

| | |
|---|---|
| modified_base | 13<br>mod_base = OTHER<br>note = 2'-O-methyl adenosine |
| modified_base | 14<br>mod_base = OTHER<br>note = 2'-O-methyl adenosine |
| modified_base | 15<br>mod_base = OTHER<br>note = 2'-O-methyl guanosine |
| modified_base | 16<br>mod_base = OTHER<br>note = 2'-O-methyl guanosine |
| modified_base | 17<br>mod_base = OTHER<br>note = 2'-O-methyl uridine |
| modified_base | 18<br>mod_base = OTHER<br>note = 2'-O-methyl guanosine |
| modified_base | 19<br>mod_base = OTHER<br>note = 2'-O-methyl adenosine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl cytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER<br>note = 2'-O-methyl guanosine |
| modified_base | 32<br>mod_base = OTHER<br>note = 2'-O-methyl guanosine |
| modified_base | 33<br>mod_base = OTHER<br>note = 2'-O-methyl cytidine |
| modified_base | 34<br>mod_base = OTHER<br>note = 2'-O-methyl uridine |
| modified_base | 35<br>mod_base = OTHER<br>note = 2'-O-methyl guanosine |
| modified_base | 36<br>mod_base = OTHER<br>note = 2'-O-methyl cytidine |
| source | 1..36<br>mol_type = other RNA<br>organism = synthetic construct |

SEQUENCE: 631
gaggtgtcct tcaaggtgaa gcagccgaaa ggctgc                                    36

SEQ ID NO: 632        moltype = RNA   length = 36

-continued

```
FEATURE              Location/Qualifiers
misc_feature         1..36
                     note = synthetic construct
misc_feature         1..2
                     note = linked via phosphorothioate
modified_base        1
                     mod_base = OTHER
                     note = 2'-O-methyl cytidine
modified_base        2
                     mod_base = OTHER
                     note = 2'-O-methyl uridine
modified_base        3
                     mod_base = OTHER
                     note = 2'-O-methyl cytidine
modified_base        4
                     mod_base = OTHER
                     note = 2'-O-methyl adenosine
modified_base        5
                     mod_base = OTHER
                     note = 2'-O-methyl cytidine
modified_base        6
                     mod_base = OTHER
                     note = 2'-O-methyl cytidine
modified_base        7
                     mod_base = OTHER
                     note = 2'-O-methyl uridine
modified_base        8
                     mod_base = OTHER
                     note = 2'-fluoro guanosine
modified_base        9
                     mod_base = OTHER
                     note = 2'-fluoro cytidine
modified_base        10
                     mod_base = OTHER
                     note = 2'-fluoro uridine
modified_base        11
                     mod_base = OTHER
                     note = 2'-fluoro uridine
modified_base        12
                     mod_base = OTHER
                     note = 2'-O-methyl cytidine
modified_base        13
                     mod_base = OTHER
                     note = 2'-O-methyl uridine
modified_base        14
                     mod_base = OTHER
                     note = 2'-O-methyl uridine
modified_base        15
                     mod_base = OTHER
                     note = 2'-O-methyl cytidine
modified_base        16
                     mod_base = OTHER
                     note = 2'-O-methyl uridine
modified_base        17
                     mod_base = OTHER
                     note = 2'-O-methyl guanosine
modified_base        18
                     mod_base = OTHER
                     note = 2'-O-methyl guanosine
modified_base        19
                     mod_base = OTHER
                     note = 2'-O-methyl uridine
modified_base        20
                     mod_base = OTHER
                     note = 2'-O-methyl adenosine
modified_base        21
                     mod_base = OTHER
                     note = 2'-O-methyl guanosine
modified_base        22
                     mod_base = OTHER
                     note = 2'-O-methyl cytidine
modified_base        23
                     mod_base = OTHER
                     note = 2'-O-methyl adenosine
modified_base        24
                     mod_base = OTHER
                     note = 2'-O-methyl guanosine
modified_base        25
                     mod_base = OTHER
```

```
                    note = 2'-O-methyl cytidine
modified_base       26
                    mod_base = OTHER
                    note = 2'-O-methyl cytidine
modified_base       27
                    mod_base = OTHER
                    note = 2'-O-methyl guanosine
modified_base       28
                    mod_base = OTHER
                    note = 2'-aminodiethoxymethanol-Adenine-GalNAc
modified_base       29
                    mod_base = OTHER
                    note = 2'-aminodiethoxymethanol-Adenine-GalNAc
modified_base       30
                    mod_base = OTHER
                    note = 2'-aminodiethoxymethanol-Adenine-GalNAc
modified_base       31
                    mod_base = OTHER
                    note = 2'-O-methyl guanosine
modified_base       32
                    mod_base = OTHER
                    note = 2'-O-methyl guanosine
modified_base       33
                    mod_base = OTHER
                    note = 2'-O-methyl cytidine
modified_base       34
                    mod_base = OTHER
                    note = 2'-O-methyl uridine
modified_base       35
                    mod_base = OTHER
                    note = 2'-O-methyl guanosine
modified_base       36
                    mod_base = OTHER
                    note = 2'-O-methyl cytidine
source              1..36
                    mol_type = other RNA
                    organism = synthetic construct
SEQUENCE: 632
ctcacctgct tcttctggta gcagccgaaa ggctgc                            36

SEQ ID NO: 633      moltype = RNA  length = 36
FEATURE             Location/Qualifiers
misc_feature        1..36
                    note = synthetic construct
misc_feature        1..2
                    note = linked via phosphorothioate
modified_base       1
                    mod_base = OTHER
                    note = 2'-O-methyl uridine
modified_base       2
                    mod_base = OTHER
                    note = 2'-O-methyl cytidine
modified_base       3
                    mod_base = OTHER
                    note = 2'-O-methyl adenosine
modified_base       4
                    mod_base = OTHER
                    note = 2'-O-methyl cytidine
modified_base       5
                    mod_base = OTHER
                    note = 2'-O-methyl cytidine
modified_base       6
                    mod_base = OTHER
                    note = 2'-O-methyl uridine
modified_base       7
                    mod_base = OTHER
                    note = 2'-O-methyl guanosine
modified_base       8
                    mod_base = OTHER
                    note = 2'-fluoro cytidine
modified_base       9
                    mod_base = OTHER
                    note = 2'-fluoro uridine
modified_base       10
                    mod_base = OTHER
                    note = 2'-fluoro uridine
modified_base       11
                    mod_base = OTHER
                    note = 2'-fluoro cytidine
```

| | |
|---|---|
| modified_base | 12<br>mod_base = OTHER<br>note = 2'-O-methyl uridine |
| modified_base | 13<br>mod_base = OTHER<br>note = 2'-O-methyl uridine |
| modified_base | 14<br>mod_base = OTHER<br>note = 2'-O-methyl cytidine |
| modified_base | 15<br>mod_base = OTHER<br>note = 2'-O-methyl uridine |
| modified_base | 16<br>mod_base = OTHER<br>note = 2'-O-methyl guanosine |
| modified_base | 17<br>mod_base = OTHER<br>note = 2'-O-methyl guanosine |
| modified_base | 18<br>mod_base = OTHER<br>note = 2'-O-methyl uridine |
| modified_base | 19<br>mod_base = OTHER<br>note = 2'-O-methyl uridine |
| modified_base | 20<br>mod_base = OTHER<br>note = 2'-O-methyl adenosine |
| modified_base | 21<br>mod_base = OTHER<br>note = 2'-O-methyl guanosine |
| modified_base | 22<br>mod_base = OTHER<br>note = 2'-O-methyl cytidine |
| modified_base | 23<br>mod_base = OTHER<br>note = 2'-O-methyl adenosine |
| modified_base | 24<br>mod_base = OTHER<br>note = 2'-O-methyl guanosine |
| modified_base | 25<br>mod_base = OTHER<br>note = 2'-O-methyl cytidine |
| modified_base | 26<br>mod_base = OTHER<br>note = 2'-O-methyl cytidine |
| modified_base | 27<br>mod_base = OTHER<br>note = 2'-O-methyl guanosine |
| modified_base | 28<br>mod_base = OTHER<br>note = 2'-aminodiethoxymethanol-Adenine-GalNAc |
| modified_base | 29<br>mod_base = OTHER<br>note = 2'-aminodiethoxymethanol-Adenine-GalNAc |
| modified_base | 30<br>mod_base = OTHER<br>note = 2'-aminodiethoxymethanol-Adenine-GalNAc |
| modified_base | 31<br>mod_base = OTHER<br>note = 2'-O-methyl guanosine |
| modified_base | 32<br>mod_base = OTHER<br>note = 2'-O-methyl guanosine |
| modified_base | 33<br>mod_base = OTHER<br>note = 2'-O-methyl cytidine |
| modified_base | 34<br>mod_base = OTHER<br>note = 2'-O-methyl uridine |
| modified_base | 35<br>mod_base = OTHER<br>note = 2'-O-methyl guanosine |
| modified_base | 36<br>mod_base = OTHER<br>note = 2'-O-methyl cytidine |
| source | 1..36<br>mol_type = other RNA<br>organism = synthetic construct |
| SEQUENCE: 633 | | tcacctgctt cttctggtta gcagccgaaa ggctgc                         36

SEQ ID NO: 634          moltype = RNA   length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl uridine
modified_base           2
                        mod_base = OTHER
                        note = 2'-O-methyl cytidine
modified_base           3
                        mod_base = OTHER
                        note = 2'-O-methyl uridine
modified_base           4
                        mod_base = OTHER
                        note = 2'-O-methyl guanosine
modified_base           5
                        mod_base = OTHER
                        note = 2'-O-methyl guanosine
modified_base           6
                        mod_base = OTHER
                        note = 2'-O-methyl uridine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-fluoro adenosine
modified_base           10
                        mod_base = OTHER
                        note = 2'-fluoro uridine
modified_base           11
                        mod_base = OTHER
                        note = 2'-fluoro uridine
modified_base           12
                        mod_base = OTHER
                        note = 2'-O-methyl cytidine
modified_base           13
                        mod_base = OTHER
                        note = 2'-O-methyl uridine
modified_base           14
                        mod_base = OTHER
                        note = 2'-O-methyl cytidine
modified_base           15
                        mod_base = OTHER
                        note = 2'-O-methyl cytidine
modified_base           16
                        mod_base = OTHER
                        note = 2'-O-methyl adenosine
modified_base           17
                        mod_base = OTHER
                        note = 2'-O-methyl adenosine
modified_base           18
                        mod_base = OTHER
                        note = 2'-O-methyl adenosine
modified_base           19
                        mod_base = OTHER
                        note = 2'-O-methyl uridine
modified_base           20
                        mod_base = OTHER
                        note = 2'-O-methyl adenosine
modified_base           21
                        mod_base = OTHER
                        note = 2'-O-methyl guanosine
modified_base           22
                        mod_base = OTHER
                        note = 2'-O-methyl cytidine
modified_base           23
                        mod_base = OTHER
                        note = 2'-O-methyl adenosine
modified_base           24
                        mod_base = OTHER

```
                          note = 2'-O-methyl guanosine
modified_base             25
                          mod_base = OTHER
                          note = 2'-O-methyl cytidine
modified_base             26
                          mod_base = OTHER
                          note = 2'-O-methyl cytidine
modified_base             27
                          mod_base = OTHER
                          note = 2'-O-methyl guanosine
modified_base             28
                          mod_base = OTHER
                          note = 2'-aminodiethoxymethanol-Adenine-GalNAc
modified_base             29
                          mod_base = OTHER
                          note = 2'-aminodiethoxymethanol-Adenine-GalNAc
modified_base             30
                          mod_base = OTHER
                          note = 2'-aminodiethoxymethanol-Adenine-GalNAc
modified_base             31
                          mod_base = OTHER
                          note = 2'-O-methyl guanosine
modified_base             32
                          mod_base = OTHER
                          note = 2'-O-methyl guanosine
modified_base             33
                          mod_base = OTHER
                          note = 2'-O-methyl cytidine
modified_base             34
                          mod_base = OTHER
                          note = 2'-O-methyl uridine
modified_base             35
                          mod_base = OTHER
                          note = 2'-O-methyl guanosine
modified_base             36
                          mod_base = OTHER
                          note = 2'-O-methyl cytidine
source                    1..36
                          mol_type = other RNA
                          organism = synthetic construct
SEQUENCE: 634
tctggttcat tctccaaata gcagccgaaa ggctgc                                 36

SEQ ID NO: 635           moltype = RNA   length = 36
FEATURE                  Location/Qualifiers
misc_feature             1..36
                          note = synthetic construct
misc_feature             1..2
                          note = linked via phosphorothioate
modified_base             1
                          mod_base = OTHER
                          note = 2'-O-methyl guonosine
modified_base             2
                          mod_base = OTHER
                          note = 2'-O-methyl uridine
modified_base             3
                          mod_base = OTHER
                          note = 2'-O-methyl uridine
modified_base             4
                          mod_base = OTHER
                          note = 2'-O-methyl cytidine
modified_base             5
                          mod_base = OTHER
                          note = 2'-O-methyl adenosine
modified_base             6
                          mod_base = OTHER
                          note = 2'-O-methyl uridine
modified_base             7
                          mod_base = OTHER
                          note = 2'-O-methyl uridine
modified_base             8
                          mod_base = OTHER
                          note = 2'-fluoro cytidine
modified_base             9
                          mod_base = OTHER
                          note = 2'-fluoro uridine
modified_base             10
                          mod_base = OTHER
                          note = 2'-fluoro cytidine
```

```
modified_base    11
                 mod_base = OTHER
                 note = 2'-fluoro cytidine
modified_base    12
                 mod_base = OTHER
                 note = 2'-O-methyl adenosine
modified_base    13
                 mod_base = OTHER
                 note = 2'-O-methyl adenosine
modified_base    14
                 mod_base = OTHER
                 note = 2'-O-methyl adenosine
modified_base    15
                 mod_base = OTHER
                 note = 2'-O-methyl uridine
modified_base    16
                 mod_base = OTHER
                 note = 2'-O-methyl cytidine
modified_base    17
                 mod_base = OTHER
                 note = 2'-O-methyl cytidine
modified_base    18
                 mod_base = OTHER
                 note = 2'-O-methyl cytidine
modified_base    19
                 mod_base = OTHER
                 note = 2'-O-methyl cytidine
modified_base    20
                 mod_base = OTHER
                 note = 2'-O-methyl adenosine
modified_base    21
                 mod_base = OTHER
                 note = 2'-O-methyl guonosine
modified_base    22
                 mod_base = OTHER
                 note = 2'-O-methyl cytidine
modified_base    23
                 mod_base = OTHER
                 note = 2'-O-methyl adenosine
modified_base    24
                 mod_base = OTHER
                 note = 2'-O-methyl guonosine
modified_base    25
                 mod_base = OTHER
                 note = 2'-O-methyl cytidine
modified_base    26
                 mod_base = OTHER
                 note = 2'-O-methyl cytidine
modified_base    27
                 mod_base = OTHER
                 note = 2'-O-methyl guonosine
modified_base    28
                 mod_base = OTHER
                 note = 2'-aminodiethoxymethanol-Adenine-GalNAc
modified_base    29
                 mod_base = OTHER
                 note = 2'-aminodiethoxymethanol-Adenine-GalNAc
modified_base    30
                 mod_base = OTHER
                 note = 2'-aminodiethoxymethanol-Adenine-GalNAc
modified_base    31
                 mod_base = OTHER
                 note = 2'-O-methyl guonosine
modified_base    32
                 mod_base = OTHER
                 note = 2'-O-methyl guonosine
modified_base    33
                 mod_base = OTHER
                 note = 2'-O-methyl cytidine
modified_base    34
                 mod_base = OTHER
                 note = 2'-O-methyl uridine
modified_base    35
                 mod_base = OTHER
                 note = 2'-O-methyl guonosine
modified_base    36
                 mod_base = OTHER
                 note = 2'-O-methyl cytidine
source           1..36
```

```
                        mol_type = other RNA
                        organism = synthetic construct
SEQUENCE: 635
gttcattctc caaatcccca gcagccgaaa ggctgc                          36

SEQ ID NO: 636          moltype = RNA   length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl adenosine
modified_base           2
                        mod_base = OTHER
                        note = 2'-O-methyl adenosine
modified_base           3
                        mod_base = OTHER
                        note = 2'-O-methyl adenosine
modified_base           4
                        mod_base = OTHER
                        note = 2'-O-methyl guanosine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine
modified_base           8
                        mod_base = OTHER
                        note = 2'-fluoro adenosine
modified_base           9
                        mod_base = OTHER
                        note = 2'-fluoro uridine
modified_base           10
                        mod_base = OTHER
                        note = 2'-fluoro guanosine
modified_base           11
                        mod_base = OTHER
                        note = 2'-fluoro uridine
modified_base           12
                        mod_base = OTHER
                        note = 2'-O-methyl guanosine
modified_base           13
                        mod_base = OTHER
                        note = 2'-O-methyl cytidine
modified_base           14
                        mod_base = OTHER
                        note = 2'-O-methyl adenosine
modified_base           15
                        mod_base = OTHER
                        note = 2'-O-methyl guanosine
modified_base           16
                        mod_base = OTHER
                        note = 2'-O-methyl uridine
modified_base           17
                        mod_base = OTHER
                        note = 2'-O-methyl uridine
modified_base           18
                        mod_base = OTHER
                        note = 2'-O-methyl guanosine
modified_base           19
                        mod_base = OTHER
                        note = 2'-O-methyl adenosine
modified_base           20
                        mod_base = OTHER
                        note = 2'-O-methyl adenosine
modified_base           21
                        mod_base = OTHER
                        note = 2'-O-methyl guanosine
modified_base           22
                        mod_base = OTHER
                        note = 2'-O-methyl cytidine
modified_base           23
                        mod_base = OTHER
```

```
                        note = 2'-O-methyl adenosine
modified_base           24
                        mod_base = OTHER
                        note = 2'-O-methyl guanosine
modified_base           25
                        mod_base = OTHER
                        note = 2'-O-methyl cytidine
modified_base           26
                        mod_base = OTHER
                        note = 2'-O-methyl cytidine
modified_base           27
                        mod_base = OTHER
                        note = 2'-O-methyl guanosine
modified_base           28
                        mod_base = OTHER
                        note = 2'-aminodiethoxymethanol-Adenine-GalNAc
modified_base           29
                        mod_base = OTHER
                        note = 2'-aminodiethoxymethanol-Adenine-GalNAc
modified_base           30
                        mod_base = OTHER
                        note = 2'-aminodiethoxymethanol-Adenine-GalNAc
modified_base           31
                        mod_base = OTHER
                        note = 2'-O-methyl guanosine
modified_base           32
                        mod_base = OTHER
                        note = 2'-O-methyl guanosine
modified_base           33
                        mod_base = OTHER
                        note = 2'-O-methyl cytidine
modified_base           34
                        mod_base = OTHER
                        note = 2'-O-methyl uridine
modified_base           35
                        mod_base = OTHER
                        note = 2'-O-methyl guanosine
modified_base           36
                        mod_base = OTHER
                        note = 2'-O-methyl cytidine
source                  1..36
                        mol_type = other RNA
                        organism = synthetic construct
SEQUENCE: 636
aaagtggatg tgcagttgaa gcagccgaaa ggctgc                                    36

SEQ ID NO: 637          moltype = RNA   length = 36
FEATURE                 Location/Qualifiers
misc_feature            1..36
                        note = synthetic construct
misc_feature            1..2
                        note = linked via phosphorothioate
modified_base           1
                        mod_base = OTHER
                        note = 2'-O-methyl adenosine
modified_base           2
                        mod_base = OTHER
                        note = 2'-O-methyl adenosine
modified_base           3
                        mod_base = OTHER
                        note = 2'-O-methyl cytidine
modified_base           4
                        mod_base = OTHER
                        note = 2'-O-methyl uridine
modified_base           5
                        mod_base = OTHER
                        note = 2'-O-methyl cytidine
modified_base           6
                        mod_base = OTHER
                        note = 2'-O-methyl cytidine
modified_base           7
                        mod_base = OTHER
                        note = 2'-O-methyl adenosine
modified_base           8
                        mod_base = OTHER
                        note = 2'-fluoro guanosine
modified_base           9
                        mod_base = OTHER
                        note = 2'-fluoro cytidine
```

-continued

```
modified_base    10
                 mod_base = OTHER
                 note = 2'-fluoro uridine
modified_base    11
                 mod_base = OTHER
                 note = 2'-fluoro cytidine
modified_base    12
                 mod_base = OTHER
                 note = 2'-O-methyl cytidine
modified_base    13
                 mod_base = OTHER
                 note = 2'-O-methyl guanosine
modified_base    14
                 mod_base = OTHER
                 note = 2'-O-methyl uridine
modified_base    15
                 mod_base = OTHER
                 note = 2'-O-methyl cytidine
modified_base    16
                 mod_base = OTHER
                 note = 2'-O-methyl uridine
modified_base    17
                 mod_base = OTHER
                 note = 2'-O-methyl adenosine
modified_base    18
                 mod_base = OTHER
                 note = 2'-O-methyl uridine
modified_base    19
                 mod_base = OTHER
                 note = 2'-O-methyl uridine
modified_base    20
                 mod_base = OTHER
                 note = 2'-O-methyl adenosine
modified_base    21
                 mod_base = OTHER
                 note = 2'-O-methyl guanosine
modified_base    22
                 mod_base = OTHER
                 note = 2'-O-methyl cytidine
modified_base    23
                 mod_base = OTHER
                 note = 2'-O-methyl adenosine
modified_base    24
                 mod_base = OTHER
                 note = 2'-O-methyl guanosine
modified_base    25
                 mod_base = OTHER
                 note = 2'-O-methyl cytidine
modified_base    26
                 mod_base = OTHER
                 note = 2'-O-methyl cytidine
modified_base    27
                 mod_base = OTHER
                 note = 2'-O-methyl guanosine
modified_base    28
                 mod_base = OTHER
                 note = 2'-aminodiethoxymethanol-Adenine-GalNAc
modified_base    29
                 mod_base = OTHER
                 note = 2'-aminodiethoxymethanol-Adenine-GalNAc
modified_base    30
                 mod_base = OTHER
                 note = 2'-aminodiethoxymethanol-Adenine-GalNAc
modified_base    31
                 mod_base = OTHER
                 note = 2'-O-methyl guanosine
modified_base    32
                 mod_base = OTHER
                 note = 2'-O-methyl guanosine
modified_base    33
                 mod_base = OTHER
                 note = 2'-O-methyl cytidine
modified_base    34
                 mod_base = OTHER
                 note = 2'-O-methyl uridine
modified_base    35
                 mod_base = OTHER
                 note = 2'-O-methyl guanosine
modified_base    36
```

-continued

```
                         mod_base = OTHER
                         note = 2'-O-methyl cytidine
source                   1..36
                         mol_type = other RNA
                         organism = synthetic construct
SEQUENCE: 637
aactccagct ccgtctatta gcagccgaaa ggctgc                              36

SEQ ID NO: 638           moltype = RNA  length = 36
FEATURE                  Location/Qualifiers
misc_feature             1..36
                         note = synthetic construct
misc_feature             1..2
                         note = linked via phosphorothioate
modified_base            1
                         mod_base = OTHER
                         note = 2'-O-methyl adenosine
modified_base            2
                         mod_base = OTHER
                         note = 2'-O-methyl cytidine
modified_base            3
                         mod_base = OTHER
                         note = 2'-O-methyl cytidine
modified_base            4
                         mod_base = OTHER
                         note = 2'-O-methyl uridine
modified_base            5
                         mod_base = OTHER
                         note = 2'-O-methyl guanosine
modified_base            6
                         mod_base = OTHER
                         note = 2'-O-methyl cytidine
modified_base            7
                         mod_base = OTHER
                         note = 2'-O-methyl uridine
modified_base            8
                         mod_base = OTHER
                         note = 2'-fluoro uridine
modified_base            9
                         mod_base = OTHER
                         note = 2'-fluoro cytidine
modified_base            10
                         mod_base = OTHER
                         note = 2'-fluoro uridine
modified_base            11
                         mod_base = OTHER
                         note = 2'-fluoro uridine
modified_base            12
                         mod_base = OTHER
                         note = 2'-O-methyl cytidine
modified_base            13
                         mod_base = OTHER
                         note = 2'-O-methyl uridine
modified_base            14
                         mod_base = OTHER
                         note = 2'-O-methyl guanosine
modified_base            15
                         mod_base = OTHER
                         note = 2'-O-methyl guanosine
modified_base            16
                         mod_base = OTHER
                         note = 2'-O-methyl uridine
modified_base            17
                         mod_base = OTHER
                         note = 2'-O-methyl uridine
modified_base            18
                         mod_base = OTHER
                         note = 2'-O-methyl cytidine
modified_base            19
                         mod_base = OTHER
                         note = 2'-O-methyl adenosine
modified_base            20
                         mod_base = OTHER
                         note = 2'-O-methyl adenosine
modified_base            21
                         mod_base = OTHER
                         note = 2'-O-methyl guanosine
modified_base            22
                         mod_base = OTHER
```

```
                                    note = 2'-O-methyl cytidine
modified_base                       23
                                    mod_base = OTHER
                                    note = 2'-O-methyl adenosine
modified_base                       24
                                    mod_base = OTHER
                                    note = 2'-O-methyl guanosine
modified_base                       25
                                    mod_base = OTHER
                                    note = 2'-O-methyl cytidine
modified_base                       26
                                    mod_base = OTHER
                                    note = 2'-O-methyl cytidine
modified_base                       27
                                    mod_base = OTHER
                                    note = 2'-O-methyl guanosine
modified_base                       28
                                    mod_base = OTHER
                                    note = 2'-aminodiethoxymethanol-Adenine-GalNAc
modified_base                       29
                                    mod_base = OTHER
                                    note = 2'-aminodiethoxymethanol-Adenine-GalNAc
modified_base                       30
                                    mod_base = OTHER
                                    note = 2'-aminodiethoxymethanol-Adenine-GalNAc
modified_base                       31
                                    mod_base = OTHER
                                    note = 2'-O-methyl guanosine
modified_base                       32
                                    mod_base = OTHER
                                    note = 2'-O-methyl guanosine
modified_base                       33
                                    mod_base = OTHER
                                    note = 2'-O-methyl cytidine
modified_base                       34
                                    mod_base = OTHER
                                    note = 2'-O-methyl uridine
modified_base                       35
                                    mod_base = OTHER
                                    note = 2'-O-methyl guanosine
modified_base                       36
                                    mod_base = OTHER
                                    note = 2'-O-methyl cytidine
source                              1..36
                                    mol_type = other RNA
                                    organism = synthetic construct
SEQUENCE: 638
acctgcttct tctggttcaa gcagccgaaa ggctgc                                      36

SEQ ID NO: 639                      moltype = RNA  length = 36
FEATURE                             Location/Qualifiers
misc_feature                        1..36
                                    note = synthetic construct
misc_feature                        1..2
                                    note = linked via phosphorothioate
modified_base                       1
                                    mod_base = OTHER
                                    note = 2'-O-methyl adenosine
modified_base                       2
                                    mod_base = OTHER
                                    note = 2'-O-methyl guanosine
modified_base                       3
                                    mod_base = OTHER
                                    note = 2'-O-methyl uridine
modified_base                       4
                                    mod_base = OTHER
                                    note = 2'-O-methyl guanosine
modified_base                       5
                                    mod_base = OTHER
                                    note = 2'-O-methyl uridine
modified_base                       6
                                    mod_base = OTHER
                                    note = 2'-O-methyl guanosine
modified_base                       7
                                    mod_base = OTHER
                                    note = 2'-O-methyl adenosine
modified_base                       8
                                    mod_base = OTHER
                                    note = 2'-fluoro adenosine
```

-continued

| | | |
|---|---|---|
| modified_base | 9 | |
| | mod_base = OTHER | |
| | note = 2'-fluoro adenosine | |
| modified_base | 10 | |
| | mod_base = OTHER | |
| | note = 2'-fluoro guanosine | |
| modified_base | 11 | |
| | mod_base = OTHER | |
| | note = 2'-fluoro adenosine | |
| modified_base | 12 | |
| | mod_base = OTHER | |
| | note = 2'-O-methyl cytidine | |
| modified_base | 13 | |
| | mod_base = OTHER | |
| | note = 2'-O-methyl adenosine | |
| modified_base | 14 | |
| | mod_base = OTHER | |
| | note = 2'-O-methyl uridine | |
| modified_base | 15 | |
| | mod_base = OTHER | |
| | note = 2'-O-methyl adenosine | |
| modified_base | 16 | |
| | mod_base = OTHER | |
| | note = 2'-O-methyl guanosine | |
| modified_base | 17 | |
| | mod_base = OTHER | |
| | note = 2'-O-methyl cytidine | |
| modified_base | 18 | |
| | mod_base = OTHER | |
| | note = 2'-O-methyl uridine | |
| modified_base | 19 | |
| | mod_base = OTHER | |
| | note = 2'-O-methyl guanosine | |
| modified_base | 20 | |
| | mod_base = OTHER | |
| | note = 2'-O-methyl adenosine | |
| modified_base | 21 | |
| | mod_base = OTHER | |
| | note = 2'-O-methyl guanosine | |
| modified_base | 22 | |
| | mod_base = OTHER | |
| | note = 2'-O-methyl cytidine | |
| modified_base | 23 | |
| | mod_base = OTHER | |
| | note = 2'-O-methyl adenosine | |
| modified_base | 24 | |
| | mod_base = OTHER | |
| | note = 2'-O-methyl guanosine | |
| modified_base | 25 | |
| | mod_base = OTHER | |
| | note = 2'-O-methyl cytidine | |
| modified_base | 26 | |
| | mod_base = OTHER | |
| | note = 2'-O-methyl cytidine | |
| modified_base | 27 | |
| | mod_base = OTHER | |
| | note = 2'-O-methyl guanosine | |
| modified_base | 28 | |
| | mod_base = OTHER | |
| | note = 2'-aminodiethoxymethanol-Adenine-GalNAc | |
| modified_base | 29 | |
| | mod_base = OTHER | |
| | note = 2'-aminodiethoxymethanol-Adenine-GalNAc | |
| modified_base | 30 | |
| | mod_base = OTHER | |
| | note = 2'-aminodiethoxymethanol-Adenine-GalNAc | |
| modified_base | 31 | |
| | mod_base = OTHER | |
| | note = 2'-O-methyl guanosine | |
| modified_base | 32 | |
| | mod_base = OTHER | |
| | note = 2'-O-methyl guanosine | |
| modified_base | 33 | |
| | mod_base = OTHER | |
| | note = 2'-O-methyl cytidine | |
| modified_base | 34 | |
| | mod_base = OTHER | |
| | note = 2'-O-methyl uridine | |
| modified_base | 35 | |

```
                        mod_base = OTHER
                        note = 2'-O-methyl guanosine
modified_base           36
                        mod_base = OTHER
                        note = 2'-O-methyl cytidine
source                  1..36
                        mol_type = other RNA
                        organism = synthetic construct
SEQUENCE: 639
agtgtgaaag acatagctga gcagccgaaa ggctgc                          36

SEQ ID NO: 640          moltype = RNA   length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro uridine
modified_base           4
                        mod_base = OTHER
                        note = 2'-fluoro uridine
modified_base           5
                        mod_base = OTHER
                        note = 2'-fluoro cytidine
modified_base           6
                        mod_base = OTHER
                        note = 2'-O-methyl uridine
modified_base           7
                        mod_base = OTHER
                        note = 2'-fluoro cytidine
modified_base           8
                        mod_base = OTHER
                        note = 2'-O-methyl uridine
modified_base           9
                        mod_base = OTHER
                        note = 2'-O-methyl uridine
modified_base           10
                        mod_base = OTHER
                        note = 2'-fluoro guanosine
modified_base           11
                        mod_base = OTHER
                        note = 2'-O-methyl guanosine
modified_base           12
                        mod_base = OTHER
                        note = 2'-O-methyl adenosine
modified_base           13
                        mod_base = OTHER
                        note = 2'-O-methyl guanosine
modified_base           14
                        mod_base = OTHER
                        note = 2'-fluoro uridine
modified_base           15
                        mod_base = OTHER
                        note = 2'-O-methyl cytidine
modified_base           16
                        mod_base = OTHER
                        note = 2'-O-methyl cytidine
modified_base           17
                        mod_base = OTHER
                        note = 2'-O-methyl uridine
modified_base           18
                        mod_base = OTHER
                        note = 2'-O-methyl modified
modified_base           18
                        mod_base = OTHER
                        note = 2'-O-methyl cytidine
misc_feature            18..20
                        note = linked via phosphorothioate
modified_base           19
                        mod_base = OTHER
                        note = 2'-O-methyl adenosine
```

```
modified_base      20
                   mod_base = OTHER
                   note = 2'-O-methyl cytidine
modified_base      21
                   mod_base = OTHER
                   note = 2'-O-methyl guanosine
modified_base      22
                   mod_base = OTHER
                   note = 2'-O-methyl guanosine
source             1..22
                   mol_type = other RNA
                   organism = synthetic construct
SEQUENCE: 640
ttttctcttg gagtcctcac gg                                              22

SEQ ID NO: 641     moltype = RNA  length = 22
FEATURE            Location/Qualifiers
misc_feature       1..22
                   note = synthetic construct
misc_feature       1..4
                   note = linked via phosphorothioate
modified_base      1
                   mod_base = OTHER
                   note = 5'-methoxyphosphonate-4-oxy uridine
modified_base      2
                   mod_base = OTHER
                   note = 2'-fluoro adenosine
modified_base      3
                   mod_base = OTHER
                   note = 2'-fluoro adenosine
modified_base      4
                   mod_base = OTHER
                   note = 2'-fluoro adenosine
modified_base      5
                   mod_base = OTHER
                   note = 2'-fluoro uridine
modified_base      6
                   mod_base = OTHER
                   note = 2'-O-methyl adenosine
modified_base      7
                   mod_base = OTHER
                   note = 2'-fluoro cytidine
modified_base      8
                   mod_base = OTHER
                   note = 2'-O-methyl cytidine
modified_base      9
                   mod_base = OTHER
                   note = 2'-O-methyl adenosine
modified_base      10
                   mod_base = OTHER
                   note = 2'-fluoro guanosine
modified_base      11
                   mod_base = OTHER
                   note = 2'-O-methyl adenosine
modified_base      12
                   mod_base = OTHER
                   note = 2'-O-methyl guanosine
modified_base      13
                   mod_base = OTHER
                   note = 2'-O-methyl uridine
modified_base      14
                   mod_base = OTHER
                   note = 2'-fluoro adenosine
modified_base      15
                   mod_base = OTHER
                   note = 2'-O-methyl guanosine
modified_base      16
                   mod_base = OTHER
                   note = 2'-O-methyl cytidine
modified_base      17
                   mod_base = OTHER
                   note = 2'-O-methyl adenosine
modified_base      18
                   mod_base = OTHER
                   note = 2'-O-methyl cytidine
misc_feature       18..20
                   note = linked via phosphorothioate
modified_base      19
                   mod_base = OTHER
```

```
                    note = 2'-O-methyl cytidine
modified_base       20
                    mod_base = OTHER
                    note = 2'-O-methyl cytidine
modified_base       21
                    mod_base = OTHER
                    note = 2'-O-methyl guanosine
modified_base       22
                    mod_base = OTHER
                    note = 2'-O-methyl guanosine
source              1..22
                    mol_type = other RNA
                    organism = synthetic construct
SEQUENCE: 641
taaataccag agtagcaccc gg                                              22

SEQ ID NO: 642      moltype = RNA  length = 22
FEATURE             Location/Qualifiers
misc_feature        1..22
                    note = synthetic construct
misc_feature        1..4
                    note = linked via phosphorothioate
modified_base       1
                    mod_base = OTHER
                    note = 5'-methoxyphosphonate-4-oxy uridine
modified_base       2
                    mod_base = OTHER
                    note = 2'-fluoro guanosine
modified_base       3
                    mod_base = OTHER
                    note = 2'-fluoro adenosine
modified_base       4
                    mod_base = OTHER
                    note = 2'-fluoro adenosine
modified_base       5
                    mod_base = OTHER
                    note = 2'-fluoro adenosine
modified_base       6
                    mod_base = OTHER
                    note = 2'-O-methyl uridine
modified_base       7
                    mod_base = OTHER
                    note = 2'-fluoro adenosine
modified_base       8
                    mod_base = OTHER
                    note = 2'-O-methyl cytidine
modified_base       9
                    mod_base = OTHER
                    note = 2'-O-methyl cytidine
modified_base       10
                    mod_base = OTHER
                    note = 2'-fluoro adenosine
modified_base       11
                    mod_base = OTHER
                    note = 2'-O-methyl guanosine
modified_base       12
                    mod_base = OTHER
                    note = 2'-O-methyl adenosine
modified_base       13
                    mod_base = OTHER
                    note = 2'-O-methyl guanosine
modified_base       14
                    mod_base = OTHER
                    note = 2'-fluoro uridine
modified_base       15
                    mod_base = OTHER
                    note = 2'-O-methyl adenosine
modified_base       16
                    mod_base = OTHER
                    note = 2'-O-methyl guanosine
modified_base       17
                    mod_base = OTHER
                    note = 2'-O-methyl cytidine
modified_base       18
                    mod_base = OTHER
                    note = 2'-O-methyl adenosine
misc_feature        18..20
                    note = linked via phosphorothioate
modified_base       19
```

```
                        mod_base = OTHER
                        note = 2'-O-methyl cytidine
modified_base           20
                        mod_base = OTHER
                        note = 2'-O-methyl cytidine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 642
tgaaatacca gagtagcacc gg                                                  22

SEQ ID NO: 643          moltype = RNA  length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro adenosine
modified_base           4
                        mod_base = OTHER
                        note = 2'-fluoro guanosine
modified_base           5
                        mod_base = OTHER
                        note = 2'-fluoro guanosine
modified_base           6
                        mod_base = OTHER
                        note = 2'-O-methyl adenosine
modified_base           7
                        mod_base = OTHER
                        note = 2'-fluoro adenosine
modified_base           8
                        mod_base = OTHER
                        note = 2'-O-methyl adenosine
modified_base           9
                        mod_base = OTHER
                        note = 2'-O-methyl uridine
modified_base           10
                        mod_base = OTHER
                        note = 2'-fluoro adenosine
modified_base           11
                        mod_base = OTHER
                        note = 2'-O-methyl cytidine
modified_base           12
                        mod_base = OTHER
                        note = 2'-O-methyl cytidine
modified_base           13
                        mod_base = OTHER
                        note = 2'-O-methyl adenosine
modified_base           14
                        mod_base = OTHER
                        note = 2'-fluoro guanosine
modified_base           15
                        mod_base = OTHER
                        note = 2'-O-methyl adenosine
modified_base           16
                        mod_base = OTHER
                        note = 2'-O-methyl guanosine
modified_base           17
                        mod_base = OTHER
                        note = 2'-O-methyl uridine
modified_base           18
                        mod_base = OTHER
                        note = 2'-O-methyl adenosine
misc_feature            18..20
                        note = linked via phosphorothioate
```

```
modified_base        19
                     mod_base = OTHER
                     note = 2'-O-methyl guanosine
modified_base        20
                     mod_base = OTHER
                     note = 2'-O-methyl cytidine
modified_base        21
                     mod_base = OTHER
                     note = 2'-O-methyl guanosine
modified_base        22
                     mod_base = OTHER
                     note = 2'-O-methyl guanosine
source               1..22
                     mol_type = other RNA
                     organism = synthetic construct
SEQUENCE: 643
ttaggaaata ccagagtagc gg                                        22

SEQ ID NO: 644       moltype = RNA  length = 22
FEATURE              Location/Qualifiers
misc_feature         1..22
                     note = synthetic construct
misc_feature         1..4
                     note = linked via phosphorothioate
modified_base        1
                     mod_base = OTHER
                     note = 5'-methoxyphosphonate-4-oxy uridine
modified_base        2
                     mod_base = OTHER
                     note = 2'-fluoro uridine
modified_base        3
                     mod_base = OTHER
                     note = 2'-fluoro uridine
modified_base        4
                     mod_base = OTHER
                     note = 2'-fluoro guanosine
modified_base        5
                     mod_base = OTHER
                     note = 2'-fluoro uridine
modified_base        6
                     mod_base = OTHER
                     note = 2'-O-methyl adenosine
modified_base        7
                     mod_base = OTHER
                     note = 2'-fluoro cytidine
modified_base        8
                     mod_base = OTHER
                     note = 2'-O-methyl cytidine
modified_base        9
                     mod_base = OTHER
                     note = 2'-O-methyl cytidine
modified_base        10
                     mod_base = OTHER
                     note = 2'-fluoro uridine
modified_base        11
                     mod_base = OTHER
                     note = 2'-O-methyl adenosine
modified_base        12
                     mod_base = OTHER
                     note = 2'-O-methyl guanosine
modified_base        13
                     mod_base = OTHER
                     note = 2'-O-methyl guanosine
modified_base        14
                     mod_base = OTHER
                     note = 2'-fluoro adenosine
modified_base        15
                     mod_base = OTHER
                     note = 2'-O-methyl adenosine
modified_base        16
                     mod_base = OTHER
                     note = 2'-O-methyl adenosine
modified_base        17
                     mod_base = OTHER
                     note = 2'-O-methyl uridine
modified_base        18
                     mod_base = OTHER
                     note = 2'-O-methyl adenosine
misc_feature         18..20
```

```
                         note = linked via phosphorothioate
modified_base            19
                         mod_base = OTHER
                         note = 2'-O-methyl cytidine
modified_base            20
                         mod_base = OTHER
                         note = 2'-O-methyl cytidine
modified_base            21
                         mod_base = OTHER
                         note = 2'-O-methyl guanosine
modified_base            22
                         mod_base = OTHER
                         note = 2'-O-methyl guanosine
source                   1..22
                         mol_type = other RNA
                         organism = synthetic construct
SEQUENCE: 644
tttgtaccct aggaaatacc gg                                                22

SEQ ID NO: 645           moltype = RNA  length = 22
FEATURE                  Location/Qualifiers
misc_feature             1..22
                         note = synthetic construct
misc_feature             1..4
                         note = linked via phosphorothioate
modified_base            1
                         mod_base = OTHER
                         note = 5'-methoxyphosphonate-4-oxy uridine
modified_base            2
                         mod_base = OTHER
                         note = 2'-fluoro guanosine
modified_base            3
                         mod_base = OTHER
                         note = 2'-fluoro adenosine
modified_base            4
                         mod_base = OTHER
                         note = 2'-fluoro adenosine
modified_base            5
                         mod_base = OTHER
                         note = 2'-fluoro cytidine
modified_base            6
                         mod_base = OTHER
                         note = 2'-O-methyl cytidine
modified_base            7
                         mod_base = OTHER
                         note = 2'-fluoro adenosine
modified_base            8
                         mod_base = OTHER
                         note = 2'-O-methyl guanosine
modified_base            9
                         mod_base = OTHER
                         note = 2'-O-methyl adenosine
modified_base            10
                         mod_base = OTHER
                         note = 2'-fluoro adenosine
modified_base            11
                         mod_base = OTHER
                         note = 2'-O-methyl guanosine
modified_base            12
                         mod_base = OTHER
                         note = 2'-O-methyl adenosine
modified_base            13
                         mod_base = OTHER
                         note = 2'-O-methyl adenosine
modified_base            14
                         mod_base = OTHER
                         note = 2'-fluoro guanosine
modified_base            15
                         mod_base = OTHER
                         note = 2'-O-methyl cytidine
modified_base            16
                         mod_base = OTHER
                         note = 2'-O-methyl adenosine
modified_base            17
                         mod_base = OTHER
                         note = 2'-O-methyl guanosine
modified_base            18
                         mod_base = OTHER
                         note = 2'-O-methyl guanosine
```

```
misc_feature            18..20
                        note = linked via phosphorothioate
modified_base           19
                        mod_base = OTHER
                        note = 2'-O-methyl uridine
modified_base           20
                        mod_base = OTHER
                        note = 2'-O-methyl guanosine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 645
tgaaccagaa gaagcaggtg gg                                          22

SEQ ID NO: 646          moltype = RNA  length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro guanosine
modified_base           4
                        mod_base = OTHER
                        note = 2'-fluoro uridine
modified_base           5
                        mod_base = OTHER
                        note = 2'-fluoro cytidine
modified_base           6
                        mod_base = OTHER
                        note = 2'-O-methyl uridine
modified_base           7
                        mod_base = OTHER
                        note = 2'-fluoro uridine
modified_base           8
                        mod_base = OTHER
                        note = 2'-O-methyl uridine
modified_base           9
                        mod_base = OTHER
                        note = 2'-O-methyl cytidine
modified_base           10
                        mod_base = OTHER
                        note = 2'-fluoro adenosine
modified_base           11
                        mod_base = OTHER
                        note = 2'-O-methyl cytidine
modified_base           12
                        mod_base = OTHER
                        note = 2'-O-methyl adenosine
modified_base           13
                        mod_base = OTHER
                        note = 2'-O-methyl cytidine
modified_base           14
                        mod_base = OTHER
                        note = 2'-fluoro uridine
modified_base           15
                        mod_base = OTHER
                        note = 2'-O-methyl guanosine
modified_base           16
                        mod_base = OTHER
                        note = 2'-O-methyl guanosine
modified_base           17
                        mod_base = OTHER
                        note = 2'-O-methyl cytidine
modified_base           18
                        mod_base = OTHER
```

```
                        note = 2'-O-methyl uridine
misc_feature            18..20
                        note = linked via phosphorothioate
modified_base           19
                        mod_base = OTHER
                        note = 2'-O-methyl uridine
modified_base           20
                        mod_base = OTHER
                        note = 2'-O-methyl cytidine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 646
ttgtctttca cactggcttc gg                                                 22

SEQ ID NO: 647          moltype = RNA  length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro adenosine
modified_base           4
                        mod_base = OTHER
                        note = 2'-fluoro guanosine
modified_base           5
                        mod_base = OTHER
                        note = 2'-fluoro uridine
modified_base           6
                        mod_base = OTHER
                        note = 2'-O-methyl adenosine
modified_base           7
                        mod_base = OTHER
                        note = 2'-fluoro guanosine
modified_base           8
                        mod_base = OTHER
                        note = 2'-O-methyl cytidine
modified_base           9
                        mod_base = OTHER
                        note = 2'-O-methyl uridine
modified_base           10
                        mod_base = OTHER
                        note = 2'-fluoro guanosine
modified_base           11
                        mod_base = OTHER
                        note = 2'-O-methyl guanosine
modified_base           12
                        mod_base = OTHER
                        note = 2'-O-methyl guanosine
modified_base           13
                        mod_base = OTHER
                        note = 2'-O-methyl guanosine
modified_base           14
                        mod_base = OTHER
                        note = 2'-fluoro adenosine
modified_base           15
                        mod_base = OTHER
                        note = 2'-O-methyl adenosine
modified_base           16
                        mod_base = OTHER
                        note = 2'-O-methyl guanosine
modified_base           17
                        mod_base = OTHER
                        note = 2'-O-methyl uridine
modified_base           18
```

|  |  |
|---|---|
| | mod_base = OTHER |
| | note = 2'-O-methyl adenosine |
| misc_feature | 18..20 |
| | note = linked via phosphorothioate |
| modified_base | 19 |
| | mod_base = OTHER |
| | note = 2'-O-methyl cytidine |
| modified_base | 20 |
| | mod_base = OTHER |
| | note = 2'-O-methyl guanosine |
| modified_base | 21 |
| | mod_base = OTHER |
| | note = 2'-O-methyl guanosine |
| modified_base | 22 |
| | mod_base = OTHER |
| | note = 2'-O-methyl guanosine |
| source | 1..22 |
| | mol_type = other RNA |
| | organism = synthetic construct |
| SEQUENCE: 647 | |
| ttagtagctg gggaagtacg gg | 22 |
| | |
| SEQ ID NO: 648 | moltype = RNA   length = 22 |
| FEATURE | Location/Qualifiers |
| misc_feature | 1..22 |
| | note = synthetic construct |
| misc_feature | 1..4 |
| | note = linked via phosphorothioate |
| modified_base | 1 |
| | mod_base = OTHER |
| | note = 5'-methoxyphosphonate-4-oxy uridine |
| modified_base | 2 |
| | mod_base = OTHER |
| | note = 2'-fluoro adenosine |
| modified_base | 3 |
| | mod_base = OTHER |
| | note = 2'-fluoro adenosine |
| modified_base | 4 |
| | mod_base = OTHER |
| | note = 2'-fluoro adenosine |
| modified_base | 5 |
| | mod_base = OTHER |
| | note = 2'-fluoro uridine |
| modified_base | 6 |
| | mod_base = OTHER |
| | note = 2'-O-methyl cytidine |
| modified_base | 7 |
| | mod_base = OTHER |
| | note = 2'-fluoro adenosine |
| modified_base | 8 |
| | mod_base = OTHER |
| | note = 2'-O-methyl uridine |
| modified_base | 9 |
| | mod_base = OTHER |
| | note = 2'-O-methyl adenosine |
| modified_base | 10 |
| | mod_base = OTHER |
| | note = 2'-fluoro cytidine |
| modified_base | 11 |
| | mod_base = OTHER |
| | note = 2'-O-methyl uridine |
| modified_base | 12 |
| | mod_base = OTHER |
| | note = 2'-O-methyl uridine |
| modified_base | 13 |
| | mod_base = OTHER |
| | note = 2'-O-methyl cytidine |
| modified_base | 14 |
| | mod_base = OTHER |
| | note = 2'-fluoro uridine |
| modified_base | 15 |
| | mod_base = OTHER |
| | note = 2'-O-methyl guanosine |
| modified_base | 16 |
| | mod_base = OTHER |
| | note = 2'-O-methyl cytidine |
| modified_base | 17 |
| | mod_base = OTHER |
| | note = 2'-O-methyl cytidine |

```
modified_base       18
                    mod_base = OTHER
                    note = 2'-O-methyl uridine
misc_feature        18..20
                    note = linked via phosphorothioate
modified_base       19
                    mod_base = OTHER
                    note = 2'-O-methyl cytidine
modified_base       20
                    mod_base = OTHER
                    note = 2'-O-methyl cytidine
modified_base       21
                    mod_base = OTHER
                    note = 2'-O-methyl guanosine
modified_base       22
                    mod_base = OTHER
                    note = 2'-O-methyl guanosine
source              1..22
                    mol_type = other RNA
                    organism = synthetic construct
SEQUENCE: 648
taaatcatac ttctgcctcc gg                                             22

SEQ ID NO: 649      moltype = RNA  length = 22
FEATURE             Location/Qualifiers
misc_feature        1..22
                    note = synthetic construct
misc_feature        1..4
                    note = linked via phosphorothioate
modified_base       1
                    mod_base = OTHER
                    note = 5'-methoxyphosphonate-4-oxy uridine
modified_base       2
                    mod_base = OTHER
                    note = 2'-fluoro uridine
modified_base       3
                    mod_base = OTHER
                    note = 2'-fluoro adenosine
modified_base       4
                    mod_base = OTHER
                    note = 2'-fluoro cytidine
modified_base       5
                    mod_base = OTHER
                    note = 2'-fluoro adenosine
modified_base       6
                    mod_base = OTHER
                    note = 2'-O-methyl adenosine
modified_base       7
                    mod_base = OTHER
                    note = 2'-fluoro guanosine
modified_base       8
                    mod_base = OTHER
                    note = 2'-O-methyl cytidine
modified_base       9
                    mod_base = OTHER
                    note = 2'-O-methyl cytidine
modified_base       10
                    mod_base = OTHER
                    note = 2'-fluoro adenosine
modified_base       11
                    mod_base = OTHER
                    note = 2'-O-methyl uridine
modified_base       12
                    mod_base = OTHER
                    note = 2'-O-methyl adenosine
modified_base       13
                    mod_base = OTHER
                    note = 2'-O-methyl guanosine
modified_base       14
                    mod_base = OTHER
                    note = 2'-fluoro uridine
modified_base       15
                    mod_base = OTHER
                    note = 2'-O-methyl guanosine
modified_base       16
                    mod_base = OTHER
                    note = 2'-O-methyl cytidine
modified_base       17
                    mod_base = OTHER
```

```
                              note = 2'-O-methyl adenosine
modified_base                 18
                              mod_base = OTHER
                              note = 2'-O-methyl cytidine
misc_feature                  18..20
                              note = linked via phosphorothioate
modified_base                 19
                              mod_base = OTHER
                              note = 2'-O-methyl cytidine
modified_base                 20
                              mod_base = OTHER
                              note = 2'-O-methyl cytidine
modified_base                 21
                              mod_base = OTHER
                              note = 2'-O-methyl guanosine
modified_base                 22
                              mod_base = OTHER
                              note = 2'-O-methyl guanosine
source                        1..22
                              mol_type = other RNA
                              organism = synthetic construct
SEQUENCE: 649
ttacaagcca tagtgcaccc gg                                              22

SEQ ID NO: 650                moltype = RNA  length = 22
FEATURE                       Location/Qualifiers
misc_feature                  1..22
                              note = synthetic construct
misc_feature                  1..4
                              note = linked via phosphorothioate
modified_base                 1
                              mod_base = OTHER
                              note = 5'-methoxyphosphonate-4-oxy uridine
modified_base                 2
                              mod_base = OTHER
                              note = 2'-fluoro guanosine
modified_base                 3
                              mod_base = OTHER
                              note = 2'-fluoro uridine
modified_base                 4
                              mod_base = OTHER
                              note = 2'-fluoro uridine
modified_base                 5
                              mod_base = OTHER
                              note = 2'-fluoro guanosine
modified_base                 6
                              mod_base = OTHER
                              note = 2'-O-methyl uridine
modified_base                 7
                              mod_base = OTHER
                              note = 2'-fluoro adenosine
modified_base                 8
                              mod_base = OTHER
                              note = 2'-O-methyl cytidine
modified_base                 9
                              mod_base = OTHER
                              note = 2'-O-methyl adenosine
modified_base                 10
                              mod_base = OTHER
                              note = 2'-fluoro adenosine
modified_base                 11
                              mod_base = OTHER
                              note = 2'-O-methyl guanosine
modified_base                 12
                              mod_base = OTHER
                              note = 2'-O-methyl cytidine
modified_base                 13
                              mod_base = OTHER
                              note = 2'-O-methyl cytidine
modified_base                 14
                              mod_base = OTHER
                              note = 2'-fluoro adenosine
modified_base                 15
                              mod_base = OTHER
                              note = 2'-O-methyl uridine
modified_base                 16
                              mod_base = OTHER
                              note = 2'-O-methyl adenosine
modified_base                 17
```

```
                        mod_base = OTHER
                        note = 2'-O-methyl guanosine
modified_base           18
                        mod_base = OTHER
                        note = 2'-O-methyl uridine
misc_feature            18..20
                        note = linked via phosphorothioate
modified_base           19
                        mod_base = OTHER
                        note = 2'-O-methyl guanosine
modified_base           20
                        mod_base = OTHER
                        note = 2'-O-methyl cytidine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 650
tgttgtacaa gccatagtgc gg                                                  22

SEQ ID NO: 651          moltype = RNA   length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro adenosine
modified_base           3
                        mod_base = OTHER
                        note = 2'-fluoro adenosine
modified_base           4
                        mod_base = OTHER
                        note = 2'-fluoro adenosine
modified_base           5
                        mod_base = OTHER
                        note = 2'-fluoro cytidine
modified_base           6
                        mod_base = OTHER
                        note = 2'-O-methyl guanosine
modified_base           7
                        mod_base = OTHER
                        note = 2'-fluoro cytidine
modified_base           8
                        mod_base = OTHER
                        note = 2'-O-methyl adenosine
modified_base           9
                        mod_base = OTHER
                        note = 2'-O-methyl guanosine
modified_base           10
                        mod_base = OTHER
                        note = 2'-fluoro uridine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl cytidine
modified_base           14
                        mod_base = OTHER
                        note = 2'-fluoro uridine
modified_base           15
                        mod_base = OTHER
                        note = 2'-O-methyl cytidine
modified_base           16
                        mod_base = OTHER
                        note = 2'-O-methyl uridine
```

```
modified_base        17
                     mod_base = OTHER
                     note = 2'-O-methyl cytidine
modified_base        18
                     mod_base = OTHER
                     note = 2'-O-methyl adenosine
misc_feature         18..20
                     note = linked via phosphorothioate
modified_base        19
                     mod_base = OTHER
                     note = 2'-O-methyl uridine
modified_base        20
                     mod_base = OTHER
                     note = 2'-O-methyl cytidine
modified_base        21
                     mod_base = OTHER
                     note = 2'-O-methyl guanosine
modified_base        22
                     mod_base = OTHER
                     note = 2'-O-methyl guanosine
source               1..22
                     mol_type = other RNA
                     organism = synthetic construct
SEQUENCE: 651
taaacgcagt ttctctcatc gg                                              22

SEQ ID NO: 652       moltype = RNA  length = 22
FEATURE              Location/Qualifiers
misc_feature         1..22
                     note = synthetic construct
misc_feature         1..4
                     note = linked via phosphorothioate
modified_base        1
                     mod_base = OTHER
                     note = 5'-methoxyphosphonate-4-oxy uridine
modified_base        2
                     mod_base = OTHER
                     note = 2'-fluoro uridine
modified_base        3
                     mod_base = OTHER
                     note = 2'-fluoro cytidine
modified_base        4
                     mod_base = OTHER
                     note = 2'-fluoro adenosine
modified_base        5
                     mod_base = OTHER
                     note = 2'-fluoro cytidine
modified_base        6
                     mod_base = OTHER
                     note = 2'-O-methyl cytidine
modified_base        7
                     mod_base = OTHER
                     note = 2'-fluoro uridine
modified_base        8
                     mod_base = OTHER
                     note = 2'-O-methyl uridine
modified_base        9
                     mod_base = OTHER
                     note = 2'-O-methyl guanosine
modified_base        10
                     mod_base = OTHER
                     note = 2'-fluoro adenosine
modified_base        11
                     mod_base = OTHER
                     note = 2'-O-methyl adenosine
modified_base        12
                     mod_base = OTHER
                     note = 2'-O-methyl guanosine
modified_base        13
                     mod_base = OTHER
                     note = 2'-O-methyl guanosine
modified_base        14
                     mod_base = OTHER
                     note = 2'-fluoro adenosine
modified_base        15
                     mod_base = OTHER
                     note = 2'-O-methyl cytidine
modified_base        16
                     mod_base = OTHER
```

```
                            note = 2'-O-methyl adenosine
modified_base               17
                            mod_base = OTHER
                            note = 2'-O-methyl cytidine
modified_base               18
                            mod_base = OTHER
                            note = 2'-O-methyl cytidine
misc_feature                18..20
                            note = linked via phosphorothioate
modified_base               19
                            mod_base = OTHER
                            note = 2'-O-methyl uridine
modified_base               20
                            mod_base = OTHER
                            note = 2'-O-methyl cytidine
modified_base               21
                            mod_base = OTHER
                            note = 2'-O-methyl guanosine
modified_base               22
                            mod_base = OTHER
                            note = 2'-O-methyl guanosine
source                      1..22
                            mol_type = other RNA
                            organism = synthetic construct
SEQUENCE: 652
ttcaccttga aggacacctc gg                                               22

SEQ ID NO: 653              moltype = RNA  length = 22
FEATURE                     Location/Qualifiers
misc_feature                1..22
                            note = synthetic construct
misc_feature                1..4
                            note = linked via phosphorothioate
modified_base               1
                            mod_base = OTHER
                            note = 5'-methoxyphosphonate-4-oxy uridine
modified_base               2
                            mod_base = OTHER
                            note = 2'-fluoro adenosine
modified_base               3
                            mod_base = OTHER
                            note = 2'-fluoro cytidine
modified_base               4
                            mod_base = OTHER
                            note = 2'-fluoro cytidine
modified_base               5
                            mod_base = OTHER
                            note = 2'-fluoro adenosine
modified_base               6
                            mod_base = OTHER
                            note = 2'-O-methyl guanosine
modified_base               7
                            mod_base = OTHER
                            note = 2'-fluoro adenosine
modified_base               8
                            mod_base = OTHER
                            note = 2'-O-methyl adenosine
modified_base               9
                            mod_base = OTHER
                            note = 2'-O-methyl guanosine
modified_base               10
                            mod_base = OTHER
                            note = 2'-fluoro adenosine
modified_base               11
                            mod_base = OTHER
                            note = 2'-O-methyl adenosine
modified_base               12
                            mod_base = OTHER
                            note = 2'-O-methyl guanosine
modified_base               13
                            mod_base = OTHER
                            note = 2'-O-methyl cytidine
modified_base               14
                            mod_base = OTHER
                            note = 2'-fluoro adenosine
modified_base               15
                            mod_base = OTHER
                            note = 2'-O-methyl guanosine
modified_base               16
```

|  |  |
|---|---|
| | mod_base = OTHER |
| | note = 2'-O-methyl guanosine |
| modified_base | 17 |
| | mod_base = OTHER |
| | note = 2'-O-methyl uridine |
| modified_base | 18 |
| | mod_base = OTHER |
| | note = 2'-O-methyl guanosine |
| misc_feature | 18..20 |
| | note = linked via phosphorothioate |
| modified_base | 19 |
| | mod_base = OTHER |
| | note = 2'-O-methyl adenosine |
| modified_base | 20 |
| | mod_base = OTHER |
| | note = 2'-O-methyl guanosine |
| modified_base | 21 |
| | mod_base = OTHER |
| | note = 2'-O-methyl guanosine |
| modified_base | 22 |
| | mod_base = OTHER |
| | note = 2'-O-methyl guanosine |
| source | 1..22 |
| | mol_type = other RNA |
| | organism = synthetic construct |

SEQUENCE: 653
taccagaaga agcaggtgag gg                                              22

| | |
|---|---|
| SEQ ID NO: 654 | moltype = RNA  length = 22 |
| FEATURE | Location/Qualifiers |
| misc_feature | 1..22 |
| | note = synthetic construct |
| misc_feature | 1..4 |
| | note = linked via phosphorothioate |
| modified_base | 1 |
| | mod_base = OTHER |
| | note = 5'-methoxyphosphonate-4-oxy uridine |
| modified_base | 2 |
| | mod_base = OTHER |
| | note = 2'-fluoro adenosine |
| modified_base | 3 |
| | mod_base = OTHER |
| | note = 2'-fluoro adenosine |
| modified_base | 4 |
| | mod_base = OTHER |
| | note = 2'-fluoro cytidine |
| modified_base | 5 |
| | mod_base = OTHER |
| | note = 2'-fluoro cytidine |
| modified_base | 6 |
| | mod_base = OTHER |
| | note = 2'-O-methyl adenosine |
| modified_base | 7 |
| | mod_base = OTHER |
| | note = 2'-fluoro guanosine |
| modified_base | 8 |
| | mod_base = OTHER |
| | note = 2'-O-methyl adenosine |
| modified_base | 9 |
| | mod_base = OTHER |
| | note = 2'-O-methyl adenosine |
| modified_base | 10 |
| | mod_base = OTHER |
| | note = 2'-fluoro guanosine |
| modified_base | 11 |
| | mod_base = OTHER |
| | note = 2'-O-methyl adenosine |
| modified_base | 12 |
| | mod_base = OTHER |
| | note = 2'-O-methyl adenosine |
| modified_base | 13 |
| | mod_base = OTHER |
| | note = 2'-O-methyl guanosine |
| modified_base | 14 |
| | mod_base = OTHER |
| | note = 2'-fluoro cytidine |
| modified_base | 15 |
| | mod_base = OTHER |
| | note = 2'-O-methyl adenosine |

```
modified_base        16
                     mod_base = OTHER
                     note = 2'-O-methyl guanosine
modified_base        17
                     mod_base = OTHER
                     note = 2'-O-methyl guanosine
modified_base        18
                     mod_base = OTHER
                     note = 2'-O-methyl uridine
misc_feature         18..20
                     note = linked via phosphorothioate
modified_base        19
                     mod_base = OTHER
                     note = 2'-O-methyl guanosine
modified_base        20
                     mod_base = OTHER
                     note = 2'-O-methyl adenosine
modified_base        21
                     mod_base = OTHER
                     note = 2'-O-methyl guanosine
modified_base        22
                     mod_base = OTHER
                     note = 2'-O-methyl guanosine
source               1..22
                     mol_type = other RNA
                     organism = synthetic construct
SEQUENCE: 654
taaccagaag aagcaggtga gg                                              22

SEQ ID NO: 655       moltype = RNA   length = 22
FEATURE              Location/Qualifiers
misc_feature         1..22
                     note = synthetic construct
misc_feature         1..4
                     note = linked via phosphorothioate
modified_base        1
                     mod_base = OTHER
                     note = 5'-methoxyphosphonate-4-oxy uridine
modified_base        2
                     mod_base = OTHER
                     note = 2'-fluoro adenosine
modified_base        3
                     mod_base = OTHER
                     note = 2'-fluoro uridine
modified_base        4
                     mod_base = OTHER
                     note = 2'-fluoro uridine
modified_base        5
                     mod_base = OTHER
                     note = 2'-fluoro uridine
modified_base        6
                     mod_base = OTHER
                     note = 2'-O-methyl guanosine
modified_base        7
                     mod_base = OTHER
                     note = 2'-fluoro guanosine
modified_base        8
                     mod_base = OTHER
                     note = 2'-O-methyl adenosine
modified_base        9
                     mod_base = OTHER
                     note = 2'-O-methyl guanosine
modified_base        10
                     mod_base = OTHER
                     note = 2'-fluoro adenosine
modified_base        11
                     mod_base = OTHER
                     note = 2'-O-methyl adenosine
modified_base        12
                     mod_base = OTHER
                     note = 2'-O-methyl uridine
modified_base        13
                     mod_base = OTHER
                     note = 2'-O-methyl guanosine
modified_base        14
                     mod_base = OTHER
                     note = 2'-fluoro adenosine
modified_base        15
                     mod_base = OTHER
```

| | |
|---|---|
| | note = 2'-O-methyl adenosine |
| modified_base | 16 |
| | mod_base = OTHER |
| | note = 2'-O-methyl cytidine |
| modified_base | 17 |
| | mod_base = OTHER |
| | note = 2'-O-methyl cytidine |
| modified_base | 18 |
| | mod_base = OTHER |
| | note = 2'-O-methyl adenosine |
| misc_feature | 18..20 |
| | note = linked via phosphorothioate |
| modified_base | 19 |
| | mod_base = OTHER |
| | note = 2'-O-methyl guanosine |
| modified_base | 20 |
| | mod_base = OTHER |
| | note = 2'-O-methyl adenosine |
| modified_base | 21 |
| | mod_base = OTHER |
| | note = 2'-O-methyl guanosine |
| modified_base | 22 |
| | mod_base = OTHER |
| | note = 2'-O-methyl guanosine |
| source | 1..22 |
| | mol_type = other RNA |
| | organism = synthetic construct |
| SEQUENCE: 655 | |
| tatttggaga atgaaccaga gg | 22 |
| | |
| SEQ ID NO: 656 | moltype = RNA length = 22 |
| FEATURE | Location/Qualifiers |
| misc_feature | 1..22 |
| | note = synthetic construct |
| misc_feature | 1..4 |
| | note = linked via phosphorothioate |
| modified_base | 1 |
| | mod_base = OTHER |
| | note = 5'-methoxyphosphonate-4-oxy uridine |
| modified_base | 2 |
| | mod_base = OTHER |
| | note = 2'-fluoro guanosine |
| modified_base | 3 |
| | mod_base = OTHER |
| | note = 2'-fluoro guanosine |
| modified_base | 4 |
| | mod_base = OTHER |
| | note = 2'-fluoro guanosine |
| modified_base | 5 |
| | mod_base = OTHER |
| | note = 2'-fluoro guanosine |
| modified_base | 6 |
| | mod_base = OTHER |
| | note = 2'-O-methyl adenosine |
| modified_base | 7 |
| | mod_base = OTHER |
| | note = 2'-fluoro uridine |
| modified_base | 8 |
| | mod_base = OTHER |
| | note = 2'-O-methyl uridine |
| modified_base | 9 |
| | mod_base = OTHER |
| | note = 2'-O-methyl uridine |
| modified_base | 10 |
| | mod_base = OTHER |
| | note = 2'-fluoro guanosine |
| modified_base | 11 |
| | mod_base = OTHER |
| | note = 2'-O-methyl guanosine |
| modified_base | 12 |
| | mod_base = OTHER |
| | note = 2'-O-methyl adenosine |
| modified_base | 13 |
| | mod_base = OTHER |
| | note = 2'-O-methyl guanosine |
| modified_base | 14 |
| | mod_base = OTHER |
| | note = 2'-fluoro adenosine |
| modified_base | 15 |

```
                        mod_base = OTHER
                        note = 2'-O-methyl adenosine
modified_base           16
                        mod_base = OTHER
                        note = 2'-O-methyl uridine
modified_base           17
                        mod_base = OTHER
                        note = 2'-O-methyl guanosine
modified_base           18
                        mod_base = OTHER
                        note = 2'-O-methyl adenosine
misc_feature            18..20
                        note = linked via phosphorothioate
modified_base           19
                        mod_base = OTHER
                        note = 2'-O-methyl adenosine
modified_base           20
                        mod_base = OTHER
                        note = 2'-O-methyl cytidine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 656
tggggatttg gagaatgaac gg                                                  22

SEQ ID NO: 657          moltype = RNA  length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro cytidine
modified_base           4
                        mod_base = OTHER
                        note = 2'-fluoro adenosine
modified_base           5
                        mod_base = OTHER
                        note = 2'-fluoro adenosine
modified_base           6
                        mod_base = OTHER
                        note = 2'-O-methyl cytidine
modified_base           7
                        mod_base = OTHER
                        note = 2'-fluoro uridine
modified_base           8
                        mod_base = OTHER
                        note = 2'-O-methyl guanosine
modified_base           9
                        mod_base = OTHER
                        note = 2'-O-methyl cytidine
modified_base           10
                        mod_base = OTHER
                        note = 2'-fluoro adenosine
modified_base           11
                        mod_base = OTHER
                        note = 2'-O-methyl cytidine
modified_base           12
                        mod_base = OTHER
                        note = 2'-O-methyl adenosine
modified_base           13
                        mod_base = OTHER
                        note = 2'-O-methyl uridine
modified_base           14
                        mod_base = OTHER
                        note = 2'-fluoro cytidine
```

```
modified_base      15
                   mod_base = OTHER
                   note = 2'-O-methyl cytidine
modified_base      16
                   mod_base = OTHER
                   note = 2'-O-methyl adenosine
modified_base      17
                   mod_base = OTHER
                   note = 2'-O-methyl cytidine
modified_base      18
                   mod_base = OTHER
                   note = 2'-O-methyl uridine
misc_feature       18..20
                   note = linked via phosphorothioate
modified_base      19
                   mod_base = OTHER
                   note = 2'-O-methyl uridine
modified_base      20
                   mod_base = OTHER
                   note = 2'-O-methyl uridine
modified_base      21
                   mod_base = OTHER
                   note = 2'-O-methyl guanosine
modified_base      22
                   mod_base = OTHER
                   note = 2'-O-methyl guanosine
source             1..22
                   mol_type = other RNA
                   organism = synthetic construct
SEQUENCE: 657
ttcaactgca catccacttt gg                                              22

SEQ ID NO: 658     moltype = RNA  length = 22
FEATURE            Location/Qualifiers
misc_feature       1..22
                   note = synthetic construct
misc_feature       1..4
                   note = linked via phosphorothioate
modified_base      1
                   mod_base = OTHER
                   note = 5'-methoxyphosphonate-4-oxy uridine
modified_base      2
                   mod_base = OTHER
                   note = 2'-fluoro adenosine
modified_base      3
                   mod_base = OTHER
                   note = 2'-fluoro adenosine
modified_base      4
                   mod_base = OTHER
                   note = 2'-fluoro uridine
modified_base      5
                   mod_base = OTHER
                   note = 2'-fluoro adenosine
modified_base      6
                   mod_base = OTHER
                   note = 2'-O-methyl guanosine
modified_base      7
                   mod_base = OTHER
                   note = 2'-fluoro adenosine
modified_base      8
                   mod_base = OTHER
                   note = 2'-O-methyl cytidine
modified_base      9
                   mod_base = OTHER
                   note = 2'-O-methyl guanosine
modified_base      10
                   mod_base = OTHER
                   note = 2'-fluoro guanosine
modified_base      11
                   mod_base = OTHER
                   note = 2'-O-methyl adenosine
modified_base      12
                   mod_base = OTHER
                   note = 2'-O-methyl guanosine
modified_base      13
                   mod_base = OTHER
                   note = 2'-O-methyl cytidine
modified_base      14
                   mod_base = OTHER
```

```
                        note = 2'-fluoro uridine
modified_base           15
                        mod_base = OTHER
                        note = 2'-O-methyl guanosine
modified_base           16
                        mod_base = OTHER
                        note = 2'-O-methyl guanosine
modified_base           17
                        mod_base = OTHER
                        note = 2'-O-methyl adenosine
modified_base           18
                        mod_base = OTHER
                        note = 2'-O-methyl guanosine
misc_feature            18..20
                        note = linked via phosphorothioate
modified_base           19
                        mod_base = OTHER
                        note = 2'-O-methyl uridine
modified_base           20
                        mod_base = OTHER
                        note = 2'-O-methyl uridine
modified_base           21
                        mod_base = OTHER
                        note = 2'-O-methyl guanosine
modified_base           22
                        mod_base = OTHER
                        note = 2'-O-methyl guanosine
source                  1..22
                        mol_type = other RNA
                        organism = synthetic construct
SEQUENCE: 658
taatagacgg agctggagtt gg                                              22

SEQ ID NO: 659          moltype = RNA   length = 22
FEATURE                 Location/Qualifiers
misc_feature            1..22
                        note = synthetic construct
misc_feature            1..4
                        note = linked via phosphorothioate
modified_base           1
                        mod_base = OTHER
                        note = 5'-methoxyphosphonate-4-oxy uridine
modified_base           2
                        mod_base = OTHER
                        note = 2'-fluoro uridine
modified_base           3
                        mod_base = OTHER
                        note = 2'-fluoro guanosine
modified_base           4
                        mod_base = OTHER
                        note = 2'-fluoro adenosine
modified_base           5
                        mod_base = OTHER
                        note = 2'-fluoro adenosine
modified_base           6
                        mod_base = OTHER
                        note = 2'-O-methyl cytidine
modified_base           7
                        mod_base = OTHER
                        note = 2'-fluoro cytidine
modified_base           8
                        mod_base = OTHER
                        note = 2'-O-methyl adenosine
modified_base           9
                        mod_base = OTHER
                        note = 2'-O-methyl guanosine
modified_base           10
                        mod_base = OTHER
                        note = 2'-fluoro adenosine
modified_base           11
                        mod_base = OTHER
                        note = 2'-O-methyl adenosine
modified_base           12
                        mod_base = OTHER
                        note = 2'-O-methyl guanosine
modified_base           13
                        mod_base = OTHER
                        note = 2'-O-methyl adenosine
modified_base           14
```

```
                         mod_base = OTHER
                         note = 2'-fluoro adenosine
modified_base            15
                         mod_base = OTHER
                         note = 2'-O-methyl guanosine
modified_base            16
                         mod_base = OTHER
                         note = 2'-O-methyl cytidine
modified_base            17
                         mod_base = OTHER
                         note = 2'-O-methyl adenosine
modified_base            18
                         mod_base = OTHER
                         note = 2'-O-methyl guanosine
misc_feature             18..20
                         note = linked via phosphorothioate
modified_base            19
                         mod_base = OTHER
                         note = 2'-O-methyl guanosine
modified_base            20
                         mod_base = OTHER
                         note = 2'-O-methyl uridine
modified_base            21
                         mod_base = OTHER
                         note = 2'-O-methyl guanosine
modified_base            22
                         mod_base = OTHER
                         note = 2'-O-methyl guanosine
source                   1..22
                         mol_type = other RNA
                         organism = synthetic construct
SEQUENCE: 659
ttgaaccaga agaagcaggt gg                                                  22

SEQ ID NO: 660          moltype = RNA  length = 22
FEATURE                 Location/Qualifiers
misc_feature            1..22
                         note = synthetic construct
misc_feature             1..4
                         note = linked via phosphorothioate
modified_base            1
                         mod_base = OTHER
                         note = 5'-methoxyphosphonate-4-oxy uridine
modified_base            2
                         mod_base = OTHER
                         note = 2'-fluoro cytidine
modified_base            3
                         mod_base = OTHER
                         note = 2'-fluoro adenosine
modified_base            4
                         mod_base = OTHER
                         note = 2'-fluoro guanosine
modified_base            5
                         mod_base = OTHER
                         note = 2'-fluoro cytidine
modified_base            6
                         mod_base = OTHER
                         note = 2'-O-methyl uridine
modified_base            7
                         mod_base = OTHER
                         note = 2'-fluoro adenosine
modified_base            8
                         mod_base = OTHER
                         note = 2'-O-methyl uridine
modified_base            9
                         mod_base = OTHER
                         note = 2'-O-methyl guanosine
modified_base            10
                         mod_base = OTHER
                         note = 2'-fluoro uridine
modified_base            11
                         mod_base = OTHER
                         note = 2'-O-methyl cytidine
modified_base            12
                         mod_base = OTHER
                         note = 2'-O-methyl uridine
modified_base            13
                         mod_base = OTHER
                         note = 2'-O-methyl uridine
```

```
modified_base       14
                    mod_base = OTHER
                    note = 2'-fluoro uridine
modified_base       15
                    mod_base = OTHER
                    note = 2'-O-methyl cytidine
modified_base       16
                    mod_base = OTHER
                    note = 2'-O-methyl adenosine
modified_base       17
                    mod_base = OTHER
                    note = 2'-O-methyl cytidine
modified_base       18
                    mod_base = OTHER
                    note = 2'-O-methyl adenosine
misc_feature        18..20
                    note = linked via phosphorothioate
modified_base       19
                    mod_base = OTHER
                    note = 2'-O-methyl cytidine
modified_base       20
                    mod_base = OTHER
                    note = 2'-O-methyl uridine
modified_base       21
                    mod_base = OTHER
                    note = 2'-O-methyl guanosine
modified_base       22
                    mod_base = OTHER
                    note = 2'-O-methyl guanosine
source              1..22
                    mol_type = other RNA
                    organism = synthetic construct
SEQUENCE: 660
tcagctatgt ctttcacact gg                                            22

SEQ ID NO: 661          moltype = RNA   length = 19
FEATURE                 Location/Qualifiers
source                  1..19
                        mol_type = other RNA
                        organism = synthetic construct
SEQUENCE: 661
tgtccttcaa ggtgagccg                                                19

SEQ ID NO: 662          moltype = RNA   length = 19
FEATURE                 Location/Qualifiers
source                  1..19
                        mol_type = other RNA
                        organism = synthetic construct
SEQUENCE: 662
gtgtccttca aggtgagcc                                                19

SEQ ID NO: 663          moltype = RNA   length = 19
FEATURE                 Location/Qualifiers
source                  1..19
                        mol_type = other RNA
                        organism = synthetic construct
SEQUENCE: 663
ggtgtccttc aaggtgagc                                                19

SEQ ID NO: 664          moltype = RNA   length = 19
FEATURE                 Location/Qualifiers
source                  1..19
                        mol_type = other RNA
                        organism = synthetic construct
SEQUENCE: 664
aggtgtcctt caaggtgag                                                19

SEQ ID NO: 665          moltype = RNA   length = 19
FEATURE                 Location/Qualifiers
source                  1..19
                        mol_type = other RNA
                        organism = synthetic construct
SEQUENCE: 665
gaggtgtcct tcaaggtga                                                19

SEQ ID NO: 666          moltype = RNA   length = 19
FEATURE                 Location/Qualifiers
source                  1..19
                        mol_type = other RNA
```

-continued

```
                        organism = synthetic construct
SEQUENCE: 666
aggaggacag catggcctc                                                        19

SEQ ID NO: 667          moltype = RNA   length = 19
FEATURE                 Location/Qualifiers
source                  1..19
                        mol_type = other RNA
                        organism = synthetic construct
SEQUENCE: 667
caggaggaca gcatggcct                                                        19

SEQ ID NO: 668          moltype = RNA   length = 19
FEATURE                 Location/Qualifiers
source                  1..19
                        mol_type = other RNA
                        organism = synthetic construct
SEQUENCE: 668
ccaggaggac agcatggcc                                                        19

SEQ ID NO: 669          moltype = RNA   length = 19
FEATURE                 Location/Qualifiers
source                  1..19
                        mol_type = other RNA
                        organism = synthetic construct
SEQUENCE: 669
tccaggagga cagcatggc                                                        19

SEQ ID NO: 670          moltype = RNA   length = 19
FEATURE                 Location/Qualifiers
source                  1..19
                        mol_type = other RNA
                        organism = synthetic construct
SEQUENCE: 670
ttccaggagg acagcatgg                                                        19

SEQ ID NO: 671          moltype = RNA   length = 19
FEATURE                 Location/Qualifiers
source                  1..19
                        mol_type = other RNA
                        organism = synthetic construct
SEQUENCE: 671
cttccaggag gacagcatg                                                        19

SEQ ID NO: 672          moltype = RNA   length = 19
FEATURE                 Location/Qualifiers
source                  1..19
                        mol_type = other RNA
                        organism = synthetic construct
SEQUENCE: 672
gcttccagga ggacagcat                                                        19

SEQ ID NO: 673          moltype = RNA   length = 19
FEATURE                 Location/Qualifiers
source                  1..19
                        mol_type = other RNA
                        organism = synthetic construct
SEQUENCE: 673
tgcttccagg aggacagca                                                        19

SEQ ID NO: 674          moltype = RNA   length = 19
FEATURE                 Location/Qualifiers
source                  1..19
                        mol_type = other RNA
                        organism = synthetic construct
SEQUENCE: 674
tcatcgctga ccgctgggt                                                        19

SEQ ID NO: 675          moltype = RNA   length = 19
FEATURE                 Location/Qualifiers
source                  1..19
                        mol_type = other RNA
                        organism = synthetic construct
SEQUENCE: 675
ctcatcgctg accgctggg                                                        19

SEQ ID NO: 676          moltype = RNA   length = 19
FEATURE                 Location/Qualifiers
source                  1..19
```

```
SEQUENCE: 676
tgtgactgtg gcctccagg                                                      19

SEQ ID NO: 677         moltype = RNA   length = 19
FEATURE                Location/Qualifiers
source                 1..19
                       mol_type = other RNA
                       organism = synthetic construct
SEQUENCE: 677
actgtgactg tggcctcca                                                      19

SEQ ID NO: 678         moltype = RNA   length = 19
FEATURE                Location/Qualifiers
source                 1..19
                       mol_type = other RNA
                       organism = synthetic construct
SEQUENCE: 678
cactgtgact gtggcctcc                                                      19

SEQ ID NO: 679         moltype = RNA   length = 19
FEATURE                Location/Qualifiers
source                 1..19
                       mol_type = other RNA
                       organism = synthetic construct
SEQUENCE: 679
cctcccagat ctccctcac                                                      19

SEQ ID NO: 680         moltype = RNA   length = 19
FEATURE                Location/Qualifiers
source                 1..19
                       mol_type = other RNA
                       organism = synthetic construct
SEQUENCE: 680
tcacctccca gatctccct                                                      19

SEQ ID NO: 681         moltype = RNA   length = 19
FEATURE                Location/Qualifiers
source                 1..19
                       mol_type = other RNA
                       organism = synthetic construct
SEQUENCE: 681
ttcacctccc agatctccc                                                      19

SEQ ID NO: 682         moltype = RNA   length = 19
FEATURE                Location/Qualifiers
source                 1..19
                       mol_type = other RNA
                       organism = synthetic construct
SEQUENCE: 682
ggtatttcct agggtacaa                                                      19

SEQ ID NO: 683         moltype = RNA   length = 19
FEATURE                Location/Qualifiers
source                 1..19
                       mol_type = other RNA
                       organism = synthetic construct
SEQUENCE: 683
tggtatttcc tagggtaca                                                      19

SEQ ID NO: 684         moltype = RNA   length = 19
FEATURE                Location/Qualifiers
source                 1..19
                       mol_type = other RNA
                       organism = synthetic construct
SEQUENCE: 684
gctaccgcaa gggcaagaa                                                      19

SEQ ID NO: 685         moltype = RNA   length = 19
FEATURE                Location/Qualifiers
source                 1..19
                       mol_type = other RNA
                       organism = synthetic construct
SEQUENCE: 685
ggctaccgca agggcaaga                                                      19

SEQ ID NO: 686         moltype = RNA   length = 19
FEATURE                Location/Qualifiers
```

```
source                     1..19
                           mol_type = other RNA
                           organism = synthetic construct
SEQUENCE: 686
catggcaggc cagcctcca                                             19

SEQ ID NO: 687             moltype = RNA   length = 19
FEATURE                    Location/Qualifiers
source                     1..19
                           mol_type = other RNA
                           organism = synthetic construct
SEQUENCE: 687
agggtgagtg gccatggca                                             19

SEQ ID NO: 688             moltype = RNA   length = 19
FEATURE                    Location/Qualifiers
source                     1..19
                           mol_type = other RNA
                           organism = synthetic construct
SEQUENCE: 688
cgagggtgag tggccatgg                                             19

SEQ ID NO: 689             moltype = RNA   length = 19
FEATURE                    Location/Qualifiers
source                     1..19
                           mol_type = other RNA
                           organism = synthetic construct
SEQUENCE: 689
gtcctccgag ggtgagtgg                                             19

SEQ ID NO: 690             moltype = RNA   length = 19
FEATURE                    Location/Qualifiers
source                     1..19
                           mol_type = other RNA
                           organism = synthetic construct
SEQUENCE: 690
tgtcctccga gggtgagtg                                             19

SEQ ID NO: 691             moltype = RNA   length = 19
FEATURE                    Location/Qualifiers
source                     1..19
                           mol_type = other RNA
                           organism = synthetic construct
SEQUENCE: 691
gtgtcctccg agggtgagt                                             19

SEQ ID NO: 692             moltype = RNA   length = 19
FEATURE                    Location/Qualifiers
source                     1..19
                           mol_type = other RNA
                           organism = synthetic construct
SEQUENCE: 692
gcctggatga gagaaactg                                             19

SEQ ID NO: 693             moltype = RNA   length = 19
FEATURE                    Location/Qualifiers
source                     1..19
                           mol_type = other RNA
                           organism = synthetic construct
SEQUENCE: 693
ggcctggatg agagaaact                                             19

SEQ ID NO: 694             moltype = RNA   length = 19
FEATURE                    Location/Qualifiers
source                     1..19
                           mol_type = other RNA
                           organism = synthetic construct
SEQUENCE: 694
ctctggacta cggcttggc                                             19

SEQ ID NO: 695             moltype = RNA   length = 19
FEATURE                    Location/Qualifiers
source                     1..19
                           mol_type = other RNA
                           organism = synthetic construct
SEQUENCE: 695
tctctggact acggcttgg                                             19

SEQ ID NO: 696             moltype = RNA   length = 19
```

-continued

```
FEATURE              Location/Qualifiers
source               1..19
                     mol_type = other RNA
                     organism = synthetic construct
SEQUENCE: 696
tcacctgctt cttctggtt                                                  19

SEQ ID NO: 697       moltype = RNA   length = 19
FEATURE              Location/Qualifiers
source               1..19
                     mol_type = other RNA
                     organism = synthetic construct
SEQUENCE: 697
ctcacctgct tcttctggt                                                  19

SEQ ID NO: 698       moltype = RNA   length = 19
FEATURE              Location/Qualifiers
source               1..19
                     mol_type = other RNA
                     organism = synthetic construct
SEQUENCE: 698
caaagcccag aagatgctc                                                  19

SEQ ID NO: 699       moltype = RNA   length = 19
FEATURE              Location/Qualifiers
source               1..19
                     mol_type = other RNA
                     organism = synthetic construct
SEQUENCE: 699
ccaaagccca gaagatgct                                                  19

SEQ ID NO: 700       moltype = RNA   length = 19
FEATURE              Location/Qualifiers
source               1..19
                     mol_type = other RNA
                     organism = synthetic construct
SEQUENCE: 700
gccaaagccc agaagatgc                                                  19

SEQ ID NO: 701       moltype = RNA   length = 19
FEATURE              Location/Qualifiers
source               1..19
                     mol_type = other RNA
                     organism = synthetic construct
SEQUENCE: 701
tttggaataa agctgcctg                                                  19

SEQ ID NO: 702       moltype = RNA   length = 19
FEATURE              Location/Qualifiers
source               1..19
                     mol_type = other RNA
                     organism = synthetic construct
SEQUENCE: 702
ctttggaata aagctgcct                                                  19

SEQ ID NO: 703       moltype = RNA   length = 19
FEATURE              Location/Qualifiers
source               1..19
                     mol_type = other RNA
                     organism = synthetic construct
SEQUENCE: 703
ccctttggaa taaagctgc                                                  19

SEQ ID NO: 704       moltype = RNA   length = 19
FEATURE              Location/Qualifiers
source               1..19
                     mol_type = other RNA
                     organism = synthetic construct
SEQUENCE: 704
gccctttgga ataaagctg                                                  19

SEQ ID NO: 705       moltype = RNA   length = 19
FEATURE              Location/Qualifiers
source               1..19
                     mol_type = other RNA
                     organism = synthetic construct
SEQUENCE: 705
tgccctttgg aataaagct                                                  19
```

| | | |
|---|---|---|
| SEQ ID NO: 706<br>FEATURE<br>source | moltype = RNA   length = 19<br>Location/Qualifiers<br>1..19<br>mol_type = other RNA<br>organism = synthetic construct | |
| SEQUENCE: 706<br>agctgccctt tggaataaa | | 19 |
| SEQ ID NO: 707<br>FEATURE<br>source | moltype = RNA   length = 19<br>Location/Qualifiers<br>1..19<br>mol_type = other RNA<br>organism = synthetic construct | |
| SEQUENCE: 707<br>cagctgccct ttggaataa | | 19 |
| SEQ ID NO: 708<br>FEATURE<br>source | moltype = RNA   length = 19<br>Location/Qualifiers<br>1..19<br>mol_type = other RNA<br>organism = synthetic construct | |
| SEQUENCE: 708<br>tgagctcagc tgccctttg | | 19 |
| SEQ ID NO: 709<br>FEATURE<br>source | moltype = RNA   length = 19<br>Location/Qualifiers<br>1..19<br>mol_type = other RNA<br>organism = synthetic construct | |
| SEQUENCE: 709<br>gtgagctcag ctgcccttt | | 19 |
| SEQ ID NO: 710<br>FEATURE<br>source | moltype = RNA   length = 19<br>Location/Qualifiers<br>1..19<br>mol_type = other RNA<br>organism = synthetic construct | |
| SEQUENCE: 710<br>agcttcggaa gccctggt | | 19 |
| SEQ ID NO: 711<br>FEATURE<br>source | moltype = RNA   length = 19<br>Location/Qualifiers<br>1..19<br>mol_type = other RNA<br>organism = synthetic construct | |
| SEQUENCE: 711<br>tcagcagcaa gaatgctgg | | 19 |
| SEQ ID NO: 712<br>FEATURE<br>source | moltype = RNA   length = 19<br>Location/Qualifiers<br>1..19<br>mol_type = other RNA<br>organism = synthetic construct | |
| SEQUENCE: 712<br>ctcagcagca agaatgctg | | 19 |
| SEQ ID NO: 713<br>FEATURE<br>source | moltype = RNA   length = 19<br>Location/Qualifiers<br>1..19<br>mol_type = other RNA<br>organism = synthetic construct | |
| SEQUENCE: 713<br>gctcagcagc aagaatgct | | 19 |
| SEQ ID NO: 714<br>FEATURE<br>source | moltype = RNA   length = 19<br>Location/Qualifiers<br>1..19<br>mol_type = other RNA<br>organism = synthetic construct | |
| SEQUENCE: 714<br>tggctcagca gcaagaatg | | 19 |
| SEQ ID NO: 715<br>FEATURE<br>source | moltype = RNA   length = 19<br>Location/Qualifiers<br>1..19<br>mol_type = other RNA<br>organism = synthetic construct | |
| SEQUENCE: 715<br>gtggctcagc agcaagaat | | 19 |

```
SEQ ID NO: 716            moltype = RNA   length = 19
FEATURE                   Location/Qualifiers
source                    1..19
                          mol_type = other RNA
                          organism = synthetic construct
SEQUENCE: 716
gatgtctgct ccagtgatg                                                    19

SEQ ID NO: 717            moltype = RNA   length = 19
FEATURE                   Location/Qualifiers
source                    1..19
                          mol_type = other RNA
                          organism = synthetic construct
SEQUENCE: 717
tgatgtctgc tccagtgat                                                    19

SEQ ID NO: 718            moltype = RNA   length = 19
FEATURE                   Location/Qualifiers
source                    1..19
                          mol_type = other RNA
                          organism = synthetic construct
SEQUENCE: 718
ctgatgtctg ctccagtga                                                    19

SEQ ID NO: 719            moltype = RNA   length = 19
FEATURE                   Location/Qualifiers
source                    1..19
                          mol_type = other RNA
                          organism = synthetic construct
SEQUENCE: 719
ccctgatgtc tgctccagt                                                    19

SEQ ID NO: 720            moltype = RNA   length = 19
FEATURE                   Location/Qualifiers
source                    1..19
                          mol_type = other RNA
                          organism = synthetic construct
SEQUENCE: 720
aagtggtgac ctgaggaac                                                    19

SEQ ID NO: 721            moltype = RNA   length = 19
FEATURE                   Location/Qualifiers
source                    1..19
                          mol_type = other RNA
                          organism = synthetic construct
SEQUENCE: 721
caagtggtga cctgaggaa                                                    19

SEQ ID NO: 722            moltype = RNA   length = 19
FEATURE                   Location/Qualifiers
source                    1..19
                          mol_type = other RNA
                          organism = synthetic construct
SEQUENCE: 722
gcaagtggtg acctgagga                                                    19

SEQ ID NO: 723            moltype = RNA   length = 19
FEATURE                   Location/Qualifiers
source                    1..19
                          mol_type = other RNA
                          organism = synthetic construct
SEQUENCE: 723
agcaagtggt gacctgagg                                                    19

SEQ ID NO: 724            moltype = RNA   length = 19
FEATURE                   Location/Qualifiers
source                    1..19
                          mol_type = other RNA
                          organism = synthetic construct
SEQUENCE: 724
cagcaagtgg tgacctgag                                                    19

SEQ ID NO: 725            moltype = RNA   length = 19
FEATURE                   Location/Qualifiers
source                    1..19
                          mol_type = other RNA
                          organism = synthetic construct
SEQUENCE: 725
```

-continued

```
ccagcaagtg gtgacctga                                               19

SEQ ID NO: 726          moltype = RNA   length = 19
FEATURE                 Location/Qualifiers
source                  1..19
                        mol_type = other RNA
                        organism = synthetic construct SEQUENCE: 726
atccagcaag tggtgacct                                               19

SEQ ID NO: 727          moltype = RNA   length = 19
FEATURE                 Location/Qualifiers
source                  1..19
                        mol_type = other RNA
                        organism = synthetic construct SEQUENCE: 727
tggatccagc aagtggtga                                               19

SEQ ID NO: 728          moltype = RNA   length = 19
FEATURE                 Location/Qualifiers
source                  1..19
                        mol_type = other RNA
                        organism = synthetic construct SEQUENCE: 728
ctggatccag caagtggtg                                               19

SEQ ID NO: 729          moltype = RNA   length = 19
FEATURE                 Location/Qualifiers
source                  1..19
                        mol_type = other RNA
                        organism = synthetic construct SEQUENCE: 729
cccgcatcac aggtgtgat                                               19

SEQ ID NO: 730          moltype = RNA   length = 19
FEATURE                 Location/Qualifiers
source                  1..19
                        mol_type = other RNA
                        organism = synthetic construct SEQUENCE: 730
acccgcatca caggtgtga                                               19

SEQ ID NO: 731          moltype = RNA   length = 19
FEATURE                 Location/Qualifiers
source                  1..19
                        mol_type = other RNA
                        organism = synthetic construct SEQUENCE: 731
aactacttcg gcgtctaca                                               19

SEQ ID NO: 732          moltype = RNA   length = 19
FEATURE                 Location/Qualifiers
source                  1..19
                        mol_type = other RNA
                        organism = synthetic construct SEQUENCE: 732
ttgatcccac aggacctgt                                               19

SEQ ID NO: 733          moltype = RNA   length = 19
FEATURE                 Location/Qualifiers
source                  1..19
                        mol_type = other RNA
                        organism = synthetic construct SEQUENCE: 733
tgcagttgat cccacagga                                               19

SEQ ID NO: 734          moltype = RNA   length = 19
FEATURE                 Location/Qualifiers
source                  1..19
                        mol_type = other RNA
                        organism = synthetic construct SEQUENCE: 734
agaggtgtcc ttcaaggtg                                               19

SEQ ID NO: 735          moltype = RNA   length = 19
FEATURE                 Location/Qualifiers
source                  1..19
                        mol_type = other RNA
                        organism = synthetic construct
```

```
SEQUENCE: 735
gagaggtgtc cttcaaggt                                                        19

SEQ ID NO: 736         moltype = RNA  length = 19
FEATURE                Location/Qualifiers
source                 1..19
                       mol_type = other RNA
                       organism = synthetic construct SEQUENCE: 736
ctggagaggt gtccttcaa                                                        19

SEQ ID NO: 737         moltype = RNA  length = 19
FEATURE                Location/Qualifiers
source                 1..19
                       mol_type = other RNA
                       organism = synthetic construct SEQUENCE: 737
aggttcgggg tcgacacat                                                        19

SEQ ID NO: 738         moltype = RNA  length = 19
FEATURE                Location/Qualifiers
source                 1..19
                       mol_type = other RNA
                       organism = synthetic construct SEQUENCE: 738
attcaccttc cagtgtgag                                                        19

SEQ ID NO: 739         moltype = RNA  length = 19
FEATURE                Location/Qualifiers
source                 1..19
                       mol_type = other RNA
                       organism = synthetic construct SEQUENCE: 739
cattcacctt ccagtgtga                                                        19

SEQ ID NO: 740         moltype = RNA  length = 19
FEATURE                Location/Qualifiers
source                 1..19
                       mol_type = other RNA
                       organism = synthetic construct SEQUENCE: 740
acattcacct tccagtgtg                                                        19

SEQ ID NO: 741         moltype = RNA  length = 19
FEATURE                Location/Qualifiers
source                 1..19
                       mol_type = other RNA
                       organism = synthetic construct SEQUENCE: 741
gacattcacc ttccagtgt                                                        19

SEQ ID NO: 742         moltype = RNA  length = 19
FEATURE                Location/Qualifiers
source                 1..19
                       mol_type = other RNA
                       organism = synthetic construct SEQUENCE: 742
ggacattcac cttccagtg                                                        19

SEQ ID NO: 743         moltype = RNA  length = 19
FEATURE                Location/Qualifiers
source                 1..19
                       mol_type = other RNA
                       organism = synthetic construct SEQUENCE: 743
gcagagccac attccagtg                                                        19

SEQ ID NO: 744         moltype = RNA  length = 19
FEATURE                Location/Qualifiers
source                 1..19
                       mol_type = other RNA
                       organism = synthetic construct SEQUENCE: 744
tgcagagcca cattccagt                                                        19

SEQ ID NO: 745         moltype = RNA  length = 19
FEATURE                Location/Qualifiers
source                 1..19
                       mol_type = other RNA
```

SEQUENCE: 745
ttgcagagcc acattccag                                                19

SEQ ID NO: 746          moltype = RNA   length = 19
FEATURE                 Location/Qualifiers
source                  1..19
                        mol_type = other RNA
                        organism = synthetic construct
SEQUENCE: 746
tttgcagagc cacattcca                                                19

SEQ ID NO: 747          moltype = RNA   length = 19
FEATURE                 Location/Qualifiers
source                  1..19
                        mol_type = other RNA
                        organism = synthetic construct
SEQUENCE: 747
aaactgcgtt tgcagagcc                                                19

SEQ ID NO: 748          moltype = RNA   length = 19
FEATURE                 Location/Qualifiers
source                  1..19
                        mol_type = other RNA
                        organism = synthetic construct
SEQUENCE: 748
gaaactgcgt ttgcagagc                                                19

SEQ ID NO: 749          moltype = RNA   length = 19
FEATURE                 Location/Qualifiers
source                  1..19
                        mol_type = other RNA
                        organism = synthetic construct
SEQUENCE: 749
agaaactgcg tttgcagag                                                19

SEQ ID NO: 750          moltype = RNA   length = 19
FEATURE                 Location/Qualifiers
source                  1..19
                        mol_type = other RNA
                        organism = synthetic construct
SEQUENCE: 750
gagaaactgc gtttgcaga                                                19

SEQ ID NO: 751          moltype = RNA   length = 19
FEATURE                 Location/Qualifiers
source                  1..19
                        mol_type = other RNA
                        organism = synthetic construct
SEQUENCE: 751
agagaaactg cgtttgcag                                                19

SEQ ID NO: 752          moltype = RNA   length = 19
FEATURE                 Location/Qualifiers
source                  1..19
                        mol_type = other RNA
                        organism = synthetic construct
SEQUENCE: 752
gagagaaact gcgtttgca                                                19

SEQ ID NO: 753          moltype = RNA   length = 19
FEATURE                 Location/Qualifiers
source                  1..19
                        mol_type = other RNA
                        organism = synthetic construct
SEQUENCE: 753
tgagagaaac tgcgtttgc                                                19

SEQ ID NO: 754          moltype = RNA   length = 19
FEATURE                 Location/Qualifiers
source                  1..19
                        mol_type = other RNA
                        organism = synthetic construct
SEQUENCE: 754
atgagagaaa ctgcgtttg                                                19

SEQ ID NO: 755          moltype = RNA   length = 19
FEATURE                 Location/Qualifiers
source                  1..19

```
                        mol_type = other RNA
                        organism = synthetic construct
SEQUENCE: 755
gatgagagaa actgcgttt                                                  19

SEQ ID NO: 756          moltype = RNA  length = 19
FEATURE                 Location/Qualifiers
source                  1..19
                        mol_type = other RNA
                        organism = synthetic construct
SEQUENCE: 756
ggatgagaga aactgcgtt                                                  19

SEQ ID NO: 757          moltype = RNA  length = 19
FEATURE                 Location/Qualifiers
source                  1..19
                        mol_type = other RNA
                        organism = synthetic construct
SEQUENCE: 757
tggatgagag aaactgcgt                                                  19

SEQ ID NO: 758          moltype = RNA  length = 19
FEATURE                 Location/Qualifiers
source                  1..19
                        mol_type = other RNA
                        organism = synthetic construct
SEQUENCE: 758
ctggatgaga gaaactgcg                                                  19

SEQ ID NO: 759          moltype = RNA  length = 19
FEATURE                 Location/Qualifiers
source                  1..19
                        mol_type = other RNA
                        organism = synthetic construct
SEQUENCE: 759
cctggatgag agaaactgc                                                  19

SEQ ID NO: 760          moltype = RNA  length = 19
FEATURE                 Location/Qualifiers
source                  1..19
                        mol_type = other RNA
                        organism = synthetic construct
SEQUENCE: 760
cctgtgatgg ggtcaagga                                                  19

SEQ ID NO: 761          moltype = RNA  length = 19
FEATURE                 Location/Qualifiers
source                  1..19
                        mol_type = other RNA
                        organism = synthetic construct
SEQUENCE: 761
ttgtacaacc agtcggacc                                                  19

SEQ ID NO: 762          moltype = RNA  length = 19
FEATURE                 Location/Qualifiers
source                  1..19
                        mol_type = other RNA
                        organism = synthetic construct
SEQUENCE: 762
cttgtacaac cagtcggac                                                  19

SEQ ID NO: 763          moltype = RNA  length = 19
FEATURE                 Location/Qualifiers
source                  1..19
                        mol_type = other RNA
                        organism = synthetic construct
SEQUENCE: 763
gcttgtacaa ccagtcgga                                                  19

SEQ ID NO: 764          moltype = RNA  length = 19
FEATURE                 Location/Qualifiers
source                  1..19
                        mol_type = other RNA
                        organism = synthetic construct
SEQUENCE: 764
tggcttgtac aaccagtcg                                                  19

SEQ ID NO: 765          moltype = RNA  length = 19
FEATURE                 Location/Qualifiers
```

```
source                    1..19
                          mol_type = other RNA
                          organism = synthetic construct
SEQUENCE: 765
atggcttgta caaccagtc                                                        19

SEQ ID NO: 766            moltype = RNA   length = 19
FEATURE                   Location/Qualifiers
source                    1..19
                          mol_type = other RNA
                          organism = synthetic construct
SEQUENCE: 766
tatggcttgt acaaccagt                                                        19

SEQ ID NO: 767            moltype = RNA   length = 19
FEATURE                   Location/Qualifiers
source                    1..19
                          mol_type = other RNA
                          organism = synthetic construct
SEQUENCE: 767
ctatggcttg tacaaccag                                                        19

SEQ ID NO: 768            moltype = RNA   length = 19
FEATURE                   Location/Qualifiers
source                    1..19
                          mol_type = other RNA
                          organism = synthetic construct
SEQUENCE: 768
actatggctt gtacaacca                                                        19

SEQ ID NO: 769            moltype = RNA   length = 19
FEATURE                   Location/Qualifiers
source                    1..19
                          mol_type = other RNA
                          organism = synthetic construct
SEQUENCE: 769
cactatggct tgtacaacc                                                        19

SEQ ID NO: 770            moltype = RNA   length = 19
FEATURE                   Location/Qualifiers
source                    1..19
                          mol_type = other RNA
                          organism = synthetic construct
SEQUENCE: 770
gcactatggc ttgtacaac                                                        19

SEQ ID NO: 771            moltype = RNA   length = 19
FEATURE                   Location/Qualifiers
source                    1..19
                          mol_type = other RNA
                          organism = synthetic construct
SEQUENCE: 771
tgcactatgg cttgtacaa                                                        19

SEQ ID NO: 772            moltype = RNA   length = 19
FEATURE                   Location/Qualifiers
source                    1..19
                          mol_type = other RNA
                          organism = synthetic construct
SEQUENCE: 772
gtgcactatg gcttgtaca                                                        19

SEQ ID NO: 773            moltype = RNA   length = 19
FEATURE                   Location/Qualifiers
source                    1..19
                          mol_type = other RNA
                          organism = synthetic construct
SEQUENCE: 773
ggtgcactat ggcttgtac                                                        19

SEQ ID NO: 774            moltype = RNA   length = 19
FEATURE                   Location/Qualifiers
source                    1..19
                          mol_type = other RNA
                          organism = synthetic construct
SEQUENCE: 774
gggtgcacta tggcttgta                                                        19

SEQ ID NO: 775            moltype = RNA   length = 19
```

```
                              -continued

FEATURE                 Location/Qualifiers
source                  1..19
                        mol_type = other RNA
                        organism = synthetic construct
SEQUENCE: 775
cgggtgcact atggcttgt                                                 19

SEQ ID NO: 776          moltype = RNA   length = 19
FEATURE                 Location/Qualifiers
source                  1..19
                        mol_type = other RNA
                        organism = synthetic construct
SEQUENCE: 776
tgcgggtgca ctatggctt                                                 19

SEQ ID NO: 777          moltype = RNA   length = 19
FEATURE                 Location/Qualifiers
source                  1..19
                        mol_type = other RNA
                        organism = synthetic construct
SEQUENCE: 777
gtgtgcgggt gcactatgg                                                 19

SEQ ID NO: 778          moltype = RNA   length = 19
FEATURE                 Location/Qualifiers
source                  1..19
                        mol_type = other RNA
                        organism = synthetic construct
SEQUENCE: 778
tggacgatcc agaacagga                                                 19

SEQ ID NO: 779          moltype = RNA   length = 19
FEATURE                 Location/Qualifiers
source                  1..19
                        mol_type = other RNA
                        organism = synthetic construct
SEQUENCE: 779
cagtggacga tccagaaca                                                 19

SEQ ID NO: 780          moltype = RNA   length = 19
FEATURE                 Location/Qualifiers
source                  1..19
                        mol_type = other RNA
                        organism = synthetic construct
SEQUENCE: 780
aagtatgatt tgccgtgca                                                 19

SEQ ID NO: 781          moltype = RNA   length = 19
FEATURE                 Location/Qualifiers
source                  1..19
                        mol_type = other RNA
                        organism = synthetic construct
SEQUENCE: 781
gaagtatgat ttgccgtgc                                                 19

SEQ ID NO: 782          moltype = RNA   length = 19
FEATURE                 Location/Qualifiers
source                  1..19
                        mol_type = other RNA
                        organism = synthetic construct
SEQUENCE: 782
agaagtatga tttgccgtg                                                 19

SEQ ID NO: 783          moltype = RNA   length = 19
FEATURE                 Location/Qualifiers
source                  1..19
                        mol_type = other RNA
                        organism = synthetic construct
SEQUENCE: 783
cagaagtatg atttgccgt                                                 19

SEQ ID NO: 784          moltype = RNA   length = 19
FEATURE                 Location/Qualifiers
source                  1..19
                        mol_type = other RNA
                        organism = synthetic construct
SEQUENCE: 784
ggcagaagta tgatttgcc                                                 19
```

```
SEQ ID NO: 785         moltype = RNA   length = 19
FEATURE                Location/Qualifiers
source                 1..19
                       mol_type = other RNA
                       organism = synthetic construct
SEQUENCE: 785
aggcagaagt atgatttgc                                                    19

SEQ ID NO: 786         moltype = RNA   length = 19
FEATURE                Location/Qualifiers
source                 1..19
                       mol_type = other RNA
                       organism = synthetic construct
SEQUENCE: 786
gaggcagaag tatgatttg                                                    19

SEQ ID NO: 787         moltype = RNA   length = 19
FEATURE                Location/Qualifiers
source                 1..19
                       mol_type = other RNA
                       organism = synthetic construct
SEQUENCE: 787
ggaggcagaa gtatgattt                                                    19

SEQ ID NO: 788         moltype = RNA   length = 19
FEATURE                Location/Qualifiers
source                 1..19
                       mol_type = other RNA
                       organism = synthetic construct
SEQUENCE: 788
acttccccag ctactactc                                                    19

SEQ ID NO: 789         moltype = RNA   length = 19
FEATURE                Location/Qualifiers
source                 1..19
                       mol_type = other RNA
                       organism = synthetic construct
SEQUENCE: 789
cgtacttccc cagctacta                                                    19

SEQ ID NO: 790         moltype = RNA   length = 19
FEATURE                Location/Qualifiers
source                 1..19
                       mol_type = other RNA
                       organism = synthetic construct
SEQUENCE: 790
tgcacagcta ctacgaccc                                                    19

SEQ ID NO: 791         moltype = RNA   length = 19
FEATURE                Location/Qualifiers
source                 1..19
                       mol_type = other RNA
                       organism = synthetic construct
SEQUENCE: 791
agaagggcct gcacagcta                                                    19

SEQ ID NO: 792         moltype = RNA   length = 19
FEATURE                Location/Qualifiers
source                 1..19
                       mol_type = other RNA
                       organism = synthetic construct
SEQUENCE: 792
accgactggc catgtatga                                                    19

SEQ ID NO: 793         moltype = RNA   length = 19
FEATURE                Location/Qualifiers
source                 1..19
                       mol_type = other RNA
                       organism = synthetic construct
SEQUENCE: 793
gttgttaccg ctacagcta                                                    19

SEQ ID NO: 794         moltype = RNA   length = 19
FEATURE                Location/Qualifiers
source                 1..19
                       mol_type = other RNA
                       organism = synthetic construct
SEQUENCE: 794
gggttgttac cgctacagc                                                    19
```

| | | |
|---|---|---|
| SEQ ID NO: 795<br>FEATURE<br>source | moltype = RNA   length = 19<br>Location/Qualifiers<br>1..19<br>mol_type = other RNA<br>organism = synthetic construct | |
| SEQUENCE: 795<br>tgggttgtta ccgctacag | | 19 |
| SEQ ID NO: 796<br>FEATURE<br>source | moltype = RNA   length = 19<br>Location/Qualifiers<br>1..19<br>mol_type = other RNA<br>organism = synthetic construct | |
| SEQUENCE: 796<br>ctgggttgtt accgctaca | | 19 |
| SEQ ID NO: 797<br>FEATURE<br>source | moltype = RNA   length = 19<br>Location/Qualifiers<br>1..19<br>mol_type = other RNA<br>organism = synthetic construct | |
| SEQUENCE: 797<br>attccacgct gggttgtta | | 19 |
| SEQ ID NO: 798<br>FEATURE<br>source | moltype = RNA   length = 19<br>Location/Qualifiers<br>1..19<br>mol_type = other RNA<br>organism = synthetic construct | |
| SEQUENCE: 798<br>aattccacgc tgggttgtt | | 19 |
| SEQ ID NO: 799<br>FEATURE<br>source | moltype = RNA   length = 19<br>Location/Qualifiers<br>1..19<br>mol_type = other RNA<br>organism = synthetic construct | |
| SEQUENCE: 799<br>tgtgaaagac atagctgca | | 19 |
| SEQ ID NO: 800<br>FEATURE<br>source | moltype = RNA   length = 19<br>Location/Qualifiers<br>1..19<br>mol_type = other RNA<br>organism = synthetic construct | |
| SEQUENCE: 800<br>gtgtgaaaga catagctgc | | 19 |
| SEQ ID NO: 801<br>FEATURE<br>source | moltype = RNA   length = 19<br>Location/Qualifiers<br>1..19<br>mol_type = other RNA<br>organism = synthetic construct | |
| SEQUENCE: 801<br>agtgtgaaag acatagctg | | 19 |
| SEQ ID NO: 802<br>FEATURE<br>source | moltype = RNA   length = 19<br>Location/Qualifiers<br>1..19<br>mol_type = other RNA<br>organism = synthetic construct | |
| SEQUENCE: 802<br>cagtgtgaaa gacatagct | | 19 |
| SEQ ID NO: 803<br>FEATURE<br>source | moltype = RNA   length = 19<br>Location/Qualifiers<br>1..19<br>mol_type = other RNA<br>organism = synthetic construct | |
| SEQUENCE: 803<br>ccagtgtgaa agacatagc | | 19 |
| SEQ ID NO: 804<br>FEATURE<br>source | moltype = RNA   length = 19<br>Location/Qualifiers<br>1..19<br>mol_type = other RNA<br>organism = synthetic construct | |
| SEQUENCE: 804 | | | gccagtgtga aagacatag                                                                           19

SEQ ID NO: 805          moltype = RNA   length = 19
FEATURE                 Location/Qualifiers
source                  1..19
                        mol_type = other RNA
                        organism = synthetic construct
SEQUENCE: 805
agccagtgtg aaagacata                                                                           19

SEQ ID NO: 806          moltype = RNA   length = 19
FEATURE                 Location/Qualifiers
source                  1..19
                        mol_type = other RNA
                        organism = synthetic construct
SEQUENCE: 806
aagccagtgt gaaagacat                                                                           19

SEQ ID NO: 807          moltype = RNA   length = 19
FEATURE                 Location/Qualifiers
source                  1..19
                        mol_type = other RNA
                        organism = synthetic construct
SEQUENCE: 807
gaagccagtg tgaaagaca                                                                           19

SEQ ID NO: 808          moltype = RNA   length = 19
FEATURE                 Location/Qualifiers
source                  1..19
                        mol_type = other RNA
                        organism = synthetic construct
SEQUENCE: 808
ctgctgtcca cagtcaaca                                                                           19

SEQ ID NO: 809          moltype = RNA   length = 19
FEATURE                 Location/Qualifiers
source                  1..19
                        mol_type = other RNA
                        organism = synthetic construct
SEQUENCE: 809
agctgctgtc cacagtcaa                                                                           19

SEQ ID NO: 810          moltype = RNA   length = 19
FEATURE                 Location/Qualifiers
source                  1..19
                        mol_type = other RNA
                        organism = synthetic construct
SEQUENCE: 810
gttcattctc caaatcccc                                                                           19

SEQ ID NO: 811          moltype = RNA   length = 19
FEATURE                 Location/Qualifiers
source                  1..19
                        mol_type = other RNA
                        organism = synthetic construct
SEQUENCE: 811
ggttcattct ccaaatccc                                                                           19

SEQ ID NO: 812          moltype = RNA   length = 19
FEATURE                 Location/Qualifiers
source                  1..19
                        mol_type = other RNA
                        organism = synthetic construct
SEQUENCE: 812
tggttcattc tccaaatcc                                                                           19

SEQ ID NO: 813          moltype = RNA   length = 19
FEATURE                 Location/Qualifiers
source                  1..19
                        mol_type = other RNA
                        organism = synthetic construct
SEQUENCE: 813
ctggttcatt ctccaaatc                                                                           19

SEQ ID NO: 814          moltype = RNA   length = 19
FEATURE                 Location/Qualifiers
source                  1..19
                        mol_type = other RNA
                        organism = synthetic construct

```
SEQUENCE: 814
tctggttcat tctccaaat                                                    19

SEQ ID NO: 815        moltype = RNA   length = 19
FEATURE               Location/Qualifiers
source                1..19
                      mol_type = other RNA
                      organism = synthetic construct
SEQUENCE: 815
ttctggttca ttctccaaa                                                    19

SEQ ID NO: 816        moltype = RNA   length = 19
FEATURE               Location/Qualifiers
source                1..19
                      mol_type = other RNA
                      organism = synthetic construct
SEQUENCE: 816
cttctggttc attctccaa                                                    19

SEQ ID NO: 817        moltype = RNA   length = 19
FEATURE               Location/Qualifiers
source                1..19
                      mol_type = other RNA
                      organism = synthetic construct
SEQUENCE: 817
cttcttctgg ttcattctc                                                    19

SEQ ID NO: 818        moltype = RNA   length = 19
FEATURE               Location/Qualifiers
source                1..19
                      mol_type = other RNA
                      organism = synthetic construct
SEQUENCE: 818
gcttcttctg gttcattct                                                    19

SEQ ID NO: 819        moltype = RNA   length = 19
FEATURE               Location/Qualifiers
source                1..19
                      mol_type = other RNA
                      organism = synthetic construct
SEQUENCE: 819
tgcttcttct ggttcattc                                                    19

SEQ ID NO: 820        moltype = RNA   length = 19
FEATURE               Location/Qualifiers
source                1..19
                      mol_type = other RNA
                      organism = synthetic construct
SEQUENCE: 820
ctgcttcttc tggttcatt                                                    19

SEQ ID NO: 821        moltype = RNA   length = 19
FEATURE               Location/Qualifiers
source                1..19
                      mol_type = other RNA
                      organism = synthetic construct
SEQUENCE: 821
cctgcttctt ctggttcat                                                    19

SEQ ID NO: 822        moltype = RNA   length = 19
FEATURE               Location/Qualifiers
source                1..19
                      mol_type = other RNA
                      organism = synthetic construct
SEQUENCE: 822
acctgcttct tctggttca                                                    19

SEQ ID NO: 823        moltype = RNA   length = 19
FEATURE               Location/Qualifiers
source                1..19
                      mol_type = other RNA
                      organism = synthetic construct
SEQUENCE: 823
cacctgcttc ttctggttc                                                    19

SEQ ID NO: 824        moltype = RNA   length = 19
FEATURE               Location/Qualifiers
source                1..19
                      mol_type = other RNA
```

-continued

```
                     organism = synthetic construct
SEQUENCE: 824
cagctccgtc tattcctttt                                                 19

SEQ ID NO: 825          moltype = RNA  length = 19
FEATURE                 Location/Qualifiers
source                  1..19
                        mol_type = other RNA
                        organism = synthetic construct
SEQUENCE: 825
actccagctc cgtctattc                                                  19

SEQ ID NO: 826          moltype = RNA  length = 19
FEATURE                 Location/Qualifiers
source                  1..19
                        mol_type = other RNA
                        organism = synthetic construct
SEQUENCE: 826
aactccagct ccgtctatt                                                  19

SEQ ID NO: 827          moltype = RNA  length = 19
FEATURE                 Location/Qualifiers
source                  1..19
                        mol_type = other RNA
                        organism = synthetic construct
SEQUENCE: 827
agatgctcaa ggagctcat                                                  19

SEQ ID NO: 828          moltype = RNA  length = 19
FEATURE                 Location/Qualifiers
source                  1..19
                        mol_type = other RNA
                        organism = synthetic construct
SEQUENCE: 828
aagatgctca aggagctca                                                  19

SEQ ID NO: 829          moltype = RNA  length = 19
FEATURE                 Location/Qualifiers
source                  1..19
                        mol_type = other RNA
                        organism = synthetic construct
SEQUENCE: 829
gaaagatgctc aaggagctc                                                 19

SEQ ID NO: 830          moltype = RNA  length = 19
FEATURE                 Location/Qualifiers
source                  1..19
                        mol_type = other RNA
                        organism = synthetic construct
SEQUENCE: 830
agaagatgct caaggagct                                                  19

SEQ ID NO: 831          moltype = RNA  length = 19
FEATURE                 Location/Qualifiers
source                  1..19
                        mol_type = other RNA
                        organism = synthetic construct
SEQUENCE: 831
cagaagatgc tcaaggagc                                                  19

SEQ ID NO: 832          moltype = RNA  length = 19
FEATURE                 Location/Qualifiers
source                  1..19
                        mol_type = other RNA
                        organism = synthetic construct
SEQUENCE: 832
ccagaagatg ctcaaggag                                                  19

SEQ ID NO: 833          moltype = RNA  length = 19
FEATURE                 Location/Qualifiers
source                  1..19
                        mol_type = other RNA
                        organism = synthetic construct
SEQUENCE: 833
cccagaagat gctcaagga                                                  19

SEQ ID NO: 834          moltype = RNA  length = 19
FEATURE                 Location/Qualifiers
source                  1..19
```

```
                          mol_type = other RNA
                          organism = synthetic construct
SEQUENCE: 834
aagcccagaa gatgctcaa                                                 19

SEQ ID NO: 835            moltype = RNA   length = 19
FEATURE                   Location/Qualifiers
source                    1..19
                          mol_type = other RNA
                          organism = synthetic construct
SEQUENCE: 835
aaagcccaga agatgctca                                                 19

SEQ ID NO: 836            moltype = RNA   length = 19
FEATURE                   Location/Qualifiers
source                    1..19
                          mol_type = other RNA
                          organism = synthetic construct
SEQUENCE: 836
gtcagccagg tgtactcag                                                 19

SEQ ID NO: 837            moltype = RNA   length = 19
FEATURE                   Location/Qualifiers
source                    1..19
                          mol_type = other RNA
                          organism = synthetic construct
SEQUENCE: 837
ggtcagccag gtgtactca                                                 19

SEQ ID NO: 838            moltype = RNA   length = 19
FEATURE                   Location/Qualifiers
source                    1..19
                          mol_type = other RNA
                          organism = synthetic construct
SEQUENCE: 838
actctggtat ttcctaggg                                                 19

SEQ ID NO: 839            moltype = RNA   length = 19
FEATURE                   Location/Qualifiers
source                    1..19
                          mol_type = other RNA
                          organism = synthetic construct
SEQUENCE: 839
tactctggta tttcctagg                                                 19

SEQ ID NO: 840            moltype = RNA   length = 19
FEATURE                   Location/Qualifiers
source                    1..19
                          mol_type = other RNA
                          organism = synthetic construct
SEQUENCE: 840
ctactctggt atttcctag                                                 19

SEQ ID NO: 841            moltype = RNA   length = 19
FEATURE                   Location/Qualifiers
source                    1..19
                          mol_type = other RNA
                          organism = synthetic construct
SEQUENCE: 841
gctactctgg tatttccta                                                 19

SEQ ID NO: 842            moltype = RNA   length = 19
FEATURE                   Location/Qualifiers
source                    1..19
                          mol_type = other RNA
                          organism = synthetic construct
SEQUENCE: 842
tgctactctg gtatttcct                                                 19

SEQ ID NO: 843            moltype = RNA   length = 19
FEATURE                   Location/Qualifiers
source                    1..19
                          mol_type = other RNA
                          organism = synthetic construct
SEQUENCE: 843
gtgctactct ggtatttcc                                                 19

SEQ ID NO: 844            moltype = RNA   length = 19
FEATURE                   Location/Qualifiers
```

-continued

```
source                     1..19
                           mol_type = other RNA
                           organism = synthetic construct
SEQUENCE: 844
ggtgctactc tggtatttc                                                        19

SEQ ID NO: 845             moltype = RNA   length = 19
FEATURE                    Location/Qualifiers
source                     1..19
                           mol_type = other RNA
                           organism = synthetic construct
SEQUENCE: 845
gggtgctact ctggtattt                                                        19

SEQ ID NO: 846             moltype = RNA   length = 19
FEATURE                    Location/Qualifiers
source                     1..19
                           mol_type = other RNA
                           organism = synthetic construct
SEQUENCE: 846
ggactccaag agaaaagcc                                                        19

SEQ ID NO: 847             moltype = RNA   length = 19
FEATURE                    Location/Qualifiers
source                     1..19
                           mol_type = other RNA
                           organism = synthetic construct
SEQUENCE: 847
aggactccaa gagaaaagc                                                        19

SEQ ID NO: 848             moltype = RNA   length = 19
FEATURE                    Location/Qualifiers
source                     1..19
                           mol_type = other RNA
                           organism = synthetic construct
SEQUENCE: 848
tgaggactcc aagagaaaa                                                        19

SEQ ID NO: 849             moltype = RNA   length = 19
FEATURE                    Location/Qualifiers
source                     1..19
                           mol_type = other RNA
                           organism = synthetic construct
SEQUENCE: 849
gtgaggactc caagagaaa                                                        19

SEQ ID NO: 850             moltype = RNA   length = 19
FEATURE                    Location/Qualifiers
source                     1..19
                           mol_type = other RNA
                           organism = synthetic construct
SEQUENCE: 850
tgtgaggact ccaagagaa                                                        19

SEQ ID NO: 851             moltype = RNA   length = 19
FEATURE                    Location/Qualifiers
source                     1..19
                           mol_type = other RNA
                           organism = synthetic construct
SEQUENCE: 851
ctgtgaggac tccaagaga                                                        19

SEQ ID NO: 852             moltype = RNA   length = 19
FEATURE                    Location/Qualifiers
source                     1..19
                           mol_type = other RNA
                           organism = synthetic construct
SEQUENCE: 852
cctgtgagga ctccaagag                                                        19

SEQ ID NO: 853             moltype = DNA   length = 2475
FEATURE                    Location/Qualifiers
source                     1..2475
                           mol_type = other DNA
                           organism = Homo sapiens
SEQUENCE: 853
atgcccgtgg ccgaggcccc ccaggtggct ggcgggcagg gggacggagg tgatggcgag           60
gaagcggagc cggaggggat gttcaaggcc tgtgaggact ccaagagaaa agcccggggc          120
tacctccgcc tggtgcccct gtttgtgctg ctggccctgc tcgtgctggc ttcggcgggg          180
```

```
gtgctactct ggtatttcct agggtacaag gcggaggtga tggtcagcca ggtgtactca    240
ggcagtctgc gtgtactcaa tcgccacttc tcccaggatc ttacccgccg ggaatctagt    300
gccttccgca gtgaaaccgc caaagcccag aagatgctca aggagctcat caccagcacc    360
cgcctggaa cttactacaa ctccagctcc gtctattcct ttggggaggg acccctcacc     420
tgcttcttct ggttcattct ccaaatcccc gagcaccgcc ggctgatgct gagccccgag    480
gtggtgcagg cactgctggt ggaggagctg ctgtccacag tcaacagctc ggctgccgtc    540
ccctacaggg ccgagtacga agtgacccc gagggcctag tgatcctgga agccagtgtg     600
aaagacatag ctgcattgaa ttccacgctg ggttgttacc gctacagcta cgtgggccag    660
ggccaggtcc tccggctgaa ggggcctgac cacctggcct ccagctgcct gtggcacctg    720
cagggcccca aggacctcat gctcaaactc cggctggagt ggacgctggc agagtgccga    780
gaccgactgg ccatgtatga cgtggccggg cccctggaga agaggctcat cacctcggtg    840
tacgctgca gccgccagga gcccgtggtg gaggttctgg cgtcggggc catcatggcg       900
gtcgtctgga agaagggcct gcacagctac tacgacccct tcgtgctctc cgtgcagccg    960
gtggtcttcc aggcctgtga agtgaacctg acgctggaca acaggctcga ctcccaggge    1020
gtcctcagca ccccgtactt ccccagctac tactcgcccc aaacccactg ctcctggcac    1080
ctcacggtgc cctctctgga ctacggcttg gccctctggt ttgatgccta tgcactgagg    1140
aggcagaagt atgatttgcc gtgcacccag ggccagtgga cgatccagaa caggaggctg    1200
tgtggcttgc gcatcctgca gccctacgcc gagaggatcc ccgtggtggc cacggccggg    1260
atcaccatca acttcacctc ccagatctcc ctcaccgggc ccggtgtgcg ggtgcactat    1320
ggcttgtaca accagtcgga cccctgccct ggagagttcc tctgttctgt gaatgactc     1380
tgtgtccctg cctgtgatgg ggtcaaggac tgccccaacg gcctgatga gagaaactgc     1440
gtttgcagag ccacattcca gtgcaaagag gacagccact gcatctccat gcccaaggtc    1500
tgtgatgggc agcctgattg tctcaacggc agcgacgaag agcagtgcca ggaagggtg     1560
ccatgtggga cattcaccett ccagtgtgag gaccggagct gcgtgaagaa gcccaacccg    1620
cagtgtgatg ggcggcccga ctgcagggac ggctcggatg aggagcactg tgactgtggc    1680
ctccagggcc cctccagccg cattgttggt ggagctggtgt cctccgaggg tgagtggcca    1740
tggcaggcca gcctccaggt tcggggtcga cacatctgtg gggggcct catcgctgac      1800
cgctgggtga taacagctgc ccactgcttc caggaggaca gcatgcctc cacggtgctg      1860
tggaccgtgt tcctgggcaa ggtgtggcag aactcgcgct ggcctggaga ggtgtccttc    1920
aaggtgagcc gcctgctcct gcacccgtac cacgaagagg acagccatga ctacgacgtg    1980
gcgctgctgc agctcgacca cccggtggtg cgctcggccg ccgtgcgccc cgtctgcctg    2040
cccgcgcgct cccacttctt cgagcccggc ctgcactgct ggattacggg ctggggcgcc    2100
ttgcgcgagg gcgccctacg gcggatgct gtggccctat tttatggatg gagaaaccaa     2160
ggctcagaga catgttgctg ccccatcagc aacgctctgc agaaagtgga tgtgcagttg    2220
atcccacagg acctgtgcag cgaggtctat cgctaccagg tgacgccacg catgctgtgt    2280
gccggctacc gcaagggcaa gaaggatgcc tgtcagggtg actcaggtgg tccgctggtg    2340
tgcaaggcac tcagtggccg ctggttcctg gcggggctgg tcagctgggg cctgggctgt    2400
ggccggccta actacttcgg cgtctacacc cgcatcacag gtgtgatcag ctggatccag    2460
caagtggtga cctga                                                      2475

SEQ ID NO: 854        moltype = DNA   length = 2400
FEATURE               Location/Qualifiers
source                1..2400
                      mol_type = other DNA
                      organism = Mus musculus
SEQUENCE: 854
atgcccacca ccgaggtccc ccaagcggct gatggtcagg gcgatgcggg tgatggagag    60
gaagctgctg agccagaggg gaagttcaag ccccccaaaaa acaccaagag aaaaaaccgg    120
gactacgtcc gcttcacgcc actgttgctg gtcttggctg cgctggtctc agcaggggtc    180
atgctttggt atttctagg gtacaaagcg gaagtgaccg taagccaggt gtactctggc    240
agcctccggg tgctcaaccg tcatttctcc caggacctgg gccgacggga gtctattgct    300
ttccgcagtg aatctgccaa agcccagaag atgctccaag aactggttgc cagcacccgc    360
ctgggtactt actacaactc tagttctgtc tactccttg ggaggggacc cctcacctgc     420
ttcttctggt ttatccttga catccctgag taccagcgac tgaccctgag ccctgaagta    480
gtgcgcgagc tcctggtgga tgagctactg tccaacagct caaccctgcc ttcctataag    540
accgaatatg aggtggaccc ggaaggcctg tgatcctgg aagccagtgt gaacgacata     600
gtcgtactga attccacgct gggctgttat cgctacagct atgtgaaccc aggccaggtc    660
ctcccattga aggggcctga ccagcagacc acaagctgcc tgtggcatct gcaagggccc    720
gaagacctca tgatcaaagt gcggctggag tggaccccggg tcgattgcag agacaggtg    780
gcgatgtacg acgcagctgg gcccctggag aagagactta tcacctccgt ctatgggtgt    840
agccgccagg aacctgtgat ggaggtgctg gcatcgggct ccgtcatggc cgtggtgtgg    900
aaaaagggca tgcatagcta ctatgaccct ttcctgctct cagtgaagtc tgtggccttc    960
caggactgcc aggtgaacct gacactggag ggccggctgg acacacaggg cttcctccgt    1020
acaccctact acccccagtta ctactctccc agtacccact gctcctcacggta            1080
ccctctctgg actacggctt ggcgctctgg ttcgatgcct acgcactgag gaggcagaag    1140
tacaaccgac tgtgtactca gggccagtgg atgatccaga acaggaggct gtgtggcttc    1200
cgtaccctgc agccatatgc tgagaggatc cccatggtgg cctcagatgg tgtcaccatc    1260
aacttcacct cccagatctc cctcacaggc ccggtgtgc aagtgtacta cagcttgtac     1320
aaccaatcag accctgccc tggtgagttc tctgctctg tgaattggact gtgtgtccct    1380
gcgtgtgacg ggatcaagga ctgccccaat ggcctggatg agagaaactg tgtctgcaga    1440
gccatgttcc agtgccaaga ggacagcacg tgcatttcac tgcctagagt ctgtgaccgg    1500
cagcccgact gtctcaatgg cagtgacgaa gaacagtgcc agaaggagt gcctgtggg     1560
acattcactt tccagtgtga ggaccggagc tgtgtgaaga gcccaaccc agagtgtgac    1620
ggcagtgag attgcagaga cggctcagat gagcaacact gtgactgtgg cctccaggc    1680
ctctccagcc gtattgtggg cgggaccgtg tcctccgagg gtgagtggcc atggcaggcc    1740
agcctccaga ttcggggtcg acacatctgt gggggggctc tcatcgctga ccgctgggtc    1800
ataacgccg cccactgctt ccaggaggac agcatgcct cccgaagct gtggaccgtg      1860
ttcctgggaa agatgcggca gaactcgcgc tggccaggcg aggtgtcctt caaggtgagc    1920
cgtctgttcc tgcacccgta ccacgaggag gacagccatg actacgacgt ggccctgctg    1980
```

```
cagctcgacc accccgtggt gtactcggcc actgtgcgcc ccgtctgcct gcctgcccgc    2040
tcccacttct ttgagccagg ccagcactgc tggatcacag gctggggagc ccagcgagag    2100
ggtggtccgg tgagcaacac cctgcagaag gtggacgtac agctggtccc tcaggacctc    2160
tgcagtgagg cctaccgcta ccaggtgtcc ccacgcatgc tctgtgctgg ctaccgcaag    2220
ggcaagaaag atgcctgcca gggtgactct ggaggccgac tggtttgcag ggagcccagt    2280
ggccgctggt tcctggcagg gttgttagc tggggcctgg gctgtggccg acccaatttc    2340
tttggcgtct acacccgtgt cacacgtgtg atcaactgga tccagcaggt gctgacctga    2400
```

SEQ ID NO: 855           moltype = DNA  length = 2403
FEATURE                  Location/Qualifiers
source                   1..2403
                         mol_type = other DNA
                         organism = Macaca mulatta
SEQUENCE: 855
```
atgcctgtgg ccaaggcccc ccaggtggct ggcgggcagg gggacggagg tgatggcgag    60
gaagcggagc cagaggggat gttcgaggcc cgtgaggact ccaagagaaa agcccggggc    120
tacctccgcc tggcgcccct gtggctgacc ctggttgtgc tgacttcagt gggggtgcta    180
ctctggtatt tcctagggta caaggcggag gtgacggtca gccaggtgta ctcaggcagc    240
cttcgcgtgc tcaatcgcca cttctcccag gatcttaccc gccgggaatc cagtgccttc    300
cgcagtgaaa ccgccaaagc ccagaagatg ctcaaggagc tcatcgccag cacccgcctg    360
ggaacttatt acaactccag ctccgtctat tcctttgggg agggaccgct cacctgcttc    420
ttctggttca ttctccaaat ccccgagcac cgccggccag tctgagccc gtggctggtg    480
caggcactgc tggtggagga gctgctgtcc acagtcaaca gctcggcggc cgtccctac    540
agggccgagt acgaagtgga ccccgagggc ctagtgatcc tagaagccag tgtgaaagac    600
atagctgcac tgaattccac gctgggttgt taccgctaca gctacgtggg ccagggtcag    660
gtcctccggc tgaagggacc cgaccacctg gcctccagcc gcctgtgcca cctgcagggc    720
cccgaagacc tcatgctgaa actccggctg gagtggacgc tggccgagtg ccgggaccga    780
ctggccatgt atgacgtggc tgggcccctg gagaagaggc tcatcaccct ggtgtatggc    840
tgcagccgcc aggagcctgt ggtggaagtc ctggcatcgg gggccatcat ggcggtggtc    900
tggaagaagg gcctgcacag ctactacgac cccttttatgc tctccgtgca gtcggtggtc    960
ttccaggcct gcgaggtaaa cctgacgctg gatgacaggc tggactccca gggcgtcctc    1020
agcaccccgt acttccccag ctactactcg ccccgaaccc actgtctctg gcacctcacg    1080
gtgccctctc tggactacgg cttggccctc tggtttgacg cctacgcact gcggaggcag    1140
aagtatgatt tgcgtgcac ccagggcgag tggacgaccg agaacaggag gctgtgtggc    1200
ctgcgcatcc tgcagcctta cgccgagagg atccccgtgg tggccacggc cggcatcacc    1260
atcaatttca cctcccagat ctccctcaca gggcctggtg tgcgggtgca ctatggcttg    1320
tacaaccagt cggaccctg ccctggagag ttcctctgct ctgtgaacgg actctgcgtc    1380
cctgcctgtg atggggtcaa ggactgcccc aacggcctgg atgagagaaa ctgcgtttgc    1440
agagcacat tccagtgcca agaggacagc acgtgcatct cactgcttaa ggtctgtgac    1500
gggcagcctg actgtctcaa tggcagcgat gaagagcggg gccaggaagg ggtgccctgc    1560
gggacattca ccttccagtg tgaggaccag agctgcgtga agaagcccaa cccacagtgt    1620
gatgggcggc ccgactgcag ggacggctca gacgagcagc actgtgactg tggcctccag    1680
ggcccctcca gtcgcattgt tggtggggcc tgtgtcctcca agggtgagtg gccatggcag    1740
gccagcctcc aggttcgggg tcgacacatc tgtgggggcg ccctcatcgc tgaccgctgg    1800
gtgataacag ctgcccattg cttcaggag gacagcatgg cctccccggc gctgtggacg    1860
gtgttcctgg gcaaggtgtg gcagaactcg cgctggcctg gagaggtgtc cttcaaggtg    1920
agccgcctac tcctgcatcc gtatcacgaa gaggacagcc acgactacga tgtcgccctg    1980
ttgcagctcg accaccggt ggtgcgctcg gccgccgtgc gtcccgtctg cctgcccgcg    2040
cgctcccact tcttcgaacc cggcctgcac tgctggatca ctggctgggg cgccctgcgc    2100
gaaggcggcc ccaccagcaa tgctctgcag aaagtggacg tgcagttgat cccacaggac    2160
ctgtgcagcg aggcctatcg ctaccaggtg acgccacgca tgctgtgtgc cggctaccgc    2220
aagggcaaga aggatgcctg ccaggggtgac tcggtggtc cgctggtatg caaggcactc    2280
agtgccgct ggttcctggc agggctggtc agctggggcc tgggctgtgg ccggcctaac    2340
tacttcggcg tctacacccg catcacaggt gtgatcggct ggatccagca agtggtgacc    2400
tga                                                                  2403
```

SEQ ID NO: 856           moltype = RNA  length = 16
FEATURE                  Location/Qualifiers
source                   1..16
                         mol_type = other RNA
                         organism = synthetic construct
SEQUENCE: 856
gcagccgaaa ggctgc                                                    16

SEQ ID NO: 857           moltype = DNA  length = 19
FEATURE                  Location/Qualifiers
source                   1..19
                         mol_type = other DNA
                         organism = synthetic construct
SEQUENCE: 857
agcctgattg tctcaacgg                                                 19

SEQ ID NO: 858           moltype = DNA  length = 20
FEATURE                  Location/Qualifiers
source                   1..20
                         mol_type = other DNA
                         organism = synthetic construct
SEQUENCE: 858
ctggaaggtg aatgtcccac                                                20

```
SEQ ID NO: 859        moltype = DNA  length = 22
FEATURE               Location/Qualifiers
source                1..22
                      mol_type = other DNA
                      organism = synthetic construct
SEQUENCE: 859
acgaagagca gtgccaggaa gg                                                    22

SEQ ID NO: 860        moltype = DNA  length = 21
FEATURE               Location/Qualifiers
source                1..21
                      mol_type = other DNA
                      organism = synthetic construct
SEQUENCE: 860
gtactcaatc gccacttctc c                                                     21

SEQ ID NO: 861        moltype = DNA  length = 21
FEATURE               Location/Qualifiers
source                1..21
                      mol_type = other DNA
                      organism = synthetic construct
SEQUENCE: 861
gaatagacgg agctggagtt g                                                     21

SEQ ID NO: 862        moltype = DNA  length = 22
FEATURE               Location/Qualifiers
source                1..22
                      mol_type = other DNA
                      organism = synthetic construct
SEQUENCE: 862
cagtgaaacc gccaaagccc ag                                                    22
```

COMPOSITIONS AND METHODS FOR INHIBITING TRANSMEMBRANE SERINE PROTEASE 6 (TMPRSS6) EXPRESSION

CROSS-REFERENCE TO RELATED APPLICATIONS

This application claims priority under 35 U.S.C. § 119 to U.S. Provisional Application No. 63/355,210, filed Jun. 24, 2022 and European Patent Application 22209113.4, filed Nov. 23, 2022; the contents of which are incorporated herein by reference.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Jun. 1, 2023, is named "210088US02", and is 1,590 kilobytes in size.

BACKGROUND

Iron is a micronutrient that is a biologically essential component of every living organism. It is required for an adequate erythropoietic function, oxidative metabolism, cellular immune response, and numerous other cellular processes. In its free form, iron is involved in oxidation-reduction reactions, leading to the formation of free radicals, oxidative stress which may lead to organ damage. Living organisms have developed protein systems to transport free iron through the cell membranes and biological fluids and store it in a non-toxic and readily mobilizable form to avoid iron toxicity. In the human body, iron mainly exists in complex forms bound to protein as heme compounds, heme enzymes, or nonheme compounds. Iron absorption occurs by the enterocytes by divalent metal transport 1 and takes place in the duodenum and upper jejunum. Iron is then transferred across the he duodenal mucosa into the blood, where it is transported by transferrin to the cells or the bone marrow for erythropoiesis. Since iron is required for a number of diverse cellular functions, a constant balance between iron uptake, transport, storage, and utilization is required to maintain iron homeostasis. Hepcidin, a circulating peptide hormone encoded by the HAMP gene, is secreted by the liver that plays a crucial role in maintaining iron homeostasis. Hepcidin expression is directly regulated by variations in iron intake and its repression leads to an increase in bioavailable serum iron level. Hepcidin blocks iron flux into the plasma by its direct binding to ferroportin, the principal iron exporter localized at the cell membrane of duodenal enterocytes, which absorb iron from the diet, and macrophages, which recycle iron from senescent erythrocytes. Hepcidin binding to ferroportin triggers its internalization and subsequent lysosomal degradation, thereby blocking iron export to the circulatory system. Hepatic hepcidin expression is regulated by three independent pathways, where inflammation (inflammatory cytokines) and high serum iron levels result in hepcidin upregulation, whereas it is downregulated by elevated erythropoiesis facilitating high iron demand for red blood cell production. Put differently, when hepcidin levels are high, serum iron levels decrease which can result in anemia. When hepcidin levels are low, in disease states such as hemochromatosis, iron levels rise and overload can occur.

In pathological situations, prolonged repression of hepcidin often leads to primary iron overload, due to its malfunctional expression as a result of loss of function in the plasma iron-sensing signalling pathway (e.g. hereditary hemochromatosis). In situations of elevated, but dysfunctional erythropoiesis (e.g. beta thalassemia), hepcidin is down regulated resulting in secondary iron overload. The pathophysiological consequences of primary and secondary iron overload are common resulting in built-up of free plasma iron, accumulation in organs causing damage at disease progression.

TMPRSS6 (transmembrane Protease, Serine 6) encodes a type II serine protease and is expressed mainly in the liver. TMPRSS6 participates in a transmembrane signaling pathway triggered by iron deficiency and suppresses diverse pathways of the HAMP activation, the gene that encodes hepcidin.

Studies show that upregulation of hepcidin ameliorate abnormal erythropoiesis and prevents or limits iron overload in mouse models of β-thalassemia intermedia and hereditary hemochromatosis (Gardenghi et al. J. Clin. Invest., 2010; Guo et al., J. Clin. Invest., 2013, Schmidt et al. Blood 2013; Casu et al. Blood 2016; Ramos et al. Blood 2012). HFE-associated hereditary hemochromatosis is the most common type of inherited iron overload disorder, with a high prevalence of the p.C282Y mutation in northern European populations (Alexander and Kowdley, Genetics in Medicine, 2009). It is thought that impaired hepcidin production in the liver leads to iron overload in HFE-associated hemochromatosis. Iron overload in this context often leads to complications such as liver cirrhosis and diabetes, as well as failure of other affected organs.

Consistent with its role in suppressing hepcidin expression, mutations in TMPRSS6 result in disorders such as iron-refractory, iron-deficient anemia. Hepcidin expression is significantly elevated in TMPRSS6-/- mice and reduction of TMPRSS6 in Hfe-/- mice could ameliorate the iron overload phenotype (Du et al. Science 2008; Folgueras et al. Blood 2008; Finberg K E et al., Blood, 2011).

Such evidence suggests a role for targeting TMPRSS6 in the treatment of diseases associated with iron overload. Current treatment options for such diseases are limited. Accordingly, methods for effective treatment of disorders associated with iron overload are currently needed and the present invention addresses this need.

SUMMARY OF DISCLOSURE

The present disclosure is based, in part, on the discovery of oligonucleotides (e.g., RNAi oligonucleotides) that reduce TMPRSS6 expression in vitro and in vivo. Aberrant expression of TMPRSS6 has been shown to be associated with altered hepcidin expression and serum iron levels. As demonstrated herein, serum iron and serum iron saturation are reduced in vivo following administration of TMPRSS6 RNAi oligonucleotides. Without being bound by theory, inhibition of TMPRSS6 increases hepcidin expression and subsequently reduces serum iron levels preventing iron overload. Therefore, without wishing to be bound by theory, oligonucleotides targeting TMPRSS6 are useful for treating diseases or disorders associated with hepcidin deficiency or suppression.

Accordingly, in some aspects, the present disclosures provides an RNAi oligonucleotide for reducing transmembrane serine protease 6 (TMPRSS6) expression, the oligonucleotide comprising a sense strand and an antisense strand, wherein the sense strand and the antisense strand form a duplex region, wherein the antisense strand comprises a region of complementarity to a TMPRSS6 mRNA target sequence of any one of SEQ ID NOs: 661-852, and wherein the region of complementarity is at least 15 contiguous nucleotides in length.

In some embodiments the sense strand is 15 to 50 nucleotides in length. In some embodiments, the sense strand is 18 to 36 nucleotides in length.

In some embodiments, the antisense strand is 15 to 30 nucleotides in length.

In some embodiments, the antisense strand is 22 nucleotides in length and the antisense strand and the sense strand form a duplex region of at least 19 nucleotides in length, optionally at least 20 nucleotides in length. In some embodiments, the region of complementarity is at least 19 contiguous nucleotides in length. In some embodiments, the region of complementarity is at least 20 contiguous nucleotides in length.

In some aspects, the disclosure provides a double stranded RNAi oligonucleotide for reducing TMPRSS6 expression, the oligonucleotide comprising:
(i) an antisense strand of 19-30 nucleotides in length, wherein the antisense strand comprises a nucleotide sequence comprising a region of complementarity to a TMPRSS6 mRNA target sequence, wherein the region of complementarity is selected from SEQ ID NOs: 1-192, and
(ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some aspects, the disclosure provides a double stranded RNAi oligonucleotide for reducing TMPRSS6 expression, the oligonucleotide comprising:
(i) an antisense strand of 19-30 nucleotides in length, wherein the antisense strand comprises a nucleotide sequence selected from SEQ ID NOs: 1-192, and wherein the antisense strand is complementary a TMPRSS6 mRNA target sequence, and
(ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, the 3' end of the sense strand comprises a stem-loop set forth as S1-Lp-S2, wherein S1 is complementary to S2, and wherein Lp forms a loop between S1 and S2 of 3-5 nucleotides in length. In some embodiments, Lp is a triloop or a tetraloop. In some embodiments, Lp is a tetraloop. In some embodiments, the tetraloop comprises the sequence 5'-GAAA-3'. In some embodiments, the S1 and S2 are 1-10 nucleotides in length and have the same length. In some embodiments, S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length. In some embodiments, S1 and S2 are 6 nucleotides in length. In some embodiments, the stem-loop comprises the sequence 5'-GCAGCCGAAAGGCUGC-3' (SEQ ID NO: 856).

In some embodiments, the sense strand, proximal to the 3' end of the sense strand, comprises a stem-loop set forth as S1-Lp-S2, wherein S1 is complementary to S2, and wherein Lp forms a loop between S1 and S2 of 3-5 nucleotides in length. In some embodiments, Lp is a triloop or a tetraloop.

In some embodiments, Lp is a tetraloop. In some embodiments, the tetraloop comprises the sequence 5'-GAAA-3'. In some embodiments, the S1 and S2 are 1-10 nucleotides in length and have the same length. In some embodiments, S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length. In some embodiments, S1 and S2 are 6 nucleotides in length. In some embodiments, the stem-loop comprises the sequence 5'-GCAGCCGAAAGGCUGC-3' (SEQ ID NO: 856).

In some embodiments, the antisense strand comprises a 3' overhang sequence of one or more nucleotides in length. In some embodiments, the overhang comprises purine nucleotides. In some embodiments, the 3' overhang sequence is 2 nucleotides in length. In some embodiments, the 3' overhang is selected from AA, GG, AG, and GA. In some embodiments, the overhang is GG or AA. In some embodiments, the overhang is GG.

In some embodiments, the oligonucleotide comprises at least one modified nucleotide. In some embodiments, the modified nucleotide comprises a 2'-modification. In some embodiments, the 2'-modification is a modification selected from 2'-aminoethyl, 2'-fluoro, 2'-O-methyl, 2'-O-methoxyethyl, and 2'-deoxy-2'-fluoro-6-d-arabinonucleic acid. In some embodiments, the modification is a 2'-modification selected from 2'-fluoro and 2'-O-methyl. In some embodiments, about 10-15%, 10%, 11%, 12%, 13%, 14% or 15% of the nucleotides of the sense strand comprise a 2'-fluoro modification. In some embodiments, about 25-35%, 25%, 26%, 27%, 28%, 29%, 30%, 31%, 32%, 33%, 34% or 35% of the nucleotides of the antisense strand comprise a 2'-fluoro modification. In some embodiments, about 25-35%, 25%, 26%, 27%, 28%, 29%, 30%, 31%, 32%, 33%, 34% or 35% of the nucleotides of the oligonucleotide comprise a 2'-fluoro modification. In some embodiments, the sense strand comprises 36 nucleotides with positions 1-36 from 5' to 3', wherein positions 8-11 comprise a 2'-fluoro modification. In some embodiments, the antisense strand comprises 22 nucleotides with positions 1-22 from 5' to 3', and wherein positions 2, 3, 4, 5, 7, 10 and 14 comprise a 2'-fluoro modification.

In some embodiments, the oligonucleotide comprises at least one modified internucleotide linkage. In some embodiments, the at least one modified internucleotide linkage is a phosphorothioate linkage. In some embodiments, the antisense strand comprises a phosphorothioate linkage (i) between positions 1 and 2, and between positions 2 and 3; or (ii) between positions 1 and 2, between positions 2 and 3, and between positions 3 and 4, wherein positions are numbered 1-4 from 5' to 3'. In some embodiments, the antisense strand is 22 nucleotides in length, and wherein the antisense strand comprises a phosphorothioate linkage between positions 20 and 21 and between positions 21 and 22, wherein positions are numbered 1-22 from 5' to 3'. In some embodiments, the antisense strand is 22 nucleotides in length, and wherein the antisense strand comprises a phosphorothioate linkage between positions 1 and 2, between positions 2 and 3, positions 3 and 4, positions 20 and 21, and positions 21 and 22. In some embodiments, the sense strand comprises a phosphorothioate linkage between positions 1 and 2, wherein positions are numbered 5' to 3'.

In some embodiments, the 4'-carbon of the sugar of the 5'-nucleotide of the antisense strand comprises a phosphate analog. In some embodiments, the phosphate analog is oxymethyl phosphonate, vinyl phosphonate or malonyl phosphonate, optionally wherein the phosphate analog is a 4'-phosphate analog comprising 4'-oxymethylphosphonate.

In some embodiments, at least one nucleotide of the oligonucleotide is conjugated to one or more targeting ligands. In some embodiments, each targeting ligand comprises a carbohydrate, amino sugar, cholesterol, or polypeptide. In some embodiments, the stem loop comprises one or more targeting ligands conjugated to one or more nucleotides of the stem loop. In some embodiments, the one or more targeting ligands is conjugated to one or more nucleotides of the loop. In some embodiments, the loop comprises 4 nucleotides numbered 1-4 from 5' to 3', wherein nucleotides at positions 2, 3, and 4 each comprise one or more targeting ligands, wherein the targeting ligands are the same or different. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety or a tetravalent GalNAc moiety. In some embodiments, up to 4 nucleotides of Lp of the stem-loop are each conjugated to a monovalent GalNAc moiety.

In some embodiments, the region of complementarity is fully complementary to the mRNA target sequence. In some embodiments, the region of complementarity is partially complementary to the mRNA target sequence. In some embodiments, the region of complementarity comprises no more than four mismatches to the mRNA target sequence.

In some embodiments, the region of complementarity is fully complementary to the TMPRSS6 mRNA target sequence at nucleotide positions 2-8 of the antisense strand, wherein nucleotide positions are numbered 5' to 3'. In some embodiments, the region of complementarity is fully complementary to the TMPRSS6 mRNA target sequence at nucleotide positions 2-11 of the antisense strand, wherein nucleotide positions are numbered 5' to 3'.

In some embodiments, the sense strand comprises a nucleotide sequence of any one of SEQ ID NOs: 579-580, 585-587, 590 and 595-597. In some embodiments, the antisense strand comprises a nucleotide sequence of any one of SEQ ID NOs: 600-601, 606-608, 611 and 616-618.

In some embodiments, the sense strand and antisense strands comprise nucleotide sequences selected from the group consisting of:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively.

In some embodiments, the sense strand and antisense strands comprise nucleotide sequences selected from the group consisting of:
  a) SEQ ID NOs: 579 and 600, respectively;
  b) SEQ ID NOs: 580 and 601, respectively;
  c) SEQ ID NOs: 590 and 611, respectively;
  d) SEQ ID NOs: 597 and 618, respectively; and,
  e) SEQ ID NOs: 586 and 607, respectively.

In some embodiments, the sense strand comprises a nucleotide sequence as set forth in SEQ ID NO: 579, and the antisense strand comprises a nucleotide sequence as set forth in SEQ ID NO: 600. In some embodiments, the sense strand comprises a nucleotide sequence as set forth in SEQ ID NO: 580, and the antisense strand comprises a nucleotide sequence as set forth in SEQ ID NO: 601. In some embodiments, the sense strand comprises a nucleotide sequence as set forth in SEQ ID NO: 590, and the antisense strand comprises a nucleotide sequence as set forth in SEQ ID NO: 611. In some embodiments, the sense strand comprises a nucleotide sequence as set forth in SEQ ID NO: 597, and the antisense strand comprises a nucleotide sequence as set forth in SEQ ID NO: 618. In some embodiments, the sense strand comprises a nucleotide sequence as set forth in SEQ ID NO: 586, and the antisense strand comprises a nucleotide sequence as set forth in SEQ ID NO: 607.

In some embodiments, the antisense strand is 22 nucleotides in length.

In some embodiments, the antisense strand comprises a nucleotide sequence selected from SEQ ID NOs: 600-601, 606-608, 611, and 616-618.

In some embodiments, the sense strand is 36 nucleotides in length.

In some embodiments, the sense strand comprises a nucleotide sequence selected from SEQ ID NOs: 579-580, 585-587, 590, and 595-597.

In some embodiments, the sense strand and antisense strands comprise nucleotide sequences selected from the group consisting of:
  a) SEQ ID NOs: 621 and 642, respectively;
  b) SEQ ID NOs: 622 and 643, respectively;
  c) SEQ ID NOs: 637 and 658, respectively;
  d) SEQ ID NOs: 632 and 653, respectively;
  e) SEQ ID NOs: 638 and 659, respectively;
  f) SEQ ID NOs: 639 and 660, respectively;
  g) SEQ ID NOs: 627 and 648, respectively;
  h) SEQ ID NOs: 628 and 649, respectively; and,
  i) SEQ ID NOs: 629 and 650, respectively.

In some embodiments, the sense strand and antisense strands comprise nucleotide sequences selected from the group consisting of:
  a) SEQ ID NOs: 621 and 642, respectively;
  b) SEQ ID NOs: 622 and 643, respectively;
  c) SEQ ID NOs: 632 and 653, respectively;
  d) SEQ ID NOs: 639 and 660, respectively; and,
  e) SEQ ID NOs: 628 and 649, respectively.

In some embodiments, the sense strand comprises a nucleotide sequence as set forth in SEQ ID NO: 621, and the antisense strand comprises a nucleotide sequence as set forth in SEQ ID NO: 642. In some embodiments, the sense strand comprises a nucleotide sequence as set forth in SEQ ID NO: 622, and the antisense strand comprises a nucleotide sequence as set forth in SEQ ID NO: 643. In some embodiments, the sense strand comprises a nucleotide sequence as set forth in SEQ ID NO: 632, and the antisense strand comprises a nucleotide sequence as set forth in SEQ ID NO: 653. In some embodiments, the sense strand comprises a nucleotide sequence as set forth in SEQ ID NO: 639, and the antisense strand comprises a nucleotide sequence as set forth in SEQ ID NO: 660. In some embodiments, the sense strand comprises a nucleotide sequence as set forth in SEQ ID NO: 628, and the antisense strand comprises a nucleotide sequence as set forth in SEQ ID NO: 649.

In some aspects, the disclosure provides an RNAi oligonucleotide for reducing TMPRSS6 expression, the oligonucleotide comprising a sense strand and an antisense strand, wherein the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621), and wherein the antisense strand comprises the sequence and all of the modifications of 5' [MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642), wherein mC, mA, mG, mU=2'-OMe ribonucleosides; fA, fC, fG, fU=2'-F ribonucleosides; s=phosphorothioate, and wherein ademA-GalNAc=

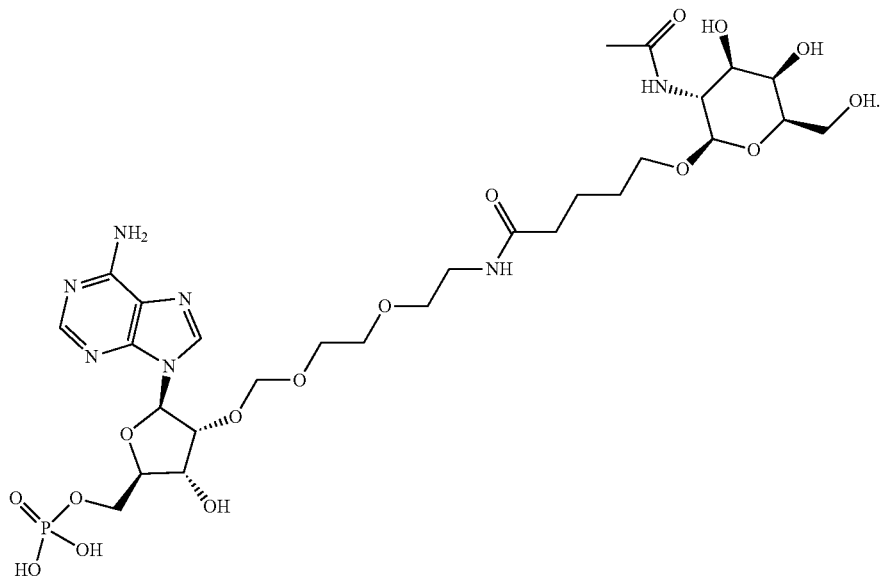 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

In some aspects, the disclosure provides an RNAi oligonucleotide for reducing TMPRSS6 expression, the oligonucleotide comprising a sense strand and an antisense strand, wherein the sense strand comprises the sequence and all of the modifications of 5' [mGs][mC][mU][mA][mC][mU][mC][fU][fG][fG][fU][mA][mU][mU][mU][mC][mC][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 622), and wherein the antisense strand comprises the sequence and all of the modifications of 5' [MePhosphonate-4O-mUs][f Us][fAs][fG][fG][mA][fA][mA][mU][fA][mC][mC][mA][fG][mA][mG][mU][mA][mG][mCs][mGs][mG]-3' (SEQ ID NO: 643), wherein mC, mA, mG, mU=2'-OMe ribonucleosides; fA, fC, fG, fU=2'-F ribonucleosides; s=phosphorothioate, and wherein ademA-GalNAc=

In some aspects, the disclosure provides an RNAi oligonucleotide for reducing TMPRSS6 expression, the oligonucleotide comprising a sense strand and an antisense strand, wherein the sense strand comprises the sequence and all of the modifications of 5'-[mCs][mU][mC][mA][mC][mC][mU][fG][fC][fU][fU][mC][mU][mU][mC][mU][mG][mG][mU][mA][mG][mC][mA][mG][mC][mC][mG][ademA-GalNAc][ademA-GalNAc][ademA-GalNAc][mG][mG][mC][mU][mG][mC]-3' (SEQ ID NO: 632), and wherein the antisense strand comprises the sequence and all of the modifications of 5'-[MePhosphonate-4O-mUs][fAs][fCs][fC][fA][mG][fA][mA][mG][fA][mA][mG][mC][fA][mG][mG][mU][mG][mA][mGs][mGs][mG]-3' (SEQ ID NO: 653), wherein mC, mA, mG, mU=2'-OMe ribonucleosides; fA, fC, fG, fU=2'-F ribonucleosides; s=phosphorothioate, and wherein ademA-GalNAc=

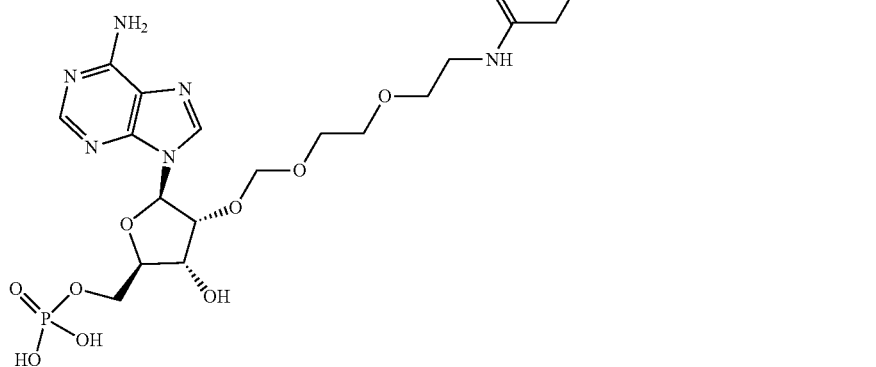

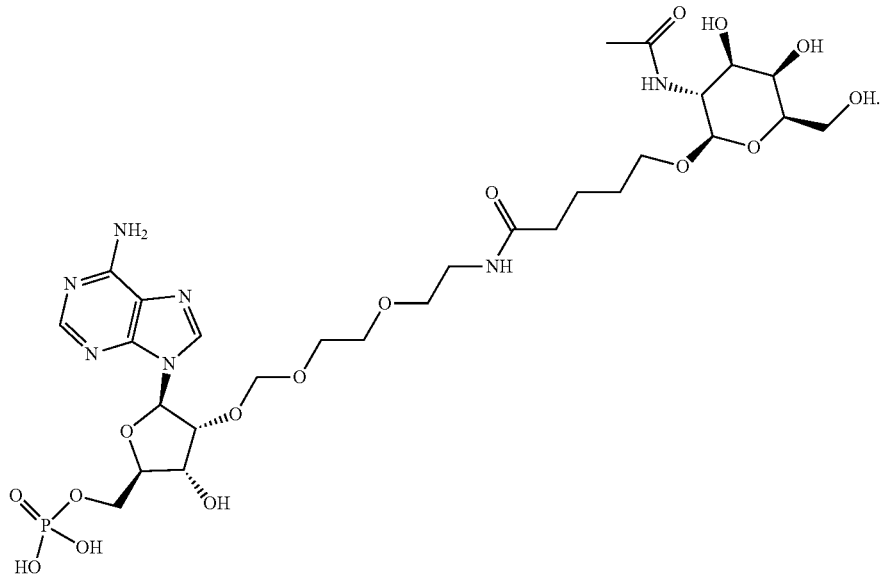 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

In some aspects, the disclosure provides an RNAi oligonucleotide for reducing TMPRSS6 expression, the oligonucleotide comprising a sense strand and an antisense strand, wherein the sense strand comprises the sequence and all of the modifications of 5'-[mAs][mG][mU][mG][mU][mG][mA][fA][fA][fG][fA][mC][mA][mU][mA][mG][mC][mU][mG][mA][mG][mC][mA][mG][mC][mC][mG][ademA-GalNAc][ademA-GalNAc][ademA-GalNAc][mG][mG][mC][mU][mG][mC]3' (SEQ ID NO: 639), and wherein the antisense strand comprises the sequence and all of the modifications of 5'-[MePhosphonate-4O-mUs][fCs][fAs][fG][fC][mU][fA][mU][mG][fU][mC][mU][mU][fU][mC][mA][mC][mA][mC][mUs][mGs][mG]-3' (SEQ ID NO: 660), wherein mC, mA, mG, mU=2'-OMe ribonucleosides; fA, fC, fG, fU=2'-F ribonucleosides; s=phosphorothioate, and wherein ademA-GalNAc=

In some aspects, the disclosure provides an RNAi oligonucleotide for reducing TMPRSS6 expression, the oligonucleotide comprising a sense strand and an antisense strand, wherein the sense strand comprises the sequence and all of the modifications of 5'-[mGs][mG][mG][mU][mG][mC][mA][fC][fU][fA][fU][mG][mG][mC][mU][mU][mG][mU][mA][mA][mG][mC][mA][mG][mC][mC][mG][ademA-GalNAc][ademA-GalNAc][ademA-GalNAc][mG][mG][mC][mU][mG][mC]3' (SEQ ID NO: 628), and wherein the antisense strand comprises the sequence and all of the modifications of 5'-[MePhosphonate-4O-mUs][fUs][fAs][fC][fA][mA][fG][mC][mC][fA][mU][mA][mG][fU][mG][mC][mA][mC][mC][mCs][mGs][mG]-3' (SEQ ID NO: 649), wherein mC, mA, mG, mU=2'-OMe ribonucleosides; fA, fC, fG, fU=2'-F ribonucleosides; s=phosphorothioate, and wherein ademA-GalNAc=

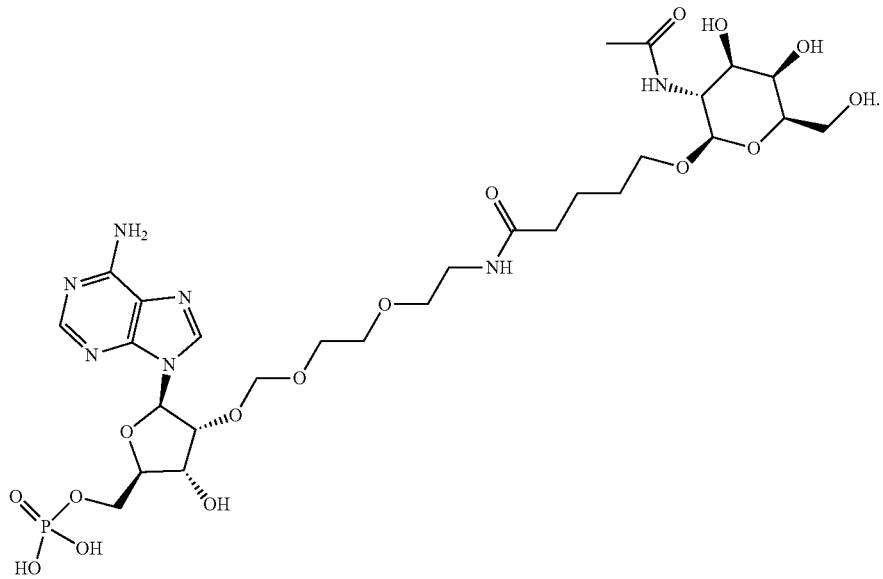 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]

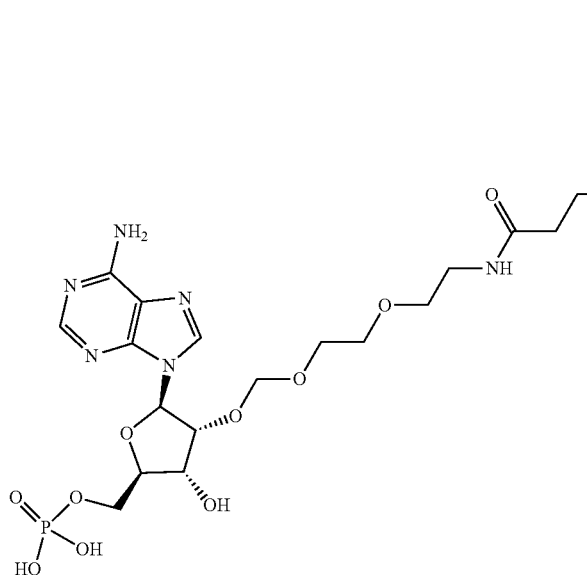

In some aspects, the disclosure provides an RNAi oligonucleotide for reducing TMPRSS6 expression, the oligonucleotide comprising a sense strand and an antisense strand, wherein the sense strand comprises SEQ ID NO: 621 and the antisense strand comprises SEQ ID NO: 642, the antisense strand comprising a region of complementarity to a TMPRSS6 RNA transcript, wherein said RNAi is in the form of a conjugate having the structure as shown in FIG. 14A.

In some aspects, the disclosure provides an RNAi oligonucleotide for reducing TMPRSS6 expression, the oligonucleotide comprising a sense strand and an antisense strand, wherein the sense strand comprises SEQ ID NO: 632 and the antisense strand comprises SEQ ID NO: 653, the antisense strand comprising a region of complementarity to a TMPRSS6 RNA transcript, wherein said RNAi is in the form of a conjugate having the structure as shown in FIG. 14B.

In some aspects, the disclosure provides an RNAi oligonucleotide for reducing TMPRSS6 expression, the oligonucleotide comprising a sense strand and an antisense strand, wherein the sense strand comprises SEQ ID NO: 639 and the antisense strand comprises SEQ ID NO: 660, the antisense strand comprising a region of complementarity to a TMPRSS6 RNA transcript, wherein said RNAi is in the form of a conjugate having the structure as shown in FIG. 14C.

In some aspects, the disclosure provides an RNAi oligonucleotide for reducing TMPRSS6 expression, the oligonucleotide comprising a sense strand and an antisense strand, wherein the sense strand comprises SEQ ID NO: 628 and the antisense strand comprises SEQ ID NO: 649, the antisense strand comprising a region of complementarity to a TMPRSS6 RNA transcript, wherein said RNAi is in the form of a conjugate having the structure as shown in FIG. 14D.

In some aspects, the disclosure provides an RNAi oligonucleotide for reducing TMPRSS6 expression, the oligonucleotide comprising a sense strand and an antisense strand, wherein the sense strand comprises SEQ ID NO: 621 and the antisense strand comprises SEQ ID NO: 642, the antisense strand comprising a region of complementarity to a TMPRSS6 RNA transcript, wherein said RNAi is in the form of a conjugate having the structure as shown in FIGS. 10A-B.

In some aspects, the disclosure provides an RNAi oligonucleotide for reducing TMPRSS6 expression, the oligonucleotide comprising a sense strand and an antisense strand, wherein the sense strand comprises SEQ ID NO: 632 and the antisense strand comprises SEQ ID NO: 653, the antisense strand comprising a region of complementarity to a TMPRSS6 RNA transcript, wherein said RNAi is in the form of a conjugate having the structure as shown in FIGS. 11A-B.

In some aspects, the disclosure provides an RNAi oligonucleotide for reducing TMPRSS6 expression, the oligonucleotide comprising a sense strand and an antisense strand, wherein the sense strand comprises SEQ ID NO: 639 and the antisense strand comprises SEQ ID NO: 660, the antisense strand comprising a region of complementarity to a TMPRSS6 RNA transcript, wherein said RNAi is in the form of a conjugate having the structure as shown in FIGS. 12A-B.

In some aspects, the disclosure provides an RNAi oligonucleotide for reducing TMPRSS6 expression, the oligonucleotide comprising a sense strand and an antisense strand, wherein the sense strand comprises SEQ ID NO: 628 and the antisense strand comprises SEQ ID NO: 649, the antisense strand comprising a region of complementarity to a TMPRSS6 RNA transcript, wherein said RNAi is in the form of a conjugate having the structure as shown in FIGS. 13A-B.

In some embodiments, the disclosure provides a pharmaceutical composition comprising an RNAi oligonucleotide described herein, and a pharmaceutically acceptable carrier, delivery agent or excipient.

In some embodiments, the disclosure provides a method for treating a subject having a disease, disorder or condition associated with hepcidin deficiency or suppression, the method comprising administering to the subject a therapeutically effective amount of an RNAi oligonucleotide or pharmaceutical composition described herein, thereby treating the subject.

In some embodiments, hepcidin expression is increased after administering the RNAi oligonucleotide. In some embodiments, iron saturation levels in the serum are decreased after administering the RNAi oligonucleotide. In some embodiments, serum iron levels are decreased after administering the RNAi oligonucleotide.

In some embodiments, the disclosure provides a method of delivering an oligonucleotide to a subject, the method comprising administering a pharmaceutical composition described herein to the subject.

In some embodiments, the disclosure provides a method for reducing TMPRSS6 expression in a cell, a population of cells or a subject, the method comprising the step of:
 i. contacting the cell or the population of cells with an RNAi oligonucleotide described herein, or a pharmaceutical composition described herein; or
 ii. administering to the subject an RNAi oligonucleotide described herein, or a pharmaceutical composition described herein.

In some embodiments, reducing TMPRSS6 expression comprises reducing an amount or level of TMPRSS6 mRNA, an amount or level of matriptase-2 protein, or both. In some embodiments, reducing TMPRSS6 expression results in an increase in hepcidin production. In some embodiments, reducing TMPRSS6 expression results in a decrease in serum iron levels. In some embodiments, reducing TMPRSS6 expression results in a decrease in serum iron saturation.

In some embodiments, the subject has a disease, disorder or condition associated with hepcidin deficiency or suppression. In some embodiments, the disease, disorder or condition associated with hepcidin deficiency is hemochromatosis or beta-thalassemia. In some embodiments, the disease, disorder or condition associated with hepcidin suppression is polycythemia vera.

In some embodiments, the RNAi oligonucleotide, or pharmaceutical composition, is administered in combination with a second composition or therapeutic agent.

In some embodiments, the disclosure provides use of an RNAi oligonucleotide or
pharmaceutical composition described herein, in the manufacture of a medicament for the treatment of a disease, disorder or condition associated with hepcidin deficiency or suppression, optionally for the treatment of hemochromatosis (e.g. hereditary hemochromatosis), polycythaemia vera or beta-thalassemia.

In some embodiments, the disclosure provides an RNAi oligonucleotide or pharmaceutical composition described herein, for use, or adaptable for use, in the treatment of a disease, disorder or condition associated with hepcidin deficiency or suppression, optionally for the treatment of hemochromatosis (e.g. hereditary hemochromatosis), polycythaemia vera or beta-thalassemia.

In some embodiments, the disclosure provides a kit comprising an RNAi oligonucleotide described herein, an optional pharmaceutically acceptable carrier, and a package insert comprising instructions for administration to a subject having a disease, disorder or condition associated with hepcidin deficiency or suppression.

In some embodiments, the disclosure provides an RNAi oligonucleotide or pharmaceutical composition for use, or adaptable for use, or a kit described herein, wherein the disease, disorder or condition associated with hepcidin deficiency or suppression is hemochromatosis (e.g. hereditary hemochromatosis), polycythaemia vera or beta-thalassemia.

BRIEF DESCRIPTION OF DRAWINGS

FIGS. 3A-3D provide schematics depicting the modification patterns of GalNAc-conjugated TMPRSS6 oligonucleotides-0416 (FIG. 3A), -0651 (FIG. 3B), -0831 (FIG. 3C), and -1546 (FIG. 3D). The sense strand includes a tetraloop structure of nucleotides 27-30 of the 36-nucleotide strand. The antisense strand is complementary and includes a 2-nucleotide overhang.

DESCRIPTION

Figure 1A:
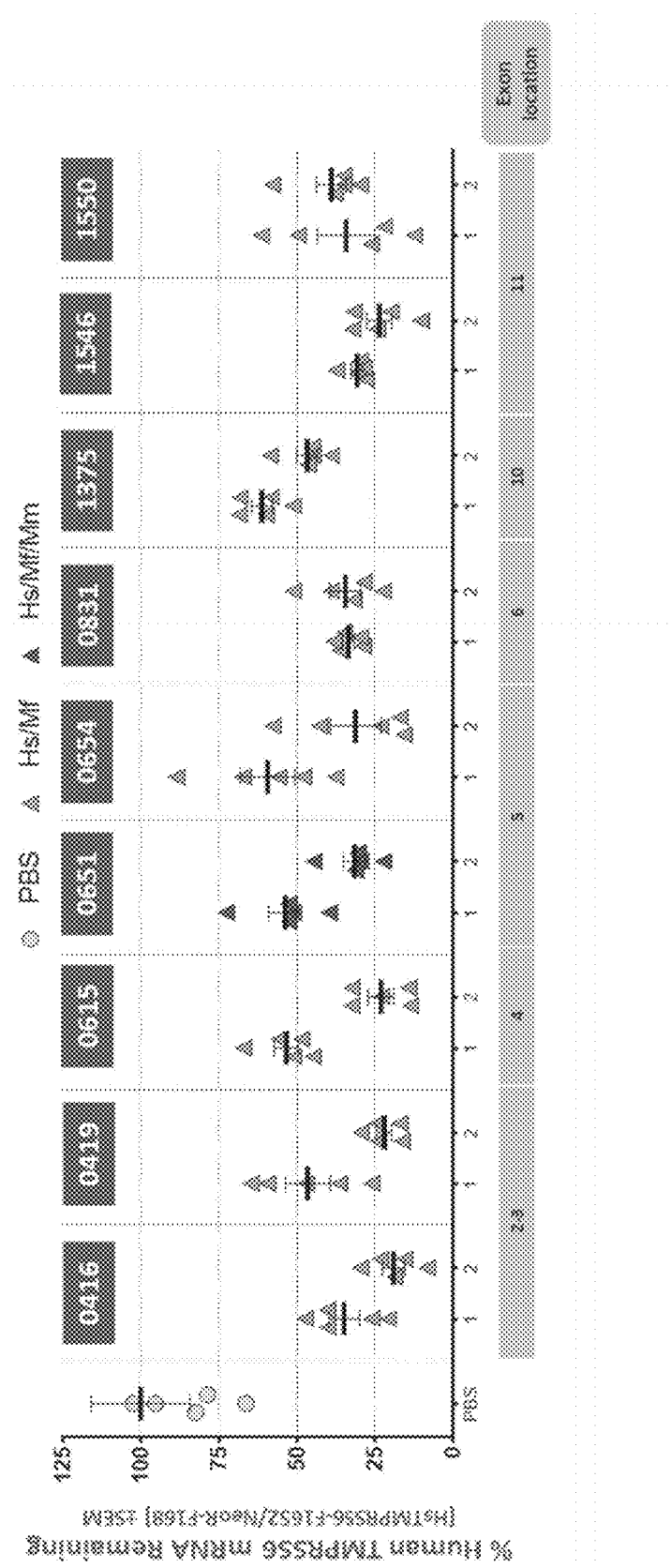
FIGS. 1A and 1B provide graphs depicting the percent (%) of human TMPRSS6 mRNA remaining in the liver of mice exogenously expressing human TMPRSS6 (hydrodynamic injection model) after treatment with GalNAc-conjugated TMPRSS6 oligonucleotides. CD-1 mice were dosed subcutaneously with 1 mg/kg or 2 mg/kg of the indicated GalNAc-conjugated TMPRSS6 oligonucleotide formulated in PBS. Four days post-dose mice were hydrodynamically injected (HDI) with a DNA plasmid encoding human TMPRSS6. The level of human TMPRSS6 mRNA was determined from livers collected 18 hours later using a 3' qPCR assay (FIG. 1A) and a 5' qPCR assay (FIG. 1B). Hs/Mf=construct is human and monkey TMPRSS6 specific; Hs-Mf-Mm=construct is human, monkey, and murine TMPRSS6 specific.

Transmembrane Serine Protease 6 (TMPRSS6) encodes the type II transmembrane serine proteinase, matriptase-2, located on the surface of cells. The matriptase-2 protein functions in iron homeostasis by regulating hepcidin.

According to some aspects, the disclosure provides oligonucleotides (e.g., RNAi oligonucleotides) that reduce TMPRSS6 expression in the liver. In some embodiments, the oligonucleotides provided herein are designed to treat diseases associated with hepcidin deficiency or suppression. In some respects, the disclosure provides methods of treating a disease associated with hepcidin deficiency or suppression by reducing TMPRSS6 expression in specific cells (e.g., cells of the liver) or in organs (e.g., liver).

Oligonucleotide Inhibitors of TMPRSS6 Expression
TMPRSS6 Target Sequences

In some embodiments, an oligonucleotide herein (e.g., an RNAi oligonucleotide) is targeted to a target sequence comprising a TMPRSS6 mRNA. In some embodiments, an oligonucleotide described herein is targeted to a target sequence within a TMPRSS6 mRNA sequence. In some embodiments, the oligonucleotide described herein corresponds to a target sequence within a TMPRSS6 mRNA sequence. In some embodiments, the oligonucleotide, or a portion, fragment, or strand thereof (e.g., an antisense strand or a guide strand of a double-stranded (ds) RNAi oligonucleotide) binds or anneals to a target sequence comprising TMPRSS6 mRNA, thereby inhibiting TMPRSS6 expression.

In some embodiments, the oligonucleotide is targeted to a TMPRSS6 target sequence for the purpose of inhibiting TMPRSS6 expression in vivo. In some embodiments, the amount or extent of inhibition of TMPRSS6 expression by an oligonucleotide targeted to a TMPRSS6 target sequence correlates with the potency of the oligonucleotide. In some embodiments, the amount or extent of inhibition of TMPRSS6 expression by an oligonucleotide targeted to a TMPRSS6 target sequence correlates with the amount or extent of therapeutic benefit in a subject or patient having a disease, disorder or condition associated with hepcidin deficiency or suppression treated with the oligonucleotide.

Through examination of the nucleotide sequence of mRNAs encoding TMPRSS6, including mRNAs of multiple different species (e.g., human, cynomolgus monkey, and mouse; see, e.g., Example 2) and as a result of in vitro and in vivo testing (see, e.g., Examples 2-5), it has been discovered that certain nucleotide sequences of TMPRSS6 mRNA are more amenable than others to oligonucleotide-based inhibition and are thus useful as target sequences for the oligonucleotides herein. In some embodiments, a TMPRSS6 target sequence comprises, or consists of, a sequence of any one of SEQ ID NOs: 661-852. In some embodiments, a TMPRSS6 target sequence comprises, or consists of, the sequence set forth in SEQ ID NO: 844, 841, 818, 794 or 762. In some embodiments, a TMPRSS6 target sequence comprises, or consists of, the sequence set forth in SEQ ID NO: 844. In some embodiments, a TMPRSS6 target sequence comprises, or consists of, the sequence set forth in SEQ ID NO: 841. In some embodiments, a TMPRSS6 target sequence comprises, or consists of, the sequence set forth in SEQ ID NO: 818. In some embodiments, a TMPRSS6 target sequence comprises, or consists of, the sequence set forth in SEQ ID NO: 794. In some embodiments, a TMPRSS6 target sequence comprises, or consists of, the sequence set forth in SEQ ID NO: 762.

TMPRSS6 Targeting Sequences

In some embodiments, the oligonucleotides herein (e.g., RNAi oligonucleotides) have regions of complementarity to TMPRSS6 mRNA (e.g., within a target sequence of TMPRSS6 mRNA) for purposes of targeting the TMPRSS6 mRNA in cells and inhibiting and/or reducing TMPRSS6 expression. In some embodiments, the oligonucleotides herein comprise a TMPRSS6 targeting sequence (e.g., an antisense strand or a guide strand of an RNAi oligonucleotide) having a region of complementarity that binds or anneals to a TMPRSS6 target sequence by complementary (Watson-Crick) base pairing. The targeting sequence or region of complementarity is generally of a suitable length and base content to enable binding or annealing of the oligonucleotide (or a strand thereof) to a TMPRSS6 mRNA for purposes of inhibiting and/or reducing TMPRSS6 expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29 or at least about 30 nucleotides in length. In some embodiments, the targeting sequence or region of complementarity is about 12 to about 30 (e.g., 12 to 30, 12 to 22, 15 to 25, 17 to 21, 18 to 27, 19 to 27, or 15 to 30) nucleotides in length. In some embodiments, the targeting sequence or region of complementarity is about 12, 13, 14, 15, 16, 17, 18, 19, 20, 21, 22, 23, 24, 25, 26, 27, 28, 29 or 30 nucleotides in length. In some embodiments, the targeting sequence or region of complementarity is 18 nucleotides in length. In some embodiments, the targeting sequence or region of complementarity is 19 nucleotides in length. In some embodiments, the targeting sequence or region of complementarity is 20 nucleotides in length. In some embodiments, the targeting sequence or region of complementarity is 21 nucleotides in length. In some embodiments, the targeting sequence or region of complementarity is 22 nucleotides in length. In some embodiments, the targeting sequence or region of complementarity is 23 nucleotides in length. In some embodiments, the targeting sequence or region of complementarity is 24 nucleotides in length. In some embodiments, an oligonucleotide comprises a targeting sequence or region of complementarity complementary to a sequence of any one of SEQ ID NOs: 661-852, and the targeting sequence or region of complementarity is 18 nucleotides in length. In some embodiments, an oligonucleotide comprises a targeting sequence or region of complementarity complementary to a sequence of any one of SEQ ID NOs: 661-852, and the targeting sequence or region of complementarity is 19 nucleotides in length. In some embodiments, an oligonucleotide comprises a targeting sequence or region of complementarity complementary to a sequence of any one of SEQ ID NOs: 193-384, and the targeting sequence or region of complementarity is 20 nucleotides in length. In some embodiments, an oligonucleotide comprises a targeting sequence or region of complementarity complementary to a sequence of any one of SEQ ID NOs: 193-384, and the targeting sequence or region of complementarity is 21 nucleotides in length. In some embodiments, an oligonucleotide comprises a targeting sequence or region of complementarity complementary to a sequence of any one of SEQ ID NOs: 193-384, and the targeting sequence or region of complementarity is 22 nucleotides in length. In some embodiments, an oligonucleotide comprises a targeting sequence or region of complementarity complementary to a sequence of any one of SEQ ID NOs: 193-384, and the targeting sequence or region of complementarity is 23 nucleotides in length. In some embodiments, an oligonucleotide comprises a targeting sequence or region of complementarity complementary to a sequence of any one of SEQ ID NOs: 193-384 and the targeting sequence or region of complementarity is 24 nucleotides in length.

In some embodiments, an oligonucleotide herein (e.g., an RNAi oligonucleotide) comprises a targeting sequence or a region of complementarity (e.g., an antisense strand or a guide strand of a double-stranded oligonucleotide) that is fully complementary to a TMPRSS6 target sequence. In some embodiments, the targeting sequence or region of complementarity is partially complementary to a TMPRSS6 target sequence. In some embodiments, the oligonucleotide comprises a targeting sequence or region of complementarity that is fully complementary to a TMPRSS6 target sequence. In some embodiments, the oligonucleotide comprises a targeting sequence or region of complementarity that is partially complementary to a TMPRSS6 target sequence.

In some embodiments, the oligonucleotide comprises a targeting sequence or region of complementarity that is fully complementary to a sequence of any one of SEQ ID NOs: 661-852. In some embodiments, the oligonucleotide comprises a targeting sequence or region of complementarity that is fully complementary to the sequence set forth in SEQ ID NOs: 844, 841, 818, 794, and 762. In some embodiments, the oligonucleotide comprises a targeting sequence or region of complementarity that is partially complementary to a sequence of any one of SEQ ID NOs: 661-852. In some embodiments, the oligonucleotide comprises a targeting sequence or region of complementarity that is partially complementary to the sequence set forth in SEQ ID NOs: 844, 841, 818, 794, and 762.

In some embodiments, an oligonucleotide herein (e.g., an RNAi oligonucleotide) comprises a targeting sequence or region of complementarity that is complementary to a contiguous sequence of nucleotides within a TMPRSS6 mRNA, wherein the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20 or 18 to 19 nucleotides in length). In some embodiments, the oligonucleotide comprises a targeting sequence or region of complementarity that is complementary to a contiguous sequence of nucleotides within a TMPRSS6 mRNA, wherein the contiguous sequence of nucleotides is 10, 11, 12, 13, 14, 15, 16, 17, 18, 19 or 20 nucleotides in length. In some embodiments, the oligonucleotide comprises a targeting sequence or region of complementarity that is complementary to a contiguous sequence of nucleotides within a TMPRSS6 mRNA, wherein the contiguous sequence of nucleotides is 19 nucleotides in length. In some embodiments, the oligonucleotide comprises a targeting sequence or region of complementarity that is complementary to a contiguous sequence of nucleotides within a TMPRSS6 mRNA, wherein the contiguous sequence of nucleotides is 20 nucleotides in length.

In some embodiments, an oligonucleotide herein (e.g., an RNAi oligonucleotide) comprises a targeting sequence or a region of complementary that is complementary to a contiguous sequence of nucleotides of any one of SEQ ID NOs: 661-852, optionally wherein the contiguous sequence of nucleotides is 19 nucleotides in length. In some embodiments, the oligonucleotide comprises a targeting sequence or a region of complementary that is complementary to a contiguous sequence of nucleotides of any one of SEQ ID NOs: 844, 841, 818, 794, and 762, wherein the contiguous sequence of nucleotides is 19 nucleotides in length. In some embodiments, the oligonucleotide comprises a targeting sequence or a region of complementary that is complementary to a contiguous sequence of nucleotides of any one of SEQ ID NOs: 376, 373, 350, 326, and 294, wherein the contiguous sequence of nucleotides is 20 nucleotides in length.

In some embodiments, an oligonucleotide herein (e.g., an RNAi oligonucleotide) comprises a targeting sequence or region of complementarity having one or more base pair (bp) mismatches with the corresponding TMPRSS6 target sequence. In some embodiments, the targeting sequence or region of complementarity may have up to about 1, up to about 2, up to about 3, up to about 4, up to about 5, etc. mismatches with the corresponding TMPRSS6 target sequence provided that the ability of the targeting sequence or region of complementarity to bind or anneal to the TMPRSS6 mRNA under appropriate hybridization conditions and/or the ability of the oligonucleotide to inhibit TMPRSS6 expression is maintained. Alternatively, the targeting sequence or region of complementarity may have no more than 1, no more than 2, no more than 3, no more than 4, or no more than 5 mismatches with the corresponding TMPRSS6 target sequence provided that the ability of the targeting sequence or region of complementarity to bind or anneal to the TMPRSS6 mRNA under appropriate hybridization conditions and/or the ability of the oligonucleotide to inhibit TMPRSS6 expression is maintained. In some embodiments, the oligonucleotide comprises a targeting sequence or region of complementarity having 1 mismatch with the corresponding target sequence. In some embodiments, the oligonucleotide comprises a targeting sequence or region of complementarity having 2 mismatches with the corresponding target sequence. In some embodiments, the oligonucleotide comprises a targeting sequence or region of complementarity having 3 mismatches with the corresponding target sequence. In some embodiments, the oligonucleotide comprises a targeting sequence or region of complementarity having 4 mismatches with the corresponding target sequence. In some embodiments, the oligonucleotide comprises a targeting sequence or region of complementarity having 5 mismatches with the corresponding target sequence. In some embodiments, the oligonucleotide comprises a targeting sequence or region of complementarity having more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein the mismatches are interspersed throughout the targeting sequence or region of complementarity. In some embodiments, the oligonucleotide comprises a targeting sequence or region of complementarity having more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or wherein at least one or more non-mismatched base pair is located between the mismatches, or a combination thereof. In some embodiments, the oligonucleotide comprises a targeting sequence or a region of complementary that is complementary to a contiguous sequence of nucleotides of any one of SEQ ID NOs: 661-852, wherein the targeting sequence or region of complementarity may have up to about 1, up to about 2, up to about 3, up to about 4, up to about 5, etc. mismatches with the corresponding TMPRSS6 target sequence. In some embodiments, the oligonucleotide comprises a targeting sequence or a region of complementary that is complementary to a contiguous sequence of nucleotides of any one of SEQ ID NOs: 661-852, wherein the targeting sequence or region of complementarity may have no more than 1, no more than 2, no more than 3, no more than 4, or no more than 5 mismatches with the corresponding TMPRSS6 target sequence. In some embodiments, the oligonucleotide comprises a targeting sequence or a region of complementary that is complementary to a contiguous sequence of nucleotides of any one of SEQ ID NOs: 661-852, wherein the targeting sequence or region of complementarity may have up to about 1, up to about 2, up to about 3, up to about 4, up to about 5, etc. mismatches with the corresponding TMPRSS6 target sequence. In some embodiments, the oligonucleotide comprises a targeting sequence or a region of complementary that is complementary to a contiguous sequence of nucleotides of any one of SEQ ID NOs: 844, 841, 818, 794, and 762, wherein the targeting sequence or region of complementarity may have no more than 1, no more than 2, no more than 3, no more than 4, or no more than 5 mismatches with the corresponding TMPRSS6 target sequence.

Types of Oligonucleotides

A variety of oligonucleotide types and/or structures are useful for targeting TMPRSS6 in the methods herein including, but not limited to, RNAi oligonucleotides, antisense oligonucleotides (ASOs), miRNAs, etc. Any of the oligonucleotide types described herein or elsewhere are contemplated for use as a framework to incorporate a TMPRSS6 targeting sequence herein for the purposes of inhibiting TMPRSS6 expression.

In some embodiments, the oligonucleotides herein inhibit TMPRSS6 expression by engaging with RNA interference (RNAi) pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended dsRNAs where at least one end of at least one strand is extended beyond a duplex targeting region, including structures where one of the strands includes a thermodynamically stabilizing tetraloop structure (see, e.g., U.S. Pat. Nos. 8,513,207 and 8,927,705, as well as Intl. Patent Application Publication No. WO 2010/033225). Such structures may include single-stranded (ss) extensions (on one or both sides of the molecule) as well as double-stranded (ds) extensions.

In some embodiments, the oligonucleotides herein engage with the RNAi pathway downstream of the involvement of Dicer (e.g., Dicer cleavage). In some embodiments, the oligonucleotides described herein are Dicer substrates. In some embodiments, upon endogenous Dicer processing, double-stranded nucleic acids of 19-23 nucleotides in length capable of reducing TMPRSS6 expression are produced. In some embodiments, the oligonucleotide has an overhang (e.g., of 1, 2, or 3 nucleotides in length) in the 3' end of the antisense strand. In some embodiments, the oligonucleotide (e.g., siRNA) comprises a 21-nucleotide guide strand that is antisense to a target RNA and a complementary passenger strand, in which both strands anneal to form a 19-bp duplex and 2 nucleotide overhangs at either or both 3' ends. Longer oligonucleotide designs also are available including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a 21 bp duplex region. See, e.g., U.S. Pat. Nos. 9,012,138; 9,012,621 and 9,193,753.

In some embodiments, the oligonucleotides herein comprise sense and antisense strands that are both in the range of about 17 to 36 (e.g., 17 to 36, 20 to 25 or 21-23) nucleotides in length. In some embodiments, the oligonucleotides described herein comprise an antisense strand of 19-30 nucleotides in length and a sense strand of 19-50 nucleotides in length, wherein the antisense and sense strands are separate strands which form an asymmetric duplex region having an overhang of 1-4 nucleotides at the 3' terminus of the antisense strand. In some embodiments, an oligonucleotide herein comprises a sense and antisense strand that are both in the range of about 19-22 nucleotides in length. In some embodiments, the sense and antisense strands are of equal length. In some embodiments, an oligonucleotide comprises sense and antisense strands, such that there is a 3'-overhang on either the sense strand or the antisense strand, or both the sense and antisense strand. In some embodiments, for oligonucleotides that have sense and antisense strands that are both in the range of about 21-23 nucleotides in length, a 3' overhang on the sense, antisense, or both sense and antisense strands is 1 or 2 nucleotides in length. In some embodiments, the oligonucleotide has a guide strand of 22 nucleotides and a passenger strand of 20 nucleotides, where there is a blunt end on the right side of the molecule (3' end of passenger strand/5' end of guide strand) and a 2 nucleotide 3'-guide strand overhang on the left side of the molecule (5' end of the passenger strand/3' end of the guide strand). In such molecules, there is a 20 bp duplex region.

Other oligonucleotide designs for use with the compositions and methods herein include: 16-mer siRNAs (see, e.g., Nucleic Acids in Chemistry and Biology, Blackburn (ed.), ROYAL SOCIETY OF CHEMISTRY, 2006), shRNAs (e.g., having 19 bp or shorter stems; see, e.g., Moore et al. (2010) Methods Mol. Biol. 629:141-158), blunt siRNAs (e.g., of 19 bps in length; see, e.g., Kraynack & Baker (2006) RNA 12:163-176), asymmetrical siRNAs (aiRNA; see, e.g., Sun et al. (2008) Nat. Biotechnol. 26:1379-82), asymmetric shorter-duplex siRNA (see, e.g., Chang et al. (2009) Mol. Ther. 17:725-32), fork siRNAs (see, e.g., Hohjoh (2004) FEBS Lett. 557:193-98), ss siRNAs (Elsner (2012) Nat. Biotechnol. 30:1063), dumbbell-shaped circular siRNAs (see, e.g., Abe et al. (2007) J. Am. Chem. Soc. 129:15108-09), and small internally segmented interfering RNA (siRNA; see, e.g., Bramsen et al. (2007) Nucleic Acids Res. 35:5886-97). Further non-limiting examples of an oligonucleotide structures that may be used in some embodiments to reduce or inhibit the expression of TMPRSS6 are microRNA (miRNA), short hairpin RNA (shRNA) and short siRNA (see, e.g., Hamilton et al. (2002) EMBO J. 21:4671-79; see also, US Patent Application Publication No. 2009/0099115).

Still, in some embodiments, an oligonucleotide for reducing or inhibiting TMPRSS6 expression herein is single-stranded (ss). Such structures may include but are not limited to single-stranded RNAi molecules. Recent efforts have demonstrated the activity of ss RNAi molecules (see, e.g., Matsui et al. (2016) Mol. Ther. 24:946-55). However, in some embodiments, oligonucleotides herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) to induce RNaseH-mediated cleavage of its target RNA in cells or (e.g., as a mixmer) to inhibit translation of the target mRNA in cells. ASOs for use herein may be modified in any suitable manner known in the art including, for example, as shown in U.S. Pat. No. 9,567,587 (including, e.g., length, sugar moieties of the nucleobase (pyrimidine, purine), and alterations of the heterocyclic portion of the nucleobase). Further, ASOs have been used for decades to reduce expression of specific target genes (see, e.g., Bennett et al. (2017) Annu. Rev. Pharmacol. 57:81-105).

In some embodiments, the antisense oligonucleotide shares a region of complementarity with TMPRSS6 mRNA. In some embodiments, the antisense oligonucleotide targets various areas of the human TMPRSS6 gene identified as NM_001289000.2. In some embodiments, the antisense oligonucleotide is 15-50 nucleotides in length. In some embodiments, the antisense oligonucleotide is 15-25 nucleotides in length. In some embodiments, the antisense oligonucleotide is 22 nucleotides in length. In some embodiments, the antisense oligonucleotide is complementary to any one of SEQ ID NOs: 661-852. In some embodiments, the antisense oligonucleotide is at least 15 contiguous nucleotides in length. In some embodiments, the antisense oligonucleotide is at least 19 contiguous nucleotides in length. In some embodiments, the antisense oligonucleotide is at least 20 contiguous nucleotides in length. In some embodiments, the antisense oligonucleotide differs by 1, 2, or 3 nucleotides from the target sequence.

Double-Stranded Oligonucleotides

In some aspects, the disclosure provides double-stranded (ds) RNAi oligonucleotides for targeting TMPRSS6 mRNA and inhibiting TMPRSS6 expression (e.g., via the RNAi pathway) comprising a sense strand (also referred to herein as a passenger strand) and an antisense strand (also referred to herein as a guide strand). In some embodiments, the sense strand and antisense strand are separate strands and are not covalently linked. In some embodiments, the sense strand and antisense strand are covalently linked. In some embodiments, the sense strand and antisense strand form a duplex region, wherein the sense strand and antisense strand, or a portion thereof, binds with one another in a complementary fashion (e.g., by Watson-Crick base pairing).

In some embodiments, a first region (R1) of the sense strand and the antisense strand form a first duplex (D1). In some embodiments, D1 is at least about 15 (e.g., at least 15, at least 16, at least 17, at least 18, at least 19, at least 20 or at least 21) nucleotides in length. In some embodiments, D1 is in the range of about 12 to 30 nucleotides in length (e.g., 12 to 30, 12 to 27, 15 to 22, 18 to 22, 18 to 25, 18 to 27, 18 to 30 or 21 to 30 nucleotides in length). In some embodiments, D1 is at least 12 nucleotides in length (e.g., at least 12, at least 15, at least 20, at least 25, or at least 30 nucleotides in length). In some embodiments, D1 is 12, 13, 14, 15, 16, 17, 18, 19, 20, 21, 22, 23, 24, 25, 26, 27, 28, 29 or 30 nucleotides in length. In some embodiments, D1 is 20 nucleotides in length. In some embodiments, D1 comprising sense strand and antisense strand does not span the entire length of the sense strand and/or antisense strand. In some embodiments, D1 comprising the sense strand and antisense strand spans the entire length of either the sense strand or antisense strand or both. In certain embodiments, D1 comprising the sense strand and antisense strand spans the entire length of both the sense strand and the antisense strand.

In some embodiments, the sense strand has a second region (R2), wherein R2 comprises a first subregion (S1), a loop (Lp), such as a tetraloop (tetraLp) or triloop (triLp), and a second subregion (S2), wherein Lp is located between S1 and S2, and wherein S1 and S2 form a second duplex (D2). D2 may have various lengths. In some embodiments, D2 is about 1-6 bp in length. In some embodiments, D2 is 2-6, 3-6, 4-6, 5-6, 1-5, 2-5, 3-5 or 4-5 bp in length. In some embodiments, D2 is 1, 2, 3, 4, 5 or 6 bp in length. In some embodiments, D2 is 6 bp in length.

In some embodiments, an oligonucleotide provided herein comprises a sense strand comprising a sequence of any one of SEQ ID NOs: 193-384 and an antisense strand comprising a sequence of any one of SEQ ID NOs: 385-576. In some embodiments, an oligonucleotide provided herein comprises a sense strand comprising a sequence of any one of SEQ ID NOs: 661-852 and an antisense strand comprising a sequence of any one of SEQ ID NOs: 1-192.

In some embodiments, an oligonucleotide provided herein (e.g., an RNAi oligonucleotide) comprises a sense strand comprising a sequence of any one of SEQ ID NOs: 577-597 and an antisense strand comprising a sequence of any one of SEQ ID NOs: 598-618 as is arranged in Table 4.

In some embodiments, an oligonucleotide provided herein (e.g., an RNAi oligonucleotide) comprises a sense strand and an antisense strand comprising nucleotide sequences selected from:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively.

In some embodiments, an oligonucleotide provided herein (e.g., an RNAi oligonucleotide) comprises a sense strand and an antisense strand comprising nucleotide sequences selected from:
  a) SEQ ID NOs: 579 and 600, respectively;
  b) SEQ ID NOs: 580 and 601, respectively;
  c) SEQ ID NOs: 590 and 611, respectively;

d) SEQ ID NOs: 597 and 618, respectively; and,
e) SEQ ID NOs: 586 and 607, respectively.

In some embodiments, the sense strand comprises the sequence of SEQ ID NO: 579 and the antisense strand comprises the sequence of SEQ ID NO: 600. In some embodiments, the sense strand comprises the sequence of SEQ ID NO: 580 and the antisense strand comprises the sequence of SEQ ID NO: 601. In some embodiments, the sense strand comprises the sequence of SEQ ID NO: 590 and the antisense strand comprises the sequence of SEQ ID NO: 611. In some embodiments, the sense strand comprises the sequence of SEQ ID NO: 597 and the antisense strand comprises the sequence of SEQ ID NO: 618. In some embodiments, the sense strand comprises the sequence of SEQ ID NO: 586 and the antisense strand comprises the sequence of SEQ ID NO: 607.

It should be appreciated that, in some embodiments, sequences presented in the Sequence Listing may be referred to in describing the structure of an oligonucleotide (e.g., an RNAi oligonucleotide) or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, an oligonucleotide herein (e.g., an RNAi oligonucleotide) comprises a sense strand and an antisense strand that, when acted upon by a Dicer enzyme, results in an antisense strand that is incorporated into the mature RISC. In some embodiments, an oligonucleotide herein (e.g., an RNAi oligonucleotide) comprises a 25-nucleotide sense strand and a 27-nucleotide antisense strand that when acted upon by a Dicer enzyme results in an antisense strand that is incorporated into the mature RISC. In some embodiments, the sense strand comprises a sequence selected from SEQ ID NOs: 193-384. In some embodiments, the 27-nucleotide antisense strand comprises a sequence selected from SEQ ID NOs: 385-576. In some embodiments, the sense strand of the oligonucleotide is longer than 27 nucleotides (e.g., 28, 29, 30, 31, 32, 33, 34, 35, 36, 37, 38, 39, 40, 41, 42, 43, 44, 45, 46, 47, 48, 49 or 50 nucleotides). In some embodiments, the sense strand of the oligonucleotide is longer than 25 nucleotides (e.g., 26, 27, 28, 29 or 30 nucleotides). In some embodiments, the sense strand of the oligonucleotide comprises a nucleotide sequence selected from SEQ ID NOs: 577-597, wherein the nucleotide sequence is longer than 27 nucleotides (e.g., 28, 29, 30, 31, 32, 33, 34, 35, 36, 37, 38, 39, 40, 41, 42, 43, 44, 45, 46, 47, 48, 49 or 50 nucleotides). In some embodiments, the sense strand of the oligonucleotide comprises a nucleotide sequence selected from SEQ ID NOs: 577-597, wherein the nucleotide sequence is longer than 25 nucleotides (e.g., 26, 27, 28, 29 or 30 nucleotides).

In some embodiments, oligonucleotides herein (e.g., RNAi oligonucleotides) have one end that is thermodynamically less stable when compared to the other 5' end. In some embodiments, an asymmetric oligonucleotide is provided that includes a blunt end at the 3' end of a sense strand and a 3'-overhang at the 3' end of an antisense strand. In some embodiments, the 3'-overhang on the antisense strand is about 1-8 nucleotides in length (e.g., 1, 2, 3, 4, 5, 6, 7 or 8 nucleotides in length). In some embodiments, the oligonucleotide has an overhang comprising two (2) nucleotides on the 3' end of the antisense (guide) strand. However, other overhangs are possible. In some embodiments, an overhang is a 3'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. However, in some embodiments, the overhang is a 5'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. In some embodiments, the oligonucleotide comprises a targeting sequence or a region of complementary that is complementary to a contiguous sequence of nucleotides of any one of SEQ ID NOs: 661-852, and a 5'-overhang comprising a length of between 1 and 6 nucleotides. In some embodiments, the oligonucleotide comprises a sense strand comprising a nucleotide sequence selected from SEQ ID NOs: 577-597, wherein the oligonucleotide comprises a 5'-overhang comprising a length of between 1 and 6 nucleotides. In some embodiments, the oligonucleotide comprises an antisense strand comprising a nucleotide sequence selected from SEQ ID NOs: 598-618, wherein the oligonucleotide comprises a 5'-overhang comprising a length of between 1 and 6 nucleotides. In some embodiments, the oligonucleotide comprises a sense strand comprising a nucleotide sequence selected from SEQ ID NOs: 577-597 and antisense strand comprising a nucleotide sequence selected from SEQ ID NOs: 598-618, wherein the oligonucleotide comprises a 5'-overhang comprising a length of between 1 and 6 nucleotides.

In some embodiments, two (2) terminal nucleotides on the 3' end of an antisense strand are modified. In some embodiments, the two (2) terminal nucleotides on the 3' end of the antisense strand are complementary with the target mRNA (e.g., TMPRSS6 mRNA). In some embodiments, the two (2) terminal nucleotides on the 3' end of the antisense strand are not complementary with the target mRNA. In some embodiments, the two (2) terminal nucleotides on the 3' end of the antisense strand of an oligonucleotide herein are unpaired. In some embodiments, the two (2) terminal nucleotides on the 3' end of the antisense strand of an oligonucleotide herein comprise an unpaired guanine (e.g., 5'-GG-3'). In some embodiments, the two (2) terminal nucleotides on the 3' end of an antisense strand of an oligonucleotide herein are not complementary to the target mRNA. In some embodiments, two (2) terminal nucleotides on each 3' end of an oligonucleotide are guanines (GG). In some embodiments, one or both of the two (2) terminal GG nucleotides on each 3' end of an oligonucleotide herein is not complementary with the target mRNA. In some embodiments, the oligonucleotide comprises a targeting sequence or a region of complementary that is complementary to a contiguous sequence of nucleotides of any one of SEQ ID NOs: 661-852, wherein the two (2) terminal nucleotides on the 3' end of the antisense strand of the oligonucleotide herein comprises an unpaired GG. In some embodiments, the oligonucleotide comprises an antisense strand comprising a nucleotide sequence selected from SEQ ID NOs: 1-192, wherein the two (2) terminal nucleotides on the 3' end of the antisense strand of the oligonucleotide comprises an unpaired GG. In some embodiments, the oligonucleotide comprises a sense strand comprising a nucleotide sequence selected from SEQ ID NOs: 577-597 and antisense strand comprising a nucleotide sequence selected from SEQ ID NOs: 598-618, wherein the two (2) terminal nucleotides on the 3' end of the antisense strand of the oligonucleotide comprises an unpaired GG.

In some embodiments, there is one or more (e.g., 1, 2, 3, 4 or 5) mismatch(es) between a sense and antisense strand comprising an oligonucleotide herein (e.g., an RNAi oligonucleotide). If there is more than one mismatch between a sense and antisense strand, they may be positioned consecutively (e.g., 2, 3 or more in a row), or interspersed throughout the region of complementarity. In some embodiments, the 3' end of the sense strand comprises one or more mismatches. In some embodiments, two (2) mismatches are incorporated at the 3' end of the sense strand. In some embodiments, base mismatches, or destabilization of segments at the 3' end of the sense strand of an oligonucleotide herein improves or increases the potency of the oligonucleotide. In some embodiments, the sense and antisense strands of an oligonucleotide herein comprise nucleotides sequences selected from the group consisting of:

a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively,
  wherein there is one or more (e.g., 1, 2, 3, 4 or 5) mismatch(es) between the sense and antisense strands.

In some embodiments, an oligonucleotide provided herein (e.g., an RNAi oligonucleotide) comprises a sense strand and an antisense strand comprising nucleotide sequences selected from the group consisting of:

a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively,
  wherein there is one or more (e.g., 1, 2, 3, 4 or 5) mismatch(es) between the sense and antisense strands.

Antisense Strands

In some embodiments, an antisense strand of an oligonucleotide herein (e.g., an RNAi oligonucleotide) is referred to as a "guide strand". For example, an antisense strand that engages with RNA-induced silencing complex (RISC) and binds to an Argonaute protein such as Ago2, or engages with or binds to one or more similar factors, and directs silencing of a target gene, as the antisense strand is referred to as a guide strand. In some embodiments, a sense strand comprising a region of complementary to a guide strand is referred to herein as a "passenger strand."

In some embodiments, an oligonucleotide herein (e.g., an RNAi oligonucleotide) comprises an antisense strand of up to about 50 nucleotides in length (e.g., up to 50, up to 40, up to 35, up to 30, up to 27, up to 25, up to 21, up to 19, up to 17 or up to 12 nucleotides in length). In some embodiments, an oligonucleotide comprises an antisense strand of at least about 12 nucleotides in length (e.g., at least 12, at least 15, at least 19, at least 21, at least 22, at least 25, at least 27, at least 30, at least 35 or at least 38 nucleotides in length). In some embodiments, an oligonucleotide comprises an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40 or 32 to 40) nucleotides in length. In some embodiments, an oligonucleotide comprises antisense strand of 15 to 30 nucleotides in length. In some embodiments, an antisense strand of any one of the oligonucleotides disclosed herein is of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, an oligonucleotide comprises an antisense strand of 22 nucleotides in length.

In some embodiments, an oligonucleotide disclosed herein (e.g., an RNAi oligonucleotide) for targeting TMPRSS6 comprises an antisense strand comprising or consisting of a sequence as set forth in any one of SEQ ID NOs: 385-576. In some embodiments, an oligonucleotide herein comprises an antisense strand comprising at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 385-576. In some embodiments, an oligonucleotide disclosed herein for targeting TMPRSS6 comprises an antisense strand comprising or consisting of a sequence as set forth in any one of SEQ ID NOs: 598-618. In some embodiments, an oligonucleotide herein comprises an antisense strand comprising at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 598-618. In some embodiments, an oligonucleotide disclosed herein for targeting TMPRSS6 comprises an antisense strand comprising or consisting of a sequence as set forth in any one of SEQ ID NOs: 598-618. In some embodiments, an oligonucleotide herein comprises an antisense strand comprising at least about 12 (e.g., at least 12, at least 13, at least 14, at least 15, at least 16, at least 17, at least 18, at least 19, at least 20, at least 21, at least 22 or at least 23) contiguous nucleotides of a sequence as set forth in any one of SEQ ID NOs: 600, 601, 611, 618, and 607. In some embodiments, an oligonucleotide disclosed herein for targeting TMPRSS6 comprises an antisense strand comprising or consisting of a sequence as set forth in any one of SEQ ID NOs: 600, 601, 611, 618, and 607.

In some embodiments, an oligonucleotide herein comprises an antisense strand comprising a nucleotide sequence selected from SEQ ID NOs: 1-192. In some embodiments, an oligonucleotide herein comprises an antisense strand comprising a nucleotide sequence selected from SEQ ID NOs: 184, 181, 158, 134, and 102.

Sense Strands

In some embodiments, an oligonucleotide disclosed herein (e.g., an RNAi oligonucleotide) for targeting TMPRSS6 mRNA and inhibiting TMPRSS6 expression comprises a sense strand sequence as set forth in any one of SEQ ID NOs: 661-852. In some embodiments, an oligonucleotide disclosed herein (e.g., an RNAi oligonucleotide) for targeting TMPRSS6 mRNA and inhibiting TMPRSS6 expression comprises a sense strand sequence as set forth in any one of SEQ ID NOs: 193-384. In some embodiments, an oligonucleotide herein has a sense strand comprised of at least about 12 (e.g., at least 13, at least 14, at least at least 16, at least 17, at least 18, at least 19, at least 20, at least 21, at least 22 or at least 23) contiguous nucleotides of a sequence as set forth in in any one of SEQ ID NOs: 193-384. In some embodiments, an oligonucleotide herein has a sense strand comprised of at least about 12 (e.g., at least 13, at least 14, at least 15, at least 16, at least 17, at least 18, or at least 19) contiguous nucleotides of a sequence as set forth in in any one of SEQ ID NOs: 661-852. In some embodiments, an oligonucleotide disclosed herein for targeting TMPRSS6 mRNA and inhibiting TMPRSS6 expression comprises a sense strand sequence as set forth in any one of SEQ ID NOs: 577-597. In some embodiments, an oligonucleotide herein has a sense strand comprised of least about 12 (e.g., at least 13, at least 14, at least 15, at least 16, at least 17, at least 18, at least 19, at least 20, at least 21, at least 22 or at least 23) contiguous nucleotides of a sequence as set forth in any one of SEQ ID NOs: 577-597. In some embodiments, an oligonucleotide disclosed herein for targeting TMPRSS6 mRNA and inhibiting TMPRSS6 expression comprises a sense strand sequence as set forth in any one of SEQ ID NOs: 579, 580, 590, 597, and 586. In some embodiments, an oligonucleotide herein has a sense strand that comprise at least about 12 (e.g., at least 13, at least 14, at least 15, at least 16, at least 17, at least 18, at least 19, at least 20, at least 21, at least 22 or at least 23) contiguous nucleotides of a sequence as set forth in any one of SEQ ID NOs: 579, 580, 590, 597, and 586. In some embodiments, an oligonucleotide disclosed herein for targeting TMPRSS6 mRNA and inhibiting TMPRSS6 expression comprises a sense strand sequence as set forth in any one of SEQ ID NOs: 844, 841, 818, 794, and 762. In some embodiments, an oligonucleotide herein has a sense strand that comprise at least about 12 (e.g., at least 13, at least 14, at least 15, at least 16, at least 17, at least 18, or at least 19) contiguous nucleotides of a sequence as set forth in any one of SEQ ID NOs: 844, 841, 818, 794, and 762.

In some embodiments, an oligonucleotide provided herein (e.g., an RNAi oligonucleotide) comprises a sense strand (or passenger strand) of up to about 50 nucleotides in length (e.g., up to 50, up to 40, up to 36, up to 30, up to 27, up to 25, up to 21, up to 19, up to 17 or up to 12 nucleotides in length). In some embodiments, an oligonucleotide herein comprises a sense strand of at least about 12 nucleotides in length (e.g., at least 12, at least 15, at least 19, at least 21, at least 25, at least 27, at least 30, at least 36 or at least 38 nucleotides in length). In some embodiments, an oligonucleotide herein comprises a sense strand in a range of about 12 to about 50 (e.g., 12 to 50, 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40 or 32 to 40) nucleotides in length. In some embodiments, an oligonucleotide herein comprises a sense strand of 15 to 50 nucleotides in length. In some embodiments, an oligonucleotide herein comprises a sense strand of 18 to 36 nucleotides in length. In some embodiments, an oligonucleotide herein comprises a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, an oligonucleotide herein comprises a sense strand of 36 nucleotides in length.

In some embodiments, an oligonucleotide provided herein (e.g., an RNAi oligonucleotide) comprises a sense strand comprising a stem-loop structure proximal the 3' end of the sense strand. In some embodiments, an oligonucleotide provided herein (e.g., an RNAi oligonucleotide) comprises a sense strand comprising a stem-loop structure at the 3' end of the first region (R1) of the sense strand. In some embodiments, the stem-loop is formed by intrastrand base pairing. In some embodiments, a sense strand comprises a stem-loop structure proximal its 5' end. In some embodiments, a sense strand comprises a stem-loop structure at the 5' end of the first region (R1). In some embodiments, the stem of the stem-loop comprises a duplex of 2, 3, 4, 5, 6, 7, 8, 9, 10, 11, 12, 13 or 14 nucleotides in length. In some embodiments, the stem of the stem-loop comprises a duplex of 2 nucleotides in length. In some embodiments, the stem of the stem-loop comprises a duplex of 3 nucleotides in length. In some embodiments, the stem of the stem-loop comprises a duplex of 4 nucleotides in length. In some embodiments, the stem of the stem-loop comprises a duplex of 5 nucleotides in length. In some embodiments, the stem of the stem-loop comprises a duplex of 6 nucleotides in length. In some embodiments, the stem of the stem-loop comprises a duplex of 7 nucleotides in length. In some embodiments, the stem of the stem-loop comprises a duplex of 8 nucleotides in length. In some embodiments, the stem of the stem-loop comprises a duplex of 9 nucleotides in length. In some embodiments, the stem of the stem-loop comprises a duplex of 10 nucleotides in length. In some embodiments, the stem of the stem-loop comprises a duplex of 11 nucleotides in length. In some embodiments, the stem of the stem-loop comprises a duplex of 12 nucleotides in length. In some embodiments, the stem of the stem-loop comprises a duplex of 13 nucleotides in length. In some embodiments, the stem of the stem-loop comprises a duplex of 14 nucleotides in length.

In some embodiments, a stem-loop provides the oligonucleotide protection against degradation (e.g., enzymatic degradation), facilitates or improves targeting and/or delivery to a target cell, tissue, or organ (e.g., the liver), or both. For example, in some embodiments, the loop of a stem-loop is comprised of nucleotides comprising one or more modifications that facilitate, improve, or increase targeting to a target mRNA (e.g., a TMPRSS6 mRNA), inhibition of target gene expression (e.g., TMPRSS6 expression), and/or delivery, uptake, and/or penetrance into a target cell, tissue, or organ (e.g., the liver), or a combination thereof. In some embodiments, the stem-loop itself or modification(s) to the stem-loop do not affect or do not substantially affect the inherent gene expression inhibition activity of the oligonucleotide, but facilitates, improves, or increases stability (e.g., provides protection against degradation) and/or delivery, uptake, and/or penetrance of the oligonucleotide to a target cell, tissue, or organ (e.g., the liver). In certain embodiments, an oligonucleotide herein comprises a sense strand comprising (e.g., at its 3' end, proximal its 3' end and/or at the 3' end of the first region (R1) of the sense strand) a stem-loop set forth as: S1-Lp-S2, in which S1 is complementary to S2, and in which Lp forms a single-stranded loop of linked nucleotides between S1 and S2 of up to about 10 nucleotides in length (e.g., 3, 4, 5, 6, 7, 8, 9 or 10 nucleotides in length). In some embodiments, the loop (Lp) is 3 nucleotides in length (referred to herein as "triloop"). In some embodiments, the loop (Lp) is 4 nucleotides in length (referred to herein as "tetraloop"). In some embodiments, the loop (Lp) is 5 nucleotides in length. In some embodiments, the loop (Lp) is 6 nucleotides in length. In some embodiments, the loop (Lp) is 7 nucleotides in length. In some embodiments, the loop (Lp) is 8 nucleotides in length. In some embodiments, the loop (Lp) is 9 nucleotides in length. In some embodiments, the loop (Lp) is 10 nucleotides in length.

In some embodiments, the tetraloop comprises the sequence 5'-GAAA-3'. In some embodiments, the stem loop comprises the sequence 5'-GCAGCCGAAAGGCUGC-3' (SEQ ID NO: 856).

In some embodiments, an oligonucleotide provided herein (e.g., an RNAi oligonucleotide) comprises a targeting sequence or a region of complementary that is complementary to a contiguous sequence of nucleotides of any one of SEQ ID NOs: 661-852, and the oligonucleotide comprises a sense strand comprising (e.g., at its 3' end, proximal its 3' end and/or at the 3' end of the first region (R1) of the sense strand) a stem-loop set forth as: S1-Lp-S2, in which S1 is complementary to S2, and in which Lp forms a single-stranded loop between S1 and S2 of up to about 10 nucleotides in length (e.g., 3, 4, 5, 6, 7, 8, 9 or 10 nucleotides in length). In some embodiments, the oligonucleotide comprises a targeting sequence or a region of complementary that is complementary to a contiguous sequence of nucleotides of any one of SEQ ID NOs: 661-852, and the oligonucleotide comprises a sense strand comprising (e.g., at its 3' end, proximal its 3' end and/or at the 3' end of the first region (R1) of the sense strand) a stem-loop set forth as: S1-Lp-S2, in which S1 is complementary to S2, and in which Lp forms a single-stranded loop between S1 and S2 of 4 nucleotides in length.

In some embodiments, a loop (Lp) of a stem-loop having the structure S1-Lp-S2 as described herein is a triloop (triLp). In some embodiments, the oligonucleotide comprises a targeting sequence or a region of complementary that is complementary to a contiguous sequence of nucleotides of any one of SEQ ID NOs: 661-852 and a triloop. In some embodiments, the triloop comprises ribonucleotides, deoxyribonucleotides, modified nucleotides, ligands (e.g., delivery ligands), and combinations thereof.

In some embodiments, a loop (Lp) of a stem-loop having the structure S1-Lp-S2 as described above is a tetraloop (tetraLp) as describe in U.S. Pat. No. 10,131,912, incorporated herein by reference. In some embodiments, an oligonucleotide herein comprises a targeting sequence or a region of complementary that is complementary to a contiguous sequence of nucleotides of any one of SEQ ID NOs: 661-852 and a tetraloop. In some embodiments, the tetraloop comprises ribonucleotides, deoxyribonucleotides, modified nucleotides, ligands (e.g., delivery ligands), and combinations thereof.

Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length). In some embodiments, a duplex formed between a sense and antisense strand is 12, 13, 14, 15, 16, 17, 18, 19, 29, 21, 22, 23, 24, 25, 26, 27, 28, 29 or 30 nucleotides in length. In some embodiments, a duplex formed between a sense and antisense strand is 12 nucleotides in length. In some embodiments, a duplex formed between a sense and antisense strand is 13 nucleotides in length. In some embodiments, a duplex formed between a sense and antisense strand is 14 nucleotides in length. In some embodiments, a duplex formed between a sense and antisense strand is 15 nucleotides in length. In some embodiments, a duplex formed between a sense and antisense strand is 16 nucleotides in length. In some embodiments, a duplex formed between a sense and antisense strand is 17 nucleotides in length. In some embodiments, a duplex formed between a sense and antisense strand is 18 nucleotides in length. In some embodiments, a duplex formed between a sense and antisense strand is 19 nucleotides in length. In some embodiments, a duplex formed between a sense and antisense strand is 20 nucleotides in length. In some embodiments, a duplex formed between a sense and antisense strand is 21 nucleotides in length. In some embodiments, a duplex formed between a sense and antisense strand is 22 nucleotides in length. In some embodiments, a duplex formed between a sense and antisense strand is 23 nucleotides in length. In some embodiments, a duplex formed between a sense and antisense strand is 24 nucleotides in length. In some embodiments, a duplex formed between a sense and antisense strand is 25 nucleotides in length. In some embodiments, a duplex formed between a sense and antisense strand is 26 nucleotides in length. In some embodiments, a duplex formed between a sense and antisense strand is 27 nucleotides in length. In some embodiments, a duplex formed between a sense and antisense strand is 28 nucleotides in length. In some embodiments, a duplex formed between a sense and antisense strand is 29 nucleotides in length. In some embodiments, a duplex formed between a sense and antisense strand is 30 nucleotides in length. In some embodiments, a duplex formed between a sense and antisense strand does not span the entire length of the sense strand and/or antisense strand. In some embodiments, a duplex between a sense and antisense strand spans the entire length of either the sense or antisense strands. In some embodiments, a duplex between a sense and antisense strand spans the entire length of both the sense strand and the antisense strand. In some embodiments, the sense and antisense strands of an oligonucleotide comprise nucleotides sequences selected from the group consisting of:

a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively,
wherein a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length)

In some embodiments, the sense and antisense strands of an oligonucleotide comprise nucleotides sequences selected from the group consisting of:

a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively,
wherein a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30 or 21 to 30 nucleotides in length)

Oligonucleotide Termini

In some embodiments, an oligonucleotide disclosed herein (e.g., an RNAi oligonucleotide) comprises a sense strand and an antisense strand, wherein the termini of either or both strands comprise a blunt end. In some embodiments, an oligonucleotide herein comprises sense and antisense strands that are separate strands which form an asymmetric duplex region having an overhang at the 3' terminus of the antisense strand. In some embodiments, an oligonucleotide herein comprises a sense strand and an antisense strand, wherein the termini of either or both strands comprise an overhang comprising one or more nucleotides. In some embodiments, the one or more nucleotides comprising the overhang are unpaired nucleotides. In some embodiments, an oligonucleotide herein comprises a sense strand and an antisense strand, wherein the 3' termini of the sense strand and the 5' termini of the antisense strand comprise a blunt end. In some embodiments, an oligonucleotide herein comprises a sense strand and an antisense strand, wherein the 5' termini of the sense strand and the 3' termini of the antisense strand comprise a blunt end.

In some embodiments, an oligonucleotide herein comprises a sense strand and an antisense strand, wherein the 3' terminus of either or both strands comprise a 3'-overhang comprising one or more nucleotides. In some embodiments, an oligonucleotide herein comprises a sense strand and an antisense strand, wherein the sense strand comprises a 3'-overhang comprising one or more nucleotides. In some embodiments, an oligonucleotide herein comprises a sense strand and an antisense strand, wherein the antisense strand comprises a 3'-overhang comprising one or more nucleotides. In some embodiments, an oligonucleotide herein comprises a sense strand and an antisense strand, wherein both the sense strand and the antisense strand comprises a 3'-overhang comprising one or more nucleotides.

In some embodiments, the 3'-overhang is about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length). In some embodiments, the 3' overhang is about one (1) to nineteen (19), one (1) to eighteen (18), one (1) to seventeen (17), one (1) to sixteen (16), one (1) to fifteen (15), one (1) to fourteen (14), one (1) to thirteen (13), one (1) to twelve (12), one (1) to eleven (11), one (1) to ten (10), one (1) to nine (9), one (1) to eight (8), one (1) to seven (7), one (1) to six (6), one (1) to five (5), one (1) to four (4), one (1) to three (3), or about one (1) to two (2) nucleotides in length. In some embodiments, the 3'-overhang is (1) nucleotide in length. In some embodiments, the 3'-overhang is two (2) nucleotides in length. In some embodiments, the 3'-overhang is three (3) nucleotides in length. In some embodiments, the 3'-overhang is four (4) nucleotides in length. In some embodiments, the 3'-overhang is five (5) nucleotides in length. In some embodiments, the 3'-overhang is six (6) nucleotides in length. In some embodiments, the 3'-overhang is seven (7) nucleotides in length. In some embodiments, the 3'-overhang is eight (8) nucleotides in length. In some embodiments, the 3'-overhang is nine (9) nucleotides in length. In some embodiments, the 3'-overhang is ten (10) nucleotides in length. In some embodiments, the 3'-overhang is eleven (11) nucleotides in length. In some embodiments, the 3'-overhang is twelve (12) nucleotides in length. In some embodiments, the 3'-overhang is thirteen (13) nucleotides in length. In some embodiments, the 3'-overhang is fourteen (14) nucleotides in length. In some embodiments, the 3'-overhang is fifteen (15) nucleotides in length. In some embodiments, the 3'-overhang is sixteen (16) nucleotides in length. In some embodiments, the 3'-overhang is seventeen (17) nucleotides in length. In some embodiments, the 3'-overhang is eighteen (18) nucleotides in length. In some embodiments, the 3'-overhang is nineteen (19) nucleotides in length. In some embodiments, the 3'-overhang is twenty (20) nucleotides in length.

In some embodiments, an oligonucleotide disclosed herein (e.g., an RNAi oligonucleotide) comprises a sense strand and an antisense strand, wherein the sense and antisense strands of the oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively,
  and wherein the antisense strand comprises a 3'-overhang about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length), optionally wherein the 3'-overhang is two (2) nucleotides in length.

In some embodiments, an oligonucleotide disclosed herein (e.g., an RNAi oligonucleotide) comprises a sense strand and an antisense strand, wherein the sense and antisense strands of the oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 590 and 611, respectively;
  d) SEQ ID NOs: 597 and 618, respectively; and,
  e) SEQ ID NOs: 586 and 607, respectively,
  and wherein the antisense strand comprises a 3'-overhang about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length), optionally wherein the 3'-overhang is two (2) nucleotides in length.

In some embodiments, an oligonucleotide herein comprises a sense strand and an antisense strand, wherein the 5' terminus of either or both strands comprise a 5'-overhang comprising one or more nucleotides. In some embodiments, an oligonucleotide herein comprises a sense strand and an antisense strand, wherein the sense strand comprises a 5'-overhang comprising one or more nucleotides. In some embodiments, an oligonucleotide herein comprises a sense strand and an antisense strand, wherein the antisense strand comprises a 5'-overhang comprising one or more nucleotides. In some embodiments, an oligonucleotide herein comprises a sense strand and an antisense strand, wherein both the sense strand and the antisense strand comprises a 5'-overhang comprising one or more nucleotides.

In some embodiments, the 5'-overhang is about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length). In some embodiments, the 5' overhang is about one (1) to nineteen (19), one (1) to eighteen (18), one (1) to seventeen (17), one (1) to sixteen (16), one (1) to fifteen (15), one (1) to fourteen (14), one (1) to thirteen (13), one (1) to twelve (12), one (1) to eleven (11), one (1) to ten (10), one (1) to nine (9), one (1) to eight (8), one (1) to seven (7), one (1) to six (6), one (1) to five (5), one (1) to four (4), one (1) to three (3), or about one (1) to two (2) nucleotides in length. In some embodiments, the 5'-overhang is (1) nucleotide in length. In some embodiments, the 5'-overhang is two (2) nucleotides in length. In some embodiments, the 5'-overhang is three (3) nucleotides in length. In some embodiments, the 5'-overhang is four (4) nucleotides in length. In some embodiments, the 5'-overhang is five (5) nucleotides in length. In some embodiments, the 5'-overhang is six (6) nucleotides in length. In some embodiments, the 5'-overhang is seven (7) nucleotides in length. In some embodiments, the 5'-overhang is eight (8) nucleotides in length. In some embodiments, the 5'-overhang is nine (9) nucleotides in length. In some embodiments, the 5'-overhang is ten (10) nucleotides in length. In some embodiments, the 5'-overhang is eleven (11) nucleotides in length. In some embodiments, the 5'-overhang is twelve (12) nucleotides in length. In some embodiments, the 5'-overhang is thirteen (13) nucleotides in length. In some embodiments, the 5'-overhang is fourteen (14) nucleotides in length.

In some embodiments, the 5'-overhang is fifteen (15) nucleotides in length. In some embodiments, the 5'-overhang is sixteen (16) nucleotides in length. In some embodiments, the 5'-overhang is seventeen (17) nucleotides in length. In some embodiments, the 5'-overhang is eighteen (18) nucleotides in length. In some embodiments, the 5'-overhang is nineteen (19) nucleotides in length. In some embodiments, the 5'-overhang is twenty (20) nucleotides in length.

In some embodiments, an oligonucleotide disclosed herein (e.g., an RNAi oligonucleotide) comprises a sense strand and an antisense strand, wherein the sense and antisense strands of the oligonucleotide comprise nucleotides sequences selected from the group consisting of:
- a) SEQ ID NOs: 579 and 600, respectively;
- b) SEQ ID NOs: 580 and 601, respectively;
- c) SEQ ID NOs: 595 and 616, respectively;
- d) SEQ ID NOs: 590 and 611, respectively;
- e) SEQ ID NOs: 596 and 617, respectively;
- f) SEQ ID NOs: 597 and 618, respectively;
- g) SEQ ID NOs: 585 and 606, respectively;
- h) SEQ ID NOs: 586 and 607, respectively; and,
- i) SEQ ID NOs: 587 and 608, respectively,
- and wherein the antisense strand comprises a 5'-overhang about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length), optionally wherein the 5'-overhang is two (2) nucleotides in length.

In some embodiments, an oligonucleotide disclosed herein (e.g., an RNAi oligonucleotide) comprises a sense strand and an antisense strand, wherein the sense and antisense strands of the oligonucleotide comprise nucleotides sequences selected from the group consisting of:
- a) SEQ ID NOs: 579 and 600, respectively;
- b) SEQ ID NOs: 580 and 601, respectively;
- c) SEQ ID NOs: 590 and 611, respectively;
- d) SEQ ID NOs: 597 and 618, respectively; and,
- e) SEQ ID NOs: 586 and 607, respectively,
- and wherein the antisense strand comprises a 5'-overhang about one (1) to twenty (20) nucleotides in length (e.g., about 1, 2, 3, 4, 5, 6, 7, 8, 9, 10, 11, 12, 13, 14, 15, 16, 17, 18, 19, or about 20 nucleotides in length), optionally wherein the 5'-overhang is two (2) nucleotides in length.

In some embodiments, one or more (e.g., 2, 3, 4, 5, or more) nucleotides comprising the 3' terminus or 5' terminus of a sense and/or antisense strand are modified. For example, in some embodiments, one or two terminal nucleotides of the 3' terminus of the antisense strand are modified. In some embodiments, the last nucleotide at the 3' terminus of an antisense strand is modified, such that it comprises 2' modification, or it comprises, a 2'-O-methoxyethyl. In some embodiments, the last one or two terminal nucleotides at the 3' terminus of an antisense strand are complementary with the target. In some embodiments, the last one or two nucleotides at the 3' terminus of the antisense strand are not complementary with the target.

In some embodiments, an oligonucleotide disclosed herein (e.g., an RNAi oligonucleotide) comprises a sense strand and an antisense strand, wherein the 3' terminus of the sense strand comprises a step-loop described herein and the 3' terminus of the antisense strand comprises a 3'-overhang described herein. In some embodiments, an oligonucleotide disclosed herein (e.g., an RNAi oligonucleotide) comprises a sense strand and an antisense strand that form a nicked tetraloop structure described herein, wherein the 3' terminus of the sense strand comprises a stem-loop, wherein the loop is a tetraloop described herein, and wherein the 3' terminus of the antisense strand comprises a 3'-overhang described herein. In some embodiments, the 3'-overhang is two (2) nucleotides in length. In some embodiments, the two (2) nucleotides comprising the 3'-overhang both comprise guanine (G) nucleobases. One or both of the nucleotides comprising the 3'-overhang of the antisense strand may not be complementary with the target mRNA. Typically, one or both of the nucleotides comprising the 3'-overhang of the antisense strand are not complementary with the target mRNA.

Oligonucleotide Modifications

In some embodiments, an oligonucleotide described herein (e.g., an RNAi oligonucleotide) comprises a modification. Oligonucleotides (e.g., RNAi oligonucleotides) may be modified in various ways to improve or control specificity, stability, delivery, bioavailability, resistance from nuclease degradation, immunogenicity, base-pairing properties, RNA distribution and cellular uptake and other features relevant to therapeutic or research use.

In some embodiments, the modification is a modified sugar. In some embodiments, the modification is a 5'-terminal phosphate group. In some embodiments, the modification is a modified internucleotide linkage. In some embodiments, the modification is a modified base. In some embodiments, an oligonucleotide described herein can comprise any one of the modifications described herein or any combination thereof. For example, in some embodiments, an oligonucleotide described herein comprises at least one modified sugar, a 5'-terminal phosphate group, at least one modified internucleotide linkage, and at least one modified base. In some embodiments, the sense and antisense strands of an oligonucleotide comprise nucleotides sequences selected from the group consisting of:
- a) SEQ ID NOs: 579 and 600, respectively;
- b) SEQ ID NOs: 580 and 601, respectively;
- c) SEQ ID NOs: 595 and 616, respectively;
- d) SEQ ID NOs: 590 and 611, respectively;
- e) SEQ ID NOs: 596 and 617, respectively;
- f) SEQ ID NOs: 597 and 618, respectively;
- g) SEQ ID NOs: 585 and 606, respectively;
- h) SEQ ID NOs: 586 and 607, respectively; and,
- i) SEQ ID NOs: 587 and 608, respectively,
- wherein the oligonucleotide comprises at least one modified sugar, a 5'-terminal phosphate group, at least one modified internucleotide linkage, and at least one modified base.

In some embodiments, the sense and antisense strands of an oligonucleotide comprise nucleotides sequences selected from the group consisting of:
- a) SEQ ID NOs: 579 and 600, respectively;
- b) SEQ ID NOs: 580 and 601, respectively;
- c) SEQ ID NOs: 590 and 611, respectively;
- d) SEQ ID NOs: 597 and 618, respectively; and,
- e) SEQ ID NOs: 586 and 607, respectively,
- wherein the oligonucleotide comprises at least one modified sugar, a 5'-terminal phosphate group, at least one modified internucleotide linkage, and at least one modified base.

The number of modifications on an oligonucleotide (e.g., an RNAi oligonucleotide) and the position of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier, it may be advantageous for at least some of the nucleotides to be modified. Accordingly, in some embodiments, all or substantially all the nucleotides of an oligonucleotide are modified. In some embodiments, more than half of the nucleotides are modified. In some embodiments, less than half of the nucleotides are modified. In some embodiments, the sugar moiety of all nucleotides comprising the oligonucleotide is modified at the 2' position. The modifications may be reversible or irreversible. In some embodiments, an oligonucleotide as disclosed herein has a number and type of modified nucleotides sufficient to cause the desired characteristics (e.g., protection from enzymatic degradation, capacity to target a desired cell after in vivo administration, and/or thermodynamic stability).

Sugar Modifications

In some embodiments, an oligonucleotide described herein (e.g., an RNAi oligonucleotide) comprises a modified sugar. In some embodiments, a modified sugar (also referred herein to a sugar analog) includes a modified deoxyribose or ribose moiety in which, for example, one or more modifications occur at the 2', 3', 4' and/or 5' carbon position of the sugar. In some embodiments, a modified sugar may also include non-natural alternative carbon structures such as those present in locked nucleic acids ("LNA"; see, e.g., Koshkin et al. (1998) Tetrahedon 54:3607-30), unlocked nucleic acids ("UNA"; see, e.g., Snead et al. (2013) Mol. Ther-Nucl. Acids 2:e103) and bridged nucleic acids ("BNA"; see, e.g., Imanishi & Obika (2002) Chem Commun. (Camb) 21:1653-59).

In some embodiments, a nucleotide modification in a sugar comprises a 2'-modification. In some embodiments, a 2'-modification may be 2'-O-propargyl, 2'-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl] (2'-O-NMA) or 2'-deoxy-2'-fluoro-6-d-arabinonucleic acid (2'-FANA). In some embodiments, the modification is 2'-F, 2'-OMe or 2'-MOE. In some embodiments, a modification in a sugar comprises a modification of the sugar ring, which may comprise modification of one or more carbons of the sugar ring. For example, a modification of a sugar of a nucleotide may comprise a 2'-oxygen of a sugar linked to a 1'-carbon or 4'-carbon of the sugar, or a 2'-oxygen linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, an oligonucleotide (e.g., an RNAi oligonucleotide) described herein comprises at least about 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand of the oligonucleotide comprises at least about 1 modified nucleotide (e.g., at least 1, at least 5, at least 10, at least 15, at least 20, at least 25, at least 30, at least 35, or more). In some embodiments, the antisense strand of the oligonucleotide comprises at least about 1 modified nucleotide (e.g., at least 1, at least 5, at least 10, at least 15, at least 20, or more).

In some embodiments, all the nucleotides of the sense strand of the oligonucleotide are modified. In some embodiments, all the nucleotides of the antisense strand of the oligonucleotide are modified. In some embodiments, all the nucleotides of the oligonucleotide (i.e., both the sense strand and the antisense strand) are modified. In some embodiments, the modified nucleotide comprises a 2'-modification (e.g., a 2'-F or 2'-OMe, 2'-MOE, and 2'-deoxy-2'-fluoro-β-d-arabinonucleic acid).

In some embodiments, the disclosure provides oligonucleotides having different modification patterns. In some embodiments, an oligonucleotide herein comprises a sense strand having a modification pattern as set forth in the Examples and Sequence Listing and an antisense strand having a modification pattern as set forth in the Examples and Sequence Listing.

In some embodiments, an oligonucleotide disclosed herein (e.g., an RNAi oligonucleotide) comprises an antisense strand having nucleotides that are modified with 2'-F. In some embodiments, an oligonucleotide herein comprises an antisense strand comprising nucleotides that are modified with 2'-F and 2'-OMe. In some embodiments, an oligonucleotide disclosed herein comprises a sense strand having nucleotides that are modified with 2'-F. In some embodiments, an oligonucleotide disclosed herein comprises a sense strand comprises nucleotides that are modified with 2'-F and 2'-OMe.

In some embodiments, an oligonucleotide described herein comprises a sense strand with about 10-15%, 10%, 11%, 12%, 13%, 14% or 15% of the nucleotides of the sense strand comprising a 2'-fluoro modification. In some embodiments, about 11% of the nucleotides of the sense strand comprise a 2'-fluoro modification. In some embodiments, an oligonucleotide described herein comprises an antisense strand with about 25-35%, 25%, 26%, 27%, 28%, 29%, 30%, 31%, 32%, 33%, 34% or 35% of the nucleotides of the antisense strand comprising a 2'-fluoro modification. In some embodiments, about 32% of the nucleotides of the antisense strand comprise a 2'-fluoro modification. In some embodiments, the oligonucleotide has about 15-25%, 15%, 16%, 17%, 18%, 19%, 20%, 21%, 22%, 23%, 24%, or 25% of its nucleotides comprising a 2'-fluoro modification. In some embodiments, about 19% of the nucleotides in the oligonucleotide comprise a 2'-fluoro modification.

As used herein, oligonucleotide numbering of the sense and antisense strand, respectively, starts at the 5' end with "position 1".

In some embodiments, one or more of positions 8, 9, 10 or 11 of the sense strand is modified with a 2'-F group. In some embodiments, one or more of positions 3, 8, 9, 10, 12, 13 and 17 of the sense strand is modified with a 2'-F group. In some embodiments, one or more of positions 2, 3, 4, 5, 7, 10 and 14 of the antisense strand is modified with a 2'-F group. In some embodiments, one or more of positions 2, 3, 4, 5, 7, 8, 10, 14, 16 and 19 is modified with a 2'-F group. In some embodiments, the sugar moiety at each of nucleotides at positions 1-7 and 12-20 in the sense strand is modified with a 2'-OMe. In some embodiments, the sugar moiety at each of nucleotides at positions 1-7, 12-27 and 31-36 in the sense strand is modified with a 2'-OMe. In some embodiments, the sugar moiety at each of nucleotides at positions 6, 9, 11-13, 15, 17, 18 and 20-22 in the sense strand is modified with a 2'-OMe.

In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;

h) SEQ ID NOs: 586 and 607, respectively; and,
i) SEQ ID NOs: 587 and 608, respectively,
wherein one or more of positions 8, 9, 10 or 11 of the sense strand is modified with a 2'-F group.

In some embodiments, the sense and antisense strands of an oligonucleotide comprise nucleotides sequences selected from the group consisting of:
a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively,
wherein one or more of positions 8, 9, 10 or 11 of the sense strand is modified with a 2'-F group.

In some embodiments, an oligonucleotide provided herein comprises an antisense strand having the sugar moiety of each of the nucleotides at positions 2, 5, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 1, 2, 5, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl, (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 2, 4, 5, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 1, 2, 3, 5, 7, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 2, 3, 4, 5, 7, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 1, 2, 3, 5, 10, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 2, 3, 4, 5, 10, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety of each of the nucleotides at positions 2, 3, 5, 7, 10, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-6-d-arabinonucleic acid (2'-FANA).

In some embodiments, an oligonucleotide provided herein comprises an antisense strand having the sugar moiety of each of the nucleotides at positions 2, 3, 4, 5, 7, 10, and 14 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-6-d-arabinonucleic acid (2'-FANA).

In some embodiments, an oligonucleotide provided herein comprises an antisense strand having the sugar moiety of each of the nucleotides at positions 2, 3, 4, 5, 7, 8, 10, 14, 16 and 19 of the antisense strand modified with 2'-F and the sugar moiety of each of the remaining nucleotides of the antisense strand modified with a modification selected from the group consisting of 2'-O-propargyl, 2'-O-propylamin, 2'-amino, 2'-ethyl, 2'-aminoethyl (EA), 2'-(2'-OMe), 2'-O-methoxyethyl (2'-MOE), 2'-O-[2-(methylamino)-2-oxoethyl] (2'-O-NMA), and 2'-deoxy-2'-fluoro-6-d-arabinonucleic acid (2'-FANA).

In some embodiments, an oligonucleotide provided herein comprises an antisense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, or position 22 modified with 2'-F.

In some embodiments, an oligonucleotide provided herein comprises an antisense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, or position 22 modified with 2'-OMe.

In some embodiments, an oligonucleotide provided herein comprises an antisense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, or position 22 modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises an antisense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, or position 22 modified with a modification selected from the group consisting of 2'-fluoro (2'-F), 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises a sense strand having the sugar moiety at positions 8-11 modified with 2'-F. In some embodiments, an oligonucleotide provided herein comprises a sense strand having the sugar moiety at positions 3, 8, 9, 10, 12, 13 and 17 modified with 2'-F. In some embodiments, an oligonucleotide provided herein comprises a sense strand having the sugar moiety at positions 1-7 and 12-17 or 12-20 modified with 2'OMe. In some embodiments, an oligonucleotide provided herein comprises a sense strand having the sugar moiety at positions 1-7, 12-27 and 31-36 modified with 2'OMe. In some embodiments, an oligonucleotide provided herein comprises a sense strand having the sugar moiety of each of the nucleotides at positions 1-7 and 12-17 or 12-20 of the sense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA). In some embodiments, an oligonucleotide provided herein comprises a sense strand having the sugar moiety at positions 1-2, 4-7, 11, 14-16 and 18-20 modified with 2'OMe. In some embodiments, an oligonucleotide provided herein comprises a sense strand having the sugar moiety of each of the nucleotides at positions 1-2, 4-7, 11, 14-16 and 18-20 of the sense strand modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-β-d-arabinonucleic acid (2'-FANA).

In some embodiments, an oligonucleotide provided herein comprises a sense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, or position 36 modified with 2'-F.

In some embodiments, an oligonucleotide provided herein comprises a sense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, or position 36 modified with 2'-OMe.

In some embodiments, an oligonucleotide provided herein comprises a sense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, or position 36 modified with a modification selected from the group consisting of 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-6-d-arabinonucleic acid (2'-FANA).

In some embodiments, an oligonucleotide provided herein comprises a sense strand having the sugar moiety at position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, or position 36 modified with a modification selected from the group consisting of 2'-fluoro (2'-F), 2'-O-propargyl, 2'-O-propylamin, 2'-amino, 2'-ethyl, 2'-aminoethyl (EA), 2'-O-methyl (2'-OMe), 2'-O-methoxyethyl (2'-MOE), 2'-O-[2-(methylamino)-2-oxoethyl] (2'-O-NMA), and 2'-deoxy-2'-fluoro-6-d-arabinonucleic acid (2'-FANA).

5'-Terminal Phosphate

In some embodiments, an oligonucleotide described herein (e.g., an RNAi oligonucleotide) comprises a sense strand and an antisense strand, wherein the antisense strand comprises a 5'-terminal phosphate. In some embodiments, 5'-terminal phosphate groups of an RNAi oligonucleotide enhance the interaction with Ago2. However, oligonucleotides comprising a 5'-phosphate group may be susceptible to degradation via phosphatases or other enzymes, which can limit their performance and/or bioavailability in vivo. In some embodiments, an oligonucleotide herein includes analogs of 5' phosphates that are resistant to such degradation. In some embodiments, the phosphate analog is oxymethyl phosphonate, vinyl phosphonate or malonyl phosphonate, or a combination thereof. In certain embodiments, the 5' terminus of an oligonucleotide strand is attached to chemical moiety that mimics the electrostatic and steric properties of a natural 5'-phosphate group ("phosphate mimic"). In some embodiments, the sense and antisense strands of an oligonucleotide comprise nucleotides sequences selected from the group consisting of:

a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively,
wherein the oligonucleotide comprises a 5'-terminal phosphate, optionally a 5'-terminal phosphate analog.

In some embodiments, the sense and antisense strands of an oligonucleotide comprise nucleotides sequences selected from the group consisting of:
a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively,
wherein the oligonucleotide comprises a 5'-terminal phosphate, optionally a 5'-terminal phosphate analog.

In some embodiments, an oligonucleotide herein (e.g., an RNAi oligonucleotide) has a phosphate analog at a 4'-carbon position of the sugar (referred to as a "4'-phosphate analog"). See, e.g., Intl. Patent Application Publication No. WO 2018/045317. In some embodiments, an oligonucleotide herein comprises a 4'-phosphate analog at a 5'-terminal nucleotide. In some embodiments, a phosphate analog is an oxymethyl phosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, a 4'-phosphate analog is an oxymethyl phosphonate. In some embodiments, an oxymethyl phosphonate is represented by the formula —O—CH$_2$—PO(OH)$_2$, —O—CH$_2$—PO(OR)$_2$, or —O—CH$_2$—PO(OH)(R), in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$ or a protecting group. In certain embodiments, the alkyl group is CH$_2$CH$_3$. More typically, R is independently selected from H, CH$_3$ or CH$_2$CH$_3$. In some embodiment, R is CH$_3$. In some embodiments, the 4'-phosphate analog is 4'-oxymethyl phosphonate.

In some embodiments, an oligonucleotide provided herein comprises an antisense strand comprising a 4'-phosphate analog at the 5'-terminal nucleotide, wherein 5'-terminal nucleotide comprises the following structure:

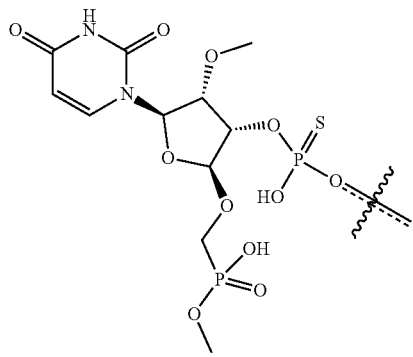

(Chem. 1)

4'-O-monomethylphosphonate-2'-O-methyluridine phosphorothioate [MePhosphonate-4O-mUs]

In some embodiments, an oligonucleotide provided herein comprises an antisense strand comprising a 4'-phosphate analog at the 5'-terminal nucleotide, wherein 5'-terminal nucleotide comprises the following structure:

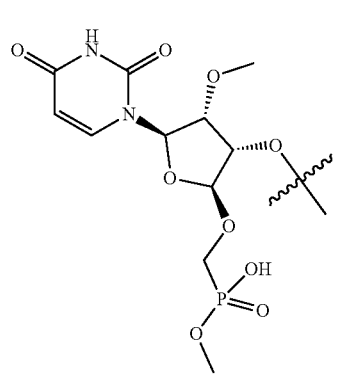

(Chem. 1a)

4'-O-monomethylphosphonate-2'-O-methyluridine [MePhosphonate-4O-mU]

Chem. 1a may be referred to as 4'-O-monomethylphosphonate-2'-O-methyluridine phosphorothioate [MePhosphonate-4O-mUs] when a phosphorothioate internucleotide linkage is provided.

Modified Internucleotide Linkage

In some embodiments, an oligonucleotide provided herein (e.g., a RNAi oligonucleotide) comprises a modified internucleotide linkage. In some embodiments, phosphate modifications or substitutions result in an oligonucleotide that comprises at least about 1 (e.g., at least 1, at least 2, at least 3 or at least 5) modified internucleotide linkage. In some embodiments, any one of the oligonucleotides disclosed herein comprises about 1 to about 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9 or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

In some embodiments, an oligonucleotide provided herein (e.g., a RNAi oligonucleotide) has a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide described herein has a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand. In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively,
  wherein the oligonucleotide comprises a modified internucleotide linkage.

In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 590 and 611, respectively;
  d) SEQ ID NOs: 597 and 618, respectively; and,
  e) SEQ ID NOs: 586 and 607, respectively,
  wherein the oligonucleotide comprises a modified internucleotide linkage.

Base Modifications

In some embodiments, an oligonucleotide provided herein (e.g., an RNAi oligonucleotides) comprises one or more modified nucleobases. In some embodiments, modified nucleobases (also referred to herein as base analogs) are linked at the 1' position of a nucleotide sugar moiety. In certain embodiments, a modified nucleobase is a nitrogenous base. In some embodiments, a modified nucleobase does not contain nitrogen atom. See, e.g., US Patent Application Publication No. 2008/0274462. In some embodiments, a modified nucleotide comprises a universal base. In some embodiments, a modified nucleotide does not contain a nucleobase (abasic). In some embodiments, the sense and antisense strands of an oligonucleotide comprise nucleotides sequences selected from the group consisting of: a) SEQ ID NOs: 579 and 600, respectively;
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively,
  wherein the oligonucleotide comprises one or more modified nucleobases.

In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 590 and 611, respectively;
  d) SEQ ID NOs: 597 and 618, respectively; and,
  e) SEQ ID NOs: 586 and 607, respectively,
  wherein the oligonucleotide comprises one or more modified nucleobases.

In some embodiments, a universal base is a heterocyclic moiety located at the 1' position of a nucleotide sugar moiety in a modified nucleotide, or the equivalent position in a nucleotide sugar moiety substitution, that, when present in a duplex, can be positioned opposite more than one type of base without substantially altering structure of the duplex. In some embodiments, compared to a reference single-stranded nucleic acid (e.g., oligonucleotide) that is fully complementary to a target nucleic acid (e.g., a TMPRSS6 mRNA), a single-stranded nucleic acid containing a universal base forms a duplex with the target nucleic acid that has a lower $T_m$ than a duplex formed with the complementary nucleic acid. In some embodiments, when compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include, but are not limited to, inosine, 1-β-D-ribofuranosyl-5-nitroindole and/or 1-βD-ribofuranosyl-3-nitropyrrole (see, US Patent Application Publication No. 2007/0254362; Van Aerschot et al. (1995) Nucleic Acids Res. 23:4363-4370; Loakes et al. (1995) Nucleic Acids Res. 23:2361-66; and Loakes & Brown (1994) Nucleic Acids Res. 22:4039-43).

Targeting Ligands

In some embodiments, it is desirable to target an oligonucleotide provided herein (e.g., an RNAi oligonucleotide) to one or more cells or cell type, tissues, organs, or anatomical regions or compartments. Such a strategy may help to avoid undesirable effects to the organism treated and/or to avoid undue loss of the oligonucleotide to cells, tissues, organs, or anatomical regions or compartments that would not benefit from the oligonucleotide or its effects (e.g., inhibition or reduction of TMPRSS6 expression). Accordingly, in some embodiments, oligonucleotides disclosed herein (e.g., RNAi oligonucleotides) are modified to facilitate targeting and/or delivery to particular cells or cell types, tissues, organs, or anatomical regions or compartments (e.g., to facilitate delivery of the oligonucleotide to the liver). In some embodiments, an oligonucleotide comprises at least one nucleotide (e.g., 1, 2, 3, 4, 5, 6 or more nucleotides) conjugated to one or more targeting ligand(s). In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 595 and 616, respectively;
  d) SEQ ID NOs: 590 and 611, respectively;
  e) SEQ ID NOs: 596 and 617, respectively;
  f) SEQ ID NOs: 597 and 618, respectively;
  g) SEQ ID NOs: 585 and 606, respectively;
  h) SEQ ID NOs: 586 and 607, respectively; and,
  i) SEQ ID NOs: 587 and 608, respectively,
  wherein the oligonucleotide comprises a targeting ligand conjugated to at least one nucleotide.

In some embodiments, the sense and antisense strands of an oligonucleotide comprise nucleotides sequences selected from the group consisting of:
  a) SEQ ID NOs: 579 and 600, respectively;
  b) SEQ ID NOs: 580 and 601, respectively;
  c) SEQ ID NOs: 590 and 611, respectively;
  d) SEQ ID NOs: 597 and 618, respectively; and,
  e) SEQ ID NOs: 586 and 607, respectively,
  wherein the oligonucleotide comprises a targeting ligand conjugated to at least one nucleotide.

In some embodiments, the targeting ligand comprises a carbohydrate, amino sugar, cholesterol, peptide, polypeptide, protein, or part of a protein (e.g., an antibody or antibody fragment), or lipid. In certain embodiments, the targeting ligand is a carbohydrate comprising at least one GalNAc moiety.

In some embodiments, 1 or more (e.g., 1, 2, 3, 4, 5 or 6) nucleotides of an oligonucleotide provided herein (e.g., an RNAi oligonucleotide) are each conjugated to a separate targeting ligand (e.g., a GalNAc moiety). In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., targeting ligands are conjugated to a 2 to 4 nucleotide overhang or extension on the 5' or 3' terminus of the sense or antisense strand) such that the targeting ligands resemble bristles of a toothbrush and the oligonucleotide resembles a toothbrush. For example, an oligonucleotide may comprise a stem-loop at either the 5' or 3' terminus of the sense strand and 1, 2, 3 or 4 nucleotides of the loop of the stem may be individually conjugated to a targeting ligand. In some embodiments, an oligonucleotide provided by the disclosure (e.g., a RNAi oligonucleotide) comprises a stem-loop at the 3' terminus of the sense strand, wherein the loop of the stem-loop comprises a triloop or a tetraloop, and wherein the 3 or 4 nucleotides comprising the triloop or tetraloop, respectively, are individually conjugated to a targeting ligand. In some embodiments, an oligonucleotide provided by the disclosure (e.g., a RNAi oligonucleotide) comprises a stem-loop at the 3' terminus of the sense strand, wherein the loop of the stem-loop comprises a tetraloop, and wherein 3 nucleotides of the tetraloop are individually conjugated to a targeting ligand.

GalNAc is a high affinity carbohydrate ligand for the asialoglycoprotein receptor (ASGPR), which is primarily expressed on the surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to oligonucleotides of the instant disclosure can be used to target these oligonucleotides to the ASGPR expressed on cells. In some embodiments, an oligonucleotide of the instant disclosure (e.g., an RNAi oligonucleotide) is conjugated to at least one or more GalNAc moieties, wherein the GalNAc moieties target the oligonucleotide to an ASGPR expressed on human liver cells (e.g., human hepatocytes). In some embodiments, the GalNAc moiety target the oligonucleotide to the liver.

In some embodiments, an oligonucleotide of the instant disclosure (e.g., an RNAi oligonucleotide) is conjugated directly or indirectly to a monovalent GalNAc moiety. In some embodiments, the oligonucleotide is conjugated directly or indirectly to more than one monovalent GalNAc (i.e., is conjugated to 2, 3 or 4 monovalent GalNAc moieties and is typically conjugated to 3 or 4 monovalent GalNAc moieties). In some embodiments, an oligonucleotide is conjugated to one or more bivalent GalNAc, trivalent GalNAc or tetravalent GalNAc moieties. In some embodiments, a bivalent, trivalent or tetravalent GalNAc moiety is conjugated to an oligonucleotide via a branched linker. In some embodiments, a monovalent GalNAc moiety is conjugated to a first nucleotide and a bivalent, trivalent, or tetravalent GalNAc moiety is conjugated to a second nucleotide via a branched linker.

In some embodiments, one (1) or more (e.g., 1, 2, 3, 4, 5 or 6) nucleotides of an oligonucleotide described herein (e.g., an RNAi oligonucleotide) are each conjugated to a GalNAc moiety. In some embodiments, two (2) to four (4) nucleotides of a tetraloop are each conjugated to a separate GalNAc moiety. In some embodiments, one (1) to three (3) nucleotides of a triloop are each conjugated to a separate GalNAc moiety. In some embodiments, targeting ligands are conjugated to two (2) to four (4) nucleotides at either ends of the sense or antisense strand (e.g., ligands are conjugated to a two (2) to four (4) nucleotide overhang or extension on the 5' or 3' terminus of the sense or antisense strand) such that the GalNAc moieties resemble bristles of a toothbrush and the oligonucleotide resembles a toothbrush. In some embodiments, GalNAc moieties are conjugated to a nucleotide of the sense strand. For example, three (3) or four (4) GalNAc moieties can be conjugated to nucleotides in the tetraloop of the sense strand where each GalNAc moiety is conjugated to one (1) nucleotide.

In some embodiments, an oligonucleotide described herein (e.g., an RNAi oligonucleotide) comprises a tetraloop, wherein the tetraloop (tetraLp) is any combination of adenine (A) and guanine (G) nucleotides. In some embodiments, the tetraloop (tetraLp) comprises a monovalent GalNAc moiety attached to any one or more guanine (G) nucleotides of the tetraloop via any linker described herein, as depicted below in Chem. 2 (X=heteroatom):

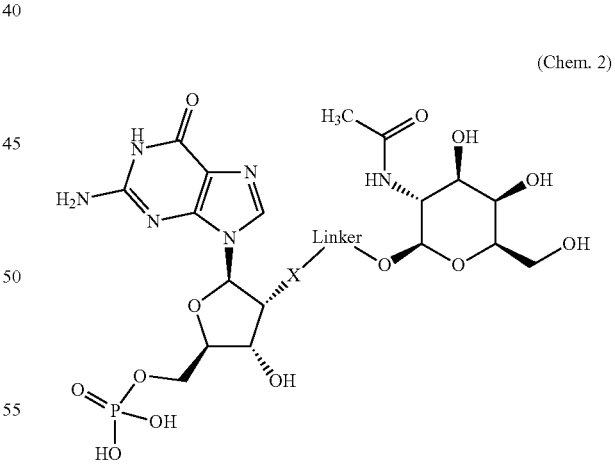

(Chem. 2)

It is understood that when comprised in an oligonucleotide, Chem. 2 may be covalently linked to neighboring nucleotides. In some embodiments, the tetraloop (tetraLp) comprises a monovalent GalNAc moiety attached to any one or more guanine (G) nucleotides of the tetraloop via any linker described herein, as depicted below in Chem. 2a (X=heteroatom):

(Chem. 2a)

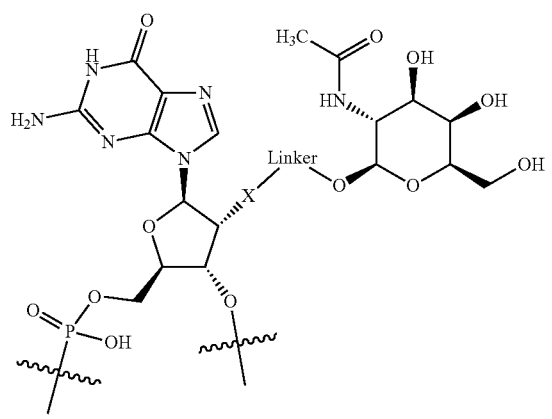

In some embodiments, the tetraloop (tetraLp) has a monovalent GalNAc attached to any one or more adenine (A) nucleotides of the tetraloop via any linker described herein, as depicted below Chem. 3 (X=heteroatom):

(Chem. 3)

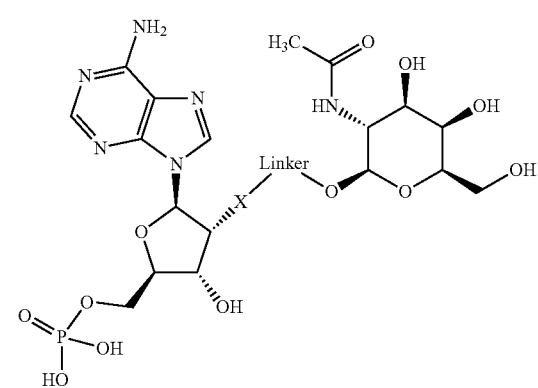

It is understood that when comprised in an oligonucleotide, Chem. 3 may be covalently linked to neighboring nucleotides. In some embodiments, the tetraloop (tetraLp) has a monovalent GalNAc attached to any one or more adenine (A) nucleotides of the tetraloop via any linker described herein, as depicted below Chem. 3a (X=heteroatom):

(Chem. 3a)

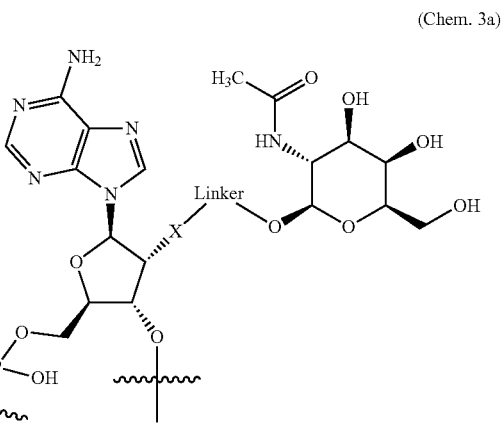

In some embodiments, an oligonucleotide herein (e.g., an RNAi oligonucleotide) comprises a monovalent GalNAc moiety attached to a guanine (G) nucleotide referred to as [ademG-GalNAc] or 2'-aminodiethoxymethanol-Guanine-GalNAc, as depicted below (Chem. 4)

(Chem. 4)

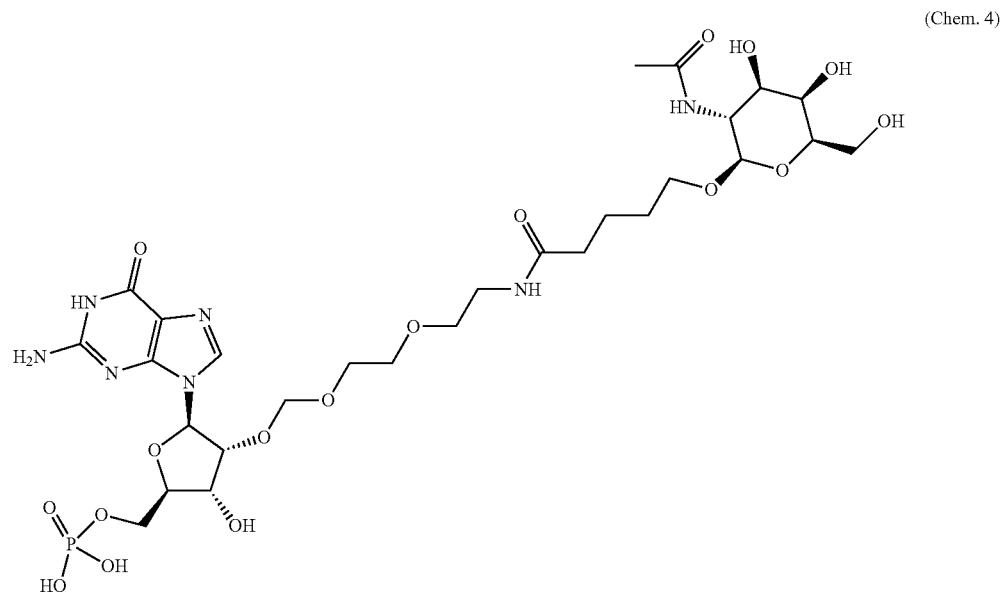 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(=O)[nH]c(N)nc32)O[C@H](CO)[C@H](O)[C@@H]1O]

It is understood that when comprised in an oligonucleotide, Chem. 4 may be linked to neighboring nucleotides such as for instance shown in Chem 4a below:

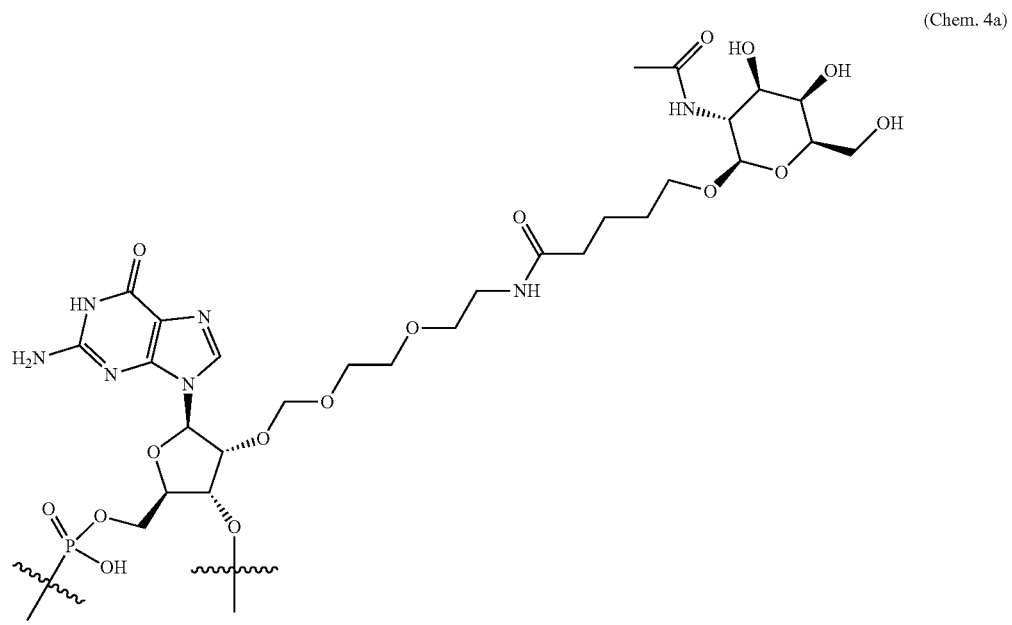 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(*)(=O)O]
(Chem. 4a)

In some embodiments, an oligonucleotide herein comprises a monovalent GalNAc moiety attached to an adenine nucleotide, referred to as [ademA-GalNAc] or 2'-aminodiethoxymethanol-Adenine-GalNAc, as depicted below (Chem. 5):

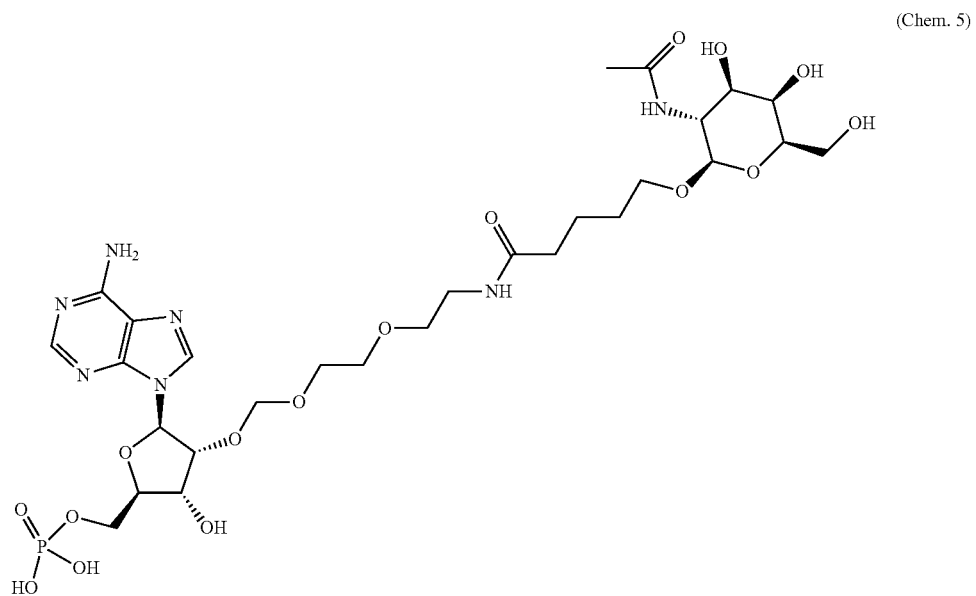 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(N)ncnc32)O[C@H](CO)[C@H](O)[C@@H]1O]
(Chem. 5)

It is understood that when comprised in an oligonucleotide, Chem. 5 may be linked to neighboring nucleotides such as for instance shown in Chem 5a below:

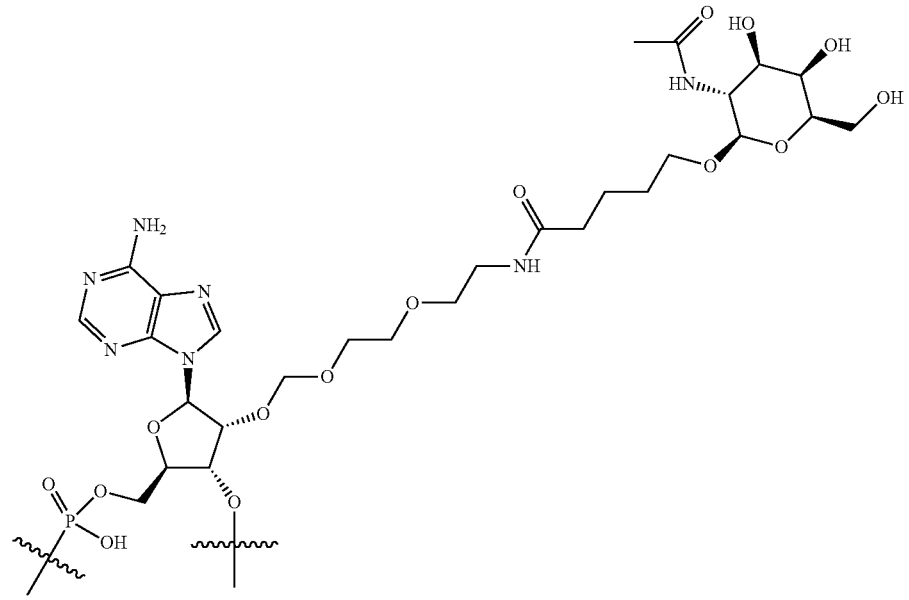

(Chem. 5a)

An example of such conjugation is shown below (Chem. 6) for a loop comprising from 5' to 3' the nucleotide sequence GAAA (L=linker, X=heteroatom). Such a loop may be present, for example, at positions 27-30 of a sense strand provided herein. In the chemical formula, ⅓ is used to describe an attachment point to the oligonucleotide strand (Chem. 6).

(Chem. 6)
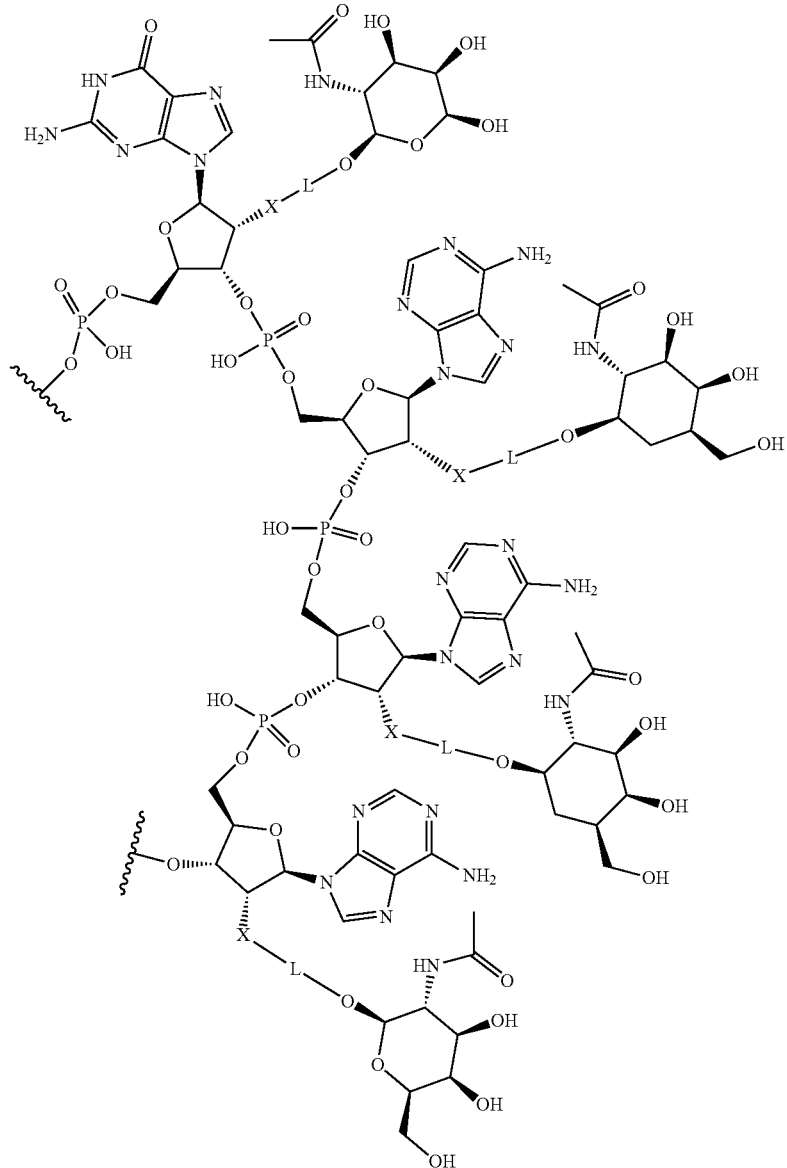
Another example of such conjugation is shown below (Chem. 6a) for a loop comprising from 5' to 3' the nucleotide sequence GAAA (L=linker, X=heteroatom). Such a loop may be present, for example, at positions 27-30 of a sense strand provided herein. In the chemical formula, ⌇ is used to describe an attachment point to the oligonucleotide strand.

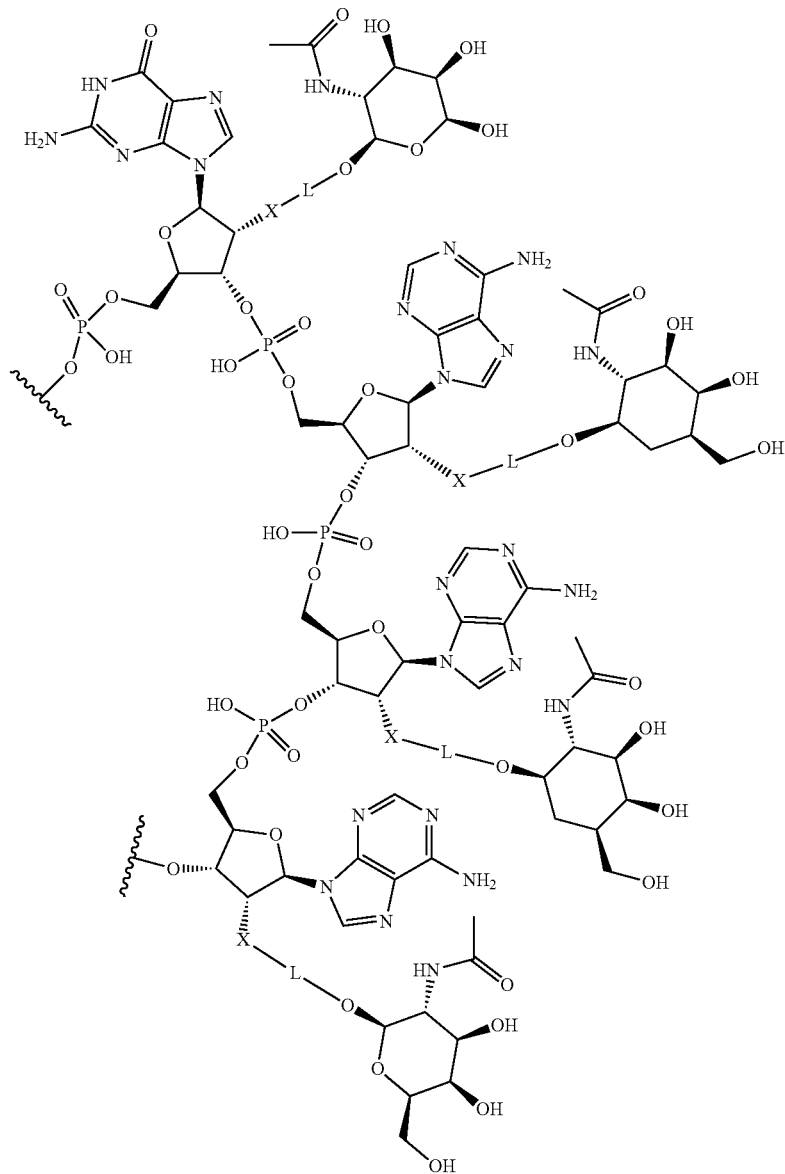

(Chem. 6a)

Appropriate methods or chemistry (e.g., click chemistry) can be used to link a targeting ligand to a nucleotide. In some embodiments, a targeting ligand is conjugated to a nucleotide comprising an oligonucleotide herein (e.g., an RNAi oligonucleotide) using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO2016/100401.

In some embodiments, the linker is a labile linker. However, in other embodiments, the linker is stable. An example is shown below for a loop comprising from 5' to 3' the nucleotides GAAA, in which GalNAc moieties are attached to nucleotides of the loop using an acetal linker (Chem. 7 and Chem. 8). Such a loop may be present, for example, at positions 27-30 of the any one of the sense strands. In the chemical formula, ⌇ is an attachment point to the oligonucleotide strand (Chem. 7 and Chem. 8).

(Chem. 7)
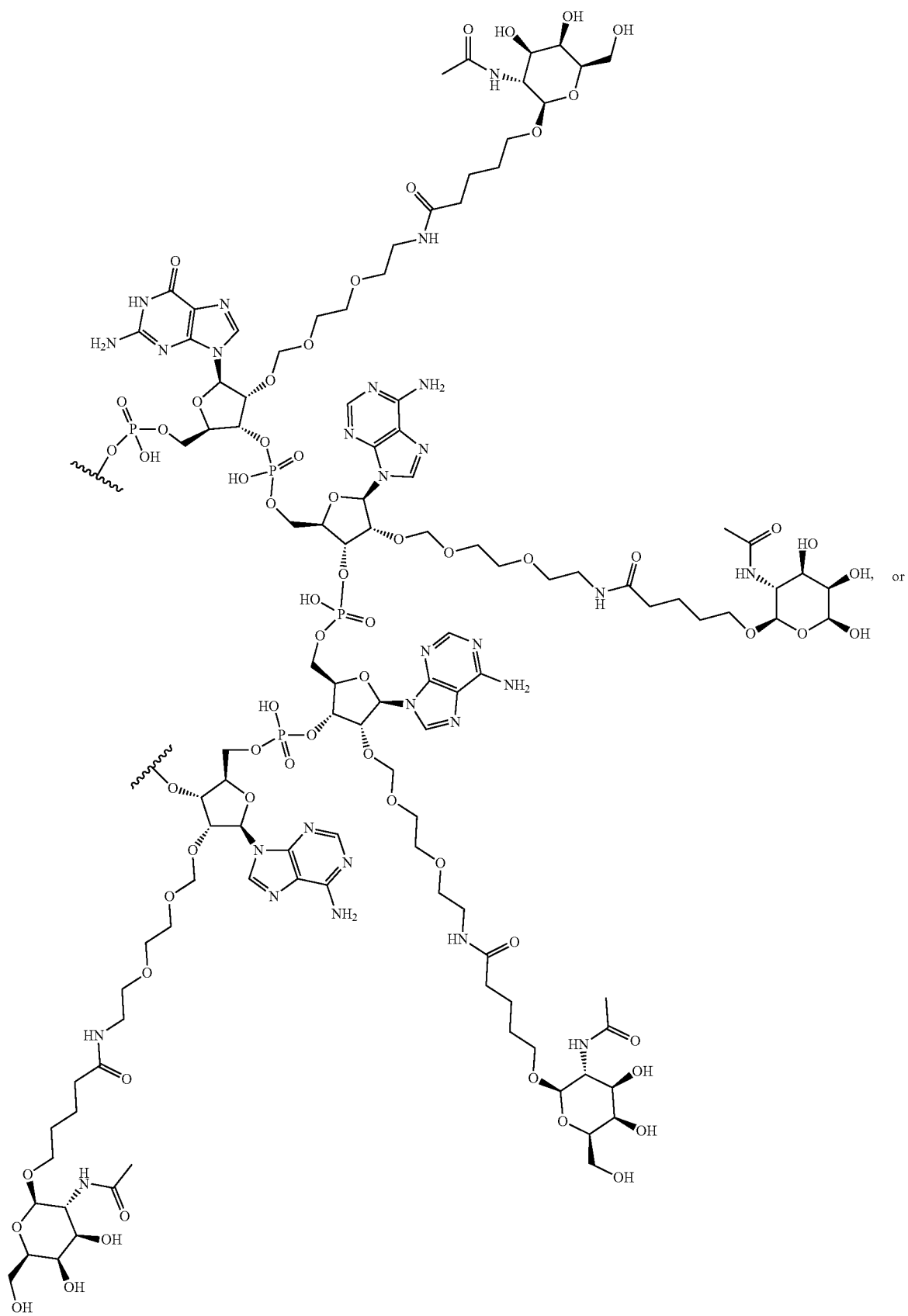

(Chem. 8)
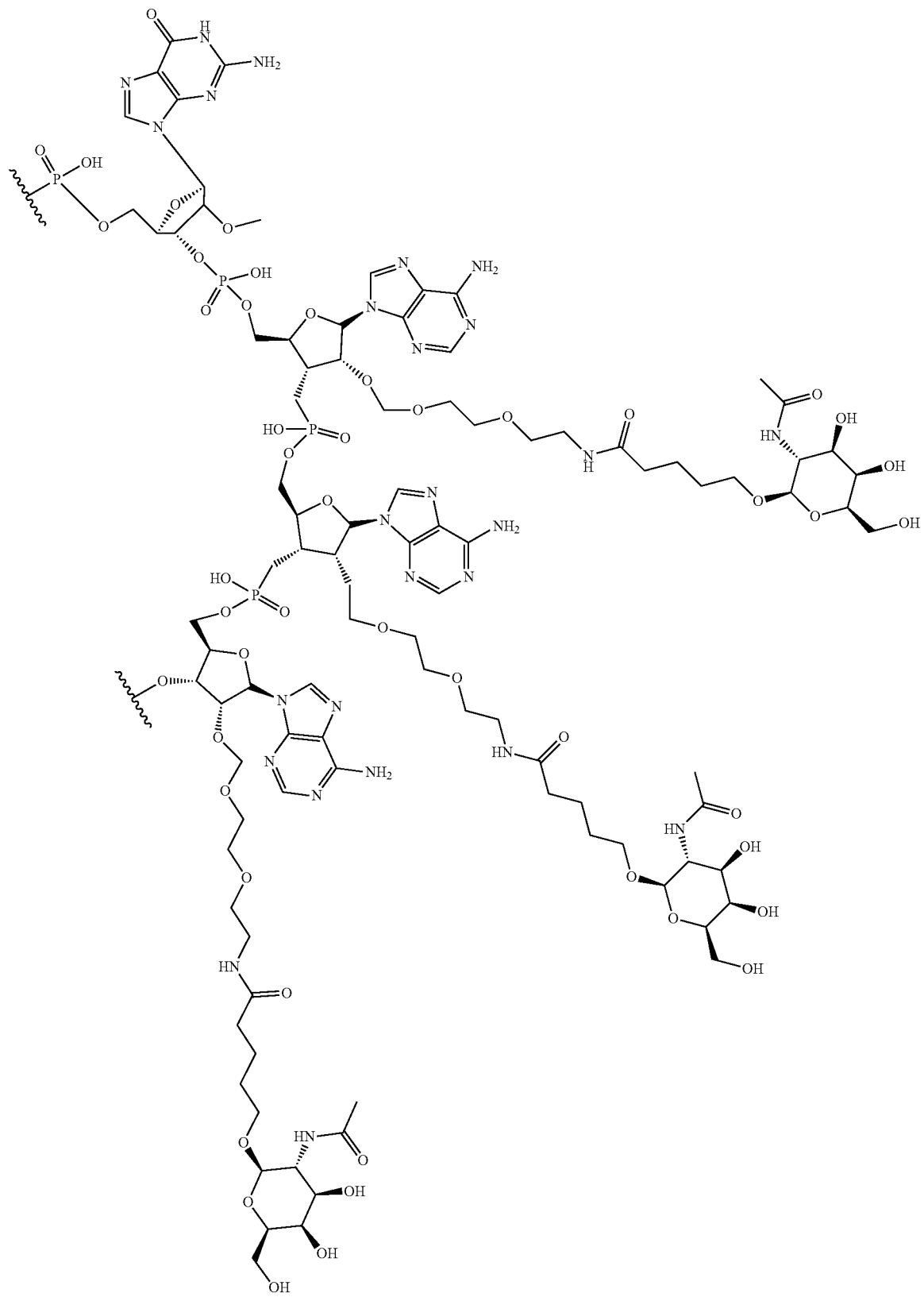

An example is shown below for a loop comprising from 5' to 3' the nucleotides GAAA, in which GalNAc moieties are attached to nucleotides of the loop using an acetal linker (Chem. 7a and Chem. 8a). Such a loop may be present, for example, at positions 27-30 of the any one of the sense strands. In the chemical formula,  is an attachment point to the oligonucleotide strand (Chem. 7a and Chem. 8a):

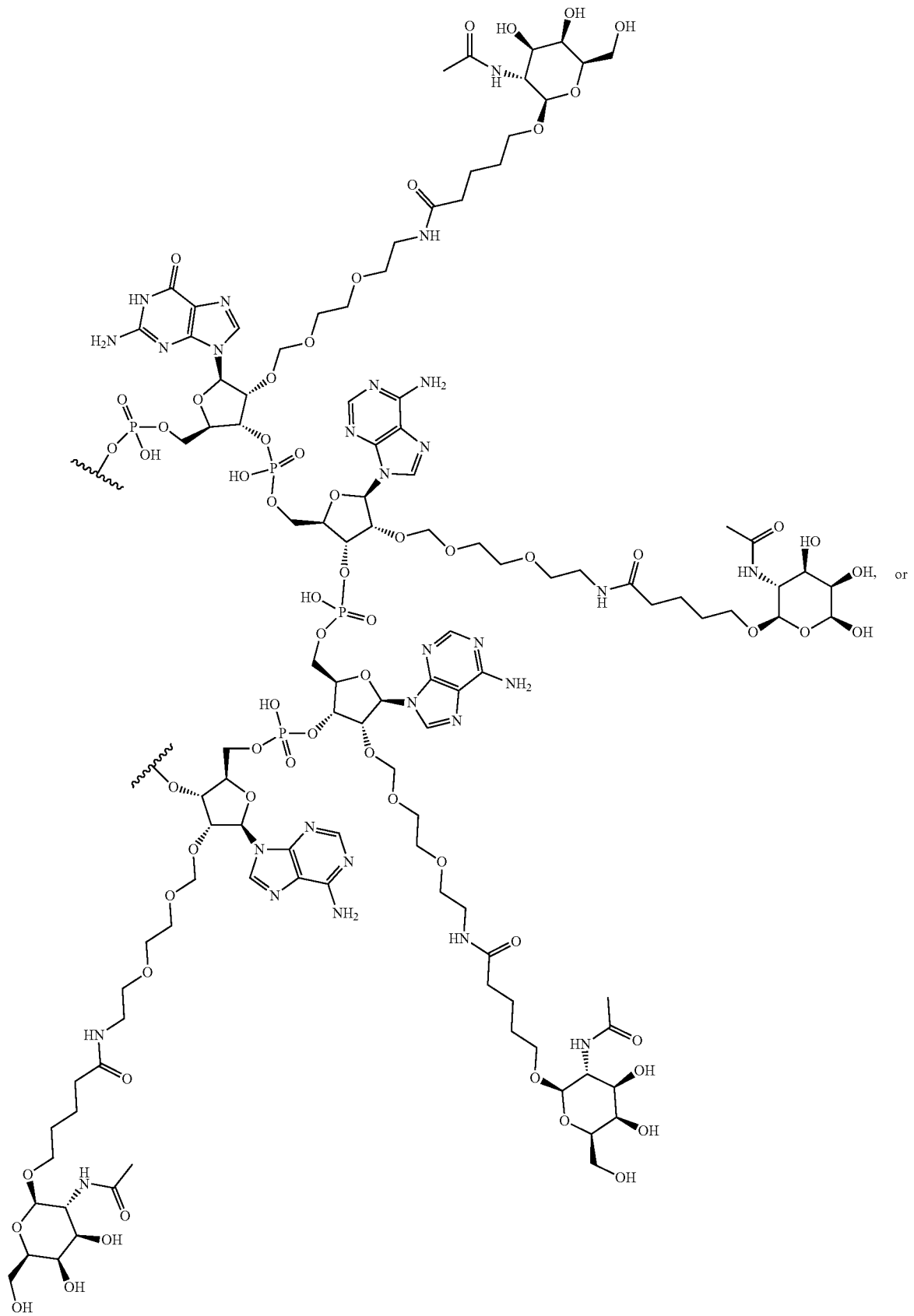
(Chem. 7a)

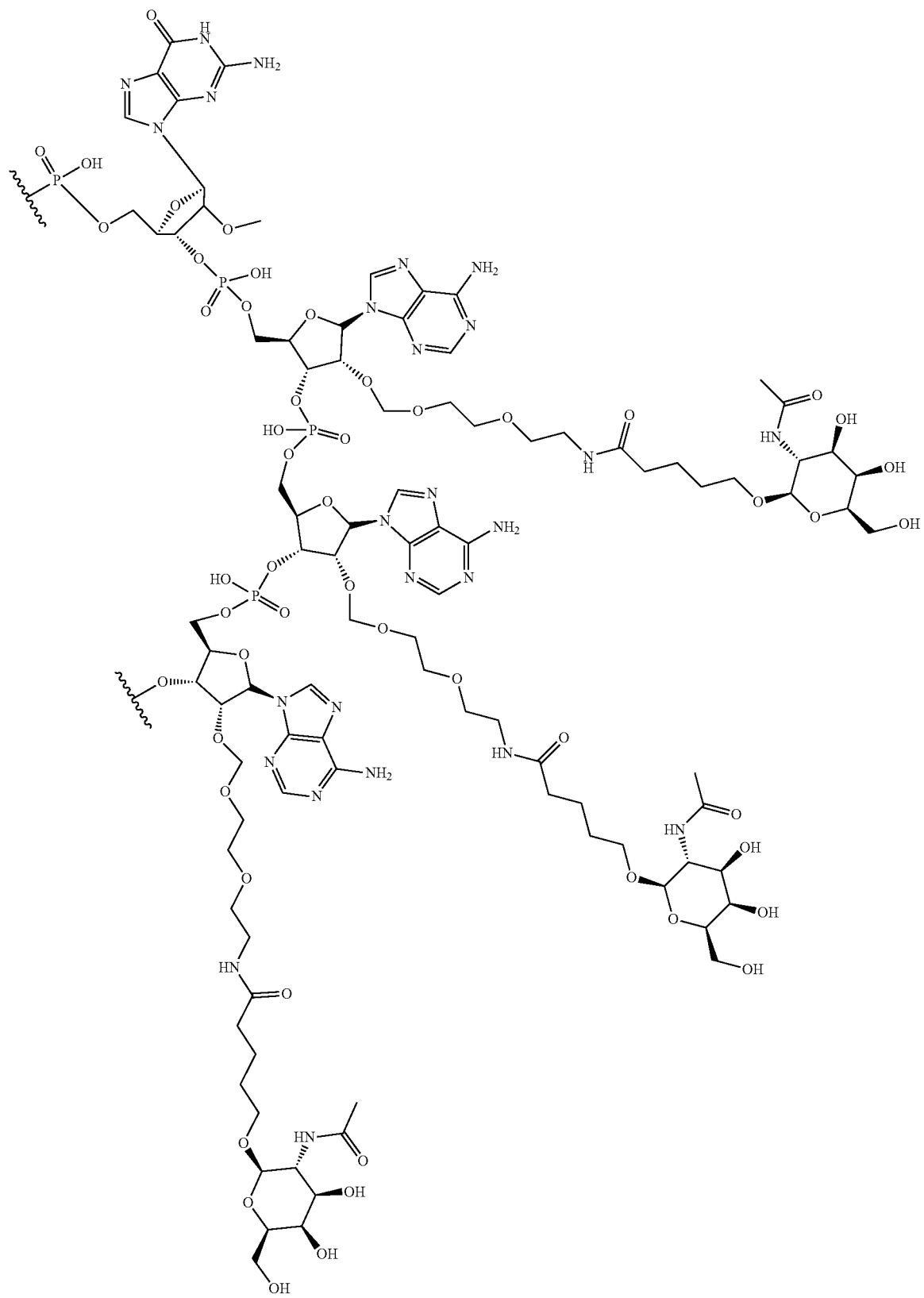
(Chem. 8a)

As mentioned, various appropriate methods or chemistry synthetic techniques (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is a stable linker.

In some embodiments, the oligonucleotides herein (e.g., RNAi oligonucleotides) do not have a GalNAc conjugated thereto.

In some embodiments, the sense and antisense strands of an oligonucleotide comprise nucleotides sequences selected from the group consisting of:
a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively,
wherein the oligonucleotide comprises at least one GalNAc moiety conjugated to a nucleotide.

In some embodiments, the sense and antisense strands of an oligonucleotide comprise nucleotides sequences selected from the group consisting of:
a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively,
wherein the oligonucleotide comprises at least one GalNAc moiety conjugated to a nucleotide.

Exemplary Oligonucleotides for Reducing TMPRSS6 Expression

In some embodiments, the TMPRSS6-targeting oligonucleotide (e.g., an RNAi oligonucleotide) for reducing TMPRSS6 expression provided by the disclosure comprise a sense strand and an antisense strand, wherein all nucleotides comprising the sense strand and antisense strand are modified, wherein the antisense strand comprises a region of complementarity to a TMPRSS6 mRNA target sequence of any one of SEQ ID NOs: 661-852 and wherein the region of complementarity is at least 15 contiguous nucleotides in length. In some embodiments, the 5'-terminal nucleotide of the antisense strand comprises 4'-O-monomethylphosphonate-2'-O-methyluridine [MePhosphonate-4O-mU], as described herein. In some embodiments, the 5'-terminal nucleotide of the antisense strand comprises a phosphorothioate linkage. In some embodiments, the antisense strand and the sense strand comprise one or more 2'-fluoro (2'-F) and 2'-O-methyl (2'-OMe) modified nucleotides and at least one phosphorothioate linkage. In some embodiments, the antisense strand comprises four (4) phosphorothioate linkages and the sense strand comprises one (1) phosphorothioate linkage. In some embodiments, the antisense strand comprises five (5) phosphorothioate linkages and the sense strand comprises one (1) phosphorothioate linkage.

In some embodiments, an oligonucleotide provided herein (e.g., an RNAi oligonucleotide) comprises a sense strand having a sequence of any one of SEQ ID NOs: 193-384 and an antisense strand comprising a complementary sequence selected from SEQ ID NOs: 385-576.

In some embodiments, an oligonucleotide provided herein (e.g., an RNAi oligonucleotide) comprises a sense strand having a sequence of any one of SEQ ID NOs: 577-597 and an antisense strand comprising a complementary sequence selected from SEQ ID NOs: 598-618.

In some embodiments, an oligonucleotide provided herein (e.g., an RNAi oligonucleotide) comprises a sense strand having a sequence of any one of SEQ ID NOs: 619-639 and an antisense strand comprising a complementary sequence selected from SEQ ID NOs: 640-660.

In some embodiments, an oligonucleotide provided herein (e.g., and RNAi oligonucleotide) for reducing TMPRSS6 expression comprises:
a sense strand of 36 nucleotides comprising a 2'-F modified nucleotide at positions 8-11, a 2'-OMe modified nucleotide at positions 1-7, 12-27, and 31-36, a GalNAc-conjugated nucleotide at position 28, 29 and 30; and a phosphorothioate linkage between positions 1 and 2;
an antisense strand of 22 nucleotides comprising a 2'-F modified nucleotide at positions 2, 3, 4, 5, 7, 10 and 14, a 2'-OMe at positions 1, 6, 8, 9, 11-13, and 15-22, a phosphorothioate linkage between positions 1 and 2, positions 2 and 3, positions 3 and 4, positions 20 and 21, and positions 21 and 22, and a 5'-terminal nucleotide at position 1 comprising a 4'-phosphate analog, optionally wherein the 5'-terminal nucleotide comprises 4'-O-monomethylphosphonate-2'-methyluridine [MePhosphonate-4O-mU]; wherein positions 1-20 of the antisense strand form a duplex region with positions 1-20 of the sense strand, wherein positions 21-36 of the sense strand form a stem-loop, wherein positions 27-30 form the loop of the stem-loop, optionally wherein positions 27-30 comprise a tetraloop, wherein positions 21 and 22 of the antisense strand comprise an overhang, and wherein the sense strand and antisense strands comprise nucleotide sequences selected from the group consisting of:
a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively.

In some embodiments, the TMPRSS6-targeting oligonucleotide (e.g., an RNAi oligonucleotide) for reducing TMPRSS6 expression comprise:
a sense strand of 36 nucleotides comprising a 2'-F modified nucleotide at positions 8-11, a 2'-OMe modified nucleotide at positions 1-7, 12-27, and 31-36, a GalNAc-conjugated nucleotide at position 28, 29 and 30; and a phosphorothioate linkage between positions 1 and 2;
an antisense strand of 22 nucleotides comprising a 2'-F modified nucleotide at positions 2, 3, 4, 5, 7, 10 and 14, a 2'-OMe at positions 1, 6, 8, 9, 11-13, and 15-22, a phosphorothioate linkage between positions 1 and 2, positions 2 and 3, positions 3 and 4, positions 20 and 21, and positions 21 and 22, and a 5'-terminal nucleotide at position 1 comprising a 4'-phosphate analog, optionally wherein the 5'-terminal nucleotide comprises 4'-O-monomethylphosphonate-2'-O-methyluridine [MePhosphonate-4O-mU]; wherein positions 1-20 of the antisense strand form a duplex region with positions 1-20 of the sense strand, wherein positions 21-36 of the sense strand form a stem-loop, wherein positions 27-30 form the loop of the stem-loop, optionally wherein positions 27-30 comprise a tetraloop, wherein positions 21 and 22 of the antisense strand comprise an overhang, and wherein the sense strand and antisense strands comprise nucleotide sequences selected from the group consisting of:
a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively.

In some embodiments, a TMPRSS6-targeting oligonucleotide for reducing TMPRSS6 expression provided by the disclosure comprises a sense strand comprising the nucleotide sequence as set forth in SEQ ID NO: 579 and an antisense strand comprising the nucleotide sequence as set forth in SEQ ID NO: 600. In some embodiments, a TMPRSS6-targeting oligonucleotide for reducing TMPRSS6 expression provided by the disclosure comprises a sense strand comprising the nucleotide sequence as set forth in SEQ ID NO: 580 and an antisense strand comprising the nucleotide sequence as set forth in SEQ ID NO: 601. In some embodiments, a TMPRSS6-targeting oligonucleotide for reducing TMPRSS6 expression provided by the disclosure comprises a sense strand comprising the nucleotide sequence as set forth in SEQ ID NO: 590 and an antisense strand comprising the nucleotide sequence as set forth in SEQ ID NO: 611. In some embodiments, a TMPRSS6-targeting oligonucleotide for reducing TMPRSS6 expression provided by the disclosure comprises a sense strand comprising the nucleotide sequence as set forth in SEQ ID NO: 597 and an antisense strand comprising the nucleotide sequence as set forth in SEQ ID NO: 618. In some embodiments, a TMPRSS6-targeting oligonucleotide for reducing TMPRSS6 expression provided by the disclosure comprises a sense strand comprising the nucleotide sequence as set forth in SEQ ID NO: 586 and an antisense strand comprising the nucleotide sequence as set forth in SEQ ID NO: 607.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 184; and (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 181; and (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 158; and (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 134; and (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 102; and (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 184; and (ii) a sense strand of 19-50 nucleotides in length comprising a region of complementarity to the antisense strand and a stem-loop at the 3' terminus, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 181; and (ii) a sense strand of 19-50 nucleotides in length comprising a region of complementarity to the antisense strand and a stem-loop at the 3'terminus, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 158; and (ii) a sense strand of 19-50 nucleotides in length comprising a region of complementarity to the antisense strand and a stem-loop at the 3' terminus, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 134; and (ii) a sense strand of 19-50 nucleotides in length comprising a region of complementarity to the antisense strand and a stem-loop at the 3'terminus, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 102; and (ii) a sense strand of 19-50 nucleotides in length comprising a region of complementarity to the antisense strand and a stem-loop at the 3' terminus, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 184; and (ii) a sense strand of 19-50 nucleotides in length comprising a region of complementarity to the antisense strand, wherein the region of complementarity to the antisense strand is set forth in SEQ ID NO: 844, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 181; and (ii) a sense strand of 19-50 nucleotides in length comprising a region of complementarity to the antisense strand, wherein the region of complementarity to the antisense strand is set forth in SEQ ID NO: 841, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 158; and (ii) a sense strand of 19-50 nucleotides in length comprising a region of complementarity to the antisense strand, wherein the region of complementarity to the antisense strand is set forth in SEQ ID NO: 818, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 134; and (ii) a sense strand of 19-50 nucleotides in length comprising a region of complementarity to the antisense strand, wherein the region of complementarity to the antisense strand is set forth in SEQ ID NO: 794, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 102; and (ii) a sense strand of 19-50 nucleotides in length comprising a region of complementarity to the antisense strand, wherein the region of complementarity to the antisense strand is set forth in SEQ ID NO: 762, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 184; and (ii) a sense strand of 19-50 nucleotides in length comprising a region of complementarity to the antisense strand and a stem-loop at the 3' terminus, wherein the region of complementarity to the antisense strand is set forth in SEQ ID NO: 844, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 181; and (ii) a sense strand of 19-50 nucleotides in length comprising a region of complementarity to the antisense strand and a stem-loop at the 3' terminus, wherein the region of complementarity to the antisense strand is set forth in SEQ ID NO: 841, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 158; and (ii) a sense strand of 19-50 nucleotides in length comprising a region of complementarity to the antisense strand and a stem-loop at the 3' terminus, wherein the region of complementarity to the antisense strand is set forth in SEQ ID NO: 818, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 134; and (ii) a sense strand of 19-50 nucleotides in length comprising a region of complementarity to the antisense strand and a stem-loop at the 3' terminus, wherein the region of complementarity to the antisense strand is set forth in SEQ ID NO: 794, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, a TMPRSS6-targeting oligonucleotide (e.g., an RNAi oligonucleotide) for reducing TMPRSS6 expression comprises (i) an antisense strand of 19-30 nucleotides in length, wherein the antisense strand comprises a nucleotide sequence comprising a region of complementarity to a TMPRSS6 mRNA target sequence, wherein the region of complementarity is set forth in SEQ ID NO: 102; and (ii) a sense strand of 19-50 nucleotides in length comprising a region of complementarity to the antisense strand and a stem-loop at the 3' terminus, wherein the region of complementarity to the antisense strand is set forth in SEQ ID NO: 762, wherein the stem-loop is set forth as S1-Lp-S2, wherein S1 is complementary to S2 and wherein Lp forms a loop between S1 and S2 of 3 to 5 nucleotides in length, wherein the antisense and sense strands are separate strands which form an asymmetric duplex region having an overhang of 1-4 nucleotides at the 3' terminus of the antisense strand.

In some embodiments, the disclosure provides an oligonucleotide (e.g., an RNAi oligonucleotide) for reducing TMPRSS6 expression, wherein the oligonucleotide comprises a sense strand and an antisense strand according to:

Sense Strand: 5'-mX-S-mX-mX-mX-mX-mX-mX-fX-fX-fX-fX-mX-mX-mX-mX-mX-mX-mX-mX-mX-mX-mX-mX-mX-mX-mX-[ademX-GalNAc]-[ademX-GalNAc]-[ademX-GalNAc]-mX-mX-mX-mX-mX-mX-3';

hybridized to:

Antisense Strand: 5'-[MePhosphonate-4O-mX]-S-fX-S-fX-S-fX-fX-mX-fX-mX-mX-fX-mX-mX-mX-fX-mX-mX-mX-mX-mX-mX-S-mX-S-mX-3';

wherein mX=2'-O-methyl modified nucleotide,
fX=2'-fluoro modified nucleotide,
—S—=phosphorothioate linkage,
-=phosphodiester linkage,
[MePhosphonate-4O-mX]=4'-O-monomethylphosphonate-2'-O-methyl modified nucleotide, and
ademX-GalNAc=GalNAc attached to a nucleotide.

In some embodiments, the disclosure provides an RNAi oligonucleotide for reducing TMPRSS6 expression, the oligonucleotide comprising a sense strand and an antisense strand, wherein the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621), and wherein the antisense strand comprises the sequence and all of the modifications of 5' [MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642), wherein mC, mA, mG, mU=2'-OMe ribonucleosides; fA, fC, fG, fU=2'-F ribonucleosides; s=phosphorothioate, and wherein ademA-GalNAc=GalNAc modified adenine nucleotide.

In some embodiments, the disclosure provides an RNAi oligonucleotide for reducing TMPRSS6 expression, the oligonucleotide comprising a sense strand and an antisense strand, wherein the sense strand comprises the sequence and all of the modifications of 5' [mGs][mC][mU][mA][mC][mU][mC][fU][fG][fG][fU][mA][mU][mU][mU][mC][mC][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 622), and wherein the antisense strand comprises the sequence and all of the modifications of 5' [MePhosphonate-4O-mUs][f Us][fAs][fG][fG][mA][fA][mA][mU][fA][mC][mC][mA][fG][mA][mG][mU][mA][mG][mCs][mGs][mG]-3' (SEQ ID NO: 643), wherein mC, mA, mG, mU=2'-OMe ribonucleosides; fA, fC, fG, fU=2'-F ribonucleosides; s=phosphorothioate, and wherein ademA-GalNAc=GalNAc modified adenine nucleotide.

In some embodiments, the disclosure provides an RNAi oligonucleotide for reducing TMPRSS6 expression, the oligonucleotide comprising a sense strand and an antisense strand, wherein the sense strand comprises the sequence and all of the modifications of 5'-[mCs][mU][mC][mA][mC][mC][mU][fG][fC][fU][fU][mC][mU][mU][mC][mU][mG][mG][mU][mA][mG][mC][mA][mG][mC][mC][mG][ademA-GalNAc][ademA-GalNAc][ademA-GalNAc][mG][mG][mC][mU][mG][mC]-3' (SEQ ID NO: 632), and wherein the antisense strand comprises the sequence and all of the modifications of 5'-[MePhosphonate-4O-mUs][fAs][fCs][fC][fA][mG][fA][mA][mG][fA][mA][mG][mC][fA][mG][mG][mU][mG][mA][mGs][mGs][mG]-3' (SEQ ID NO: 653), wherein mC, mA, mG, mU=2'-OMe ribonucleosides; fA, fC, fG, fU=2'-F ribonucleosides; s=phosphorothioate, and wherein ademA-GalNAc=GalNAc modified adenine nucleotide.

In some embodiments, the disclosure provides, an RNAi oligonucleotide for reducing TMPRSS6 expression, the oligonucleotide comprising a sense strand and an antisense strand, wherein the sense strand comprises the sequence and all of the modifications of 5'-[mAs][mG][mU][mG][mU][mG][mA][fA][fA][fG][fA][mC][mA][mU][mA][mG][mC][mU][mG][mA][mG][mC][mA][mG][mC][mC][mG][ademA-GalNAc][ademA-GalNAc][ademA-GalNAc][mG][mG][mC][mU][mG][mC]3' (SEQ ID NO: 639), and wherein the antisense strand comprises the sequence and all of the modifications of 5'-[MePhosphonate-4O-mUs][fCs][fAs][fG][fC][mU][fA][mU][mG][fU][mC][mU][mU][fU][mC][mA][mC][mA][mC][mUs][mGs][mG]-3' (SEQ ID NO: 660), wherein mC, mA, mG, mU=2'-OMe ribonucleosides; fA, fC, fG, fU=2'-F ribonucleosides; s=phosphorothioate, and wherein ademA-GalNAc=GalNAc modified adenine nucleotide.

In some embodiments, the disclosure provides, an RNAi oligonucleotide for reducing TMPRSS6 expression, the oligonucleotide comprising a sense strand and an antisense strand, wherein the sense strand comprises the sequence and all of the modifications of 5'-[mGs][mG][mG][mU][mG][mC][mA][fC][fU][fA][fU][mG][mG][mC][mU][mU][mG][mU][mA][mA][mG][mC][mA][mG][mC][mC][mG][ademA-GalNAc][ademA-GalNAc][ademA-GalNAc][mG][mG][mC][mU][mG][mC]3' (SEQ ID NO: 628), and wherein the antisense strand comprises the sequence and all of the modifications of 5'-[MePhosphonate-4O-mUs][fUs][fAs][fC][fA][mA][fG][mC][mC][fA][mU][mA][mG][fU][mG][mC][mA][mC][mC][mCs][mGs][mG]-3' (SEQ ID NO: 649), wherein mC, mA, mG, mU=2'-OMe ribonucleosides; fA, fC, fG, fU=2'-F ribonucleosides; s=phosphorothioate, and wherein ademA-GalNAc=GalNAc modified adenine nucleotide.

In some embodiments, the disclosure provides an oligonucleotide (e.g., an RNAi oligonucleotide) for reducing TMPRSS6 expression, wherein the oligonucleotide comprises a sense strand and an antisense strand comprising nucleotide sequences selected from the group consisting of:
   a) SEQ ID NOs: 621 and 642, respectively;
   b) SEQ ID NOs: 622 and 643, respectively;
   c) SEQ ID NOs: 637 and 658, respectively;
   d) SEQ ID NOs: 632 and 653, respectively;
   e) SEQ ID NOs: 638 and 659, respectively;
   f) SEQ ID NOs: 639 and 660, respectively;
   g) SEQ ID NOs: 627 and 648, respectively;
   h) SEQ ID NOs: 628 and 649, respectively; and,
   i) SEQ ID NOs: 629 and 650, respectively.

In some embodiments, a TMPRSS6-targeting oligonucleotide for reducing TMPRSS6 expression provided by the disclosure comprises a sense strand comprising the nucleotide sequence as set forth in SEQ ID NO: 621 and an antisense strand comprising the nucleotide sequence as set forth in SEQ ID NO: 642. In some embodiments, a TMPRSS6-targeting oligonucleotide for reducing TMPRSS6 expression provided by the disclosure comprises a sense strand comprising the nucleotide sequence as set forth in SEQ ID NO: 622 and an antisense strand comprising the nucleotide sequence as set forth in SEQ ID NO: 643. In some embodiments, a TMPRSS6-targeting oligonucleotide for reducing TMPRSS6 expression provided by the disclosure comprises a sense strand comprising the nucleotide sequence as set forth in SEQ ID NO: 632 and an antisense strand comprising the nucleotide sequence as set forth in SEQ ID NO: 653. In some embodiments, a TMPRSS6-targeting oligonucleotide for reducing TMPRSS6 expression provided by the disclosure comprises a sense strand comprising the nucleotide sequence as set forth in SEQ ID NO: 639 and an antisense strand comprising the nucleotide sequence as set forth in SEQ ID NO: 660. In some embodiments, a TMPRSS6-targeting oligonucleotide for reducing TMPRSS6 expression provided by the disclosure comprises a sense strand comprising the nucleotide sequence as set forth in SEQ ID NO: 628 and an antisense strand comprising the nucleotide sequence as set forth in SEQ ID NO: 649.

Figure 14A:
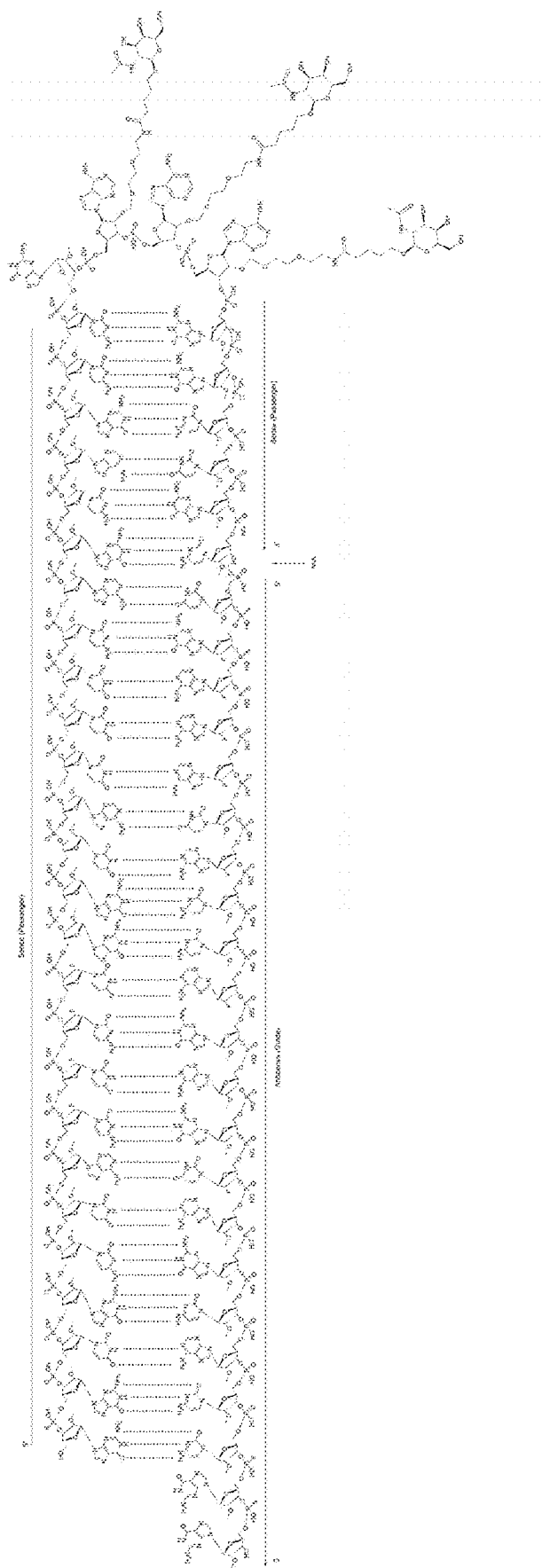
FIGS. 14A-D provides provide chemical of GalNAc-conjugated TMPRSS6 oligonucleotides −0416 (FIG. 14A), −0651 (FIG. 14B), −0831 (FIG. 14C), and −1546 (FIG. 14D).

In some embodiments, a TMPRSS6-targeting oligonucleotide for reducing TMPRSS6 expression provided by the disclosure comprises a sense strand comprising the nucleotide sequence as set forth in SEQ ID NO: 621 and an antisense strand comprising the nucleotide sequence as set forth in SEQ ID NO: 642, the antisense strand comprising a region of complementarity to a TMPRSS6 RNA transcript, wherein said RNAi is in the form of a conjugate having the structure as shown in FIG. 14A.

Figure 10A:
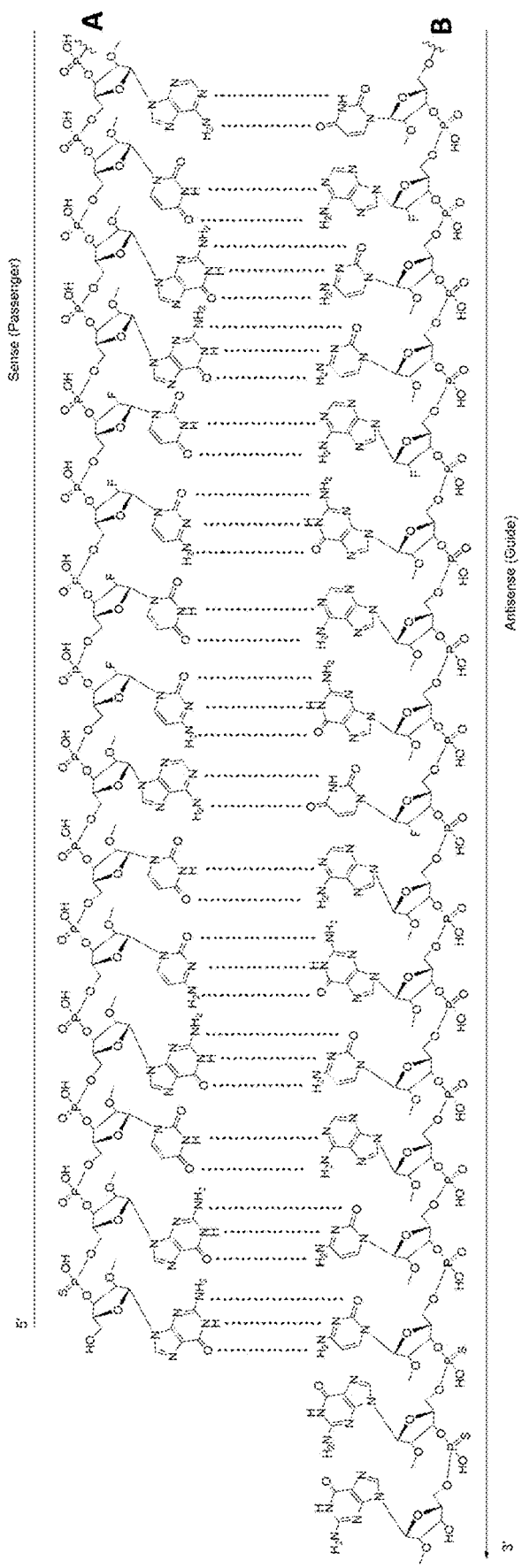
FIGS. 10A-B provide a chemical drawing of GalNAc-conjugated TMPRSS6 oligonucleotide −0416, wherein A and B identify the bonds between FIGS. 10A and 10B.
Figure 10B:
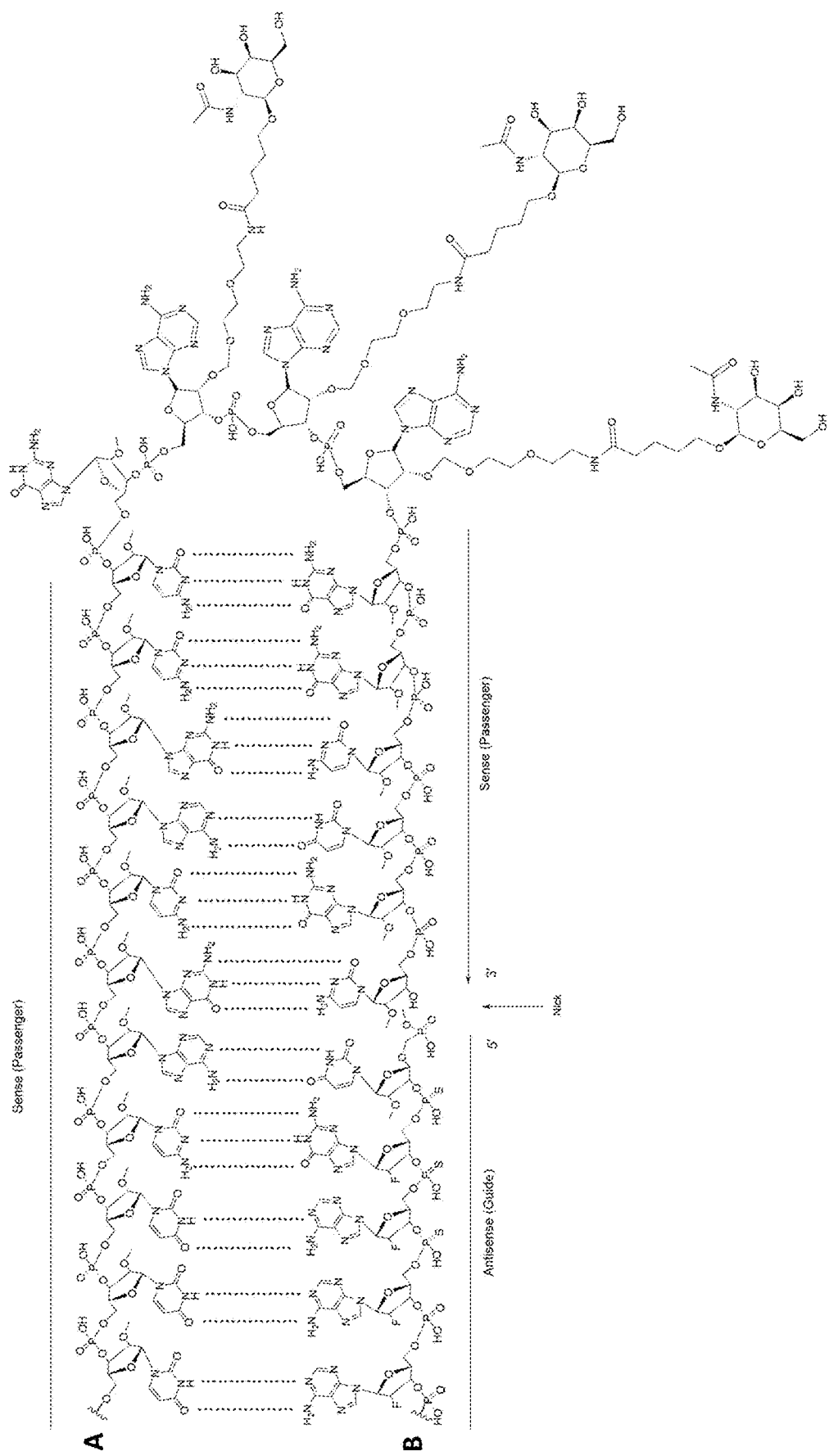

In some embodiments, a TMPRSS6-targeting oligonucleotide for reducing TMPRSS6 expression provided by the disclosure comprises a sense strand comprising the nucleotide sequence as set forth in SEQ ID NO: 621 and an antisense strand comprising the nucleotide sequence as set forth in SEQ ID NO: 642, the antisense strand comprising a region of complementarity to a TMPRSS6 RNA transcript, wherein said RNAi is in the form of a conjugate having the structure as shown in FIGS. 10A-B.

Figure 14B:
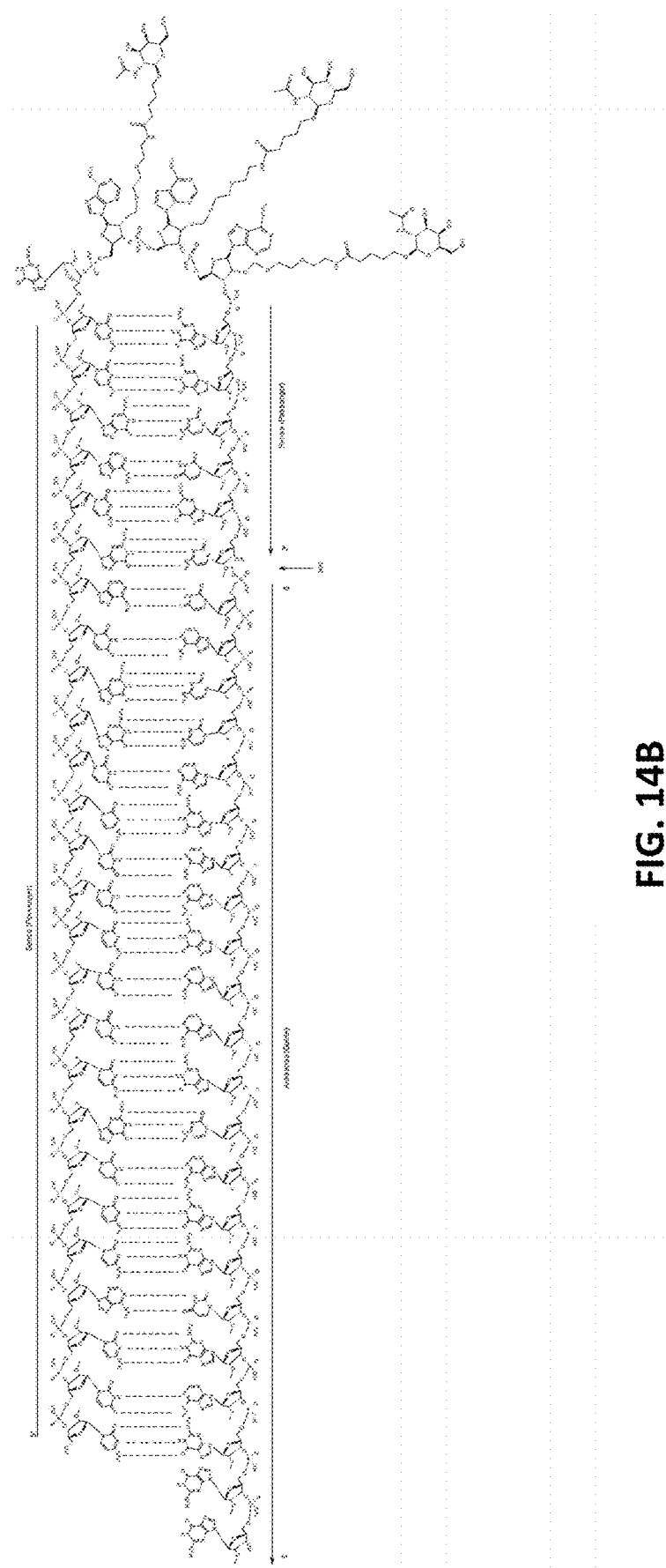

In some embodiments, a TMPRSS6-targeting oligonucleotide for reducing TMPRSS6 expression provided by the disclosure comprises a sense strand comprising the nucleotide sequence as set forth in SEQ ID NO: 632 and an antisense strand comprising the nucleotide sequence as set forth in SEQ ID NO: 653, the antisense strand comprising a region of complementarity to a TMPRSS6 RNA transcript, wherein said RNAi is in the form of a conjugate having the structure as shown in FIG. 14B.

Figure 11A:
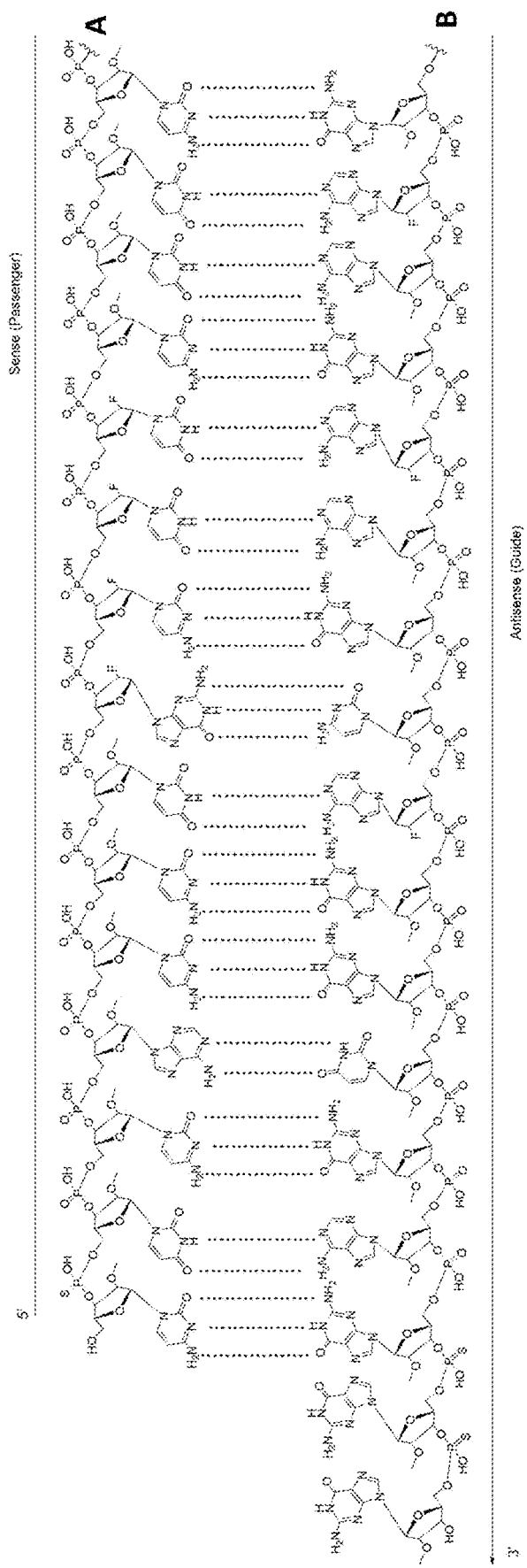
FIGS. 11A-B provide a chemical drawing of GalNAc-conjugated TMPRSS6 oligonucleotide −0651, wherein A and B identify the bonds between FIGS. 11A and 11B.
Figure 11B:
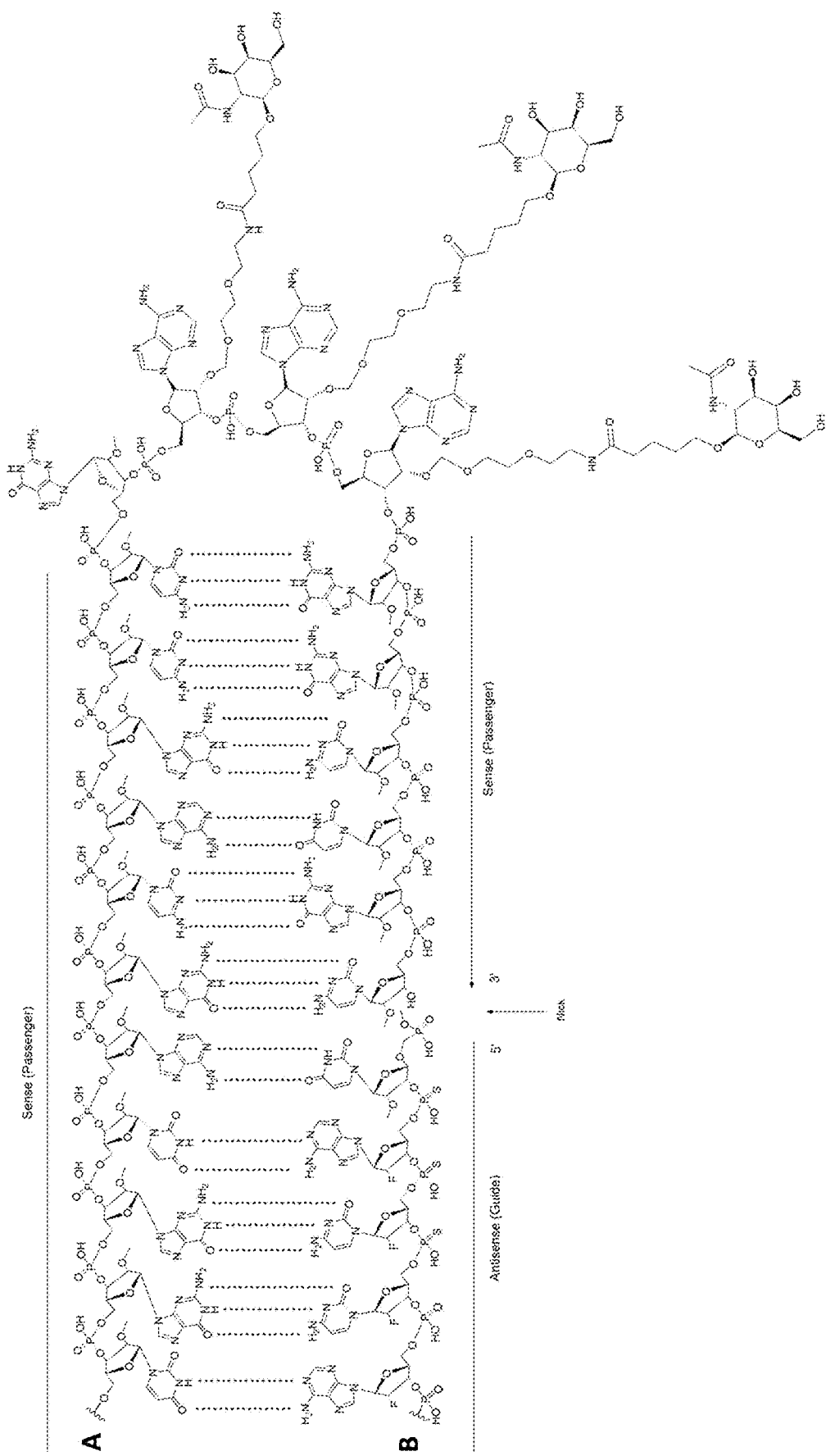

In some embodiments, a TMPRSS6-targeting oligonucleotide for reducing TMPRSS6 expression provided by the disclosure comprises a sense strand comprising the nucleotide sequence as set forth in SEQ ID NO: 632 and an antisense strand comprising the nucleotide sequence as set forth in SEQ ID NO: 653, the antisense strand comprising a region of complementarity to a TMPRSS6 RNA transcript, wherein said RNAi is in the form of a conjugate having the structure as shown in FIGS. 11A-B.

Figure 14C:
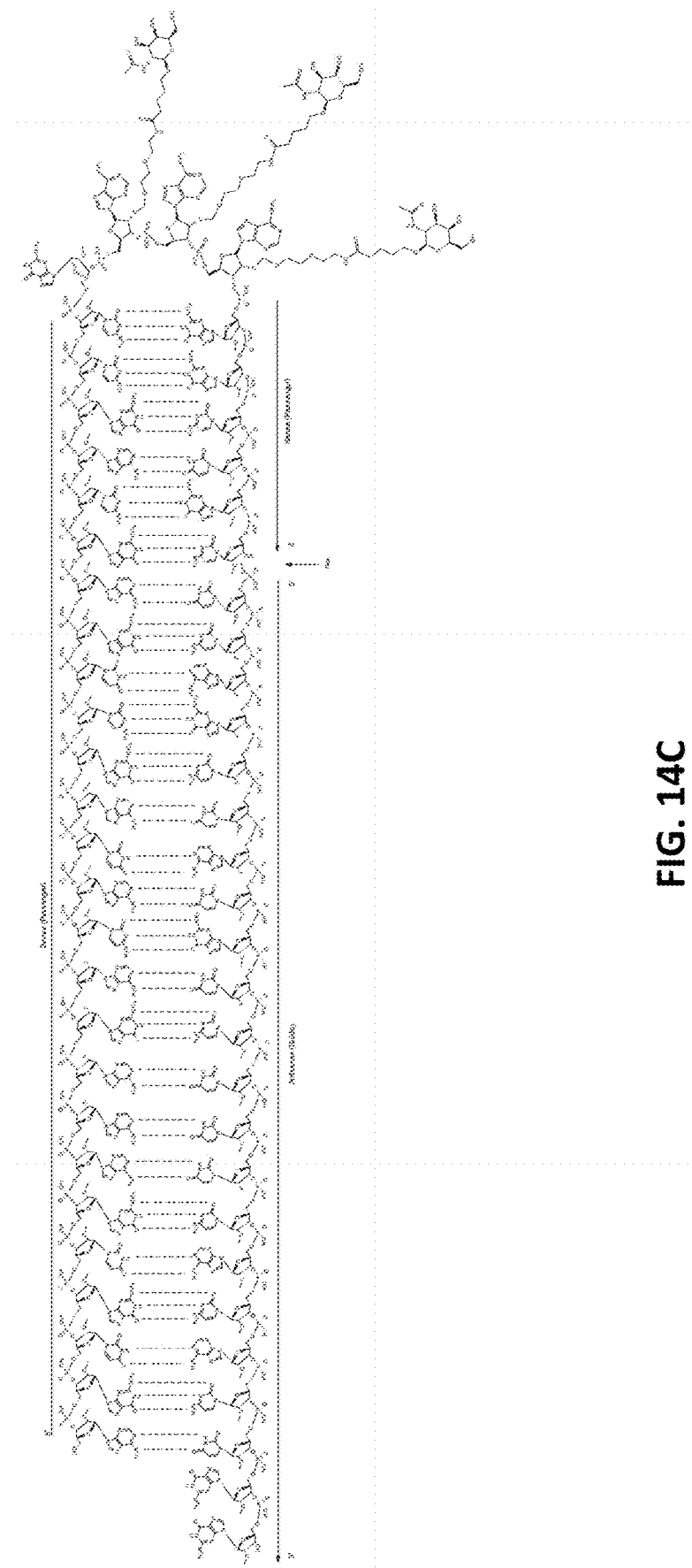

In some embodiments, a TMPRSS6-targeting oligonucleotide for reducing TMPRSS6 expression provided by the disclosure comprises a sense strand comprising the nucleotide sequence as set forth in SEQ ID NO: 639 and an antisense strand comprising the nucleotide sequence as set forth in SEQ ID NO: 660, the antisense strand comprising a region of complementarity to a TMPRSS6 RNA transcript, wherein said RNAi is in the form of a conjugate having the structure as shown in FIG. 14C.

Figure 12A:
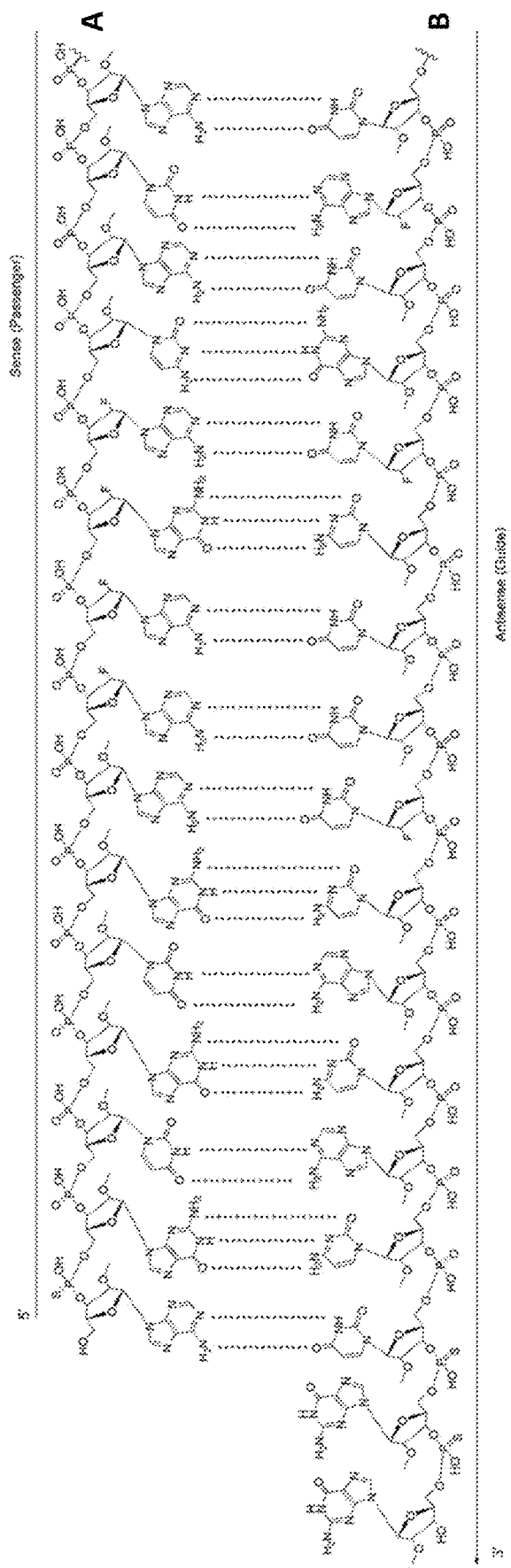
FIGS. 12A-B provide a chemical drawing of GalNAc-conjugated TMPRSS6 oligonucleotide 0831, wherein A and B identify the bonds between FIGS. 12A and 12B.
Figure 12B:
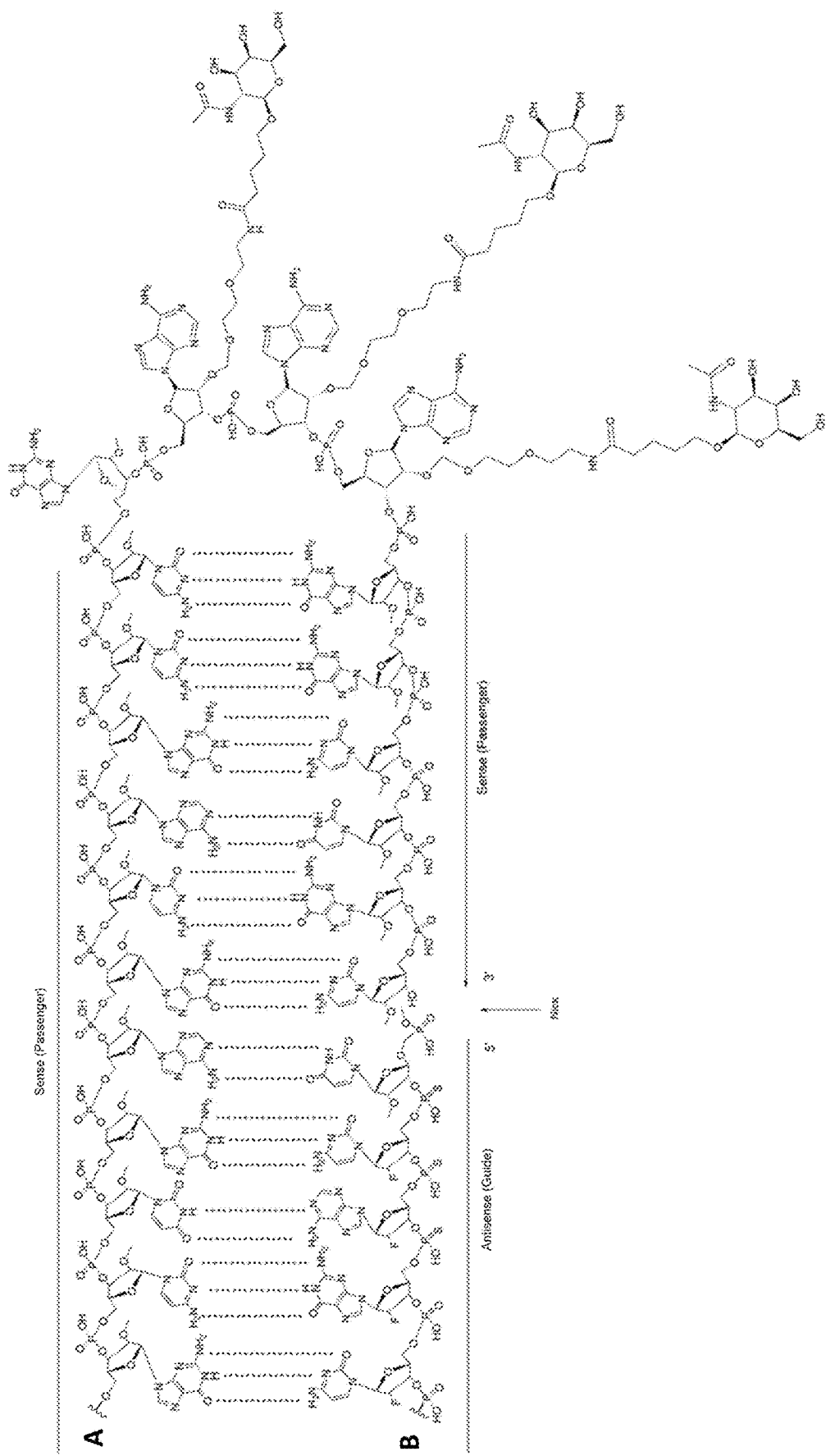

In some embodiments, a TMPRSS6-targeting oligonucleotide for reducing TMPRSS6 expression provided by the disclosure comprises a sense strand comprising the nucleotide sequence as set forth in SEQ ID NO: 639 and an antisense strand comprising the nucleotide sequence as set forth in SEQ ID NO: 660, the antisense strand comprising a region of complementarity to a TMPRSS6 RNA transcript, wherein said RNAi is in the form of a conjugate having the structure as shown in FIGS. 12A-B.

Figure 14D:
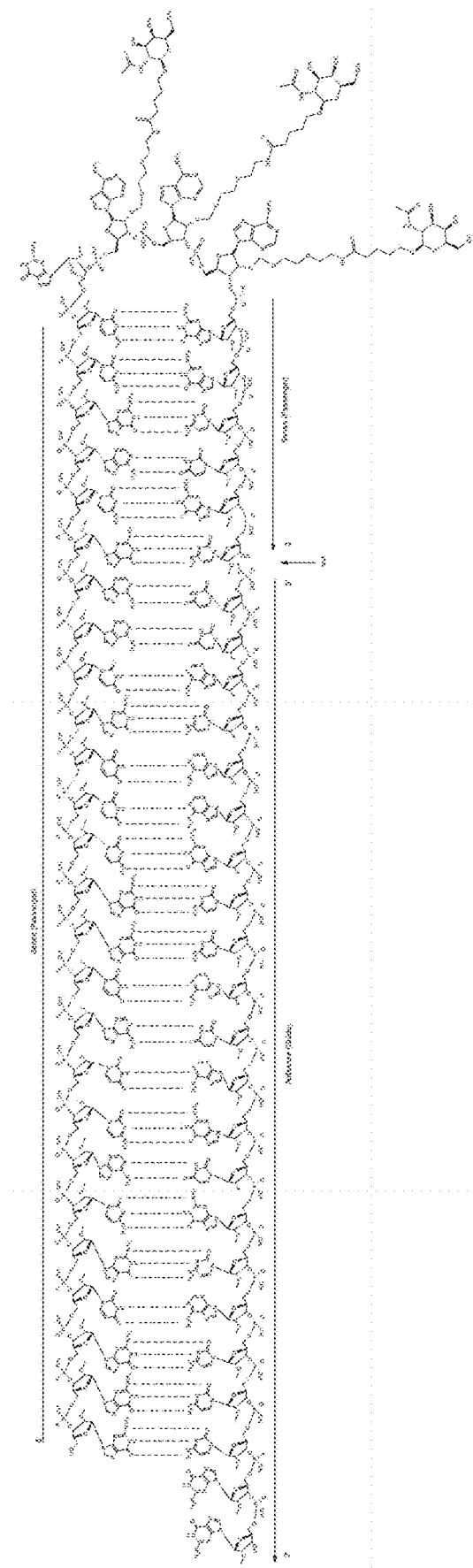

In some embodiments, a TMPRSS6-targeting oligonucleotide for reducing TMPRSS6 expression provided by the disclosure comprises a sense strand comprising the nucleotide sequence as set forth in SEQ ID NO: 628 and an antisense strand comprising the nucleotide sequence as set forth in SEQ ID NO: 649, the antisense strand comprising a region of complementarity to a TMPRSS6 RNA transcript, wherein said RNAi is in the form of a conjugate having the structure as shown in FIG. 14D.

Figure 13A:
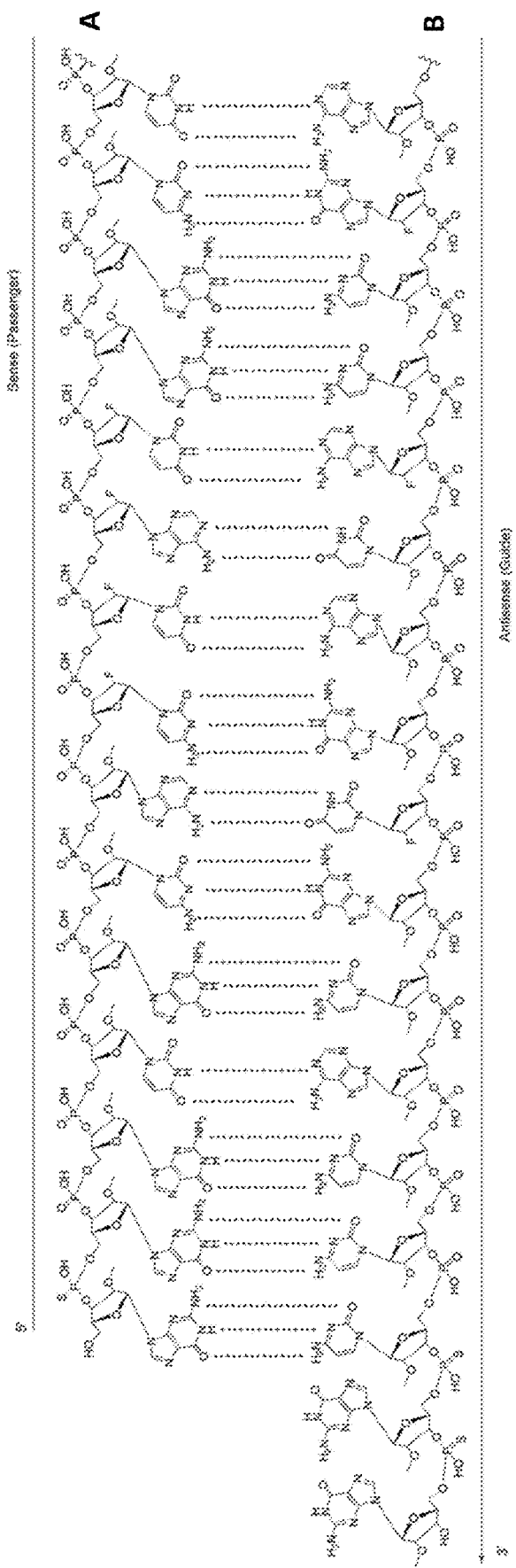
FIGS. 13A-B provide a chemical drawing of GalNAc-conjugated TMPRSS6 oligonucleotide −1546, wherein A and B identify the bonds between FIGS. 13A and 13B.
Figure 13B:
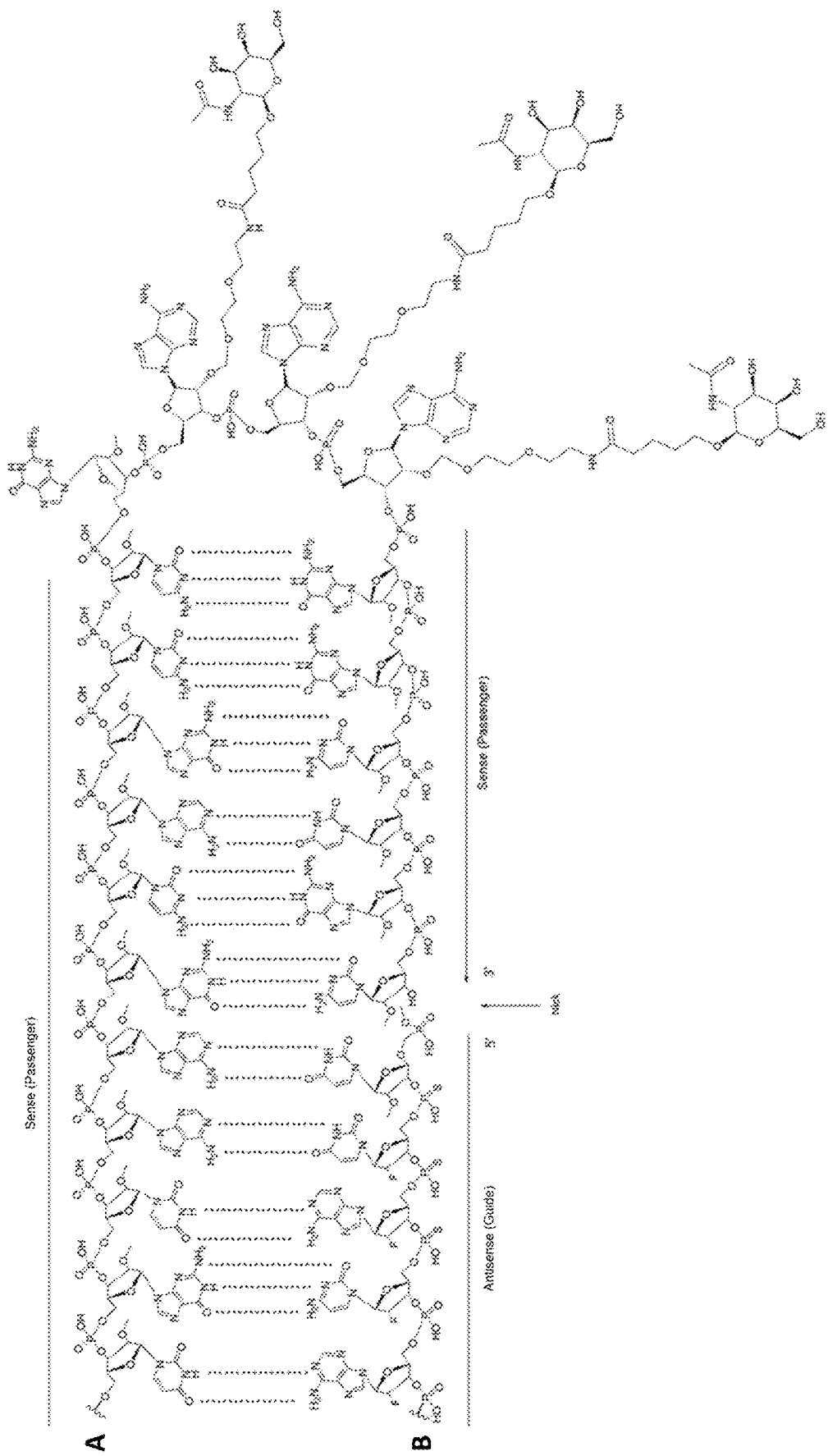

In some embodiments, a TMPRSS6-targeting oligonucleotide for reducing TMPRSS6 expression provided by the disclosure comprises a sense strand comprising the nucleotide sequence as set forth in SEQ ID NO: 628 and an antisense strand comprising the nucleotide sequence as set forth in SEQ ID NO: 649, the antisense strand comprising a region of complementarity to a TMPRSS6 RNA transcript, wherein said RNAi is in the form of a conjugate having the structure as shown in FIGS. 13A-B.

Formulations

Various formulations (e.g., pharmaceutical formulations) have been developed for oligonucleotide use. For example, oligonucleotides (e.g., RNAi oligonucleotides) can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., RNAi oligonucleotides) reduce the expression of TMPRSS6. Such compositions can be suitably formulated such that when administered to a subject, either into the immediate environment of a target cell or systemically, a sufficient portion of the oligonucleotides enter the cell to reduce TMPRSS6 expression. Any variety of suitable oligonucleotide formulations can be used to deliver oligonucleotides for the reduction of TMPRSS6 as disclosed herein. In some embodiments, an oligonucleotide is formulated in buffer solutions such as phosphate buffered saline solutions, liposomes, micellar structures, and capsids. Any of the oligonucleotides described herein may be provided not only as nucleic acids, but also in the form of a pharmaceutically acceptable salt.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013).

In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll™ or gelatin).

In some embodiments, a pharmaceutical composition is formulated to be compatible with its intended route of administration. Examples of routes of administration include parenteral (e.g., intravenous, intramuscular, intraperitoneal, intradermal, subcutaneous), oral (e.g., inhalation), transdermal (e.g., topical), transmucosal and rectal administration.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and liquid polyethylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., a RNAi oligonucleotide for reducing TMPRSS6 expression) or more, although the percentage of the active ingredient(s) may be between about 1% to about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Methods of Use

Reducing TMPRSS6 Expression

In some embodiments, the disclosure provides methods for contacting or delivering to a cell or population of cells an effective amount of oligonucleotides provided herein (e.g., RNAi oligonucleotides) to reduce TMPRSS6 expression. In some embodiments, a reduction of TMPRSS6 expression is determined by measuring a reduction in the amount or level of TMPRSS6 mRNA, matriptase-2 protein, or matriptase-2 activity in a cell. The methods include those described herein and known to one of ordinary skill in the art.

Methods provided herein are useful in any appropriate cell type. In some embodiments, a cell is any cell that expresses TMPRSS6 mRNA (e.g., hepatocytes). In some embodiments, the cell is a primary cell obtained from a subject. In some embodiments, the primary cell has undergone a limited number of passages such that the cell substantially maintains its natural phenotypic properties. In some embodiments, a cell to which the oligonucleotide is delivered is ex vivo or in vitro (i.e., can be delivered to a cell in culture or to an organism in which the cell resides).

In some embodiments, the oligonucleotides herein (e.g., RNAi oligonucleotides) are delivered to a cell or population of cells using a nucleic acid delivery method known in the art including, but not limited to, injection of a solution containing the oligonucleotides, bombardment by particles covered by the oligonucleotides, exposing the cell or population of cells to a solution containing the oligonucleotides, or electroporation of cell membranes in the presence of the oligonucleotides. Other methods known in the art for delivering oligonucleotides to cells may be used, such as lipid-mediated carrier transport, chemical-mediated transport, and cationic liposome transfection such as calcium phosphate, and others.

In some embodiments, reduction of TMPRSS6 expression is determined by an assay or technique that evaluates one or more molecules, properties, or characteristics of a cell or population of cells associated with TMPRSS6 expression, or by an assay or technique that evaluates molecules that are directly indicative of TMPRSS6 expression in a cell or population of cells (e.g., TMPRSS6 mRNA or matriptase-2 protein). In some embodiments, the extent to which an oligonucleotide provided herein reduces TMPRSS6 expression is evaluated by comparing TMPRSS6 expression in a cell or population of cells contacted with the oligonucleotide to an appropriate control (e.g., an appropriate cell or population of cells not contacted with the oligonucleotide or contacted with a control oligonucleotide). In some embodiments, a control amount or level of TMPRSS6 expression in a control cell or population of cells is predetermined, such that the control amount or level need not be measured in every instance the assay or technique is performed. The predetermined level or value can take a variety of forms. In some embodiments, a predetermined level or value can be single cut-off value, such as a median or mean.

In some embodiments, contacting or delivering an oligonucleotide described herein (e.g., an RNAi oligonucleotide) to a cell or a population of cells results in a reduction in TMPRSS6 expression in a cell or population of cells not contacted with the oligonucleotide or contacted with a control oligonucleotide. In some embodiments, the reduction in TMPRSS6 expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower relative to a control amount or level of TMPRSS6 expression. In some embodiments, the control amount or level of TMPRSS6 expression is an amount or level of TMPRSS6 mRNA and/or matriptase-2 protein in a cell or population of cells that has not been contacted with an oligonucleotide herein. In some embodiments, TMPRSS6 mRNA expression is measured using methods known in the art. In some embodiments, TMPRSS6 mRNA expression is measured by qPCR. In some embodiments, TMPRSS6 protein expression is measured using methods known in the art. In some embodiments TMPRSS6 protein expression is measured by ELISA. In some embodiments, TMPRSS6 protein expression is measured by western blot.

In some embodiments, the effect of delivery of an oligonucleotide herein to a cell or population of cells according to a method herein is assessed after any finite period or amount of time (e.g., minutes, hours, days, weeks, months). For example, in some embodiments, TMPRSS6 expression is determined in a cell or population of cells at least about 4 hours, about 8 hours, about 12 hours, about 18 hours, about 24 hours; or at least about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, about 42 days, about 49 days, about 56 days, about 63 days, about 70 days, about 77 days, or about 84 days or more after contacting or delivering the oligonucleotide to the cell or population of cells. In some embodiments, TMPRSS6 expression is determined in a cell or population of cells at least about 1 month, about 2 months, about 3 months, about 4 months, about 5 months, or about 6 months or more after contacting or delivering the oligonucleotide to the cell or population of cells.

In some embodiments, an oligonucleotide provided herein (e.g., an RNAi oligonucleotide) is delivered in the form of a transgene that is engineered to express in a cell the oligonucleotide or strands comprising the oligonucleotide (e.g., its sense and antisense strands). In some embodiments, an oligonucleotide herein is delivered using a transgene engineered to express any oligonucleotide disclosed herein. Transgenes may be delivered using viral vectors (e.g., adenovirus, retrovirus, vaccinia virus, poxvirus, adeno-associated virus, or herpes simplex virus) or non-viral vectors (e.g., plasmids or synthetic mRNAs). In some embodiments, transgenes can be injected directly to a subject.

Treatment Methods

The disclosure provides oligonucleotides (e.g., RNAi oligonucleotides) for use as a medicament, in particular for use in a method for the treatment of diseases, disorders, and conditions associated with hepcidin deficiency or suppression. The disclosure also provides oligonucleotides for use, or adaptable for use, to treat a subject (e.g., a human having a disease, disorder or condition associated with hepcidin deficiency or suppression) that would benefit from reducing TMPRSS6 expression. In some respects, the disclosure provides oligonucleotides for use, or adapted for use, to treat a subject having a disease, disorder or condition associated with hepcidin deficiency or suppression. In some embodiments, the subject in need of TMPRSS6 reduction has, or is at risk for, an iron accumulation disease, disorder or condition. In some embodiments, compositions, compounds and methods described herein are provided for use in reducing iron levels in an individual. In some embodiments, the iron accumulation is due to a disease, disorder, or condition in the subject. In some embodiments, the disease, disorder and/or condition is hemochromatosis such as hereditary hemochromatosis. In some embodiments, the disease, disorder and/or condition is β-thalassemia. In some embodiments, the disease, disorder and/or condition is polycythemia vera. The disclosure also provides oligonucleotides for use, or adaptable for use, in the manufacture of a medicament or pharmaceutical composition for treating a disease, disorder or condition associated with hepcidin deficiency or suppression. In some embodiments, the oligonucleotides for use, or adaptable for use, target TMPRSS6 mRNA and reduce TMPRSS6 expression (e.g., via the RNAi pathway). In some embodiments, the oligonucleotides for use, or adaptable for use, target TMPRSS6 mRNA and reduce the amount or level of TMPRSS6 mRNA, matriptase-2 protein and/or TMPRSS6 activity.

The disclosure also provides methods of treating a subject having, suspected of having, or at risk of developing a disease, disorder or condition associated with a hepcidin deficiency or suppression with an oligonucleotide provided herein. In some aspects, the disclosure provides methods of treating or attenuating the onset or progression of a disease, disorder or condition associated with hepcidin deficiency or suppression using the oligonucleotides herein. In other aspects, the disclosure provides methods to achieve one or more therapeutic benefits in a subject having a disease, disorder, or condition associated with hepcidin deficiency or suppression using the oligonucleotides provided herein. In some embodiments of the methods herein, the subject is treated by administering a therapeutically effective amount of any one or more of the oligonucleotides provided herein. In some embodiments, treatment comprises reducing TMPRSS6 expression. In some embodiments, the subject is treated therapeutically. In some embodiments, the subject is treated prophylactically.

In some embodiments of the methods herein, one or more oligonucleotides herein (e.g., RNAi oligonucleotides), or a pharmaceutical composition comprising one or more oligonucleotides, is administered to a subject having a disease, disorder or condition associated with hepcidin deficiency or suppression such that TMPRSS6 expression is reduced in the subject, thereby treating the subject. In some embodiments, an amount or level of TMPRSS6 mRNA is reduced in the subject. In some embodiments, an amount or level of matriptase-2 protein is reduced in the subject. In some embodiments, an amount or level of matriptase-2 activity is reduced in the subject.

In some embodiments of the methods herein, an oligonucleotide provided herein (e.g., an RNAi oligonucleotide), or a pharmaceutical composition comprising the oligonucleotide, is administered to a subject having a disease, disorder or condition associated with hepcidin deficiency or suppression such that TMPRSS6 expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to TMPRSS6 expression prior to administration of one or more oligonucleotides or pharmaceutical composition. In some embodiments, TMPRSS6 expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to TMPRSS6 expression in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide or oligonucleotides herein (e.g., RNAi oligonucleotides), or a pharmaceutical composition comprising the oligonucleotide or oligonucleotides, is administered to a subject having a disease, disorder or condition associated with hepcidin deficiency or suppression such that an amount or level of TMPRSS6 mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of TMPRSS6 mRNA prior to administration of the oligonucleotide or pharmaceutical composition. In some embodiments, an amount or level of TMPRSS6 mRNA is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of TMPRSS6 mRNA in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide or oligonucleotides herein, or a pharmaceutical composition comprising the oligonucleotide or oligonucleotides, is administered to a subject having a disease, disorder or condition associated with hepcidin deficiency or suppression such that an amount or level of matriptase-2 protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of matriptase-2 protein prior to administration of the oligonucleotide or pharmaceutical composition. In some embodiments, an amount or level of matriptase-2 protein is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of matriptase-2 protein in a subject (e.g., a reference or control subject) not receiving the oligonucleotide or oligonucleotides or pharmaceutical composition or receiving a control oligonucleotide, oligonucleotides or pharmaceutical composition or treatment.

In some embodiments of the methods herein, an oligonucleotide or oligonucleotides (e.g., RNAi oligonucleotides) herein, or a pharmaceutical composition comprising the oligonucleotide or oligonucleotides, is administered to a subject having a disease, disorder or condition associated with hepcidin deficiency or suppression such that an amount or level of TMPRSS6 gene activity/expression is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to the amount or level of TMPRSS6 activity prior to administration of the oligonucleotide or pharmaceutical composition. In some embodiments, an amount or level of TMPRSS6 activity is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to an amount or level of TMPRSS6 activity in a subject (e.g., a reference or control subject) not receiving the oligonucleotide or pharmaceutical composition or receiving a control oligonucleotide, pharmaceutical composition or treatment.

In some embodiments of the methods herein, an oligonucleotide provided herein (e.g., an RNAi oligonucleotide), or a pharmaceutical composition comprising the oligonucleotide, is administered to a subject having a disease, disorder or condition associated with hepcidin deficiency or suppression such that hepcidin production is increased in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to hepcidin production prior to administration of one or more oligonucleotides or pharmaceutical composition. In some embodiments, hepcidin production is increased in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to hepcidin production in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide provided herein (e.g., an RNAi oligonucleotide), or a pharmaceutical composition comprising the oligonucleotide, is administered to a subject having a disease, disorder or condition associated with hepcidin deficiency or suppression such that serum iron is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to serum iron prior to administration of one or more oligonucleotides or pharmaceutical composition. In some embodiments, serum iron is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to serum iron in a subject (e.g., a reference or control subject) not receiving the oligonucleotide or oligonucleotides or pharmaceutical composition or receiving a control oligonucleotide or oligonucleotides, pharmaceutical composition or treatment.

In some embodiments of the methods herein, an oligonucleotide provided herein (e.g., an RNAi oligonucleotide), or a pharmaceutical composition comprising the oligonucleotide, is administered to a subject having a disease, disorder or condition associated with hepcidin deficiency or suppression such that serum iron saturation is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to serum iron saturation prior to administration of one or more oligonucleotides or pharmaceutical composition. In some embodiments, serum iron saturation is reduced in the subject by at least about 30%, about 35%, about 40%, about 45%, about 50%, about 55%, about 60%, about 65%, about 70%, about 75%, about 80%, about 85%, about 90%, about 95%, about 99% or greater than 99% when compared to serum iron saturation in a subject (e.g., a reference or control subject) not receiving the oligonucleotide or oligonucleotides or pharmaceutical composition or receiving a control oligonucleotide or oligonucleotides, pharmaceutical composition or treatment.

Suitable methods for determining TMPRSS6 expression, the amount or level of TMPRSS6 mRNA, matriptase-2 protein, matriptase-2 activity, or a biomarker related to or affected by modulation of TMPRSS6 expression (e.g., a plasma biomarker), in the subject, or in a sample from the subject, are known in the art. Further, the Examples set forth herein illustrate methods for determining TMPRSS6 expression.

In some embodiments, TMPRSS6 expression, the amount or level of TMPRSS6 mRNA, matriptase-2 protein, matriptase-2 activity, or a biomarker related to or affected by modulation of TMPRSS6 expression, or any combination thereof, is reduced in a cell (e.g., a hepatocyte), a population or a group of cells (e.g., an organoid), an organ (e.g., liver), blood or a fraction thereof (e.g., plasma), a tissue (e.g., liver tissue), a sample (e.g., a liver biopsy sample), or any other appropriate biological material obtained or isolated from the subject. In some embodiments, TMPRSS6 expression, the amount or level of TMPRSS6 mRNA, matriptase-2 protein, matriptase-2 activity, or a biomarker related to or affected by modulation of TMPRSS6 expression, or any combination thereof, is reduced in more than one type of cell (e.g., a hepatocyte and one or more other type(s) of cell), more than one groups of cells, more than one organ (e.g., liver and one or more other organ(s)), more than one fraction of blood (e.g., plasma and one or more other blood fraction(s)), more than one type of tissue (e.g., liver tissue and one or more other type(s) of tissue), or more than one type of sample (e.g., a liver biopsy sample and one or more other type(s) of biopsy sample).

Because of their high specificity, the oligonucleotides provided herein (e.g., RNAi oligonucleotides) specifically target mRNA of target genes (e.g., TMPRSS6 mRNA) of cells and tissue(s), or organs(s) (e.g., in the liver). In preventing disease, the target gene may be one which is required for initiation or maintenance of the disease or which has been identified as being associated with a higher risk of contracting the disease. In treating disease, the oligonucleotide can be brought into contact with the cells, tissue(s), or organ(s) (e.g., liver) exhibiting or responsible for mediating the disease. For example, an oligonucleotide (e.g., an RNAi oligonucleotide) substantially identical to all or part of a wild-type (i.e., native) or mutated gene associated with a disorder or condition associated with hepcidin deficiency or suppression may be brought into contact with or introduced into a cell or tissue type of interest such as a hepatocyte or other liver cell.

Examples of a disease, disorder or condition associated with hepcidin deficiency or suppression include, but are not limited to hemochromatosis (e.g. hereditary hemochromatosis), beta-thalassemia, Polycythemia vera, iron-refractory iron deficiency anemia.

In some embodiments, the target gene may be a target gene from any mammal, such as a human target. Any target gene may be silenced according to the method described herein.

Methods described herein typically involve administering to a subject an effective amount of an oligonucleotide herein (e.g., a RNAi oligonucleotide), that is, an amount that produces or generates a desirable therapeutic result. A therapeutically acceptable amount may be an amount that therapeutically treats a disease or disorder. The appropriate dosage for any one subject will depend on certain factors, including the subject's size, body surface area, age, the composition to be administered, the active ingredient(s) in the composition, time and route of administration, general health, and other drugs being administered concurrently.

In some embodiments, a subject is administered any one of the compositions herein (e.g., a composition comprising an RNAi oligonucleotide described herein) either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides herein are administered intravenously or subcutaneously.

In some embodiments, an oligonucleotide herein (e.g., an RNAi oligonucleotide), or a pharmaceutical composition comprising the oligonucleotide, is administered alone or in combination. In some embodiments, the oligonucleotides herein are administered in combination concurrently, sequentially (in any order), or intermittently. For example, two oligonucleotides may be co-administered concurrently. Alternatively, one oligonucleotide may be administered and followed any amount of time later (e.g., one hour, one day, one week or one month) by the administration of a second oligonucleotide.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

Kits

In some embodiments, the disclosure provides a kit comprising an oligonucleotide herein (e.g., an RNAi oligonucleotide), and instructions for use. In some embodiments, the kit comprises an oligonucleotide herein, and a package insert containing instructions for use of the kit and/or any component thereof. In some embodiments, the kit comprises, in a suitable container, an oligonucleotide herein, one or more controls, and various buffers, reagents, enzymes and other standard ingredients well known in the art. In some embodiments, the container comprises at least one vial, well, test tube, flask, bottle, syringe, or other container means, into which the oligonucleotide is placed, and in some instances, suitably aliquoted. In some embodiments where an additional component is provided, the kit contains additional containers into which this component is placed. The kits can also include a means for containing the oligonucleotide and any other reagent in close confinement for commercial sale. Such containers may include injection or blow-molded plastic containers into which the desired vials are retained. Containers and/or kits can include labeling with instructions for use and/or warnings.

In some embodiments, a kit comprises an oligonucleotide herein (e.g., an RNAi oligonucleotide), and a pharmaceutically acceptable carrier, or a pharmaceutical composition comprising the oligonucleotide and instructions for treating or delaying progression of a disease, disorder or condition associated with hepcidin deficiency or suppression in a subject in need thereof.

Definitions

As used herein, the term "antisense oligonucleotide" encompasses a nucleic acid-based molecule which has a sequence complementary to all or part of the target mRNA, in particular seed sequence thereby capable of forming a duplex with a mRNA. Thus, the term "antisense oligonucleotide", as used herein, may be referred to as a "complementary nucleic acid-based inhibitor" or "guide strand".

As used herein, "approximately" or "about," as applied to one or more values of interest, refers to a value that is similar to a stated reference value. In certain embodiments, "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

As used herein, "administer," "administering," "administration" and the like refers to providing a substance (e.g., an oligonucleotide) to a subject in a manner that is pharmacologically useful (e.g., to treat a disease, disorder, or condition in the subject).

As used herein, "attenuate," "attenuating," "attenuation" and the like refers to reducing or effectively halting. As a non-limiting example, one or more of the treatments herein may reduce or effectively halt the onset or progression of iron-refractory iron deficiency anemia, hemochromatosis or beta-thalassemia in a subject. This attenuation may be exemplified by, for example, a decrease in one or more aspects (e.g., symptoms, tissue characteristics, and cellular, inflammatory, or immunological activity, etc.) of iron-refractory iron deficiency anemia, hemochromatosis, or beta-thalassemia, no detectable progression (worsening) of one or more aspects of hemochromatosis or beta-thalassemia, or no detectable aspects of iron-refractory iron deficiency anemia, hemochromatosis, or beta-thalassemia in a subject when they might otherwise be expected.

As used herein, "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other to form regions of complementarity, as described herein.

As used herein, "deoxyribonucleotide" refers to a nucleotide having a hydrogen in place of a hydroxyl at the 2' position of its pentose sugar when compared with a ribonucleotide. A modified deoxyribonucleotide is a deoxyribonucleotide having one or more modifications or substitutions of atoms other than at the 2' position, including modifications or substitutions in or of the sugar, phosphate group or base.

As used herein, "double-stranded oligonucleotide" or "ds oligonucleotide" refers to an oligonucleotide that is substantially in a duplex form. In some embodiments, the complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region (s) of a double-stranded oligonucleotide is formed from single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed (e.g., having overhangs at one or both ends). In some embodiments, a double-stranded oligonucleotide comprises antiparallel sequence of nucleotides that are partially complementary, and thus, may have one or more mismatches, which may include internal mismatches or end mismatches.

As used herein, "duplex," in reference to nucleic acids (e.g., oligonucleotides), refers to a structure formed through complementary base pairing of two antiparallel sequences of nucleotides.

As used herein, "excipient" refers to a non-therapeutic agent that may be included in a composition, for example, to provide or contribute to a desired consistency or stabilizing effect.

As used herein, "hepatocyte" or "hepatocytes" refers to cells of the parenchymal tissues of the liver. These cells make up about 70%-85% of the liver's mass and manufacture serum albumin, FBN and the prothrombin group of clotting factors (except for Factors 3 and 4). Markers for hepatocyte lineage cells include, but are not limited to, transthyretin (Ttr), glutamine synthetase (Glul), hepatocyte nuclear factor 1a (Hnf1a) and hepatocyte nuclear factor 4a (Hnf4a). Markers for mature hepatocytes may include, but are not limited to, cytochrome P450 (Cyp3a11), cytochrome P450 3A4 (CYP3A4), fumarylacetoacetate hydrolase (Fah), glucose 6-phosphate (G6p), albumin (Alb) and OC2-2F8. See, e.g., Huch et al. (2013) Nature 494:247-50.

As used herein, a "hepatotoxic agent" refers to a chemical compound, virus or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

As used herein, the term "TMPRSS6" refers to transmembrane protease serine 6. The TMPRSS6 gene encodes the matriptase-2 protein which functions in a signaling pathway with hepcidin to regulate iron balance in the body. matriptase-2

As used herein, "labile linker" refers to a linker that can be cleaved (e.g., by acidic pH). A "fairly stable linker" refers to a linker that cannot be cleaved.

As used herein, "modified internucleotide linkage" refers to an internucleotide linkage having one or more chemical modifications when compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified internucleotide linkage may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. When referring to an oligonucleotide being modified, it may be understood to refer to an oligonucleotide that comprises a at least one modified nucleotide therein. When referring to an oligonucleotide being fully modified, it may be understood to refer to an oligonucleotide wherein all nucleotides therein are modified nucleotides. Said modified nucleotides need not comprise the same modifications.

As used herein, "nicked tetraloop structure" refers to a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand. The structure is said to be nicked by a discontinuity between the backbone of the sense and antisense strand, typically by a discontinuity between the pentose sugars of the adjacent nucleotides of the sense and antisense strands. A "nicked structure" may generally be referred to with this same definition when the loop may or may not be a tetraloop (e.g., one may refer to a nicked structure when the sense strand forms a triloop, tetraloop or other type of loop as disclosed herein).

As used herein, "oligonucleotide" refers to a short nucleic acid (e.g., less than about 100 nucleotides in length). An oligonucleotide may be single-stranded (ss) or double-stranded (ds). An oligonucleotide may comprise deoxyribonucleosides, ribonucleosides, or a combination of both. In some embodiments, a double-stranded oligonucleotide comprising ribonucleosides is referred to as "dsRNA". An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (DsiRNA), antisense oligonucleotide, short siRNA or ss siRNA.

As used herein, "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at (or proximal to) the 5' terminus or 3' terminus of an oligonucleotide. In certain embodiments, the overhang is a 3' or 5' overhang on the antisense strand or sense strand of an oligonucleotide.

As used herein, features may be described as being provided "in", "on" or "at" the 3' end or 5' end of a strand. Nucleotide features described at a given strand end, such as sugar modifications, internucleotide modifications, nucleotide mismatches and overhangs for instance, are understood to refer to the nucleotide(s) of that strand proximal to the defined strand end (e.g., at 3' end of the sense strand).

As used herein, "phosphate analog" refers to a chemical moiety that mimics the electrostatic and/or steric properties of a phosphate group. In some embodiments, the phosphate analog mimics the electrostatic and/or steric properties of a phosphate group in biologic systems. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include, but are not limited to, 5' phosphonates, such as 5' methylene phosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethyl phosphonate, in which the oxygen atom of the oxymethyl group is bound to the sugar moiety (e.g., at its 4'-carbon) or analog thereof. See, e.g., US Patent Publication No. 2019-0177729. Other modifications have been developed for the 5' end of oligonucleotides (see, e.g., Intl. Patent Application No. WO 2011/133871; U.S. Pat. No. 8,927,513; and Prakash et al. (2015) NUCLEIC ACIDS RES. 43:2993-3011).

As used herein, "reduced expression" of a gene (e.g., TMPRSS6) refers to a decrease in the amount or level of RNA transcript (e.g., TMPRSS6 mRNA) or protein encoded by the gene and/or a decrease in the amount or level of activity of the gene in a cell, a population of cells, a sample, or a subject, when compared to an appropriate reference (e.g., a reference cell, population of cells, sample or subject). For example, the act of contacting a cell with an oligonucleotide herein (e.g., an oligonucleotide comprising an antisense strand having a nucleotide sequence that is complementary to a nucleotide sequence comprising TMPRSS6 mRNA) may result in a decrease in the amount or level of TMPRSS6 mRNA, matriptase-2 protein and/or activity (e.g., via degradation of TMPRSS6mRNA by the RNAi pathway) when compared to a cell that is not treated with the oligonucleotide. Similarly, and as used herein, "reducing expression" refers to an act that results in reduced expression of a gene (e.g., TMPRSS6).

As used herein, "reduction of TMPRSS6 expression" refers to a decrease in the amount or level of TMPRSS6 mRNA, matriptase-2 protein and/or matriptase-2 activity in a cell, a population of cells, a sample or a subject when compared to an appropriate reference (e.g., a reference cell, population of cells, sample, or subject).

As used herein, "region of complementarity" refers to a sequence of nucleotides of a nucleic acid (e.g., an oligonucleotide) that is sufficiently complementary to an antiparallel sequence of nucleotides to permit hybridization between the two sequences of nucleotides under appropriate hybridization conditions (e.g., in a phosphate buffer, in a cell, etc.). In some embodiments, an oligonucleotide herein comprises a targeting sequence having a region of complementary to a mRNA target sequence. A region of complementarity may be of a given length and be identified by a number of contiguous nucleotides (e.g., at least 15 contiguous nucleotides in length), referring to a number of nucleotides contiguously linked together through internucleotide linkages.

As used herein, "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

As used herein, "RNAi oligonucleotide" refers to either (a) a double-stranded oligonucleotide having a sense strand (passenger) and antisense strand (guide), in which the antisense strand or part of the antisense strand is used by the Argonaute 2 (Ago2) endonuclease in the cleavage of a target mRNA (e.g., TMPRSS6 mRNA) or (b) a single-stranded oligonucleotide having a single antisense strand, where that antisense strand (or part of that antisense strand) is used by the Ago2 endonuclease in the cleavage of a target mRNA (e.g., TMPRSS6 mRNA).

As used herein, "strand" refers to a single, contiguous sequence of nucleotides linked together through internucleotide linkages (e.g., phosphodiester linkages or phosphoro-thioate linkages). In some embodiments, a strand has two free ends (e.g., a 5' end and a 3' end).

As used herein, "subject" means any mammal, including mice, rabbits, non-human primates (NHP) and humans. In one embodiment, the subject is a human or NHP. Moreover, "individual" or "patient" may be used interchangeably with "subject."

As used herein, "synthetic" refers to a nucleic acid or other molecule that is artificially synthesized (e.g., using a machine (e.g., a solid-state nucleic acid synthesizer)) or that is otherwise not derived from a natural source (e.g., a cell or organism) that normally produces the molecule.

As used herein, "targeting ligand" refers to a molecule (e.g., a carbohydrate, amino sugar, cholesterol, polypeptide, or lipid, such as a GalNAc moiety for instance) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

As used herein, "target sequence" refers to a contiguous portion of the nucleotide sequence of an mRNA molecule formed during the transcription of a TMPRSS6 gene (e.g., SEQ ID NOs: 853, 854, and 855) including mRNA that is a product of RNA processing of a primary transcription product. In some embodiments, the target portion of the sequence will be at least long enough to serve as a substrate for RNAi-directed cleavage at or near that portion of the nucleotide sequence of an mRNA molecule formed during the transcription of a TMPRSS6 gene. In some embodiments, the target sequence is within the protein coding region of the TMPRSS6 gene. In some embodiments, the target sequence is within the 3' UTR of the TMPRSS6 gene.

As used herein, "targeting sequence" refers to a nucleotide sequence that is fully or partially complementary to a target sequence.

As used herein, "loop", "triloop", or "tetraloop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cell), the two antiparallel regions, which flank the unpaired region, hybridize to form a duplex (referred to as a "stem"). A loop increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a loop (e.g., a tetraloop or triloop) can confer a $T_m$ of at least about 50° C., at least about 55° C., at least about 56° C., at least about 58° C., at least about 60° C., at least about 65° C. or at least about 75° C. in 10 mM Na$_2$HPO$_4$ to a hairpin comprising a duplex of at least 2 base pairs (bp) in length. In some embodiments, a tetraloop can confer a T$_m$ of at least about 50° C., at least about 55° C., at least about 56° C., at least about 58° C., at least about 60° C., at least about 65° C. or at least about 75° C. in 10 mM NaH$_2$PO$_4$ to a hairpin comprising a duplex of at least 2 base pairs (bp) in length. In some embodiments, a loop may stabilize a bp in an adjacent stem duplex by stacking interactions. In addition, interactions among the nucleotides in a loop include, but are not limited to, non-Watson-Crick base pairing, stacking interactions, hydrogen bonding and contact interactions (Cheong et al. (1990) Nature 346:680-82; Heus & Pardi (1991) Science 253:191-94). In some embodiments, a loop comprises or consists of 3 to 6 nucleotides and is typically 4 to 5 nucleotides. In certain embodiments, a loop comprises or consists of 3, 4, 5 or 6 nucleotides, which may or may not be modified (e.g., which may or may not be conjugated to a targeting moiety/targeting ligand). In one embodiment, a loop consisting of 3 nucleotides is a triloop. In one embodiment, a loop consisting of 4 nucleotides is a tetraloop. Any nucleotide may be used in the tetraloop and standard IUPAC-IUB symbols for such nucleotides may be used as described in Cornish-Bowden (1985) Nucleic Acids Res. 13:3021-30. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al. (1990) Proc. Natl. Acad. Sci. USA 87:8467-71; Antao et al. (1991) Nucleic Acids Res. 19:5901-05). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, e.g., Nakano et al. (2002) Biochem. 41:14281-92; Shinji et al. (2000) Nippon Kagakkai Koen Yokoshu 78:731. In some embodiments, the tetraloop is contained within a nicked tetraloop structure.

As used herein, "treat" or "treating" refers to the act of providing care to a subject in need thereof, for example, by administering a therapeutic agent (e.g., an oligonucleotide herein) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

"Pharmaceutically acceptable" indicates that the substance or composition must be chemically and/or toxicologically suitable for the treatment of mammals.

As used herein, the symbol  is used to describe an attachment point.

List of Further Embodiments of the Invention

1. An RNAi oligonucleotide for reducing transmembrane serine protease 6 (TMPRSS6) expression, the oligonucleotide comprising a sense strand and an antisense strand, wherein the sense strand and the antisense strand form a duplex region, wherein the antisense strand comprises a region of complementarity to a TMPRSS6 mRNA target sequence of any one of SEQ ID NOs: 661-852, and wherein the region of complementarity is at least 15 contiguous nucleotides in length.
2. An RNAi oligonucleotide for reducing transmembrane serine protease 6 (TMPRSS6) expression, the oligonucleotide comprising a sense strand and an antisense strand forming a duplex region, wherein the antisense strand comprises a region of complementarity to a TMPRSS6 mRNA target sequence as set forth in any one of SEQ ID NOs: 661-852, and wherein the region of complementarity is at least 15 contiguous nucleotides in length.
3. The RNAi oligonucleotide according to embodiments 1 or 2, wherein the sense strand is 15 to 50 nucleotides in length.
4. The RNAi oligonucleotide according to any one of the preceding embodiments, wherein the sense strand is 18 to 36 nucleotides in length.
5. The RNAi oligonucleotide according to any one of the preceding embodiments, wherein the antisense strand is 15 to 30 nucleotides in length.
6. The RNAi oligonucleotide according to any one of the preceding embodiments, wherein the antisense strand is 22 nucleotides in length and wherein antisense strand and the sense strand form a duplex region of at least 19 nucleotides in length, optionally at least 20 nucleotides in length.
7. The RNAi oligonucleotide according to any one of the preceding embodiments, wherein the antisense strand is 22 nucleotides in length and wherein antisense strand and the sense strand form a duplex region of at least 20 nucleotides in length.
8. The RNAi oligonucleotide according to any one of the preceding embodiments, wherein the region of complementarity is at least 18 contiguous nucleotides in length, optionally the region of complementarity is at least 19 contiguous nucleotides in length.
9. The RNAi oligonucleotide according to any one of the preceding embodiments, wherein the region of complementarity is at least 19 contiguous nucleotides in length.
10. The RNAi oligonucleotide according to any one of the preceding embodiments, wherein the region of complementarity is at least 19 contiguous nucleotides in length.
11. The RNAi oligonucleotide according to any one of the preceding embodiments, wherein the region of complementarity is at least 20 contiguous nucleotides in length.
12. A double stranded RNAi oligonucleotide for reducing TMPRSS6 expression, the oligonucleotide comprising:
   (i) an antisense strand of 19-30 nucleotides in length, wherein the antisense strand comprises a nucleotide sequence comprising a region of complementarity to a TMPRSS6 mRNA target sequence, wherein the region of complementarity is selected from SEQ ID NOs: 1-192, and
   (ii) a sense strand of 19-50 nucleotides in length comprising a region of complementarity to the antisense strand, wherein the antisense and sense strands are separate strands which form an asymmetric duplex region having an overhang of 1-4 nucleotides at the 3' terminus of the antisense strand.
13. The RNAi oligonucleotide according to any one of the preceding embodiments, wherein the 3' end of the sense strand comprises a stem-loop set forth as S1-Lp-S2, wherein S1 is complementary to S2, and wherein Lp forms a loop between S1 and S2 of 3-5 nucleotides in length.

14. The RNAi oligonucleotide according to any one of embodiments 1-12, wherein the sense strand comprises a stem-loop set forth as S1-Lp-S2 proximal the 3' end, wherein S1 is complementary to S2, and wherein Lp forms a loop of 3-5 nucleotides in length between S1 and S2.

15. The RNAi oligonucleotide according to any one of embodiments 1-12, wherein the sense strand proximal the 3' end comprises a stem-loop set forth as S1-Lp-S2, wherein S1 is complementary to S2, and wherein Lp forms a loop of 3-5 nucleotides in length between S1 and S2.

16. The RNAi oligonucleotide according to any one of embodiments 13-15, wherein Lp is a triloop or a tetraloop.

17. The RNAi oligonucleotide according to any one of embodiments 13-16, wherein Lp is a tetraloop.

18. The RNAi oligonucleotide according to embodiment 17, wherein the tetraloop comprises the sequence 5'-GAAA-3'.

19. The RNAi oligonucleotide according to any one of embodiments 13-18, wherein the loop is a tetraloop comprising the sequence 5'-GAAA-3'.

20. The RNAi oligonucleotide according to any one of embodiments 13-19, wherein S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length.

21. The RNAi oligonucleotide according to any one of embodiments 13-19, wherein S1 and S2 are each 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length.

22. The RNAi oligonucleotide according to any one of embodiments 13-21, wherein the S1 and S2 are 1-10 nucleotides in length and have the same length.

23. The RNAi oligonucleotide according to any one of embodiments 13-22, wherein S1 and S2 are 6 nucleotides in length.

24. The RNAi oligonucleotide according to any one of embodiments 13-23, wherein the stem-loop comprises the sequence 5'-GCAGCCGAAAGGCUGC-3' (SEQ ID NO: 856).

25. The RNAi oligonucleotide according to any one of embodiments 13-24, wherein a discontinuity is formed between the sense strand and antisense strand, forming a nicked structure.

26. The RNAi oligonucleotide according to any one of embodiments 13-25, wherein a discontinuity is formed between the sense strand and antisense strand, forming a nicked tetraloop structure.

27. The RNAi oligonucleotide according to any one of the preceding embodiments, wherein the antisense strand comprises a 3' overhang sequence of one or more nucleotides in length.

28. The RNAi oligonucleotide according to embodiment 27, wherein the overhang comprises purine nucleotides.

29. The RNAi oligonucleotide according to any one of embodiments 27-28, wherein the 3' overhang sequence is 2 nucleotides in length.

30. The RNAi oligonucleotide according to any one of embodiments 27-29, wherein the 3' overhang is selected from AA, GG, AG, and GA.

31. The RNAi oligonucleotide according to embodiment 30, wherein the overhang is GG or AA.

32. The RNAi oligonucleotide according to any one of embodiments 30-31, wherein the overhang is GG.

33. The RNAi oligonucleotide according to any one of embodiments 27-29, wherein the 3' overhang is selected from 5'-AA-3', 5'-GG-3', 5'-AG-3', and 5'-GA-3'.

34. The RNAi oligonucleotide according to embodiment 33, wherein the overhang is 5'-GG-3' or 5'-AA-3'.

35. The RNAi oligonucleotide according to any one of embodiments 33-34, wherein the overhang is 5'-GG-3'.

36. The RNAi oligonucleotide according to any one of the preceding embodiments, wherein the oligonucleotide comprises at least one modified nucleotide.

37. The RNAi oligonucleotide according to any one of the preceding embodiments, wherein the oligonucleotide is fully modified.

38. The RNAi oligonucleotide according to any one of the preceding embodiments, wherein the all the nucleotides of the oligonucleotide are modified nucleotides.

39. The RNAi oligonucleotide according to any one of embodiments 1-36, wherein the oligonucleotide is partially modified.

40. The RNAi oligonucleotide according to any one of embodiments 36-39, wherein the modified oligonucleotide comprises a targeting ligand conjugated nucleotide.

41. The RNAi oligonucleotide according to any one of embodiments 36-40, wherein the modified nucleotide comprises a targeting ligand conjugated nucleotide.

42. The RNAi oligonucleotide according to any one of embodiments 36-41, wherein the oligonucleotide comprises a 2'-modification.

43. The RNAi oligonucleotide according to any one of embodiment 36-42, wherein the modified nucleotide comprises a 2'-modification.

44. The RNAi oligonucleotide according to any one of embodiments 42-43, wherein the 2'-modification is a modification selected from 2'-aminoethyl, 2'-fluoro, 2'-O-methyl, 2'-O-methoxyethyl, and 2'-deoxy-2'-fluoro-β-d-arabinonucleic acid.

45. The RNAi oligonucleotide according to any one of embodiments 42-44, wherein the 2'-modification is selected from 2'-fluoro (2'-F) and 2'-O-methyl (2'-OMe).

46. The RNAi oligonucleotide according to any one of embodiments 36-45, wherein the modification is a 2'-modification selected from 2'-fluoro (2'-F) and 2'-O-methyl (2'-OMe).

47. The RNAi oligonucleotide according to any one of embodiments 36-46, wherein about 10-15%, 10%, 11%, 12%, 13%, 14% or 15% of the nucleotides of the sense strand comprise a 2'-fluoro (2'-F) modification.

48. The RNAi oligonucleotide according to any one of embodiments 36-47, wherein about 25-35%, 25%, 26%, 27%, 28%, 29%, 30%, 31%, 32%, 33%, 34% or 35% of the nucleotides of the antisense strand comprise a 2'-fluoro (2'-F) modification.

49. The RNAi oligonucleotide according to any one of embodiments 36-48, wherein about 25-35%, 25-35%, 25%, 26%, 27%, 28%, 29%, 30%, 31%, 32%, 33%, 34% or 35% of the nucleotides of the oligonucleotide comprise a 2'-fluoro (2'-F) modification.

50. The RNAi oligonucleotide according to any one of the preceding embodiments, wherein the sense strand comprises 36 nucleotides with positions 1-36 from 5' to 3', wherein positions 8-11 comprise a 2'-fluoro (2'-F) modification.

51. The RNAi oligonucleotide according to any one of the preceding embodiments, wherein
the sense strand comprises 36 nucleotides, numbered 5' to 3'; and
all of positions 8-11 of the sense strand comprise a 2'-fluoro (2'-F) modification.

52. The RNAi oligonucleotide according to any one of the preceding embodiments, wherein
the sense strand is 36 nucleotides in length, numbered 5' to 3'; and
all of positions 8-11 of the sense strand comprise a 2'-fluoro (2'-F) modification.

53. The RNAi oligonucleotide according to any one of the preceding embodiments, wherein the antisense strand comprises 22 nucleotides with positions 1-22 from 5' to 3', and wherein positions 2, 3, 4, 5, 7, 10 and 14 comprise a 2'-fluoro (2'-F) modification.

54. The RNAi oligonucleotide according to any one of the preceding embodiments, wherein
the antisense strand comprises 22 nucleotides, numbered 5' to 3'; and
all of positions 2, 3, 4, 5, 7, 10 and 14 of the antisense strand comprise a 2'-fluoro (2'-F) modification.

55. The RNAi oligonucleotide according to any one of the preceding embodiments, wherein
the antisense strand is 22 nucleotides in length, numbered 5' to 3'; and
all of positions 2, 3, 4, 5, 7, 10 and 14 of the antisense strand comprise a 2'-fluoro (2'-F) modification.

56. The RNAi oligonucleotide according to any one of the preceding embodiments, wherein the sense strand comprises 36 nucleotides with positions 1-36 from 5' to 3', and wherein positions 1-7, 12-27, and 31-36 comprise a 2'-O-methyl modification.

57. The RNAi oligonucleotide according to any one of the preceding embodiments, wherein
the sense strand comprises 36 nucleotides, numbered 5' to 3'; and
all of positions 1-7, 12-27, and 31-36 of the sense strand comprise a 2'-O-methyl modification.

58. The RNAi oligonucleotide according to any one of the preceding embodiments, wherein
the sense strand is 36 nucleotides in length, numbered 5' to 3'; and
all of positions 1-7, 12-27, and 31-36 of the sense strand comprise a 2'-O-methyl modification.

59. The RNAi oligonucleotide according to any one of the preceding embodiments, wherein the antisense strand comprises 22 nucleotides with positions 1-22 from 5' to 3', and wherein positions 1, 6, 8, 9, 11-13, and 15-22 comprise a 2'-O-methyl modification.

60. The RNAi oligonucleotide according to any one of the preceding embodiments, wherein
the antisense strand comprises 22 nucleotides, numbered 5' to 3'; and
all of positions 1, 6, 8, 9, 11-13, and 15-22 of the antisense strand comprise a 2'-O-methyl modification.

61. The RNAi oligonucleotide according to any one of the preceding embodiments, wherein
the antisense strand is 22 nucleotides in length, numbered 5' to 3'; and
all of positions 1, 6, 8, 9, 11-13, and 15-22 of the antisense strand comprise a 2'-O-methyl modification.

62. The RNAi oligonucleotide according to any one of the preceding embodiments, wherein
the sense strand comprises 36 nucleotides and the antisense strand comprises 22 nucleotides, the nucleotides of each one of the strands being numbered 5' to 3';
all of positions 1-7, 12-27, and 31-36 of the sense strand and positions 1, 6, 8, 9, 11-13, and 15-22 of the antisense strand comprise a 2'-O-methyl modification; and
all of positions 8-11 of the sense strand and 2, 3, 4, 5, 7, 10 and 14 of the antisense strand comprise a 2'-fluoro modification.

63. The RNAi oligonucleotide according to any one of the preceding embodiments, wherein the oligonucleotide comprises at least one modified internucleotide linkage.

64. The RNAi oligonucleotide according to embodiment 63, wherein the at least one modified internucleotide linkage is a phosphorothioate linkage.

65. The RNAi oligonucleotide according to any one of the preceding embodiments, the oligonucleotide comprises at least one phosphorothioate linkage.

66. The RNAi oligonucleotide according to any one of the preceding embodiments, wherein the antisense strand comprises a phosphorothioate linkage (i) between positions 1 and 2, and between positions 2 and 3; or (ii) between positions 1 and 2, between positions 2 and 3, and between positions 3 and 4, wherein positions are numbered 1-4 from 5' to 3'.

67. The RNAi oligonucleotide according to any one of the preceding embodiments, wherein the antisense strand is 22 nucleotides in length, and wherein the antisense strand comprises a phosphorothioate linkage between positions 20 and 21 and between positions 21 and 22, wherein positions are numbered 1-22 from 5' to 3'.

68. The RNAi oligonucleotide according to any one of the preceding embodiments, wherein
the antisense strand comprises 22 nucleotides, numbered 5' to 3'; and
a phosphorothioate linkage is provided between positions 1 and 2, between positions 2 and 3, and between positions 3 and 4, between positions 20 and 21 and between positions 21 and 22 of the antisense strand.

69. The RNAi oligonucleotide according to any one of the preceding embodiments, wherein the sense strand comprises a phosphorothioate linkage between positions 1 and 2, wherein positions are numbered 5' to 3'.

70. The RNAi oligonucleotide according to any one of the preceding embodiments, wherein
the antisense strand comprises 22 nucleotides;
the nucleotides of each one of the strands are numbered 5' to 3';
a phosphorothioate linkage is provided between positions 1 and 2 of the sense strand, and between positions 1 and 2, between positions 2 and 3, and between positions 3 and 4, between positions 20 and 21 and between positions 21 and 22 of the antisense strand.

71. The RNAi oligonucleotide according to any one of the preceding embodiments, wherein the 4'-carbon of the sugar of the 5'-nucleotide of the antisense strand comprises a phosphate analog.

72. The RNAi oligonucleotide according to embodiment 71, wherein the phosphate analog is oxymethyl phosphonate, vinyl phosphonate or malonyl phosphonate, optionally wherein the phosphate analog is a 4'-phosphate analog comprising 4'-oxymethylphosphonate.

73. The RNAi oligonucleotide according to any one of the preceding embodiments, wherein the 5'-terminal nucleotide of the antisense strand comprises a structure according to Chem. 1a (MePhosphonate-4O-mU).

74. The RNAi oligonucleotide according to any one of the preceding embodiments, wherein at least one nucleotide of the oligonucleotide is conjugated to one or more targeting ligands.

75. The RNAi oligonucleotide according to embodiment 74, wherein each targeting ligand comprises a carbohydrate, amino sugar, cholesterol, or polypeptide.

76. The RNAi oligonucleotide according to any one of embodiments 13-75, wherein the stem-loop comprises one or more targeting ligands conjugated to one or more nucleotides of the stem-loop.

77. The RNAi oligonucleotide according to any one of embodiments 74-76, wherein the one or more targeting ligands is conjugated to one or more nucleotides of the loop.

78. The RNAi oligonucleotide according to any one of embodiments 13-77, wherein the loop (Lp) comprises 4 nucleotides numbered 1-4 from 5' to 3', wherein nucleotides at positions 2, 3, and 4 each comprise one or more targeting ligands, wherein the targeting ligands are the same or different.

79. The RNAi oligonucleotide according to any one of embodiments 74-78, wherein each targeting ligand comprises a N-acetylgalactosamine (GalNAc) moiety.

80. The RNAi oligonucleotide according to embodiment 79, wherein the GalNAc moiety is a monovalent GalNAc moiety, a bivalent GalNAc moiety, a trivalent GalNAc moiety or a tetravalent GalNAc moiety.

81. The RNAi oligonucleotide according to any one of embodiments 79-80, wherein the GalNAc moiety is a monovalent GalNAc moiety.

82. The RNAi oligonucleotide according to any one of embodiments 13-81, wherein up to 4 nucleotides of Lp of the stem-loop are each conjugated to a monovalent GalNAc moiety.

83. The RNAi oligonucleotide according to any one of embodiments 13-82, wherein the loop Lp is 4 nucleotides in length numbered 1-4 from 5' to 3', wherein the loop Lp nucleotides at positions 2, 3, and 4 are each conjugated to a monovalent N-acetylgalactosamine (GalNAc) moiety.

84. The RNAi oligonucleotide according to any one of embodiments 13-82, wherein the loop Lp is 4 nucleotides in length, and wherein the second, third and fourth nucleotides of the loop Lp from 5' to 3' are each conjugated to a monovalent N-acetylgalactosamine (GalNAc) moiety.

85. The RNAi oligonucleotide according to any one of the preceding embodiments, wherein the region of complementarity is fully complementary to the mRNA target sequence.

86. The RNAi oligonucleotide according to any one of embodiments 1-84, wherein the region of complementarity is partially complementary to the mRNA target sequence.

87. The RNAi oligonucleotide according to any one of embodiments 1-84 and 86, wherein the region of complementarity comprises no more than four mismatches to the mRNA target sequence.

88. The RNAi oligonucleotide according to any one of the preceding embodiments, wherein the region of complementarity is fully complementary to the TMPRSS6 mRNA target sequence at nucleotide positions 2-8 of the antisense strand, wherein nucleotide positions are numbered 5' to 3'.

89. The RNAi oligonucleotide according to any one of the preceding embodiments, wherein the region of complementarity is fully complementary to the TMPRSS6 mRNA target sequence at nucleotide positions 2-11 of the antisense strand, wherein nucleotide positions are numbered 5' to 3'.

90. The RNAi oligonucleotide according to any one of the preceding embodiments, wherein the TMPRSS6 mRNA target sequence is as set forth in SEQ ID NO: 844.

91. The RNAi oligonucleotide according to any one of the preceding embodiments, wherein the antisense strand comprises a nucleotide sequence as set forth in SEQ ID NO: 184, and optionally wherein the sense strand comprises a nucleotide sequence as set forth in SEQ ID NO: 844.

92. The RNAi oligonucleotide according to any one of the preceding embodiments, wherein the sense strand comprises a nucleotide sequence of any one of SEQ ID NOs: 579-580, 585-587, 590 and 595-597.

93. The RNAi oligonucleotide according to any one of the preceding embodiments, wherein the sense strand comprises a nucleotide sequence selected from SEQ ID NOs: 579-580, 585-587, 590, and 595-597.

94. The RNAi oligonucleotide according to any one of the preceding embodiments, wherein the antisense strand comprises a nucleotide sequence of any one of SEQ ID NOs: 600-601, 606-608, 611 and 616-618.

95. The RNAi oligonucleotide according to any one of the preceding embodiments, wherein the antisense strand comprises a nucleotide sequence selected from SEQ ID NOs: 600-601, 606-608, 611, and 616-618.

96. The RNAi oligonucleotide according to any one of the preceding embodiments, wherein the sense strand and antisense strands comprise nucleotide sequences selected from the group consisting of:
a) SEQ ID NOs: 579 and 600, respectively;
b) SEQ ID NOs: 580 and 601, respectively;
c) SEQ ID NOs: 595 and 616, respectively;
d) SEQ ID NOs: 590 and 611, respectively;
e) SEQ ID NOs: 596 and 617, respectively;
f) SEQ ID NOs: 597 and 618, respectively;
g) SEQ ID NOs: 585 and 606, respectively;
h) SEQ ID NOs: 586 and 607, respectively; and,
i) SEQ ID NOs: 587 and 608, respectively.

97. The RNAi oligonucleotide according to any one of the preceding embodiments, wherein the sense strand and antisense strands comprise nucleotide sequences selected from the group consisting of:
a) SEQ ID NOs: 579 and 600, respectively;
b) SEQ ID NOs: 580 and 601, respectively;
c) SEQ ID NOs: 590 and 611, respectively;
d) SEQ ID NOs: 597 and 618, respectively; and,
e) SEQ ID NOs: 586 and 607, respectively.

98. The RNAi oligonucleotide according to any one of the preceding embodiments, wherein the antisense strand comprises a nucleotide sequence as set forth in SEQ ID NO: 600, and optionally wherein the sense strand comprises a nucleotide sequence as set forth in SEQ ID NO: 579.

99. The RNAi oligonucleotide according to any one of the preceding embodiments, wherein the sense strand comprises a nucleotide sequence as set forth in SEQ ID NO: 579, wherein the antisense strand comprises a nucleotide sequence as set forth in SEQ ID NO: 600.

100. The RNAi oligonucleotide according to any one of embodiments 1-97, wherein the sense strand comprises a nucleotide sequence as set forth in SEQ ID NO: 580, wherein the antisense strand comprises a nucleotide sequence as set forth in SEQ ID NO: 601.

101. The RNAi oligonucleotide according to any one of embodiments 1-97, wherein the sense strand comprises a nucleotide sequence as set forth in SEQ ID NO: 590, wherein the antisense strand comprises a nucleotide sequence as set forth in SEQ ID NO: 611.

102. The RNAi oligonucleotide according to any one of embodiments 1-97, wherein the sense strand comprises a nucleotide sequence as set forth in SEQ ID NO: 597, wherein the antisense strand comprises a nucleotide sequence as set forth in SEQ ID NO: 618.

103. The RNAi oligonucleotide according to any one of embodiments 1-97, wherein the sense strand comprises a nucleotide sequence as set forth in SEQ ID NO: 586, wherein the antisense strand comprises a nucleotide sequence as set forth in SEQ ID NO: 607.

104. The RNAi oligonucleotide according to any one of the preceding embodiments, wherein the antisense strand is 22 nucleotides in length.

105. The RNAi oligonucleotide according to any one of the preceding embodiments, wherein the sense strand is 36 nucleotides in length.

106. The RNAi oligonucleotide according to any one of the preceding embodiments, wherein the sense strand and antisense strands comprise nucleotide sequences selected from the group consisting of:
a) SEQ ID NOs: 621 and 642, respectively;
b) SEQ ID NOs: 622 and 643, respectively;
c) SEQ ID NOs: 637 and 658, respectively;
d) SEQ ID NOs: 632 and 653, respectively;
e) SEQ ID NOs: 638 and 659, respectively;
f) SEQ ID NOs: 639 and 660, respectively;
g) SEQ ID NOs: 627 and 648, respectively;
h) SEQ ID NOs: 628 and 649, respectively; and,
i) SEQ ID NOs: 629 and 650, respectively.

107. The RNAi oligonucleotide according to any one of the preceding embodiments, wherein the sense strand and antisense strands comprise nucleotide sequences selected from the group consisting of:
a) SEQ ID NOs: 621 and 642, respectively;
b) SEQ ID NOs: 622 and 643, respectively;
c) SEQ ID NOs: 632 and 653, respectively;
d) SEQ ID NOs: 639 and 660, respectively; and,
e) SEQ ID NOs: 628 and 649, respectively.

108. The RNAi oligonucleotide according to any one of the preceding embodiments, wherein the sense strand comprises a nucleotide sequence as set forth in SEQ ID NO: 621, wherein the antisense strand comprises a nucleotide sequence as set forth in SEQ ID NO: 642.

109. The RNAi oligonucleotide according to any one of embodiments 1-107, wherein the antisense strand comprises a nucleotide sequence as set forth in SEQ ID NO: 642, and optionally the sense strand comprises a nucleotide sequence as set forth in SEQ ID NO: 621.

110. The RNAi oligonucleotide according to any one of embodiments 1-107, wherein the sense strand comprises a nucleotide sequence as set forth in SEQ ID NO: 622, wherein the antisense strand comprises a nucleotide sequence as set forth in SEQ ID NO: 643.

111. The RNAi oligonucleotide according to any one of embodiments 1-107, wherein the sense strand comprises a nucleotide sequence as set forth in SEQ ID NO: 632, wherein the antisense strand comprises a nucleotide sequence as set forth in SEQ ID NO: 653.

112. The RNAi oligonucleotide according to any one of embodiments 1-107, wherein the sense strand comprises a nucleotide sequence as set forth in SEQ ID NO: 639, wherein the antisense strand comprises a nucleotide sequence as set forth in SEQ ID NO: 660.

113. The RNAi oligonucleotide according to any one of embodiments 1-107, wherein the sense strand comprises a nucleotide sequence as set forth in SEQ ID NO: 628, wherein the antisense strand comprises a nucleotide sequence as set forth in SEQ ID NO: 649.

114. An RNAi oligonucleotide for reducing transmembrane serine protease 6 (TMPRSS6) expression, the oligonucleotide comprising a sense strand and an antisense strand forming a duplex region, wherein
the antisense strand comprises 22 nucleotides and comprises a nucleotide sequence as set forth in SEQ ID NO: 600, and the sense strand comprises 36 nucleotides and comprises a nucleotide sequence as set forth in SEQ ID NO: 579, the nucleotides of each one of the strands being numbered 5' to 3';
all of positions 1-7, 12-27, and 31-36 of the sense strand and positions 1, 6, 8, 9, 11-13, and 15-22 of the antisense strand comprise a 2'-O-methyl (2'-OMe) modification, and all of positions 8-11 of the sense strand and 2, 3, 4, 5, 7, 10 and 14 of the antisense strand comprise a 2'-Fluoro (2'-F) modification;
a phosphorothioate linkage is provided between positions 1 and 2 of the sense strand, and between positions 1 and 2, between positions 2 and 3, between positions 3 and 4, between positions 20 and 21 and between positions 21 and 22 of the antisense strand;
the sense strand proximal the 3' end comprises a stem-loop set forth as S1-Lp-S2, S1 being complementary to S2, Lp forming a loop of 4 nucleotides in length, and wherein the second, third and fourth nucleotides of the loop Lp from 5' to 3' are each conjugated to a monovalent N-acetylgalactosamine (GalNAc) moiety; and
the 5'-terminal nucleotide of the antisense strand comprises a structure according to Chem. 1a (MePhosphonate-4O-mU):

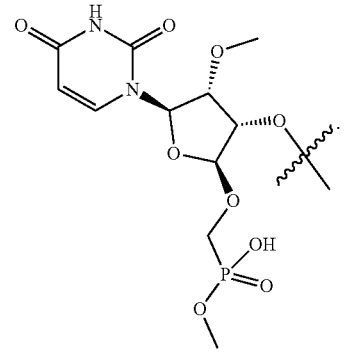 [SMILES: *O[C@@H]1[C@@H](OCP(=O)(O)OC)O[C@@H](n2ccc(=O)[nH]c2=O)[C@@H]1OC]

115. The RNAi oligonucleotide according to embodiment 114, wherein the antisense strand comprises a 3' overhang of one or more purine nucleotides in length, and optionally wherein the 3' overhang is 5'-GG-3'.

116. The RNAi oligonucleotide according to any one of embodiments 114-115, wherein the nucleotides of the loop Lp conjugated to the monovalent N-acetylgalactosamine (GalNAc) moiety each comprise a structure according to Chem. 5a:

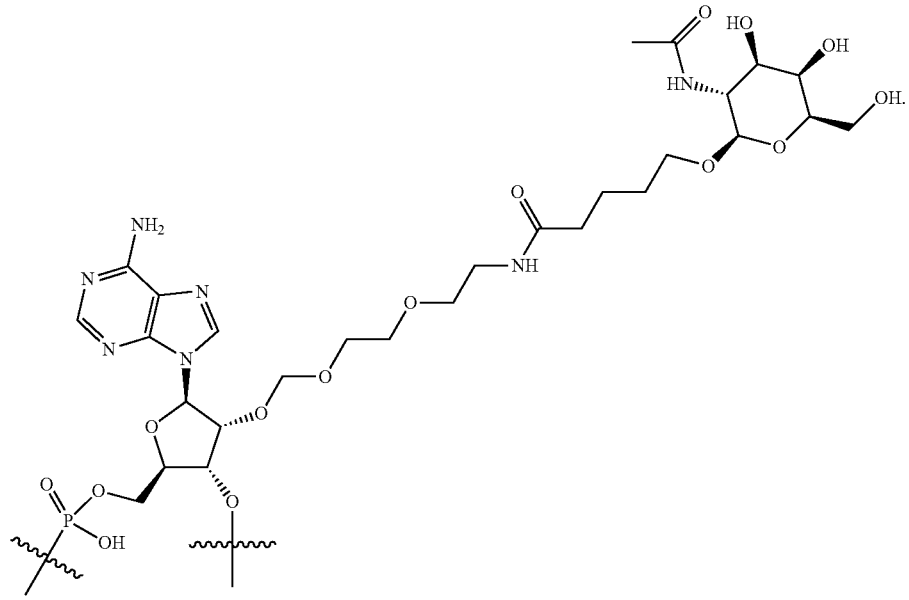 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(*)(=O)O]

117. An RNAi oligonucleotide for reducing TMPRSS6 expression, the oligonucleotide comprising a sense strand and an antisense strand, wherein the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621), and wherein the antisense strand comprises the sequence and all of the modifications of 5'-[MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642), wherein mC, mA, mG, mU=2'-OMe ribonucleosides; fA, fC, fG, fU=2'-F ribonucleosides; s=phosphorothioate, and wherein ademA-GalNAc=

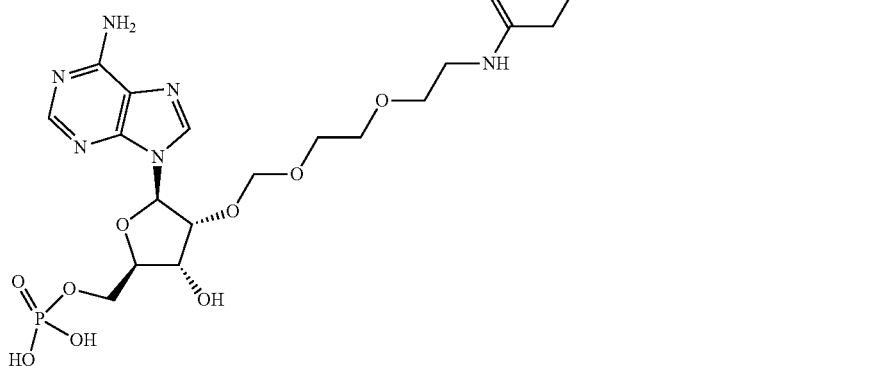

(Chem. 5)

118. An RNAi oligonucleotide for reducing TMPRSS6 expression, the oligonucleotide comprising a sense strand and an antisense strand, wherein the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621);

the antisense strand comprises the sequence and all of the modifications of 5'-[MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642);

mC, mA, mG, mU indicate 2'-O-methyl (2'-OMe) modified nucleotides;

fA, fC, fG, fU indicate 2'-Fluoro (2'-F) modified nucleotides;

s indicates a phosphorothioate internucleotide linkage; and ademA-GalNAc comprises a structure according to Chem. 5a:

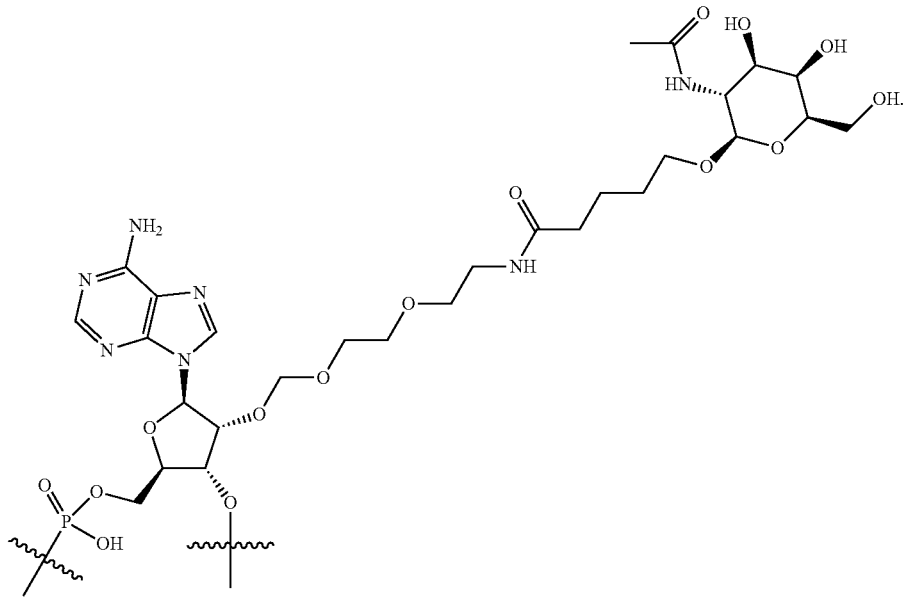 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(*)(=O)O]

119. An RNAi oligonucleotide for reducing TMPRSS6 expression, the oligonucleotide comprising a sense strand and an antisense strand, wherein the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621);

the antisense strand comprises the sequence and all of the modifications of 5'-[MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642);

mC, mA, mG, mU indicate 2'-O-methyl (2'-OMe) modified nucleotides;

fA, fC, fG, fU indicate 2'-fluoro (2'-F) modified nucleotides;

s indicates a phosphorothioate internucleotide linkage;

ademA-GalNAc comprises a structure according to Chem. 5a:

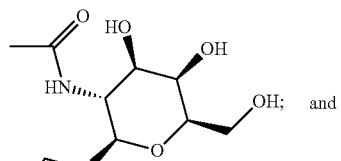

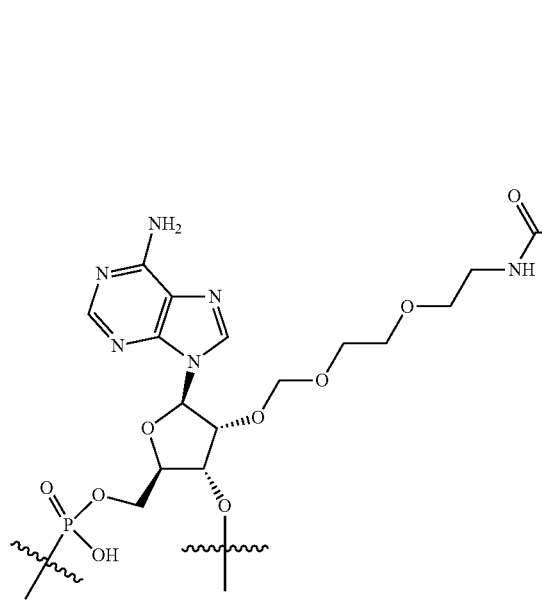

MePhosphonate-4O-mU comprises a structure according to Chem. 1a:

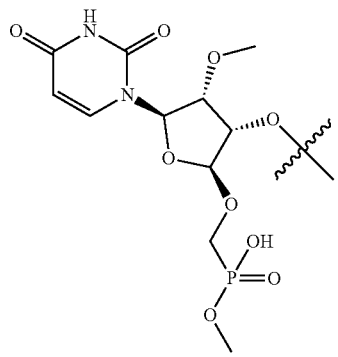

120. An RNAi oligonucleotide for reducing TMPRSS6 expression, the oligonucleotide comprising a sense strand and an antisense strand, wherein the sense strand comprises the sequence and all of the modifications of 5'-[mGs][mC][mU][mA][mC][mU][mC][fU][fG][fG][fU][mA][mU][mU][mU][mC][mC][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 622), and wherein the antisense strand comprises the sequence and all of the modifications of 5'-[MePhosphonate-4O-mUs][fUs][fAs][fG][fG][mA][fA][mA][mU][fA][mC][mC][mA][fG][mA][mG][mU][mA][mG][mCs][mGs][mG]-3' (SEQ ID NO: 643), wherein mC, mA, mG, mU=2'-OMe ribonucleosides; fA, fC, fG, fU=2'-F ribonucleosides; s=phosphorothioate, and wherein ademA-GalNAc=

(Chem. 5)

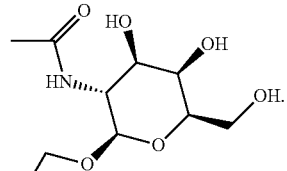

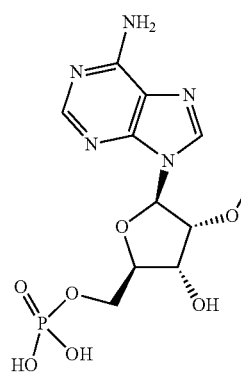

121. An RNAi oligonucleotide for reducing TMPRSS6 expression, the oligonucleotide comprising a sense strand and an antisense strand, wherein
the sense strand comprises the sequence and all of the modifications of 5'-[mGs][mC][mU][mA][mC][mU][mC][fU][fG][fG][fU][mA][mU][mU][mU][mC][mC][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 622);
the antisense strand comprises the sequence and all of the modifications of 5'-[MePhosphonate-4O-mUs][fUs][fAs][fG][fG][mA][fA][mA][mU][fA][mC][mC][mA][fG][mA][mG][mU][mA][mG][mCs][mGs][mG]-3' (SEQ ID NO: 643)

mC, mA, mG, mU indicate 2'-O-methyl (2'-OMe) modified nucleotides;

fA, fC, fG, fU indicate 2'-Fluoro (2'-F) modified nucleotides;

s indicates a phosphorothioate internucleotide linkage; and ademA-GalNAc comprises a structure according to Chem 5a:

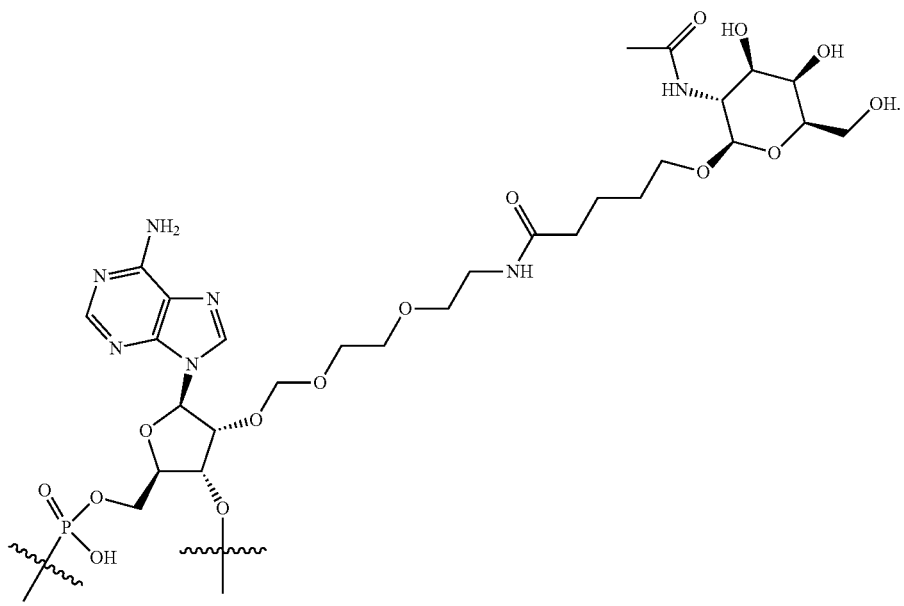 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(*)(=O)O]

122. An RNAi oligonucleotide for reducing TMPRSS6 expression, the oligonucleotide comprising a sense strand and an antisense strand, wherein the sense strand comprises the sequence and all of the modifications of 5'-[mCs][mU][mC][mA][mC][mC][mU][fG][fC][fU][fU][mC][mU][mU][mC][mU][mG][mG][mU][mA][mG][mC][mA][mG][mC][mC][mG][ademA-GalNAc][ademA-GalNAc][ademA-GalNAc][mG][mG][mC][mU][mG][mC]-3' (SEQ ID NO: 632), and wherein the antisense strand comprises the sequence and all of the modifications of 5'-[MePhosphonate-4O-mUs][fAs][fCs][fC][fA][mG][fA][mA][mG][fA][mA][mG][mC][fA][mG][mG][mU][mG][mA][mGs][mGs][mG]-3' (SEQ ID NO: 653), wherein mC, mA, mG, mU=2'-OMe ribonucleosides; fA, fC, fG, fU=2'-F ribonucleosides; s=phosphorothioate, and wherein ademA-GalNAc=

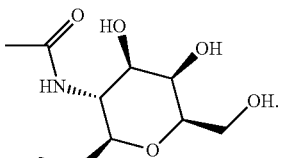

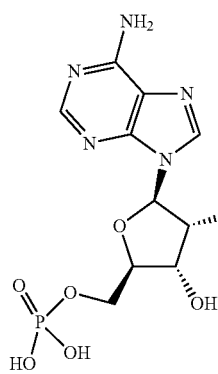

123. An RNAi oligonucleotide for reducing TMPRSS6 expression, the oligonucleotide comprising a sense strand and an antisense strand, wherein the sense strand comprises the sequence and all of the modifications of 5'-[mCs][mU][mC][mA][mC][mC][mU][fG][fC][fU][fU][mC][mU][mU][mC][mU][mG][mG][mU][mA][mG][mC][mA][mG][mC][mC][mG][ademA-GalNAc][ademA-GalNAc][ademA-GalNAc][mG][mG][mC][mU][mG][mC]-3' (SEQ ID NO: 632);

the antisense strand comprises the sequence and all of the modifications of 5'-[MePhosphonate-4O-mUs][fAs][fCs][fC][fA][mG][fA][mA][mG][fA][mA][mG][mC][fA][mG][mG][mU][mG][mA][mGs][mGs][mG]-3' (SEQ ID NO: 653);

mC, mA, mG, mU indicate 2'-O-methyl (2'-OMe) modified nucleotides;

fA, fC, fG, fU indicate 2'-Fluoro (2'-F) modified nucleotides;

s indicates a phosphorothioate internucleotide linkage; and ademA-GalNAc comprises a structure according to Chem. 5a:

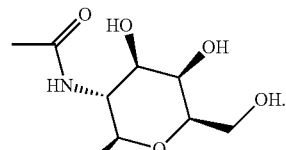

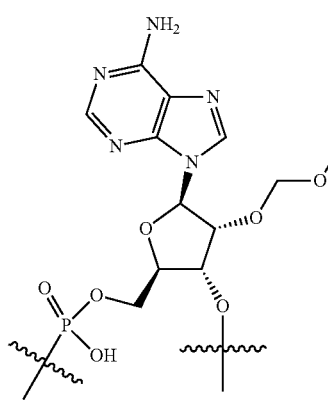

124. An RNAi oligonucleotide for reducing TMPRSS6 expression, the oligonucleotide comprising a sense strand and an antisense strand, wherein the sense strand comprises the sequence and all of the modifications of 5'-[mAs][mG][mU][mG][mU][mG][mA][fA][fA][fG][fA][mC][mA][mU][mA][mG][mC][mU][mG][mA][mG][mC][mA][mG][mC][mC][mG][ademA-GalNAc][ademA-GalNAc][ademA-GalNAc][mG][mG][mC][mU][mG][mC]-3' (SEQ ID NO: 639), and wherein the antisense strand comprises the sequence and all of the modifications of 5'-[MePhosphonate-4O-mUs][fCs][fAs][fG][fC][mU][fA][mU][mG][fU][mC][mU][mU][fU][mC][mA][mC][mA][mC][mUs][mGs][mG]-3' (SEQ ID NO: 660), wherein mC, mA, mG, mU=2'-Ome ribonucleosides; fA, fC, fG, fU=2'-F ribonucleosides; s=phosphorothioate, and wherein ademA-GalNAc=

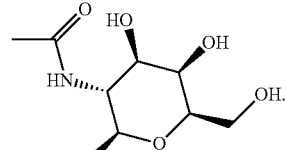

(Chem. 5)

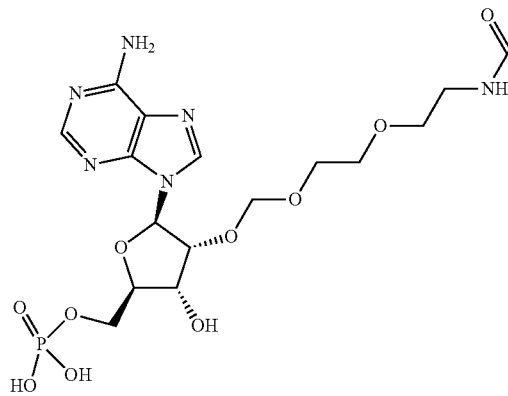

125. An RNAi oligonucleotide for reducing TMPRSS6 expression, the oligonucleotide comprising a sense strand and an antisense strand, wherein the sense strand comprises the sequence and all of the modifications of 5'-[mAs][mG][mU][mG][mU][mG][mA][fA][fA][fG][fA][mC][mA][mU][mA][mG][mC][mU][mG][mA][mG][mC][mA][mG][mC][mC][mG][ademA-GalNAc][ademA-GalNAc][ademA-GalNAc][mG][mG][mC][mU][mG][mC]-3' (SEQ ID NO: 639);

the antisense strand comprises the sequence and all of the modifications of 5'-[MePhosphonate-4O-mUs][fCs][fAs][fG][fC][mU][fA][mU][mG][fU][mC][mU][mU][fU][mC][mA][mC][mA][mC][mUs][mGs][mG]-3' (SEQ ID NO: 660);

mC, mA, mG, mU indicate 2'-O-methyl (2'-OMe) modified nucleotides;

fA, fC, fG, fU indicate 2'-Fluoro (2'-F) modified nucleotides;

s indicates a phosphorothioate internucleotide linkage; and ademA-GalNAc comprises a structure according to Chem. 5a:

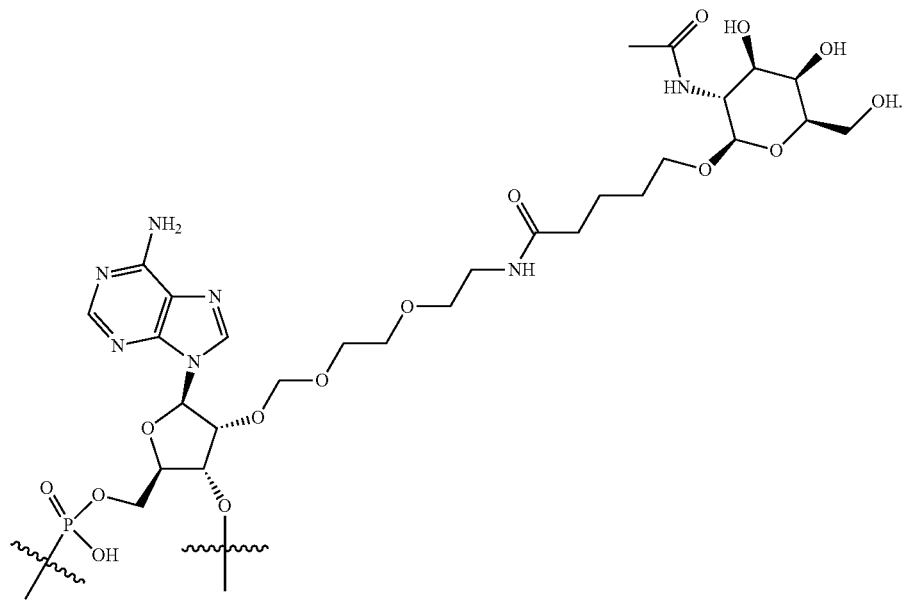 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(*)(=O)O]

126. An RNAi oligonucleotide for reducing TMPRSS6 expression, the oligonucleotide comprising a sense strand and an antisense strand, wherein the sense strand comprises the sequence and all of the modifications of 5'-[mGs][mG][mG][mU][mG][mC][mA][fC][fU][fA][fU][mG][mG][mC][mU][mU][mG][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 628), and wherein the antisense strand comprises the sequence and all of the modifications of 5'-[MePhosphonate-4O-mUs][fUs][fAs][fC][fA][mA][fG][mC][mC][fA][mU][mA][mG][fU][mG][mC][mA][mC][mC][mCs][mGs][mG]-3' (SEQ ID NO: 649), wherein mC, mA, mG, mU=2'-OMe ribonucleosides; fA, fC, fG, fU=2'-F ribonucleosides; s=phosphorothioate, and wherein ademA-GalNAc=

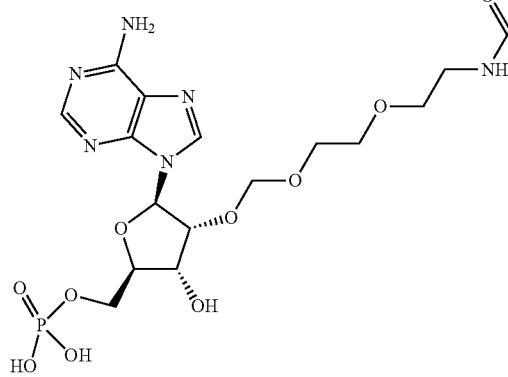

(Chem. 5)

127. An RNAi oligonucleotide for reducing TMPRSS6 expression, the oligonucleotide comprising a sense strand and an antisense strand, wherein the sense strand comprises the sequence and all of the modifications of 5'-[mGs][mG][mG][mU][mG][mC][mA][fC][fU][fA][fU][mG][mG][mC][mU][mU][mG][mU][mA][mA][mG][mC][mA][mG][mC][mC][mG][ademA-GalNAc][ademA-GalNAc][ademA-GalNAc][mG][mG][mC][mU][mG][mC]-3' (SEQ ID NO: 628);

the antisense strand comprises the sequence and all of the modifications of 5'-[MePhosphonate-4O-mUs][fUs][fAs][fC][fA][mA][fG][mC][mC][fA][mU][mA][mG][fU][mG][mC][mA][mC][mC][mCs][mGs][mG]-3' (SEQ ID NO: 649);

mC, mA, mG, mU indicate 2'-O-methyl (2'-OMe) modified nucleotides;

fA, fC, fG, fU indicate 2'-Fluoro (2'-F) modified nucleotides;

s indicates a phosphorothioate internucleotide linkage; and ademA-GalNAc comprises a structure according to Chem. 5a:

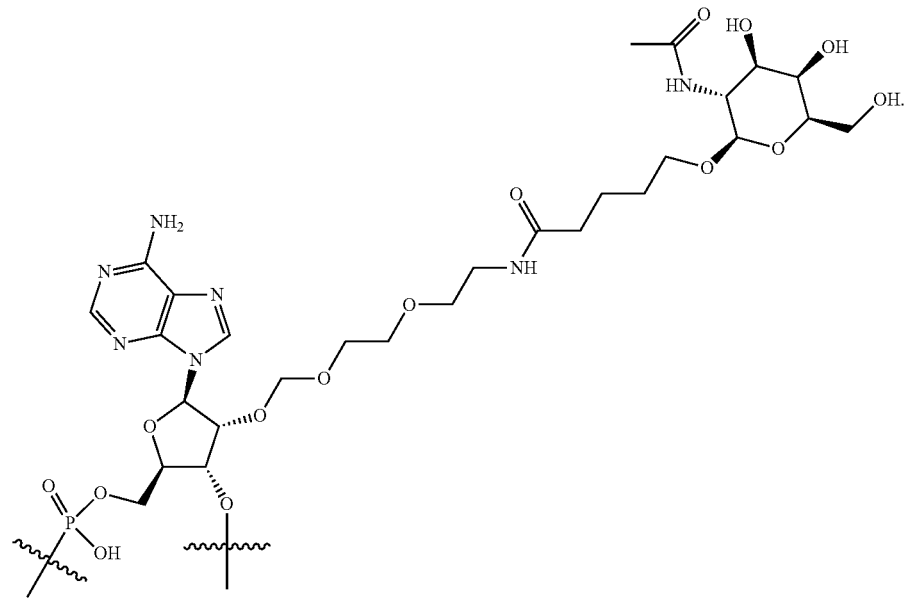 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(*)(=O)O]

128. The RNAi oligonucleotide according to any one of embodiments 116-127, wherein MePhosphonate-4O-mUs comprises a structure according to Chem. 1:

129. The RNAi oligonucleotide according to any one of embodiments 116-127, wherein MePhosphonate-4O-mU comprises a structure according to Chem. 1a:

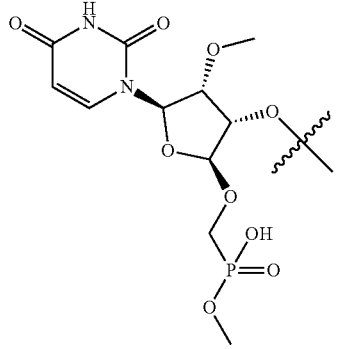

130. An RNAi oligonucleotide for reducing TMPRSS6 expression comprising a sense strand and an antisense strand, wherein the sense strand comprises SEQ ID NO: 621 and the antisense strand comprises SEQ ID NO: 642, wherein the antisense strand comprises a region of complementarity to a TMPRSS6 RNA transcript, and wherein the oligonucleotide is in the form of a conjugate having the structure as shown in FIGS. 10A-B.

131. An RNAi oligonucleotide for reducing TMPRSS6 expression comprising a sense strand and an antisense strand, wherein the sense strand comprises SEQ ID NO: 621 and the antisense strand comprises SEQ ID NO: 642, wherein the antisense strand comprises a region of complementarity to a TMPRSS6 RNA transcript, and wherein the oligonucleotide is in the form of a conjugate having the structure as shown in FIG. 14A.

132. An RNAi oligonucleotide for reducing TMPRSS6 expression comprising a sense strand and an antisense strand, wherein the sense strand comprises SEQ ID NO: 632 and the antisense strand comprises SEQ ID NO: 653, wherein the antisense strand comprises a region of complementarity to a TMPRSS6 RNA transcript, and wherein the oligonucleotide is in the form of a conjugate having the structure as shown in FIGS. 11A-B.

133. An RNAi oligonucleotide for reducing TMPRSS6 expression comprising a sense strand and an antisense strand, wherein the sense strand comprises SEQ ID NO: 632 and the antisense strand comprises SEQ ID NO: 653, wherein the antisense strand comprises a region of complementarity to a TMPRSS6 RNA transcript, and wherein the oligonucleotide is in the form of a conjugate having the structure as shown in FIG. 14B.

134. An RNAi oligonucleotide for reducing TMPRSS6 expression comprising a sense strand and an antisense strand, wherein the sense strand comprises SEQ ID NO: 639 and the antisense strand comprises SEQ ID NO: 660, wherein the antisense strand comprises a region of complementarity to a TMPRSS6 RNA transcript, and wherein the oligonucleotide is in the form of a conjugate having the structure as shown in FIGS. 12A-B.

135. An RNAi oligonucleotide for reducing TMPRSS6 expression comprising a sense strand and an antisense strand, wherein the sense strand comprises SEQ ID NO: 639 and the antisense strand comprises SEQ ID NO: 660, wherein the antisense strand comprises a region of complementarity to a TMPRSS6 RNA transcript, and wherein the oligonucleotide is in the form of a conjugate having the structure as shown in FIG. 14C.

136. An RNAi oligonucleotide for reducing TMPRSS6 expression comprising a sense strand and an antisense strand, wherein the sense strand comprises SEQ ID NO: 628 and the antisense strand comprises SEQ ID NO: 649, wherein the antisense strand comprises a region of complementarity to a TMPRSS6 RNA transcript, and wherein the oligonucleotide is in the form of a conjugate having the structure as shown in FIG. 13A-B.

137. An RNAi oligonucleotide for reducing TMPRSS6 expression comprising a sense strand and an antisense strand, wherein the sense strand comprises SEQ ID NO: 628 and the antisense strand comprises SEQ ID NO: 649, wherein the antisense strand comprises a region of complementarity to a TMPRSS6 RNA transcript, and wherein the oligonucleotide is in the form of a conjugate having the structure as shown in FIG. 14D.

138. A pharmaceutical composition comprising the RNAi oligonucleotide according to any one of the preceding embodiments, and a pharmaceutically acceptable carrier, delivery agent or excipient.

139. A method for treating a subject having a disease, disorder or condition associated with hepcidin deficiency or suppression, the method comprising administering to the subject a therapeutically effective amount of the RNAi oligonucleotide according to any one of embodiments 1-137, or the pharmaceutical composition according to embodiment 138, thereby treating the subject.

140. The method according to embodiment 139, wherein (i) hepcidin expression is increased; (ii) serum iron levels are decreased; (iii) serum iron saturation is decreased; or (iv) any combination of (i)-(iii), after administering the RNAi oligonucleotide.

141. A method of delivering an oligonucleotide to a subject, the method comprising administering pharmaceutical composition of embodiment 138 to the subject.

142. A method for reducing TMPRSS6 expression in a cell, a population of cells or a subject, the method comprising the step of:
  i) contacting the cell or the population of cells with the RNAi oligonucleotide according to any one of embodiments 1-137, or the pharmaceutical composition of embodiment 138; or
  ii) administering to the subject the RNAi oligonucleotide according to any one of embodiments 1-137, or the pharmaceutical composition of embodiment 138.

143. The method according to embodiment 142, wherein reducing TMPRSS6 expression comprises reducing an amount or level of TMPRSS6 mRNA, an amount or level of matriptase-2 protein, or both.

144. The method according to embodiment 142 or 143, wherein reducing TMPRSS6 expression results in (i) an increase in hepcidin production; (ii) a decrease in serum iron saturation; (iii) a decrease in serum iron; or (iv) any combination of (i)-(iii).

145. The method according to any one of embodiments 142-144, wherein the subject has a disease, disorder or condition associated with hepcidin deficiency or suppression.

146. The method according to any one of embodiments 139-140 and 145, wherein the disease, disorder or condition associated with hepcidin deficiency is hemochromatosis such hereditary hemochromatosis.

147. The method according to any one of embodiments 139-140 and 145, wherein the disease, disorder or condition associated with hepcidin deficiency is beta-thalassemia.

148. The method according to any one of embodiments 139-140 and 145, wherein the disease, disorder or condition associated with hepcidin suppression is polycythaemia vera.

149. The method according to any one of embodiments 139-148, wherein the RNAi oligonucleotide, or pharmaceutical composition, is administered in combination with a second composition or therapeutic agent.

150. Use of the RNAi oligonucleotide according to any one of embodiments 1-137, or the pharmaceutical composition according to embodiment 138, in the manufacture of a medicament for the treatment of a disease, disorder or condition associated with hepcidin deficiency or suppression, optionally for the treatment of hemochromatosis such as hereditary hemochromatosis, polycythaemia vera, or beta-thalassemia.

151. The RNAi oligonucleotide according to any one of embodiments 1-137, or the pharmaceutical composition according to embodiment 138, for use as a medicament.

152. The RNAi oligonucleotide according to any one of embodiments 1-137, or the pharmaceutical composition according to embodiment 138, for use as a medicament.

153. The RNAi oligonucleotide according to any one of embodiments 1-137, or the pharmaceutical composition of embodiment 138, for use, or adaptable for use, in the treatment of a disease, disorder or condition associated with hepcidin deficiency or suppression, optionally for the treatment of hemochromatosis such as hereditary hemochromatosis, polycythaemia vera, or beta-thalassemia.

154. The RNAi oligonucleotide according to any one of embodiments 1-137, or the pharmaceutical composition according to 138, for use in the treatment of hemochromatosis such as hereditary hemochromatosis.

155. The RNAi oligonucleotide according to any one of embodiments 1-137, or the pharmaceutical composition according to 138, for use in the treatment of polycythaemia vera.

156. The RNAi oligonucleotide according to any one of embodiments 1-137, or the pharmaceutical composition according to 138, for use in the treatment of beta-thalassemia.

157. The RNAi oligonucleotide according to any one of embodiments 1-137, or the pharmaceutical composition according to 138, for use in the treatment of hemochromatosis such as hereditary hemochromatosis or beta-thalassemia.

158. A kit comprising the RNAi oligonucleotide according to any one of embodiments 1-137, an optional pharmaceutically acceptable carrier, and a package insert comprising instructions for administration to a subject having a disease, disorder or condition associated with hepcidin deficiency or suppression.

159. A kit comprising the RNAi oligonucleotide according to any one of embodiments 1-137, or the pharmaceutical composition of embodiment 138, and a package insert comprising instructions for administration to a subject having a disease, disorder or condition associated with hepcidin deficiency or suppression.

160. The use of embodiment 150, the RNAi oligonucleotide or pharmaceutical composition for use, or adaptable for use, according to any one of embodiments 151-157, or the kit according to any one of embodiments 158-159, wherein the disease, disorder or condition associated with hepcidin deficiency or suppression is hemochromatosis such as hereditary hemochromatosis, polycythaemia vera, or beta-thalassemia.

EXAMPLES

Example 1: Preparation of RNAi Oligonucleotides

Oligonucleotide Synthesis and Purification

The oligonucleotides (RNAi oligonucleotides) described in the foregoing Examples were chemically synthesized using methods described herein. Generally, RNAi oligonucleotides are synthesized using solid phase oligonucleotide synthesis methods as described for 19-23mer siRNAs (see, e.g., Scaringe et al. (1990) Nucleic Acids Res. 18:5433-5441 and Usman et al. (1987) J. Am. Chem. Soc. 109:7845-45; see also, U.S. Pat. Nos. 5,804,683; 5,831,071; 5,998,203; 6,008,400; 6,111,086; 6,117,657; 6,353,098; 6,362,323; 6,437,117 and 6,469,158) in addition to using known phosphoramidite synthesis (see, e.g. Hughes and Ellington (2017) Cold Spring Harb Perspect Biol. 9(1):a023812; Beaucage S. L., Caruthers M. H. *Studies on Nucleotide Chemistry V: Deoxynucleoside Phosphoramidites—A New Class of Key Intermediates for Deoxypolynucleotide Synthesis*, Tetrahedron Lett. 1981; 22:1859-62. Doi: 10.1016/S0040-4039(01)90461-7). dsRNAi oligonucleotides having a 19mer core sequence were formatted into constructs having a 25mer sense strand and a 27mer antisense strand to allow for processing by the RNAi machinery. The 19mer core sequence is complementary to a region in the TMPRSS6 mRNA.

Individual RNA strands were synthesized and HPLC purified according to standard methods (Integrated DNA Technologies; Coralville, IA). For example, RNA oligonucleotides were synthesized using solid phase phosphoramidite chemistry, deprotected and desalted on NAP-5 columns (Amersham Pharmacia Biotech; Piscataway, NJ) using standard techniques (Damha & Olgivie (1993) Methods Mol. Biol. 20:81-114; Wincott et al. (1995) Nucleic Acids Res. 23:2677-84). The oligomers were purified using ion-exchange high performance liquid chromatography (IE-HPLC) on an Amersham Source 15Q column (1.0 cm×25 cm; Amersham Pharmacia Biotech) using a 15 min. step-linear gradient. The gradient varied from 90:10 Buffers A:B to 52:48 Buffers A:B, where Buffer A is 100 mM Tris pH 8.5 and Buffer B is 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc.; Fullerton, CA). The CE capillaries have a 100 µm inner diameter and contain ssDNA 100R Gel (Beckman-Coulter). Typically, about 0.6 nmole of oligonucleotide was injected into a capillary, run in an electric field of 444 V/cm and was detected by UV absorbance at 260 nm. Denaturing Tris-Borate-7 M-urea running buffer was purchased from Beckman-Coulter. Oligoribonucleotides were obtained that were at least 90% pure as assessed by CE for use in experiments described below. Compound identity was verified by matrix-assisted laser desorption ionization time-of-flight (MALDI-TOF) mass spectroscopy on a Voyager DE™ Biospectrometry Work Station (Applied Biosystems; Foster City, CA) following the manufacturer's recommended protocol. Relative molecular masses of all oligomers were obtained, often within 0.2% of expected molecular mass.

Preparation of Duplexes

Single strand RNA oligomers were resuspended (e.g., at 100 µM concentration) in duplex buffer consisting of 100 mM potassium acetate, 30 mM HEPES, pH 7.5. Complementary sense and antisense strands were mixed in equal molar amounts to yield a final solution of, for example, 50 µM duplex. Samples were heated to 100° C. for 5 minutes in RNA buffer (IDT) and were allowed to cool to room temperature before use. The RNAi oligonucleotides were stored at −20° C. Single strand RNA oligomers were stored lyophilized or in nuclease-free water at −80° C.

Example 2: Generation of TMPRSS6-Targeting GalNAc-Conjugated RNAi Oligonucleotides Transmembrane protease, serine 6 (TMPRSS6) is a type II transmembrane serine protease found on the cell surface. The protein functions in a signaling pathway with hepcidin to regulate iron balance in the body.

Identification of TMPRSS6 mRNA Target Sequences

To generate TMPRSS6 RNAi oligonucleotides, a computer-based algorithm was used to computationally identify TMPRSS6 mRNA target sequences suitable for assaying inhibition of TMPRSS6 expression by the RNAi pathway. The algorithm provided RNAi oligonucleotide guide (antisense) strand sequences each having a region of complementarity to a suitable TMPRSS6 mRNA target sequence of human (Hs) or murine (Mm) mRNA (e.g., SEQ ID NOs: 853 and 854, respectively; Table 1). Due to sequence conservation across species, some of the TMPRSS6 mRNA target sequences identified for human TMPRSS6 mRNA are homologous to the corresponding TMPRSS6 mRNA target sequence of murine (Mm) TMPRSS6 mRNA (SEQ ID NO:854; Table 1) and/or cynomolgus monkey (Mf) TMPRSS6 mRNA (SEQ ID NO:855; Table 1). TMPRSS6 RNAi oligonucleotides comprising a region of complementarity to homologous TMPRSS6 mRNA target sequences with nucleotide sequence similarity are predicted to have the ability to target homologous TMPRSS6 mRNAs (e.g., human TMPRSS6 and monkey TMPRSS6 mRNAs).

TABLE 1

Exemplary Human TMPRSS6, Monkey TMPRSS6, and Murine TMPRSS6 mRNA Sequences

| Species | GenBank Ref Seq # | SEQ ID NO |
|---|---|---|
| Human (Hs) | NM_001289000.2 | 853 |
| Murine (Mm) | NM_001355601.1 | 854 |
| Cynomolgus monkey (Mf) | XM_005567384.2 | 855 |

Specifically, oligonucleotides synthesized as described in Example 1 were used to generate double-stranded RNAi oligonucleotides comprising a nicked tetraloop GalNAc-conjugated structure (referred to herein as "GalNAc-conjugated TMPRSS6 oligonucleotides" or "GalNAc-TMPRSS6 oligonucleotides") having a 36-mer passenger strand and a 22-mer guide strand. Further, the nucleotide sequences comprising the passenger strand and guide strand have a distinct pattern of modified nucleotides and phosphorothioate linkages. Three of the nucleotides comprising the tetraloop were each conjugated to a GalNAc moiety (CAS #14131-60-3). The modification pattern of each strand is illustrated below:

Sense Strand: 5'-[mXs][mX][mX][mX][mX][mX][mX]
[fX][fX][fX][fX][mX][mX][mX][mX][mX][mX]
[mX][mX][mX][mX][mX][mX][mX][mX][mX][mX]
[ademX-GalNAc][ademX-GalNAc][ademX-GalNAc]
[mX][mX][mX][mX][mX][mX]-3'

Hybridized to:

Antisense Strand: 5'-[MePhosphonate-4O-mXs][fXs]
[fXs][fX][fX][mX][fX][mX][mX][fX][mX][mX][mX]
[fX][mX][mX][mX][mX][mX][mXs][mXs][mX]-3'

TABLE 2

Modification key

| Symbol | Modification/linkage |
|---|---|
| [MePhosphonate-4O-mXs] | 4'-O-monomethylphosphonate-2'-O-methyl modified nucleotide with a phosphorothioate linkage to the neighboring nucleotide |
| [ademX-GalNAc] | GalNAc attached to a nucleotide |

TABLE 2-continued

Modification key

| Symbol | Modification/linkage |
|---|---|
| [mXs] | 2'-O-methyl modified nucleotide with a phosphorothioate linkage to the neighboring nucleotide |
| [fXs] | 2'-fluoro modified nucleotide with a phosphorothioate linkage to the neighboring nucleotide |
| [mX] | 2'-O-methyl modified nucleotide with phosphodiester linkages to neighboring nucleotides |
| [fX] | 2'-fluoro modified nucleotide with phosphodiester linkages to neighboring nucleotides |

It is understood that "X" in the above modification patterns and modification key refers to nucleobases.

In Vitro Cell-Based Assays

The ability of GalNAc-conjugated TMPRSS6 oligonucleotides to reduce TMPRSS6 mRNA was measured using in vitro cell-based assays. Briefly, human Hep3B cells expressing endogenous human TMPRSS6 gene were transfected with GalNAc-conjugated TMPRSS6 oligonucleotides at 1 nM in separate wells of a multi-well cell-culture plate. Cells were maintained for 24 hours following transfection with the modified GalNAc-conjugated TMPRSS6 oligonucleotides and then the amount of remaining TMPRSS6 mRNA from the transfected cells was determined using TAQMAN®-based qPCR assays. Two qPCR assays, a 3' assay and a 5' assay, were used to determine TMPRSS6 mRNA levels as measured using PCR probes conjugated to 6-carboxy-fluorescein (FAM). These assays are identified in Table 3 below. Primer pairs were assayed for percent (%) remaining mRNA.

TABLE 3 qPCR Assays

| 3' Assay (F1652) | Forward-1652 | AGCCTGATTGTCTCAACGG | SEQ ID NO: 857 |
|---|---|---|---|
| | Reverse-1725 | CTGGAAGGTGAATGTCCCAC | SEQ ID NO: 858 |
| | Probe-1676 | ACGAAGAGCAGTGCCAGGAAGG | SEQ ID NO: 859 |
| 5' Assay (F394) | Forward-394 | GTACTCAATCGCCACTTCTCC | SEQ ID NO: 860 |
| | Reverse-539 | GAATAGACGGAGCTGGAGTTG | SEQ ID NO: 861 |
| | Probe-450 | CAGTGAAACCGCCAAAGCCCAG | SEQ ID NO: 862 |

The results indicated that GalNAc-conjugated TMPRSS6 oligonucleotides designed to target TMPRSS6 mRNA inhibited TMPRSS6 expression in cells, as determined by a reduced amount of TMPRSS6 mRNA in GalNAc-conjugated TMPRSS6 oligonucleotide-transfected cells relative to control cells, and indicated that the nucleotide sequences comprising the GalXC-conjugated oligonucleotides are useful for generating RNAi oligonucleotides to inhibit TMPRSS6 expression.

Example 3: GalNAc-Conjugated TMPRSS6 RNAi Oligonucleotides Inhibit Human and Murine TMPRSS6 Expression In Vivo To evaluate the ability of RNAi oligonucleotides to reduce TMPRSS6 expression in vivo, an HDI mouse model was used.

Nine GalNAc-conjugated TMPRSS6 oligonucleotides shown in Table 4 were evaluated. The oligonucleotides selected were based on the nucleotide sequences that were used to generate RNAi oligonucleotides to inhibit TMPRSS6 expression in the screen of Example 2.

Oligonucleotides were evaluated in mice engineered to transiently express human TMPRSS6 mRNA in hepatocytes of the mouse liver. Briefly, 6-8 week-old female CD-1 mice (n=5) were subcutaneously administered the indicated GalNAc-conjugated TMPRSS6 oligonucleotides at a concentration of 1 mg/kg or 2 mg/kg formulated in PBS. A control group of mice (n=5) were administered only PBS. Three days later (72 hours), the mice were hydrodynamically injected (HDI) with 25 µg of DNA plasmid encoding the open reading frame (ORF) human TMPRSS6 gene (pCMV6_TMPRSS6 containing NM_153609 (Cat #: SC306623, Origene)) under control of a ubiquitous cytomegalovirus (CMV) promoter sequence. One day after introduction of the DNA plasmid, liver samples from HDI mice were collected. Total RNA derived from these HDI mice were subjected to qRT-PCR analysis to determine TMPRSS6 mRNA levels. Specifically, RNA was extracted from liver tissue to determine human and endogenous murine TMPRSS6 mRNA levels by qPCR (normalized to the neoR gene). The levels of human TMPRSS6 mRNA were determined using 5' and 3' PrimeTime™ qPCR Probe Assays (IDT), which consisted of a primer pair and fluorescently labeled probe specific to human TMPRSS6 mRNA. The levels of murine TMPRSS6 were similarly measured. The percentage of human and endogenous murine TMPRSS6 mRNA remaining in the samples from treated mice was determined using the $2^{-\Delta\Delta Ct}$ ("delta-delta Ct") method (Livak and Schmittgen (2001) Methods 25:402-408). The values were normalized for transfection efficiency using the NeoR gene included on the DNA plasmid.

TABLE 4

GalNAc-Conjugated Human TMPRSS6 RNAi Oligonucleotides for HDI screen

| | Species Targets | Unmodified Sense Strand (SEQ ID NO) | Unmodified Antisense strand (SEQ ID NO) | Modified Sense Strand (SEQ ID NO) | Modified Antisense strand (SEQ ID NO) |
|---|---|---|---|---|---|
| TMPRSS6-416 | Hs/Mf | 579 | 600 | 621 | 642 |
| TMPRSS6-0419 | Hs/Mf | 580 | 601 | 622 | 643 |
| TMPRSS6-0615 | Hs/Mf | 595 | 616 | 637 | 658 |
| TMPRSS6-0651 | Hs/Mf/Mm | 590 | 611 | 632 | 653 |
| TMPRSS6-0654 | Hs/Mf | 596 | 617 | 638 | 659 |
| TMPRSS6-0831 | Hs/Mf | 597 | 618 | 639 | 660 |
| TMPRSS6-1375 | Hs/Mf | 585 | 606 | 627 | 648 |
| TMPRSS6-1546 | Hs/Mf | 586 | 607 | 628 | 649 |
| TMPRSS6-1550 | Hs/Mf | 587 | 608 | 629 | 650 |

Figure 1B:
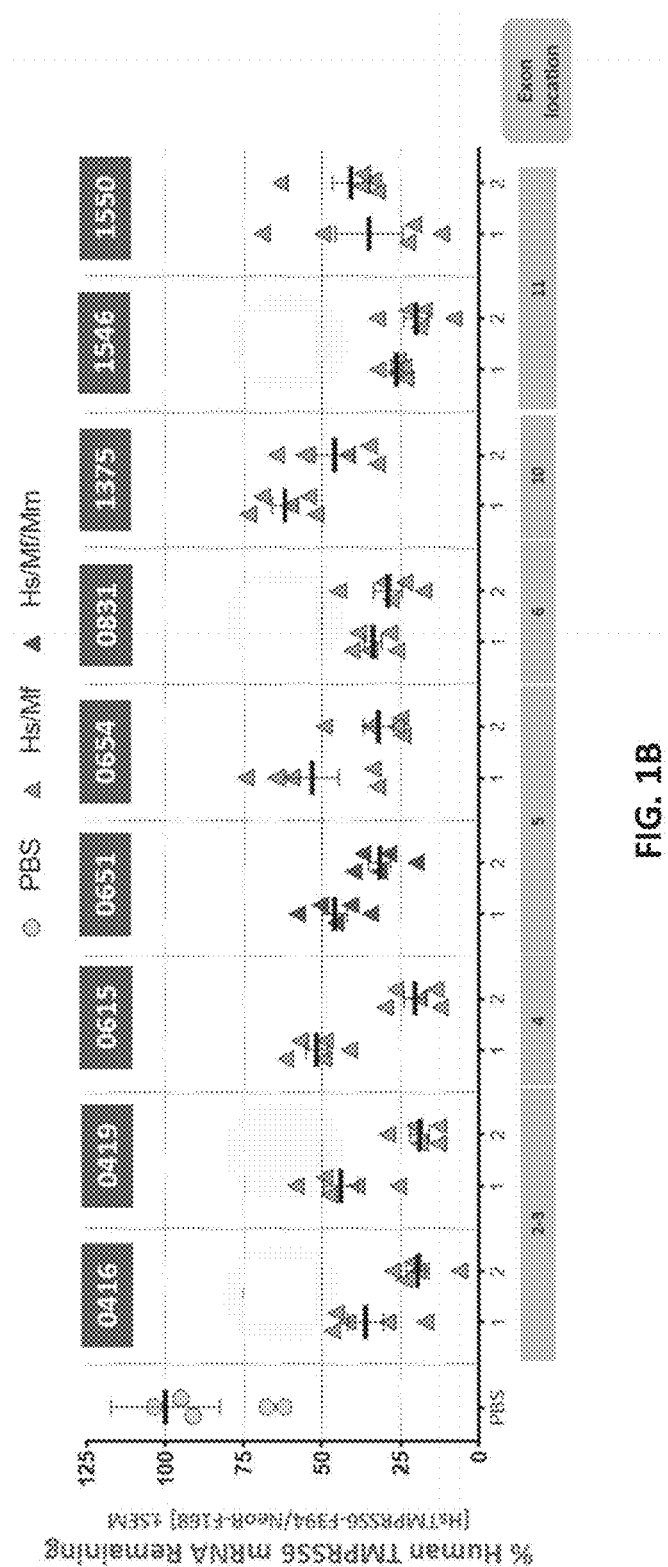

As shown in the 5' and 3' qPCR assays in FIGS. 1A and 1B, and Table 5, each oligonucleotide reduced TMPRSS6 expression by at least 50% at 2 mg/kg. TMPRSS6-0416, -0831, and -1546 were the most potent oligonucleotides and reduced TMPRSS6 expression by more than 50% at the lower 1 mg/kg concentration. This data demonstrated that GalNAc-modified oligonucleotides successfully reduced human TMPRSS6 expression in vivo.

TABLE 5

Summary of 5' and 3' assays from FIGS. 1A and 1B

| | Hs TMPRSS6-5'/F394 | | | | Hs TMPRSS6-3'/F1652 | | | |
|---|---|---|---|---|---|---|---|---|
| | 1 mg/kg | | 2 mg/kg | | 1 mg/kg | | 2 mg/kg | |
| Construct | % remaining | SEM | % remaining | SEM | % remaining | SEM | % remaining | SEM |
| TMPRSS6-416 | 36.1 | 5.7 | 19.7 | 3.6 | 34.9 | 5.0 | 18.9 | 3.6 |
| TMPRSS6-0419 | 44.0 | 5.5 | 19.0 | 3.0 | 46.6 | 7.2 | 22.0 | 2.5 |
| TMPRSS6-0615 | 51.7 | 3.5 | 20.5 | 3.4 | 53.4 | 3.8 | 23.0 | 4.1 |
| TMPRSS6-0651 | 46.0 | 4.0 | 31.7 | 3.5 | 53.9 | 5.3 | 31.5 | 3.7 |
| TMPRSS6-0654 | 53.1 | 8.5 | 32.0 | 4.7 | 59.4 | 8.7 | 31.2 | 8.2 |
| TMPRSS6-0831 | 33.8 | 2.7 | 29.1 | 4.5 | 33.4 | 1.8 | 34.5 | 5.0 |
| TMPRSS6-1375 | 61.9 | 4.2 | 46.0 | 6.1 | 61.2 | 3.3 | 46.8 | 3.2 |
| TMPRSS6-1546 | 26.4 | 1.5 | 26.1 | 3.9 | 30.6 | 1.7 | 23.5 | 4.1 |
| TMPRSS6-1550 | 35.0 | 10.7 | 40.8 | 5.7 | 34.2 | 9.2 | 39.0 | 4.9 |

Figure 2:
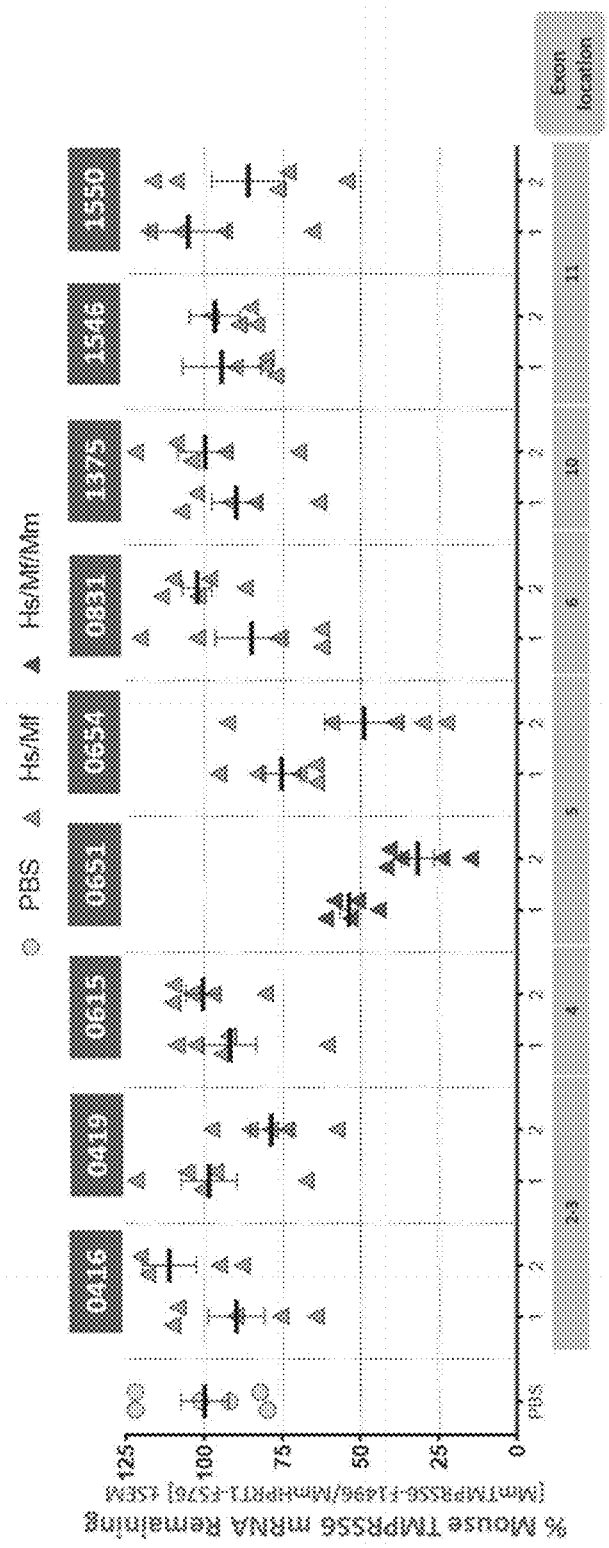
FIG. 2 provides a graph depicting the percent (%) of murine TMPRSS6 mRNA remaining in the liver of mice of FIGS. 1A-1B.
Figure 4A:
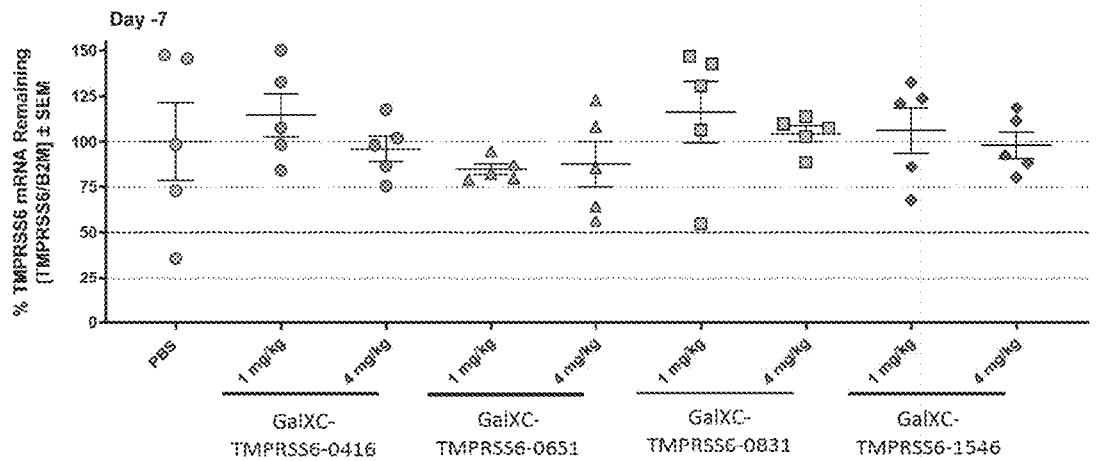
FIGS. 4A-4F provide graphs depicting the percent (%) of endogenous monkey TMPRSS6 mRNA remaining in the liver of NHP (non-human primates) after treatment with GalNAc-conjugated TMPRSS6 oligonucleotides. Macaca fascicularis were dosed subcutaneously with 1 mg/kg or 4 mg/kg of the indicated GalNAc-conjugated TMPRSS6 oligonucleotide formulated in PBS at Day 0, 28, 56, 84, and 112. Liver samples were collected at Day −7 (1 week prior to administration) (FIG. 4A); Day 28 (FIG. 4B); Day 56 (FIG. 4C); Day 84 (FIG. 4D); Day 112 (FIG. 4E); and, Day 168 (FIG. 4F) and the level of monkey TMPRSS6 mRNA was determined using a qPCR assay relative to PBS treated animals.
Figure 4B:
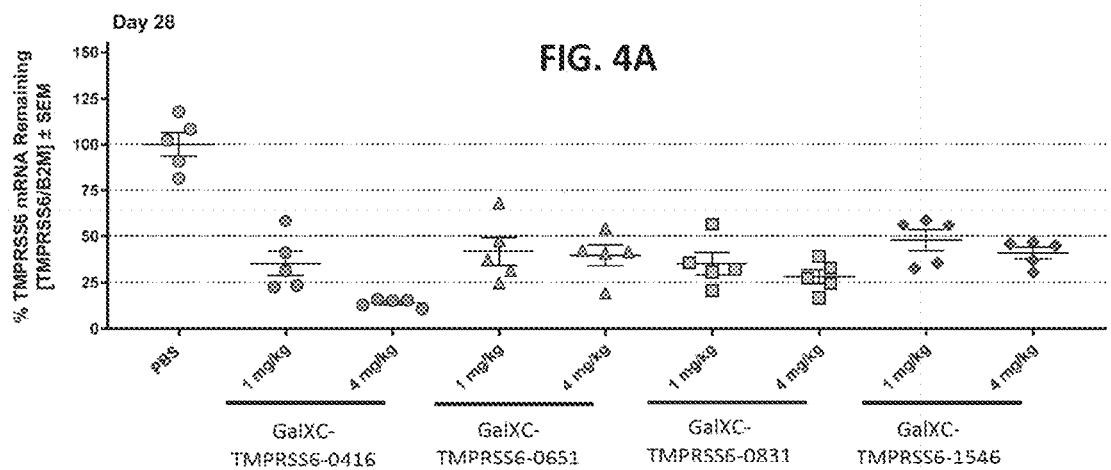
Figure 4C:
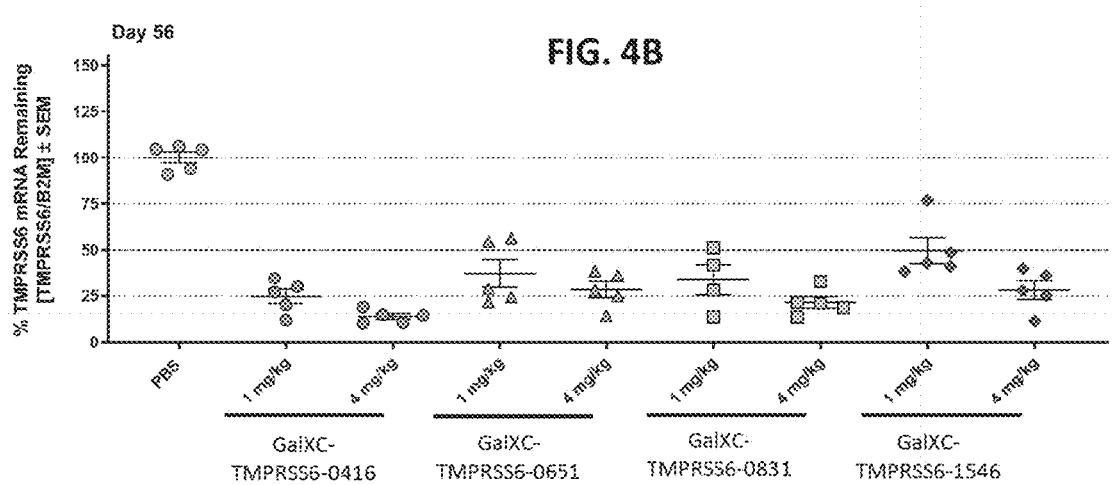
Figure 4D:
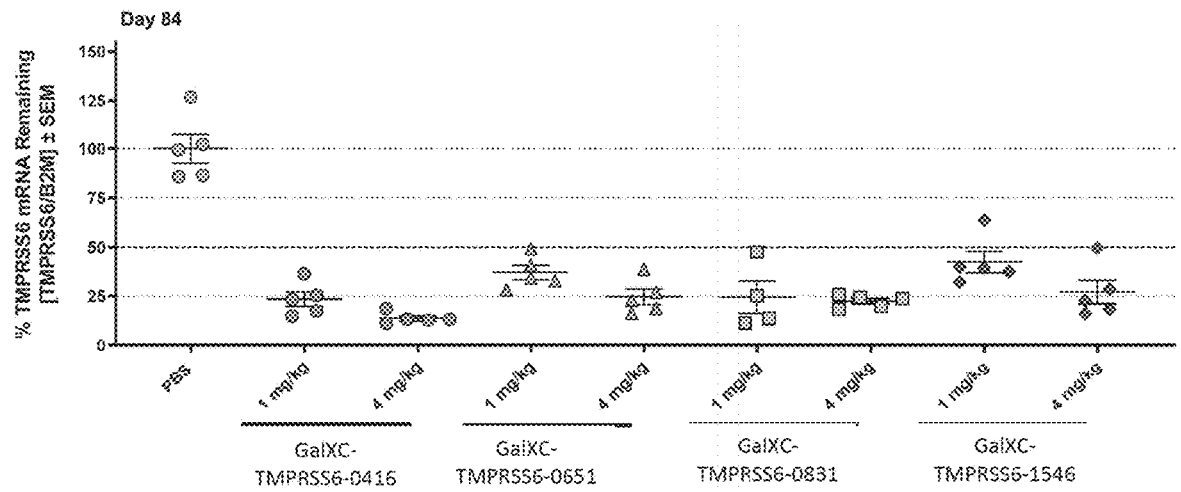
Figure 4E:
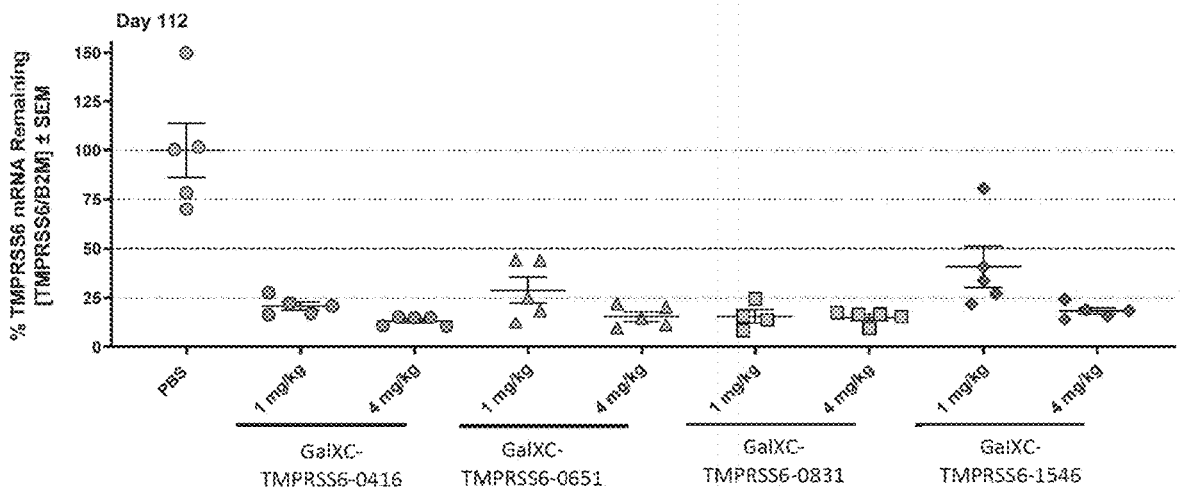
Figure 4F:
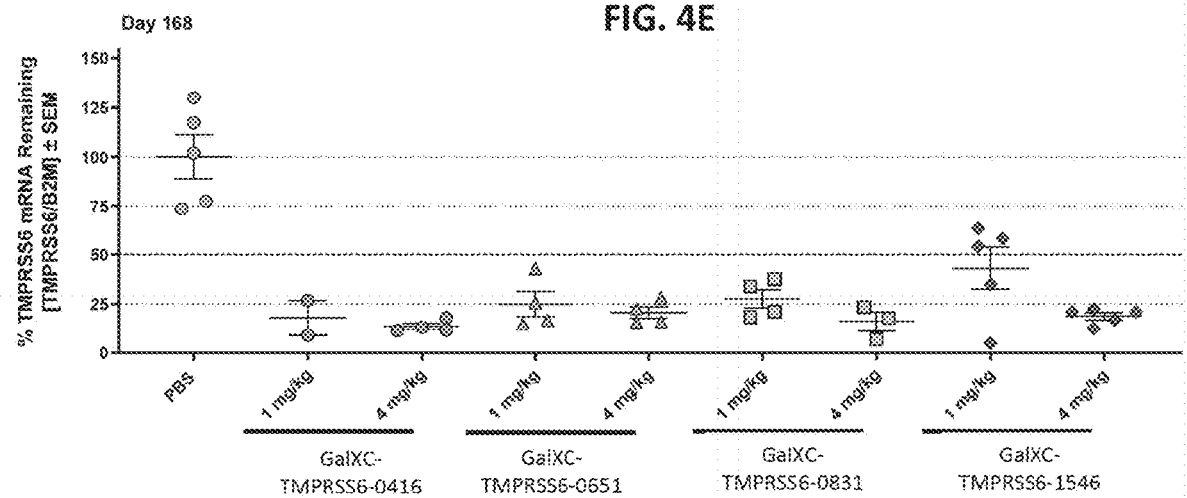
Figure 5A:
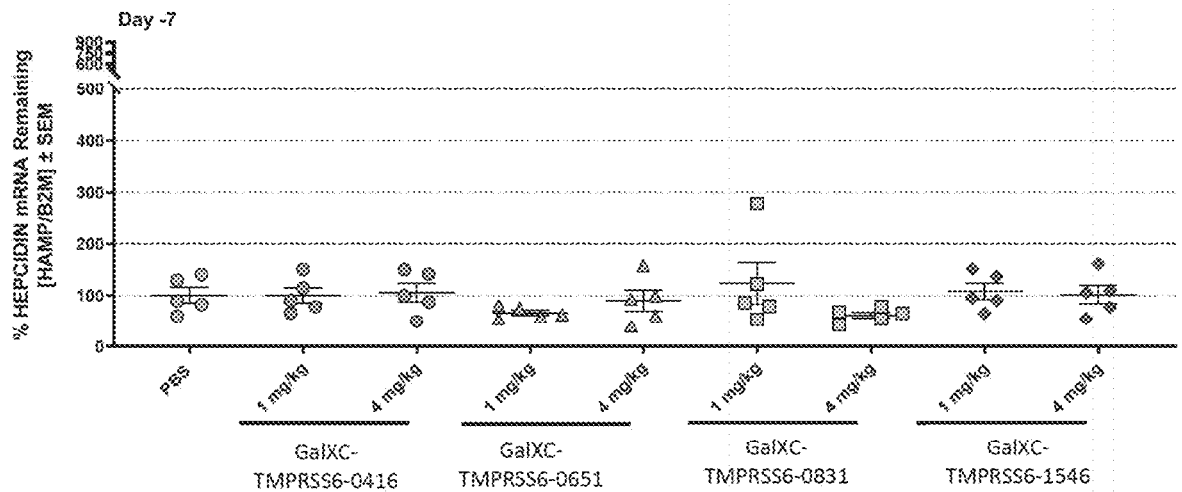
FIGS. 5A-5F provide graphs depicting the percent (%) of monkey endogenous hepcidin mRNA remaining in the liver of NHP (non-human primate) after treatment with GalNAc-conjugated TMPRSS6 oligonucleotides. Macaca fascicularis were dosed subcutaneously with 1 mg/kg or 4 mg/kg of the indicated GalNAc-conjugated TMPRSS6 oligonucleotide formulated in PBS at Day 0, 28, 56, 84, and 112. Liver samples were collected at Day −7 (1 week prior to administration) (FIG. 5A); Day 28 (FIG. 5B); Day 56 (FIG. 5C); Day 84 (FIG. 5D); Day 112 (FIG. 5E); and, Day 168 (FIG. 5F) and the level of monkey hepcidin mRNA was determined using a qPCR assay relative to PBS treated animals.
Figure 5B:
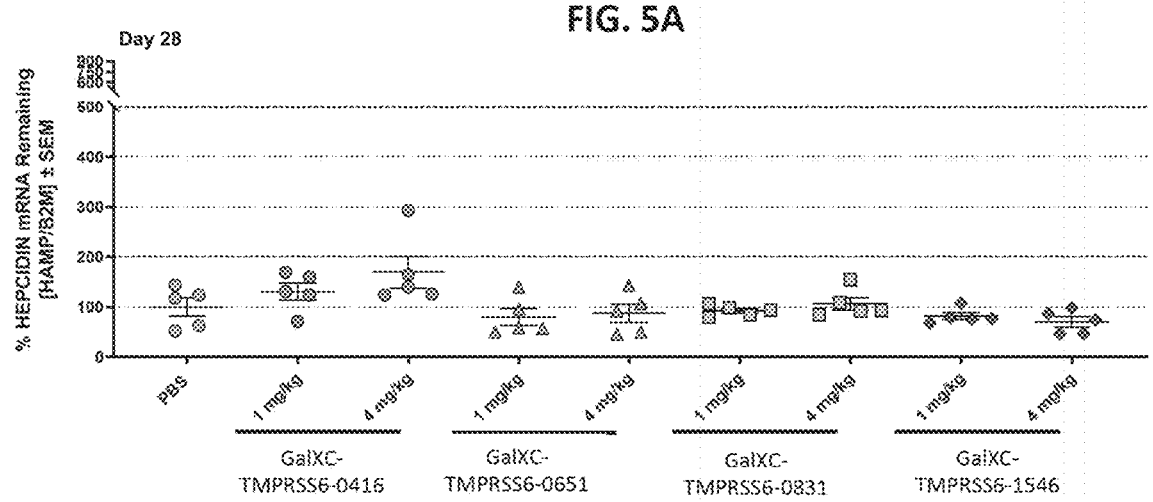
Figure 5C:
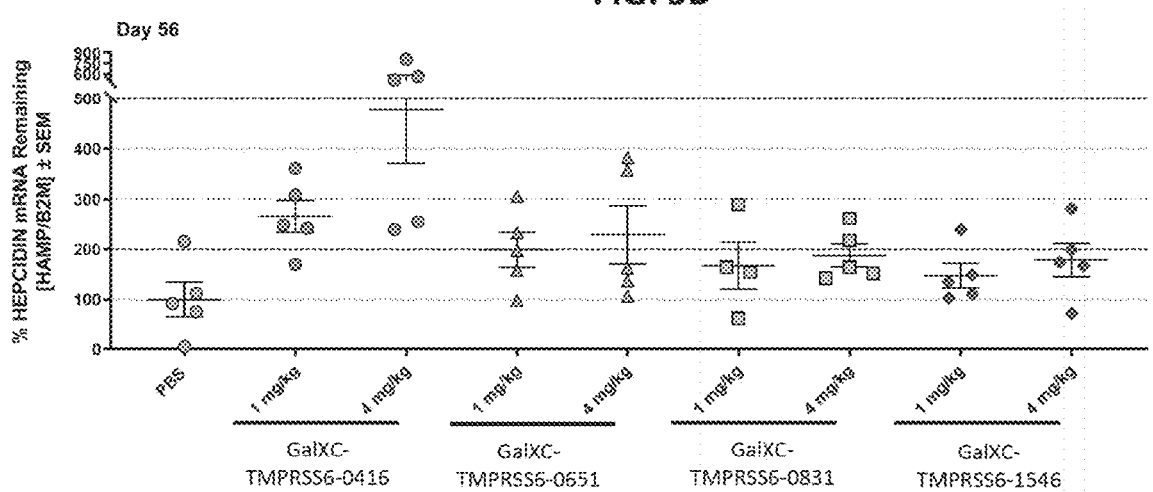
Figure 5D:
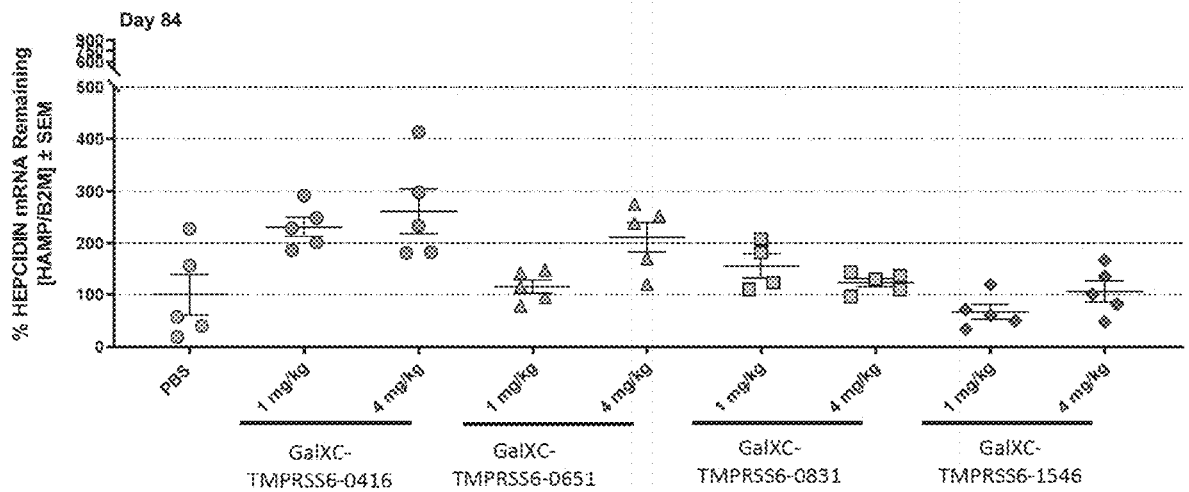
Figure 5E:
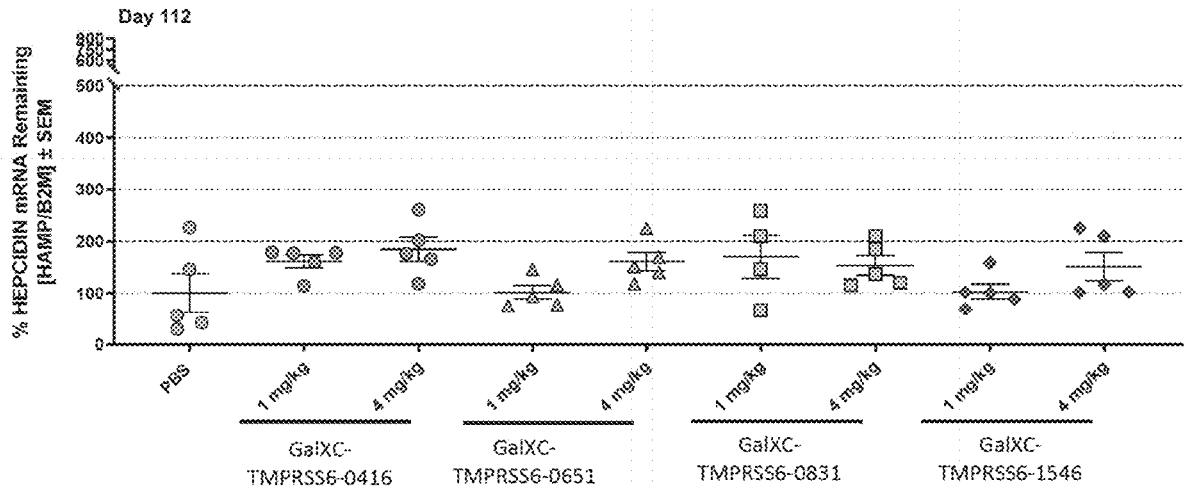
Figure 5F:
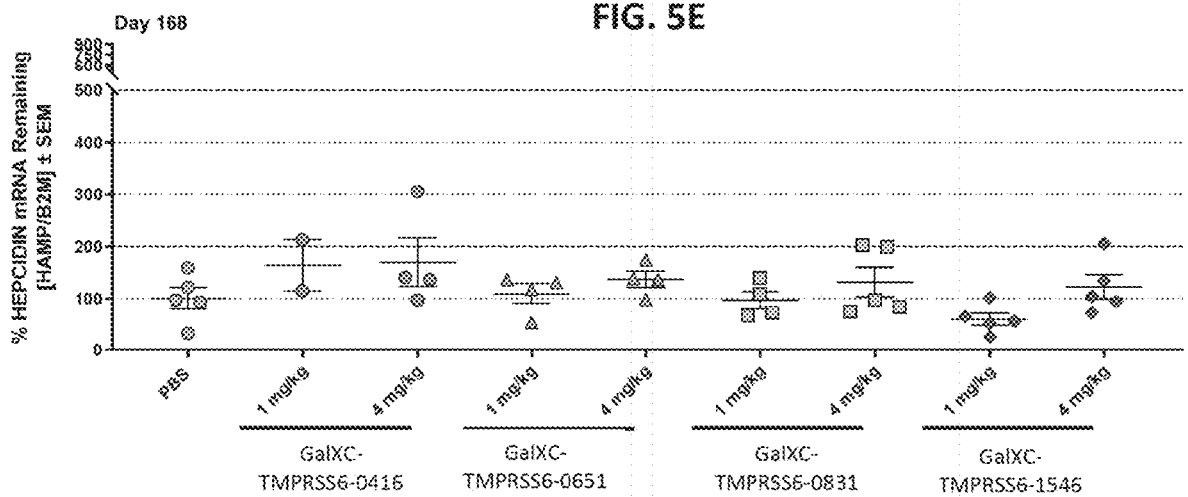
Figure 6A:
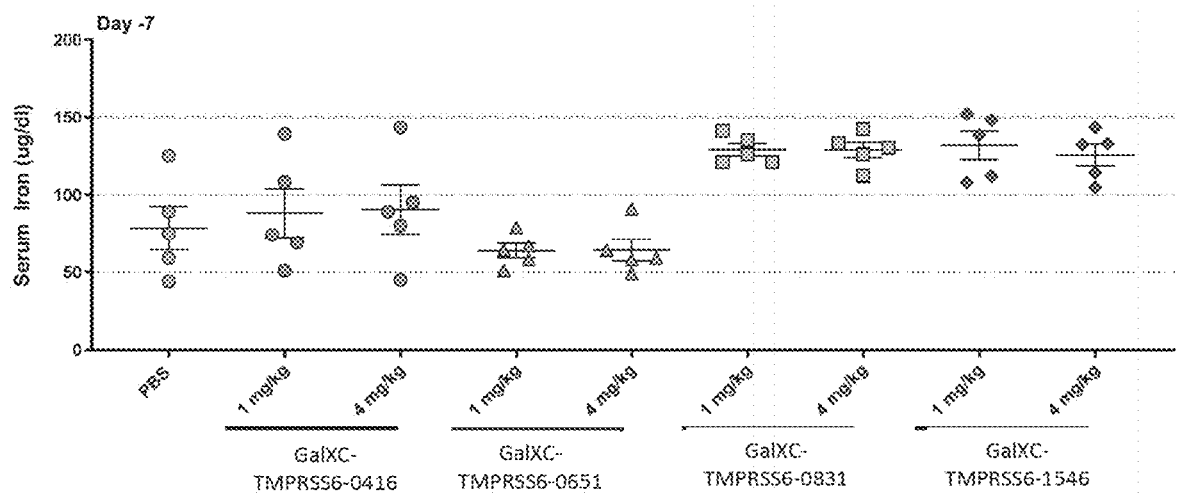
FIGS. 6A-6F provide graphs depicting serum iron levels in monkeys after treatment with GalNAc-conjugated TMPRSS6 oligonucleotides. Macaca fascicularis were dosed subcutaneously with 1 mk/kg or 4 mg/kg of the indicated GalNAc-conjugated TMPRSS6 oligonucleotide formulated in PBS at Day 0, 28, 56, 84, and 112. Serum samples were collected at Day −7 (1 week prior to administration) (FIG. 6A); Day 28 (FIG. 6B); Day 56 (FIG. 6C); Day 84 (FIG. 6D); Day 112 (FIG. 6E); and, Day 168 (FIG. 6F) and the level of serum iron level was determined.
Figure 6B:
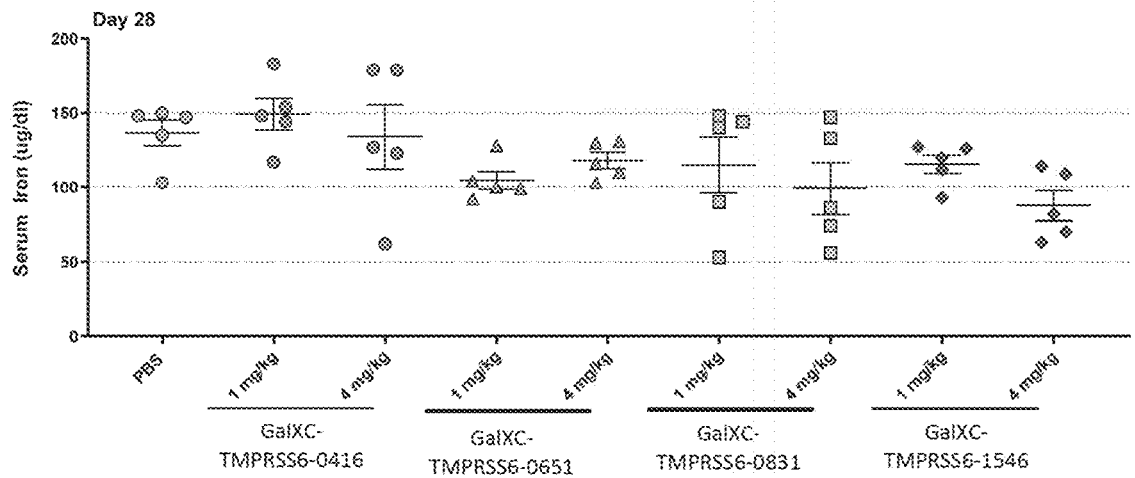
Figure 6C:
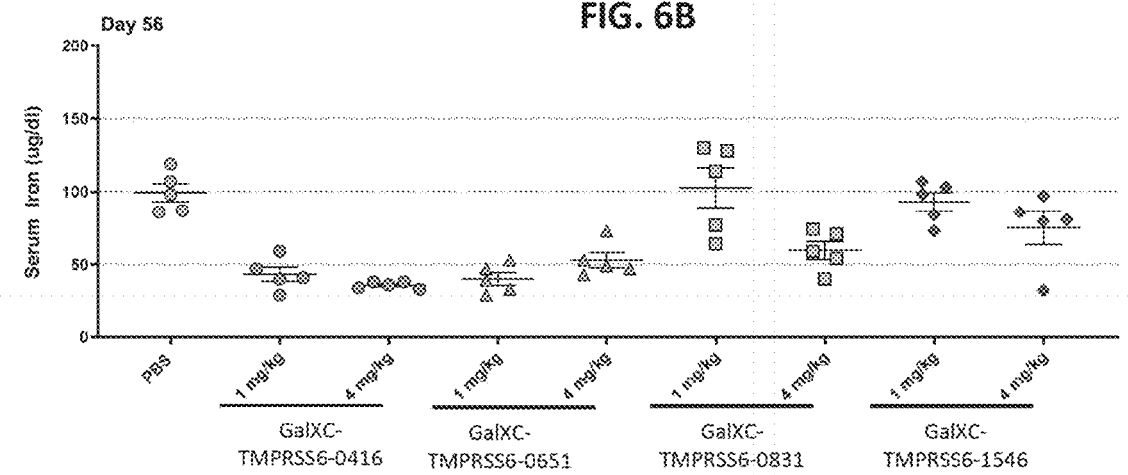
Figure 6D:
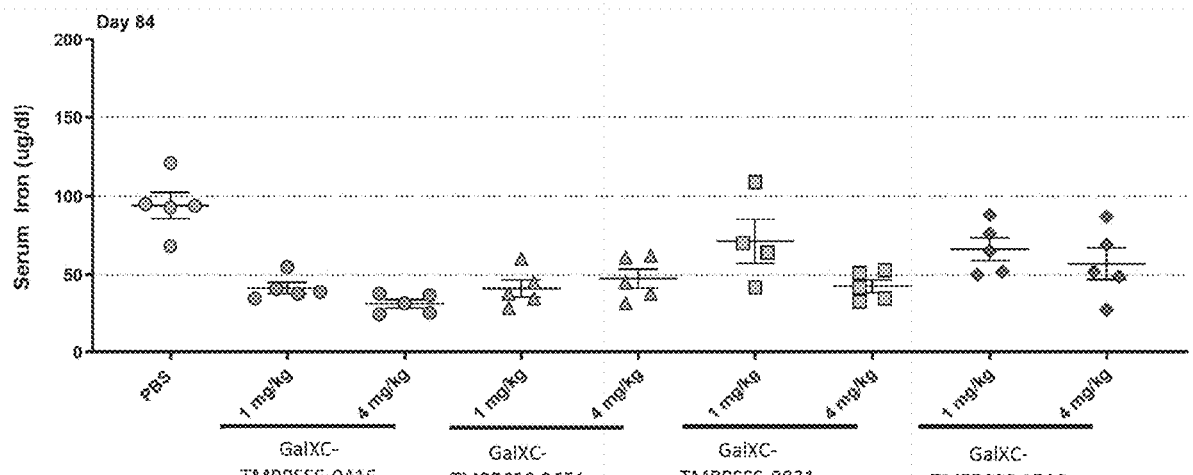
Figure 6E:
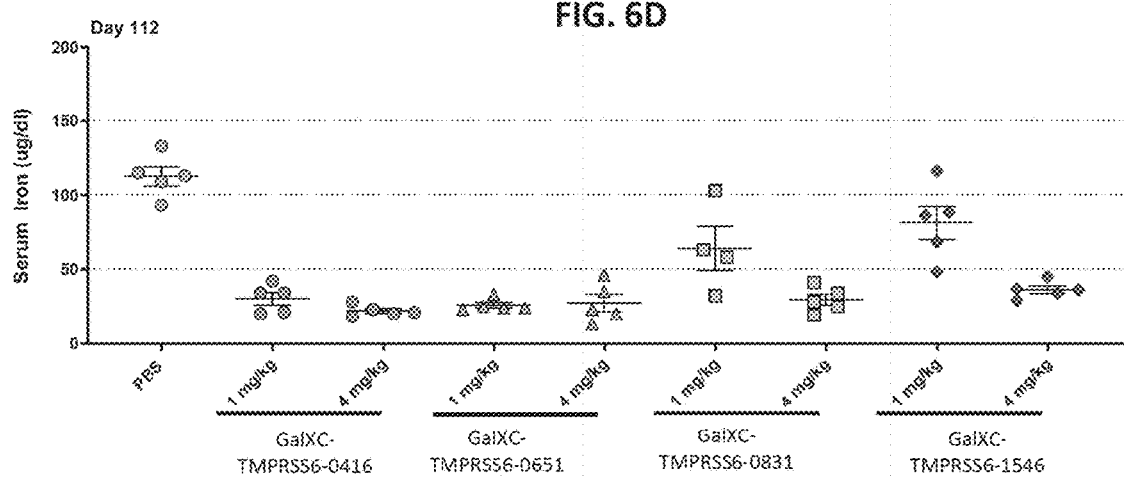
Figure 6F:
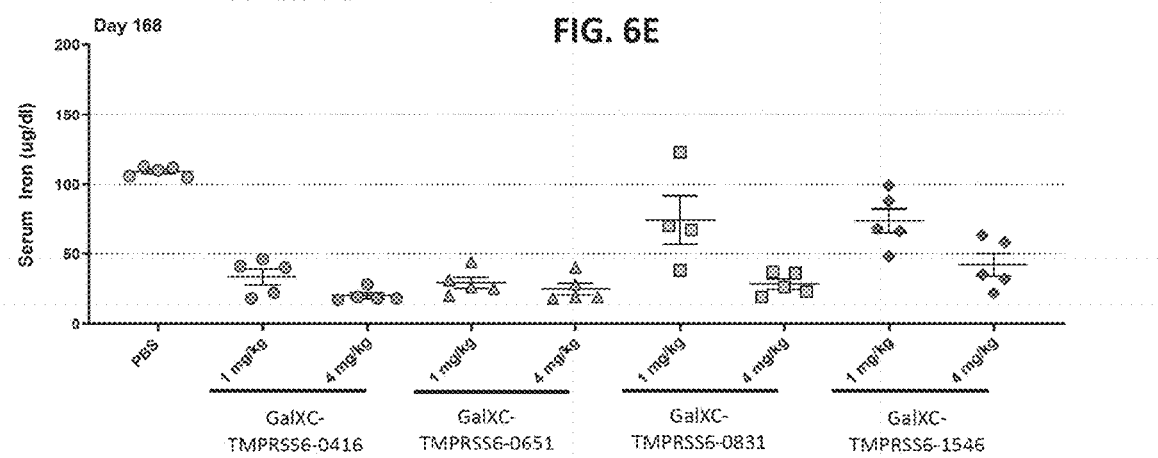
Figure 7A:
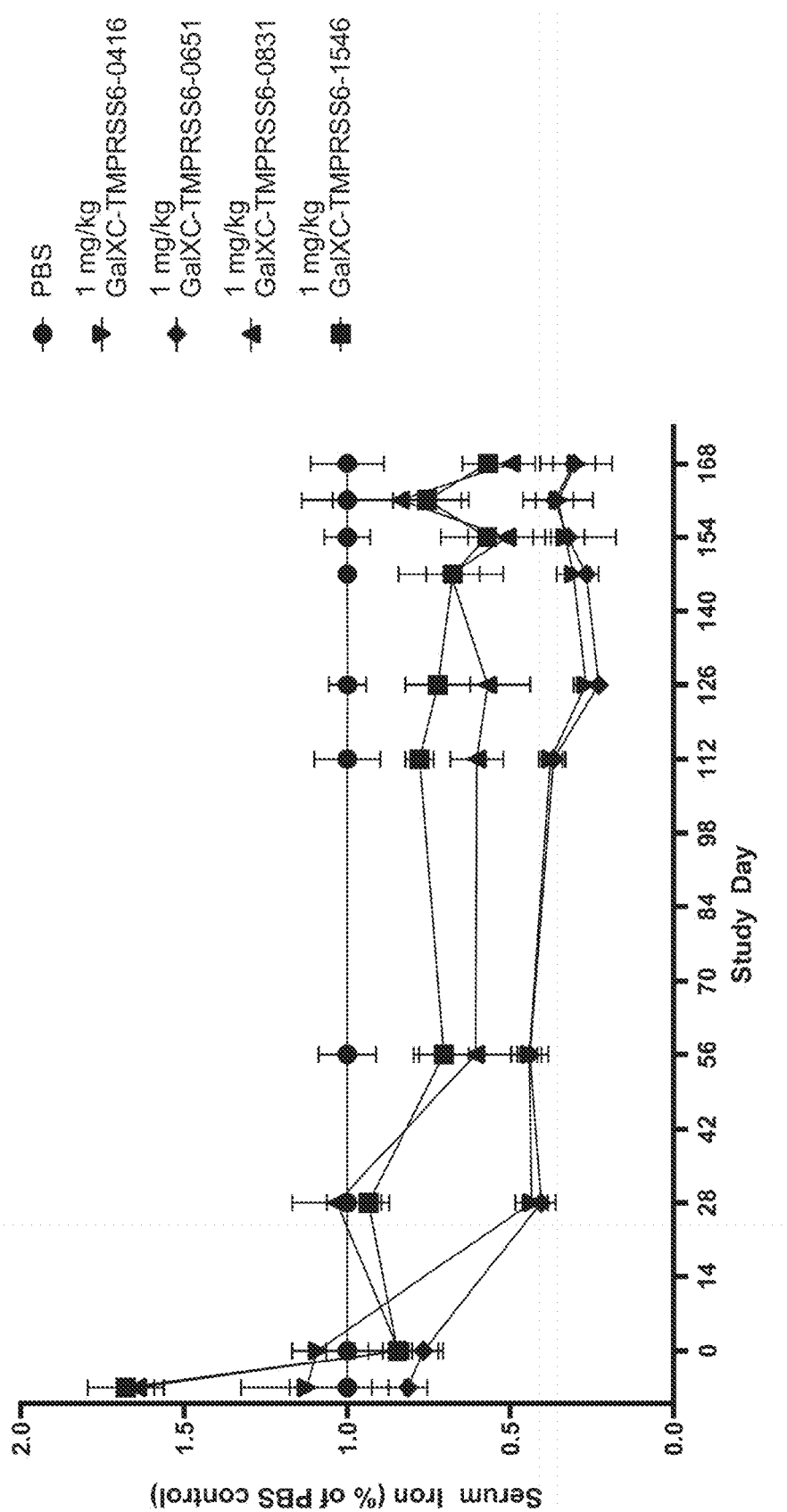
FIGS. 7A-7B provide graphs depicting the serum iron levels measured in FIGS. 6A-6F relative to PBS control treated animals for the doses of 1 mg/kg and 4 mg/kg, respectively.
Figure 7B:
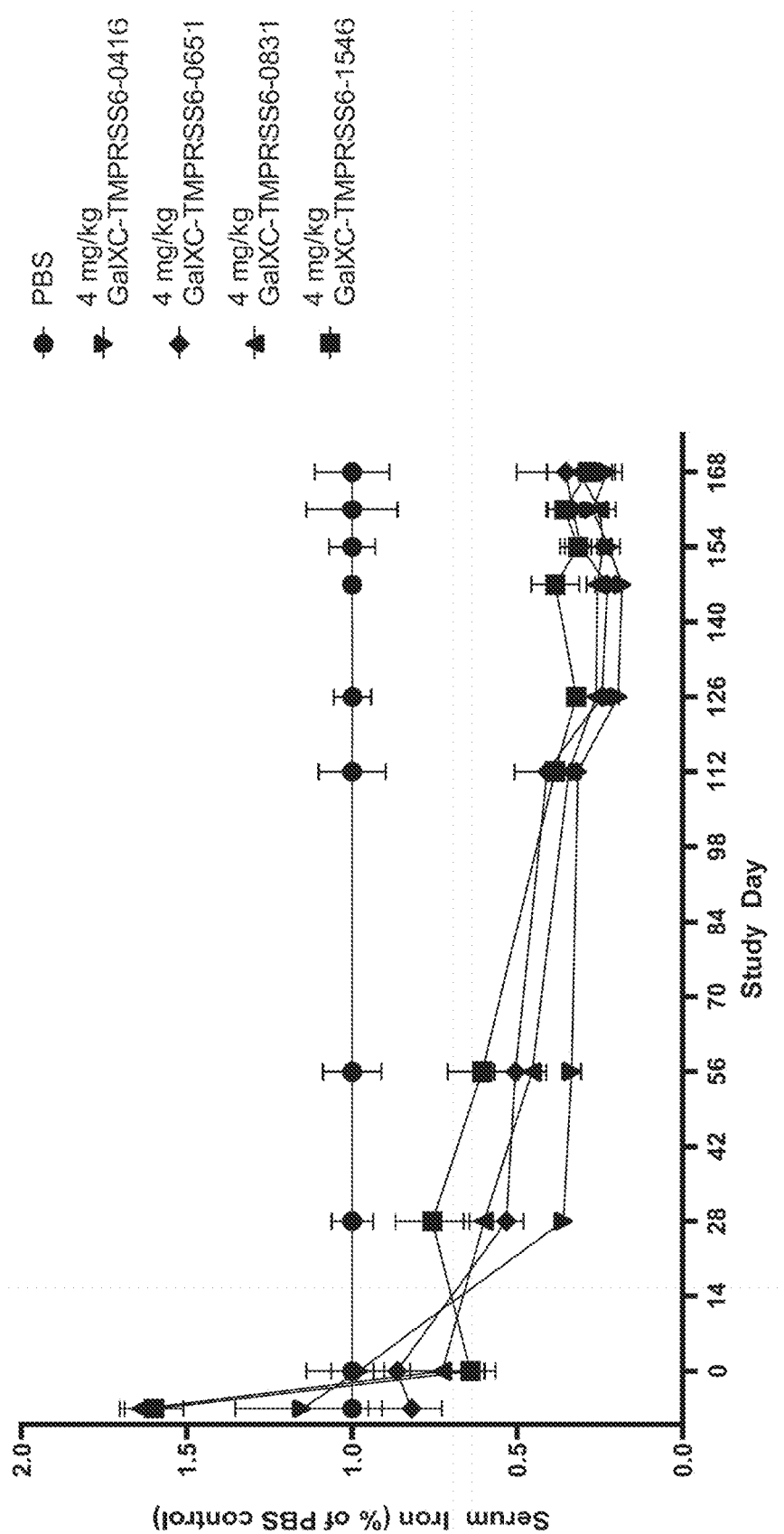
Figure 8A:
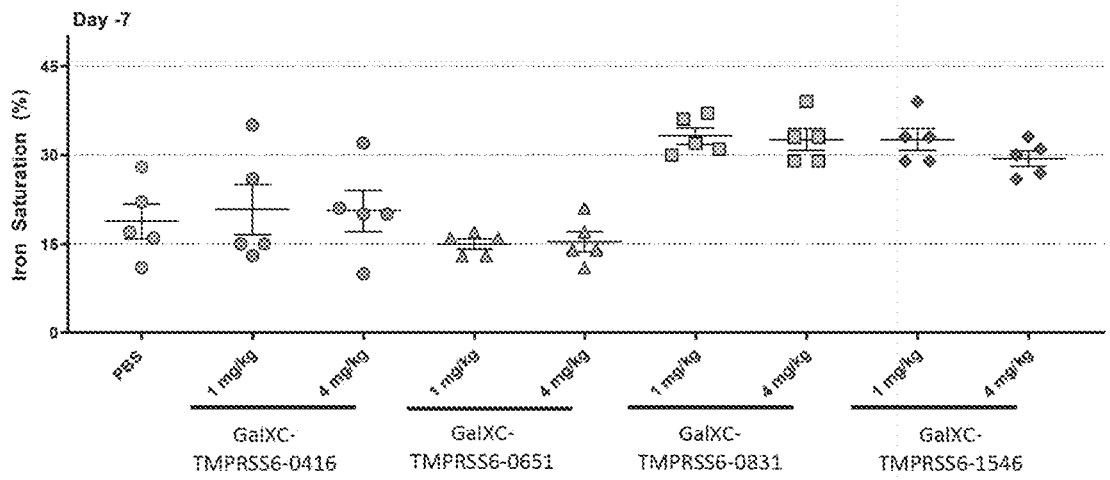
FIGS. 8A-8F provide graphs depicting serum iron saturation levels in monkeys after treatment with GalNAc-conjugated TMPRSS6 oligonucleotides. Macaca fascicularis were dosed subcutaneously with 1 mk/kg or 4 mg/kg of the indicated GalNAc-conjugated TMPRSS6 oligonucleotide formulated in PBS at Day 0, 28, 56, 84, and 112. Serum samples were collected at Day −7 (1 week prior to administration) (FIG. 8A); Day 28 (FIG. 8B); Day 56 (FIG. 8C); Day 84 (FIG. 8D); Day 112 (FIG. 8E); and, Day 168 (FIG. 8F) and serum iron saturation was determined.
Figure 8B:
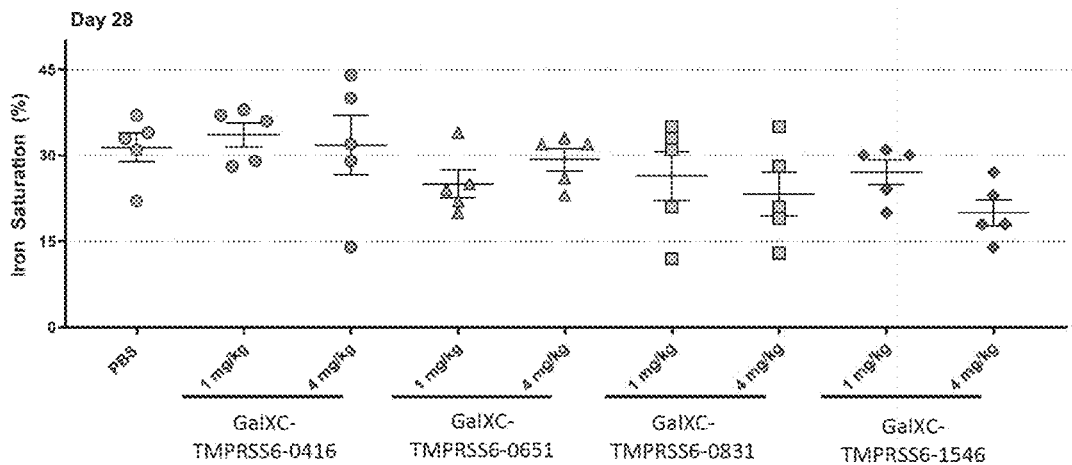
Figure 8C:
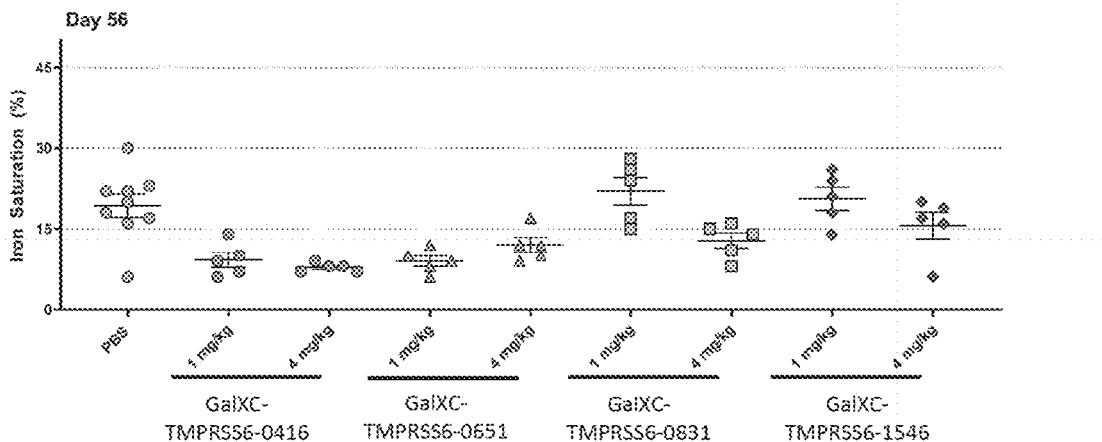
Figure 8D:
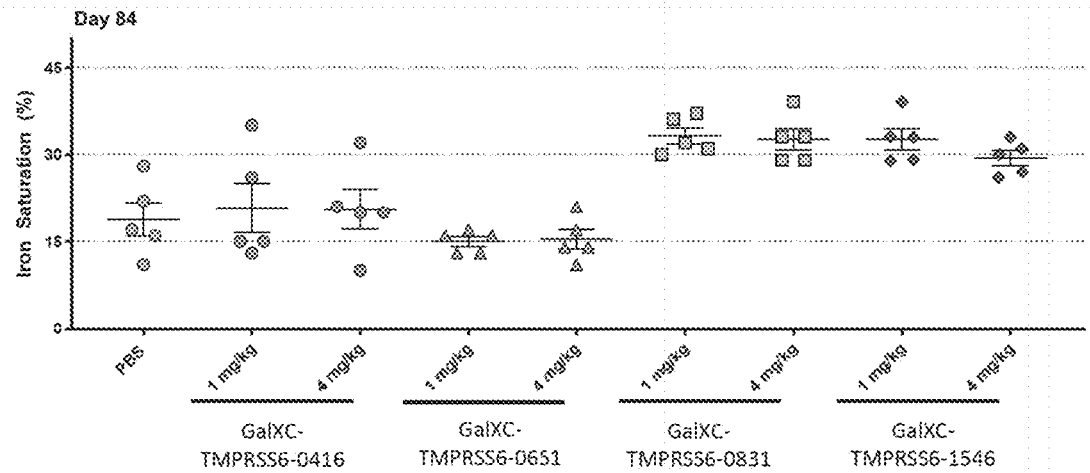
Figure 8E:
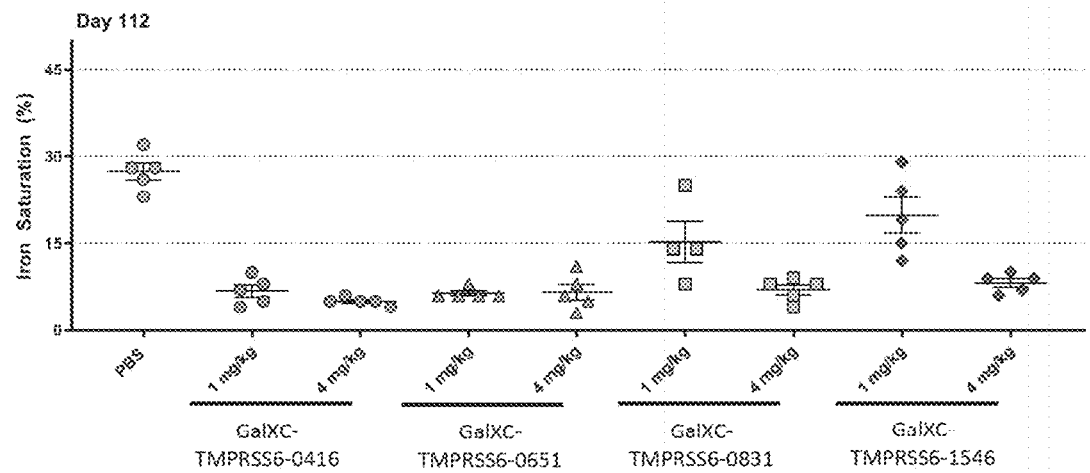
Figure 8F:
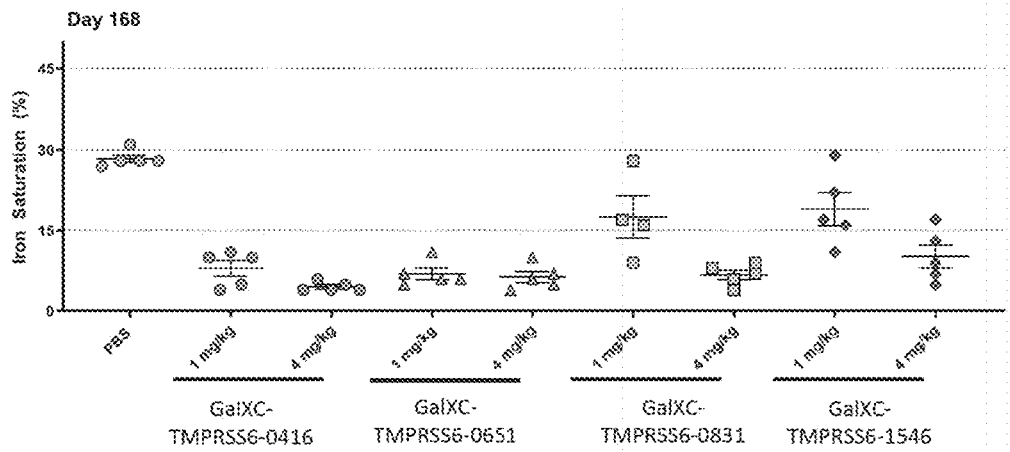
Figure 9A:
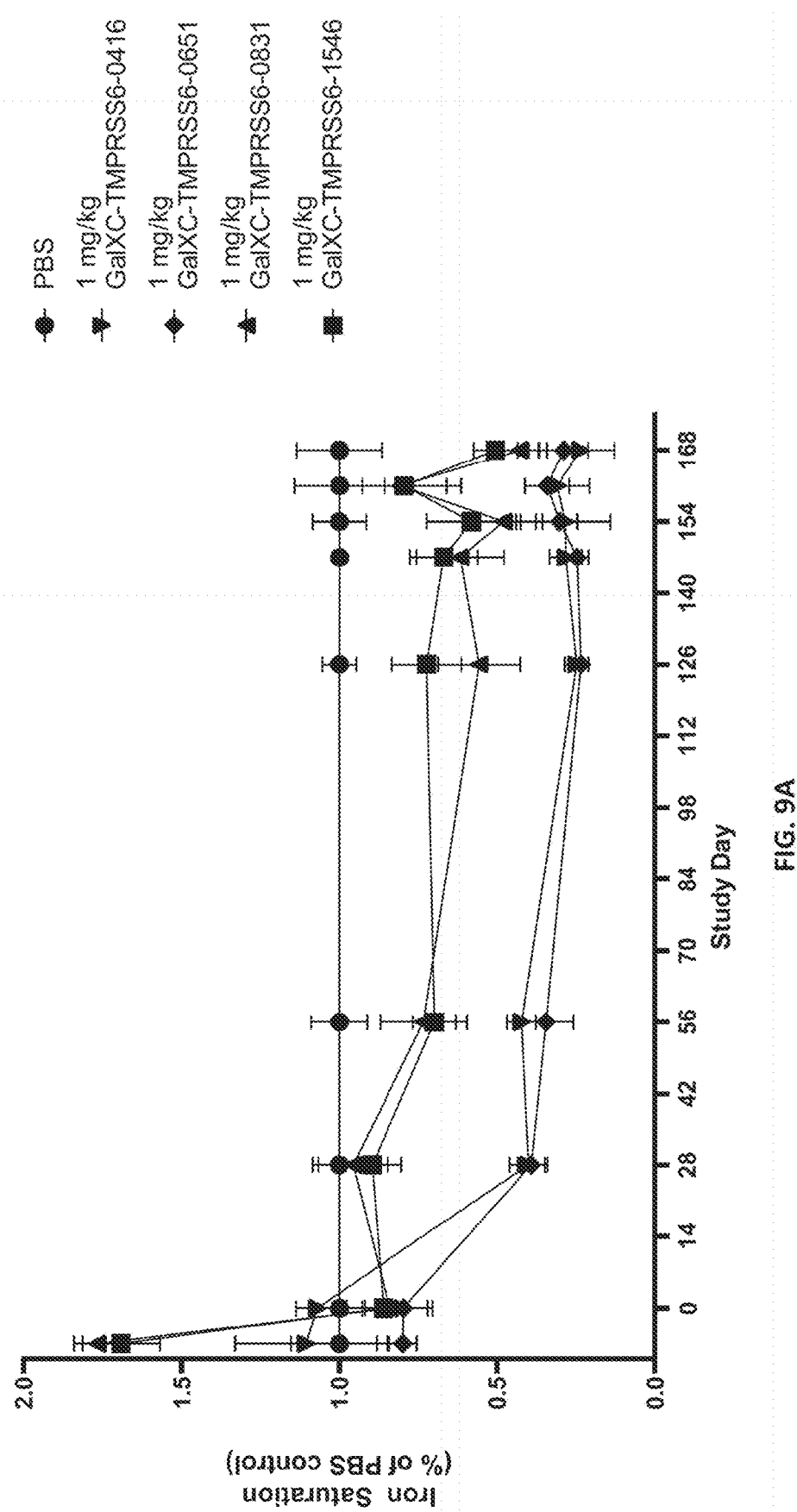
FIGS. 9A-9B provide graphs depicting the serum iron saturation measured in FIGS. 8A-8F relative to PBS control treated animals, for the doses of 1 mg/kg and 4 mg/kg, respectively.
Figure 9B:
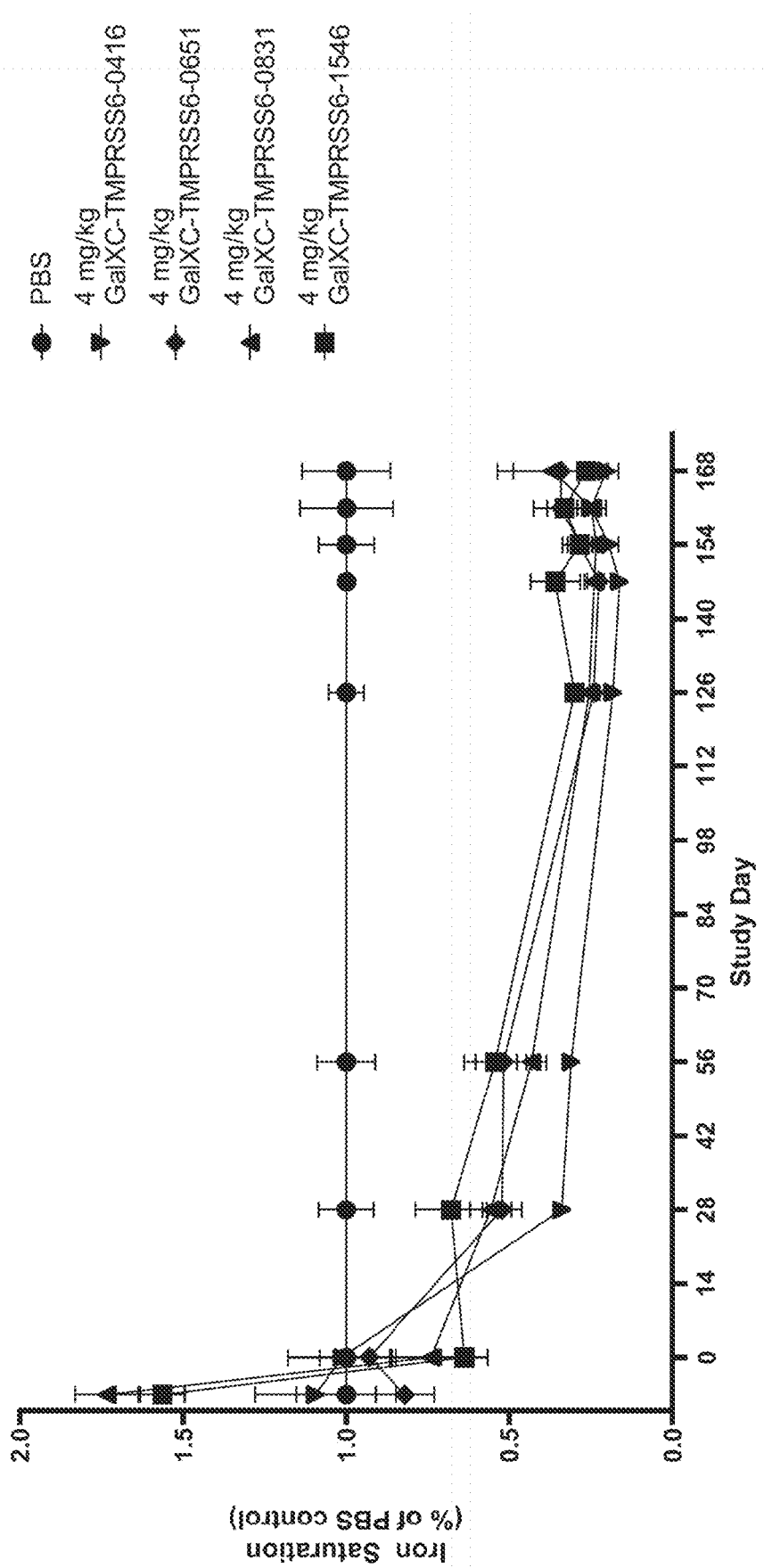

As shown in FIG. 2, GalNAc-conjugated TMPRSS6 RNAi oligonucleotide TMPRSS6-0651, having specificity for murine TMPRSS6 in addition to human TMPRSS6, reduced endogenous murine TMPRSS6 expression by at least 50% at 2 mg/kg. This data demonstrated that GalNAc-modified oligonucleotides successfully reduced endogenous murine TMPRSS6 expression in vivo.

Example 4: GalNAc-Conjugated TMPRSS6 RNAi Oligonucleotides Inhibit Monkey TMPRSS6 Expression In Vivo To evaluate the ability of RNAi oligonucleotides to reduce TMPRSS6 expression in vivo, a monkey model was used (Cynomolgus macaques).

Four modified GalNAc-conjugated TMPRSS6 oligonucleotides shown in Table 6 and depicted in FIGS. 3A-3D were evaluated. The oligonucleotides selected were based on the screen in Example 2 and results of Example 3. Briefly, cynomolgus monkeys, generally referred to herein as monkeys, were subcutaneously administered the indicated GalNAc-conjugated TMPRSS6 oligonucleotides at a concentration of 1 mg/kg or 4 mg/kg formulated in PBS at Day 0, 28, 56, 84, and 112. A control group of monkeys (n=5) were administered only PBS. Total RNA derived from these monkeys were subjected to qRT-PCR analysis to determine TMPRSS6 mRNA levels. Specifically, RNA was extracted from liver tissue to determine monkey TMPRSS6 mRNA levels by qPCR (normalized to the B2M gene) at Day −7, 28, 56, 84, 112, and 168. The levels of monkey TMPRSS6 mRNA were determined using a PrimeTime™ qPCR Probe Assay (IDT), which consisted of a primer pair and fluorescently labeled probe specific to monkey TMPRSS6 mRNA. The percentage of monkey TMPRSS6 mRNA remaining in the samples from treated monkeys was determined using the $2^{-\Delta\Delta Ct}$ ("delta-delta Ct") method (Livak and Schmittgen (2001) Methods 25:402-408).

TABLE 6

GalNAc-Conjugated Monkey TMPRSS6 RNAi Oligonucleotides for NHP screen

| | Species Targets | Unmodified Sense Strand (SEQ ID NO) | Unmodified Antisense strand (SEQ ID NO) | Modified Sense Strand (SEQ ID NO) | Modified Antisense strand (SEQ ID NO) |
|---|---|---|---|---|---|
| TMPRSS6-416 | Hs/Mf | 579 | 600 | 621 | 642 |
| TMPRSS6-0651 | Hs/Mf/Mm | 590 | 611 | 632 | 653 |
| TMPRSS6-0831 | Hs/Mf | 597 | 618 | 639 | 660 |
| TMPRSS6-1546 | Hs/Mf | 586 | 607 | 628 | 649 |

As shown in FIGS. 4A-4F, corresponding to each one of the samples at days −7, 28, 56, 84, 112, and 168 respectively, each oligonucleotide reduced TMPRSS6 expression by at least 50% at both 1 mg/kg and 4 mg/kg throughout the course of the study (i.e., out to 168 days). This data demonstrated that the GalNAc-modified oligonucleotides successfully reduced monkey TMPRSS6 expression in vivo.

Example 5: GalNAc-Conjugated TMPRSS6 RNAi Oligonucleotides Modulate Iron Homeostasis In Vivo Loss of function mutations in TMPRSS6 result in elevated hepcidin plasma levels and lead to severe disorders including iron-refractory, iron-deficient anemia. Hepcidin protein is a regulator of iron homeostasis and directs entry of iron into circulation. When levels of hepcidin are high, serum iron levels decrease which can result in anemia. When hepcidin levels are low, in disease states such as hemochromatosis, iron levels rise and overload can occur. TMPRSS6 is known to suppress hepcidin expression and thus inhibition of TMPRSS6 may modulate hepcidin expression and alter serum iron levels and saturation.

To evaluate changes in iron homeostasis, levels of hepcidin, serum iron, and serum iron saturation were measured after inhibition of TMPRSS6. The four modified GalNAc-conjugated TMPRSS6 oligonucleotides shown in Table 6 and depicted in FIGS. 3A-3D were administered to cynomolgus monkeys as described in Example 4. Total RNA derived from these monkeys were subjected to qRT-PCR analysis to determine hepcidin mRNA levels. Specifically, RNA was extracted from liver tissue to determine monkey hepcidin mRNA levels by qPCR (normalized to the B2M gene) at Day −7, 28, 56, 84, 112, and 168. The levels of monkey hepcidin mRNA were determined using a PrimeTime™ qPCR Probe Assay (IDT), which consisted of a primer pair and fluorescently labeled probe specific to monkey TMPRSS6 mRNA. The percentage of monkey hepcidin mRNA remaining in the samples from treated monkeys was determined using the $2^{-\Delta\Delta Ct}$ ("delta-delta Ct") method (Livak and Schmittgen (2001) Methods 25:402-408).

As shown in FIGS. 5A-5F, corresponding to each one of the samples at days −7, 28, 56, 84, 112, and 168 respectively, by Day 56 (FIG. 5C) a significant upregulation in hepcidin was observed for all oligonucleotides. Upregulation of hepcidin was observed for the remainder of the study to Day 168. This data demonstrates that GalNAc-modified oligonucleotides for inhibiting TMPRSS6 successfully reduce increase hepcidin expression in vivo.

To measure serum iron and serum iron saturation, serum was collected from the animals at Day −7, 28, 56, 84, 112, and 168. The levels of iron were measured using an iron panel analysis conducted at Cornell Veterinary Diagnostic Lab.

As shown in FIGS. 6A-6F and FIGS. 7A-7B, a dose dependent reduction of serum iron was observed after Day 28 and generally throughout the 168-day study for each oligonucleotide. Similarly, a dose dependent reduction of serum iron saturation was observed after Day 28 and generally throughout the 168-day study for each oligonucleotide, as shown in FIGS. 8A-8F and FIGS. 9A-9B. Together, this data demonstrated that GalNAc-modified oligonucleotides for inhibiting TMPRSS6 successfully reduced serum iron and serum iron saturation in vivo. Subsequently, reducing free iron may benefit patients with iron overload diseases, like hereditary haemochromatosis (primary iron overload) and beta-thalassemia (secondary iron overload) and would limit miss-regulated and elevated erythropoiesis as observed in polycythemia vera.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An RNAi oligonucleotide for reducing transmembrane serine protease 6 (TMPRSS6) expression, comprising a sense strand and an antisense strand, wherein the sense strand and the antisense strand form a duplex region, and wherein the sense strand comprises a nucleotide sequence as set forth in SEQ ID NO: 844 and the antisense strand comprises the nucleotide sequences as set forth in SEQ ID NO: 600.

2. The RNAi oligonucleotide according to claim 1, wherein the sense strand comprises a nucleotide sequence as set forth in SEQ ID NO: 579.

3. The RNAi oligonucleotide according to claim 1, wherein the sense strand proximal the 3' end comprises a stem-loop set forth as S1-Lp-S2, wherein S1 is complementary to S2, and wherein Lp forms a loop of 3-5 nucleotides in length between S1 and S2.

4. The RNAi oligonucleotide according to claim 2, wherein the sense strand proximal the 3' end comprises a stem-loop set forth as S1-Lp-S2, wherein S1 is complementary to S2, and wherein Lp forms a loop of 4 nucleotides in length between S1 and S2.

5. The RNAi oligonucleotide according to claim 4, wherein the oligonucleotide comprises at least one modified nucleotide.

6. The RNAi oligonucleotide according to claim 4, wherein all nucleotides of the oligonucleotide are modified nucleotides.

7. The RNAi oligonucleotide according to claim 6, wherein all nucleotides of the oligonucleotides are modified, and each one of the modified nucleotides is 2'-fluoro or 2'-O-methyl.

8. The RNAi oligonucleotide according to claim 7, wherein
the sense strand comprises 36 nucleotides and the antisense strand comprises 22 nucleotides, the nucleotides of each one of the strands being numbered 5' to 3';
all of positions 1-7, 12-27, and 31-36 of the sense strand and positions 1, 6, 8, 9, 11-13, and 15-22 of the antisense strand comprise a 2'-O-methyl (2'-OMe) modification; and
all of positions 8-11 of the sense strand and 2, 3, 4, 5, 7, 10 and 14 of the antisense strand comprise a 2'-fluoro (2'-F) modification.

9. The RNAi oligonucleotide according to claim 4, wherein at least one nucleotide of the oligonucleotide is conjugated to one or more targeting ligands.

10. The RNAi oligonucleotide according to claim 8, wherein at least one nucleotide of the oligonucleotide is conjugated to one or more targeting ligands.

11. The RNAi oligonucleotide according to claim 9, wherein each targeting ligand comprises a N-acetylgalactosamine (GalNAc) moiety.

12. The RNAi oligonucleotide according to claim 10, wherein each targeting ligand comprises a N-acetylgalactosamine (GalNAc) moiety.

13. The RNAi oligonucleotide according to claim 4, wherein the second, third and fourth nucleotides of the loop Lp from 5' to 3' are each conjugated to a monovalent N-acetylgalactosamine (GalNAc) moiety.

14. The RNAi oligonucleotide according to claim 8, wherein the second, third and fourth nucleotides of the loop Lp from 5' to 3' are each conjugated to a monovalent N-acetylgalactosamine (GalNAc) moiety.

15. The RNAi oligonucleotide according to claim 8, wherein the oligonucleotide comprises at least one phosphorothioate linkage.

16. The RNAi oligonucleotide according to claim 14, wherein the oligonucleotide comprises at least one phosphorothioate linkage.

17. The RNAi oligonucleotide according to claim 15, wherein the antisense strand comprises 22 nucleotides;
the nucleotides of each one of the strands are numbered 5' to 3'; and
a phosphorothioate linkage is provided between positions 1 and 2 of the sense strand, and between positions 1 and 2, between positions 2 and 3, between positions 3 and 4, between positions 20 and 21 and between positions 21 and 22 of the antisense strand.

18. The RNAi oligonucleotide according to claim 16, wherein
the antisense strand comprises 22 nucleotides;
the nucleotides of each one of the strands are numbered 5' to 3'; and a phosphorothioate linkage is provided between positions 1 and 2 of the sense strand, and between positions 1 and 2, between positions 2 and 3, between positions 3 and 4, between positions 20 and 21 and between positions 21 and 22 of the antisense strand.

19. The RNAi oligonucleotide according to claim 17, wherein a 5'-terminal nucleotide of the antisense strand comprises a structure according to Chem. 1a (MePhosphonate-4O-mU):

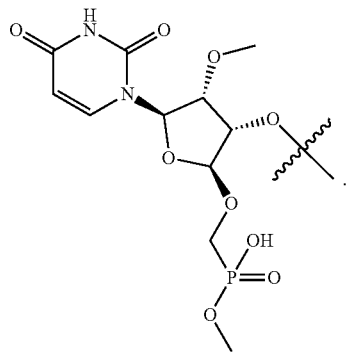 [SMILES: *O[C@@H]1[C@@H](OCP(=O)(O)OC)O[C@@H](n2ccc(=O)[nH]c2=O)[C@@H]1OC]

20. The RNAi oligonucleotide according to claim 18, wherein a 5'-terminal nucleotide of the antisense strand comprises a structure according to Chem. 1a (MePhosphonate-4O-mU):

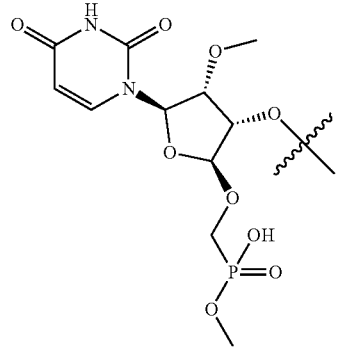

21. The RNAi oligonucleotide according to claim 14, wherein the antisense strand comprises a 3' overhang of 5'-GG-3'.

22. The RNAi oligonucleotide according to claim 20, wherein the antisense strand comprises a 3' overhang of 5'-GG-3'.

23. An RNAi oligonucleotide for reducing TMPRSS6 expression, the oligonucleotide comprising a sense strand and an antisense strand, wherein
the sense strand comprises the sequence and all of the modifications of 5'-[mGs][mG][mU][mG][mC][mU][mA][fC][fU][fC][fU][mG][mG][mU][mA][mU][mU][mU][mC][mA][mG][mC][mA][mG][mC][mC][mG][ademA-GalNAc][ademA-GalNAc][ademA-GalNAc][mG][mG][mC][mU][mG][mC]-3' (SEQ ID NO: 621), and
wherein the antisense strand comprises the sequence and all of the modifications of 5'-[MePhosphonate-4O-mUs][fGs][fAs][fA][fA][mU][fA][mC][mC][fA][mG][mA][mG][fU][mA][mG][mC][mA][mC][mCs][mGs][mG]-3' (SEQ ID NO: 642), wherein mC, mA, mG, mU=2'-OMe ribonucleosides; fA, fC, fG, fU=2'F ribonucleosides; s=phosphorothioate, and wherein ademA-GalNAc=

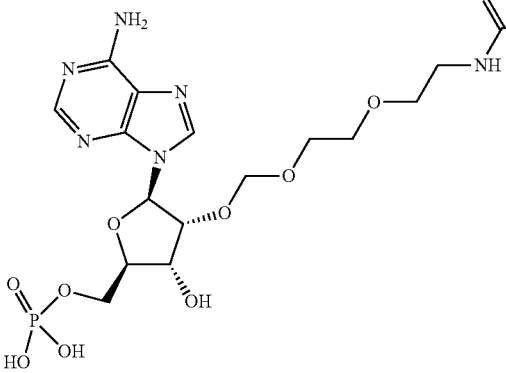

24. A pharmaceutical composition comprising the RNAi oligonucleotide according to claim 23, and a pharmaceutically acceptable carrier, delivery agent or excipient.

25. A method of treating hemochromatosis, comprising administering to a patient in need thereof the RNAi oligonucleotide of claim 23.

26. The method of claim 25, wherein the hemochromatosis is hereditary hemochromatosis or beta-thalassemia.

27. A method of treating hemochromatosis, comprising administering to a patient in need thereof the pharmaceutical composition of claim 24.

28. The method of claim 27, wherein the hemochromatosis is hereditary hemochromatosis or beta-thalassemia.

* * * * *